US012806263B2

(12) United States Patent
Kwong et al.

(10) Patent No.: US 12,806,263 B2
(45) Date of Patent: Nov. 24, 2026

(54) STABILIZED NOROVIRUS VIRUS-LIKE PARTICLES AS VACCINE IMMUNOGENS

(71) Applicants: The United States of America, as represented by the Secretary, Department of Health and Human Services, Bethesda, MD (US); The University of North Carolina at Chapel Hill, Chapel Hill, NC (US); Board of Regents, the University of Texas System, Austin, TX (US)

(72) Inventors: Peter Kwong, Washington, DC (US); Raffaello Verardi, Washington, DC (US); Yaroslav Tsybovsky, Brunswick, MD (US); Jason Gorman, Silver Spring, MD (US); Gwo-Yu Chuang, Rockville, MD (US); Li Ou, Potomac, MD (US); Lisa Lindesmith, Apex, NC (US); Ralph Baric, Haw River, NC (US); George Georgiou, Austin, TX (US)

(73) Assignees: The United States of America, as represented by the Sectetaty, Department of Health and Human Services, Bethesda, MD (US); The University of North Carolina at Chapel Hill, Chapel Hill, NC (US); Board of Regents, the University of Texas System, Austin, TX (US)

( * ) Notice: Subject to any disclaimer, the term of this patent is extended or adjusted under 35 U.S.C. 154(b) by 665 days.

(21) Appl. No.: 18/031,602

(22) PCT Filed: Oct. 14, 2021

(86) PCT No.: PCT/US2021/055018
§ 371 (c)(1),
(2) Date: Apr. 12, 2023

(87) PCT Pub. No.: WO2022/081870
PCT Pub. Date: Apr. 21, 2022

(65) Prior Publication Data
US 2023/0381293 A1 Nov. 30, 2023

Related U.S. Application Data

(60) Provisional application No. 63/091,824, filed on Oct. 14, 2020.

(51) Int. Cl.

| | |
|---|---|
| ***A61K 39/145*** | (2006.01) |
| ***A61P 37/04*** | (2006.01) |
| ***G01N 33/68*** | (2006.01) |
| *A61K 39/00* | (2006.01) |

(52) U.S. Cl.
CPC ............ *A61K 39/145* (2013.01); *A61P 37/04* (2018.01); *G01N 33/6854* (2013.01); *A61K 2039/5258* (2013.01)

(58) Field of Classification Search
None
See application file for complete search history.

(56) References Cited

U.S. PATENT DOCUMENTS 6,572,862 B1 * 6/2003 Estes ...................... C12Q 1/701 514/3.7
8,841,120 B2 * 9/2014 Richardson ............. A61P 31/12 435/320.1

FOREIGN PATENT DOCUMENTS

WO WO 2019/104439 A1 6/2019

OTHER PUBLICATIONS

Ming Xia et al. (Acs Nano, Nov. 2018, vol. 12, p. 10665-10682 in IDS on Apr. 12, 2023).*
Ming Xia et al. (Acs Nano, Nov. 2018, vol. 12, p. 10665-10682.*
Ahmed et al., "Global prevalence of norovirus in cases of gastroenteritis: a systematic review and meta-analysis," *Lancet Infect Dis.* 14.8: 725-730, Aug. 2014.
Arias et al., "Progress towards the prevention and treatment of norovirus infections," *Future Microbiol.* 8.11: 1475-1487, Nov. 2013.
Atmar et al., "Norovirus Vaccine against Experimental Human Norwalk Virus Illness," *N Engl J Med.* 365.23: 2178-2187, Dec. 2011.
Atmar et al., "Persistence of Antibodies to 2 Virus-Like Particle Norovirus Vaccine Candidate Formulations in Healthy Adults: 1-Year Follow-up With Memory Probe Vaccination," *J Infect Dis.* 220.4: 603-614, Jul. 2019.
Ausar et al., "Conformational Stability and Disassembly of Norwalk Virus-like Particles: Effect of pH and Temperature," *J Biol Chem.* 281.28: 19478-19488, Jul. 2006.
Ball et al., "Oral Immunization with Recombinant Norwalk Virus-Like Particles Induces a Systemic and Mucosal Immune Response in Mice," J. Virol. 72.2: 1345-1353, Feb. 1998.

(Continued)

*Primary Examiner* — Agnieszka Boesen
(74) *Attorney, Agent, or Firm* — Klarquist Sparkman, LLP

(57) ABSTRACT

Recombinant Norovirus Virus-Like Particles (VLPs) formed from recombinant Norovirus VP1 proteins, and methods of their use and production are disclosed. In several embodiments, the Recombinant Norovirus VLPs can be used to generate an immune response to Norovirus VP1 protein in a subject. In additional embodiments, an effective amount of the recombinant Norovirus VLPs can be administered to a subject in a method of inhibiting a Norovirus infection.

34 Claims, 32 Drawing Sheets

Specification includes a Sequence Listing.

(56) References Cited

OTHER PUBLICATIONS

Barad et al., "EMRinger: side chain-directed model and map validation for 3D cryo-electron microscopy," *Nat Methods* 12.10: 943-946, Oct. 2015.
Bertolotti-Ciarlet et al., "Structural Requirements for the Assembly of Norwalk Virus-Like Particle," *J Virol.* 76.8: 4044-4055, Apr. 2002.
Bernstein et al., "Norovirus Vaccine Against Experimental Human GII.4 Virus Illness: A Challenge Study in Healthy Adults," *J Infect Dis.* 211.6: 870-878, Mar. 2015.
Bok and Green, "Norovirus Gastroenteritis in Immunocompromised Patients," *N Engl J Med.* 368.10: 971, Mar. 2013 (12 pages).
Bundy and Swartz, "Efficient disulfide bond formation in virus-like particles," *J Biotechnol.* 154.4: 230-239, Jul. 2011.
Chen et al., "MolProbity : all-atom structure validation for macromolecular crystallography," *Acta Crystallogr D Biol. Crystallogr.* 66.Pt 1: 12-21, Jan. 2010.
Cortes-Penfield et al., "Prospects and Challenges in the Development of a Norovirus Vaccine," *Clin Ther.* 39.8: 1537-1549, Aug. 2017.
Devant et al., "Heterologous expression of human norovirus GII.4 VP1 leads to assembly of T=4 virus-like particles," *Antiviral Res.* 168: 175-182, 2019.
Emsley et al., "Features and development of Coot," *Acta Crystallogr D Biol Crystallogr.* 66.Pt 4: 486-501, Apr. 2010.
Hansman et al., "Structural Basis for Broad Detection of Genogroup II Noroviruses by a Monoclonal Antibody That Binds to a Site Occluded in the Viral Particle," *J Virol.* 86.7: 3635-3646, Apr. 2012.
International Search Report and Written Opinion mailed in International Application No. PCT/US2021/055018 by the European Searching Authority on Feb. 23, 2022 (15 pages).
Jiang et al., "Expression, self-assembly, and antigenicity of the Norwalk virus capsid protein," *J Virol.* 66.11: 6527-6532, Nov. 1992.
Jung et al., "High-resolution cryo-EM structures of outbreak strain human norovirus shells reveal size variations," *Proc Natl Acad Sci USA* 116.26: 12828-12832, Jun. 2019.
Katpally et al., "High-Resolution Cryo-Electron Microscopy Structures of Murine Norovirus 1 and Rabbit Hemorrhagic Disease Virus Reveal Marked Flexibility in the Receptor Binding Domains," *J Virol.* 84.11: 5836-5841, Jun. 2010.
Kotecha et al., "Structure-based energetics of protein interfaces guides foot-and-mouth disease virus vaccine design," *Nat Struct Mol Biol.* 22.10: 788-794, Oct. 2015.
Lander et al., "Appion: An integrated, database-driven pipeline to facilitate EM image processing," *J Struct Biol.* 166.1: 95-102, Apr. 2009.
Liebschner et al., "Macromolecular structure determination using X-rays, neutrons and electrons: recent developments in Phenix," *Acta Crystallogr D Struct Biol.* 75. Pt 10: 861-877, Oct. 2019.
Lindesmith et al., "Particle Conformation Regulates Antibody Access to a Conserved GII.4 Norovirus Blockade Epitope," *J Virol.* 88.16: 8826-8842, Aug. 2014.
Lindesmith et al., "Broad Blockade Antibody Responses in Human Volunteers after Immunization with a Multivalent Norovirus VLP Candidate Vaccine: Immunological Analyses from a Phase I Clinical Trial," *PLoS Med.* 12.13: e1001807, Mar. 2015 (32 pages).
Lindesmith et al., "Serum Immunoglobulin A Cross-Strain Blockade of Human Noroviruses," *Open Forum Infect Dis.* 2.3: ofv084, Jul. 2015 (8 pages).
Lindesmith et al., "Sera Antibody Repertoire Analyses Reveal Mechanisms of Broad and Pandemic Strain Neutralizing Responses after Human Norovirus Vaccination," *Immunity* 50: 1530-1541, Jun. 2019.
Lopman et al., "The Vast and Varied Global Burden of Norovirus: Prospects for Prevention and Control," PLoS Med. 13.4: e1001999, Apr. 2016 (12 pages).
Lu et al., "Assessing sequence plasticity of a virus-like nanoparticle by evolution toward a versatile scaffold for vaccines and drug delivery," *Proc Natl Acad Sci.* 112.40: 12360-12365, Oct. 2015.
Malik et al., "Structures of foot and mouth disease virus pentamers: Insight into capsid dissociation and unexpected pentamer reassociation," *PLOS Pathog.* 13.9: e1006607, Sep. 2017 (15 pages).
Mastronarde, "Automated electron microscope tomography using robust prediction of specimen movements," *J Struct Biol.* 152.1: 36-51, Oct. 2005.
Mateo et al., "Engineering Viable Foot-and-Mouth Disease Virus with Increased Thermostability as a Step in the Development of Improved Vaccines," *J Virol.* 82.24: 12232-12240, Dec. 2008.
Mattner et al., "Risk groups for clinical complications of norovirus infections: an outbreak investigation," *Clin Microbiol Infect.* 12.1: 69-74, Jan. 2006.
Moshen et al., "Major findings and recent advances in virus-like particle (VLP)-based vaccines," *Semin Immunol.* 34: 123-132, Dec. 2017.
Parker et al., "Identification of Genogroup I and Genogroup II Broadly Reactive Epitopes on the Norovirus Capsid," *J Virol.* 79.12: 7402-7409, Jun. 2005.
Pettersen et al., "UCSF Chimera—A visualization system for exploratory research and analysis," *J Comput Chem.* 25.13: 1605-1612, Oct. 2004.
Porta et al., "Rational Engineering of Recombinant Picornavirus Capsids to Produce Safe, Protective Vaccine Antigen," *PLOS Path.* 9.3: e1003255, Mar. 2013 (8 pages).
Prasad et al., "X-ray Crystallographic Structure of the Norwalk Virus Capsid," *Science* 286: 287-290, Oct. 1999.
Punjani et al., "cryoSPARC: algorithms for rapid unsupervised cryo-EM structure determination," *Nat Methods* 14.3: 290-296, Mar. 2017.
Ramani et al., "Mucosal and Cellular Immune Responses to Norwalk Virus," *J Infect Dis.* 212.3: 397-405, Aug. 2015.
Rohou and Grigorieff, "CTFFIND4: Fast and accurate defocus estimation from electron micrographs," *J Struct Biol.* 192.2: 216-221, Nov. 2015.
Scheres, "Relion: Implementation of a Bayesian approach to cryo-EM structure determination," *J Struct Biol.* 180.3: 519-530, Dec. 2012.
Shanker et al., "Structural basis for norovirus neutralization by an HBGA blocking human IgA antibody," *Proc Natl Acad Sci USA* 113.40: E5830-E5837, Oct. 2016.
Shiota et al., "Characterization of a Broadly Reactive Monoclonal Antibody against Norovirus Genogroups I and II: Recognition of a Novel Conformational Epitope," *J Virol.* 81.22: 12298-12306, Nov. 2007.
Slifka and Amanna, "Role of Multivalency and Antigenic Threshold in Generating Protective Antibody Responses," *Front Immunol.* 10: 956, May 2019 (16 pages).
Song et al., "Dynamic rotation of the protruding domain enhances the infectivity of norovirus," *PLoS Pathog.* 16.7: e1008619, Jul. 2020 (24 pages).
Suloway et al., "Automated molecular microscopy: The new Leginon system," J Struct Biol. 151.1: 41-60, Jul. 2005.
Tang et al., "EMAN2: An extensible image processing suite for electron microscopy," *J Struct Biol.* 157.1: 38-46, Jan. 2007.
Treanor et al., "A Novel Intramuscular Bivalent Norovirus Virus-Like Particle Vaccine Candidate-Reactogenicity, Safety, and Immunogenicity in a Phase 1 Trial in Healthy Adults," *J Infect Dis.* 210.11: 1763-1771, Dec. 2014.
Verardi et al., "Disulfide stabilization of human norovirus GI.1 virus-like particles focuses immune response toward blockade epitopes," *NPJ Vaccines* 5.1: 110, Dec. 2020 (10 pages).
Voss et al., "DoG Picker and TiltPicker: Software tools to facilitate particle selection in single particle electron microscopy," *J Struct Biol.* 166.2: 205-213, May 2009.
Xia et al., "Bioengineered Norovirus S60 Nanoparticles as a Multifunctional Vaccine Platform," *ACS Nano* 12.11: 10665-10682, Nov. 2018.
Zhang, "Gctf: Real-time CTF determination and correction," *J Struct Biol.* 193.1: 1-12, Jan. 2016.

(56) References Cited

OTHER PUBLICATIONS

Zheng et al., "MotionCor2: anisotropic correction of beam-induced motion for improved cryo-electron microscopy," *Nat Methods* 14.4: 331-332, Apr. 2017.

* cited by examiner

FIG. 7

Cryo-EM Data Collection and Refinement Statistics.

| | GI.1 DS1 (N118C-G193C) |
|---|---|
| **EMDB ID** | **TBD** |
| **PDB ID** | **TBD** |
| Data Collection | |
| Microscope | FEI Titan Krios |
| Voltage (kV) | 300 |
| Electron dose ($e^-/Å^2$) | 70.48 |
| Detector | Gatan K2 Summit |
| Pixel Size (Å) | 1.073 |
| Defocus Range (μm) | -0.11 to -3.89 |
| Magnification | 22500 |
| Reconstruction | |
| Software | cryoSparcV2.12 |
| Particles | 23,476 |
| Symmetry | Icosahedral |
| Box size (pix) | 600 |
| Resolution (Å) ($FSC_{0.143}$) | 3.86 |
| Refinement (Phenix)[#] | |
| Protein residues | 482 |
| CC (mask) | 0.784 |
| EMRinger Score | 3.38 |
| R.m.s. deviations | |
| Bond lengths (Å) | 0.01 |
| Bond angles (°) | 0.981 |
| Validation | |
| Molprobity score | 1.72 |
| Clash score | 5.25 |
| Rotamer outliers (%) | 0.24 |
| Ramachandran | |
| Favored regions (%) | 93.2 |
| Disallowed regions (%) | 0 |

GI.1 DS1 – single disulfide
(C116/C193)

GI.1 2DS – double disulfide
(C37/C44 + C116/C193)

FIG. 21A
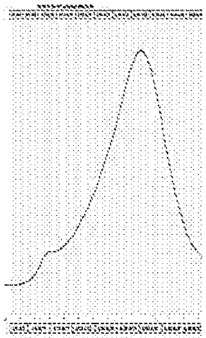
Sephacryl S500 purification of GII4.c_v7 from 100 ml of Sf9 cells infected with baculoviruses
FIG. 21B
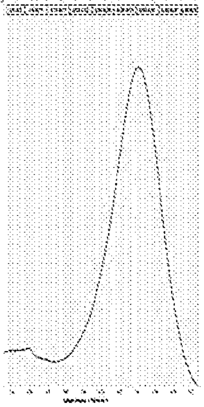
Re-run of protein on Sephacryl S500 after incubation in 20mM Diamide
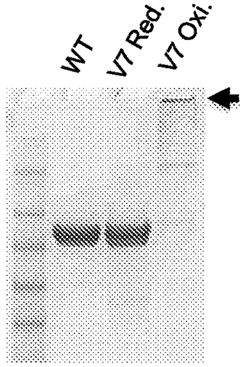
FIG. 21C
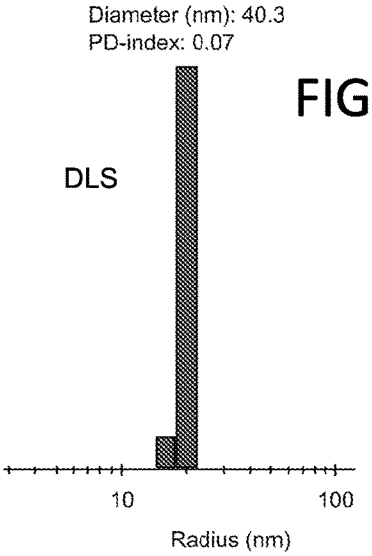
FIG. 21D
FIG. 21E
No Fab
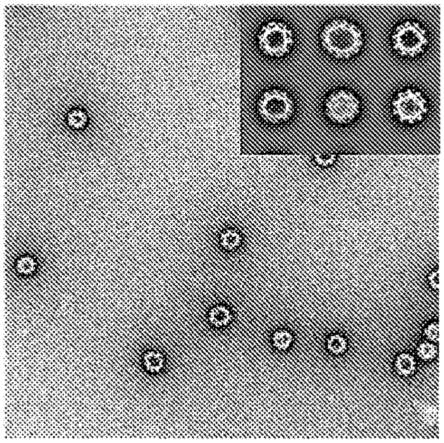
FIG. 21F
+ 1227 Fab
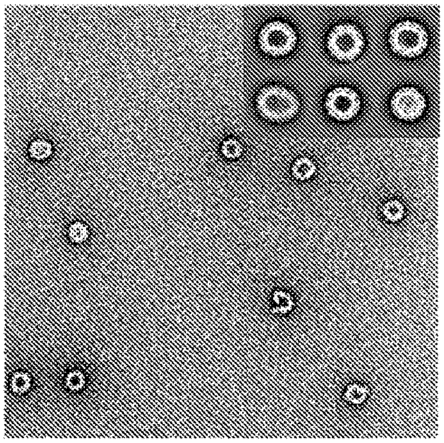

SEQUENCE LISTING

```
<160> NUMBER OF SEQ ID NOS: 56

<210> SEQ ID NO 1
<211> LENGTH: 530
<212> TYPE: PRT
<213> ORGANISM: Norovirus

<400> SEQUENCE: 1

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60
```

```
Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480
```

```
Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 2
<211> LENGTH: 546
<212> TYPE: PRT
<213> ORGANISM: Norovirus

<400> SEQUENCE: 2

Met Met Met Ala Ser Lys Asp Ala Ser Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320
```

```
Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Ile Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Gly Arg Leu Gly Val Arg
    530                 535                 540

Arg Ile
545


<210> SEQ ID NO 3
<211> LENGTH: 545
<212> TYPE: PRT
<213> ORGANISM: Norovirus

<400> SEQUENCE: 3

Met Met Met Ala Ser Lys Asp Ala Pro Pro Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ala Gln Asn Ile Ser Ile Ala Gln Ala Thr Met
```

```
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Thr
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Thr Leu Ser Asn Ser Arg Val Pro Ser Leu Ile Arg Ser Met Met Val
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Ser Val Phe His Ala Asn Gly Gly Asn Gly Tyr
    290                 295                 300

Asn Leu Thr Glu Leu Asp Gly Ser Pro Tyr His Ala Phe Glu Ser Pro
305                 310                 315                 320

Ala Pro Ile Gly Phe Pro Asp Leu Gly Glu Cys Asp Trp His Met Glu
                325                 330                 335

Ala Ser Pro Thr Thr Gln Phe Asp Thr Gly Asp Val Ile Lys Gln Ile
            340                 345                 350

Asn Val Lys Gln Glu Ala Ala Phe Ala Pro His Leu Gly Thr Ile Gln
        355                 360                 365

Ala Asp Gly Leu Ser Asp Val Ser Val Asn Thr Asn Met Ile Ala Lys
    370                 375                 380

Leu Gly Trp Val Ser Pro Val Ser Asp Gly His Arg Gly Ser Val Asp
385                 390                 395                 400

Pro Trp Val Ile Pro Arg Tyr Gly Ser Thr Leu Thr Glu Ala Ala Gln
                405                 410                 415

Leu Ala Pro Pro Ile Tyr Pro Pro Gly Phe Gly Glu Ala Ile Val Phe
            420                 425                 430

Phe Met Ser Asp Phe Pro Ile Ala His Gly Ala Asn Gly Leu Ser Val
        435                 440                 445

Pro Cys Thr Ile Pro Gln Glu Phe Val Thr His Phe Val Asn Glu Gln
    450                 455                 460

Ala Pro Thr Arg Gly Glu Ala Ala Leu Leu His Tyr Leu Asp Pro Asp
465                 470                 475                 480

Thr His Arg Asn Leu Gly Glu Phe Lys Leu Tyr Pro Glu Gly Phe Met
                485                 490                 495

Thr Cys Val Pro Asn Ser Ser Gly Thr Gly Pro Gln Thr Leu Pro Ile
            500                 505                 510

Asn Gly Val Phe Ala Phe Val Ser Trp Val Ser Arg Phe Tyr Gln Leu
        515                 520                 525

Lys Pro Val Gly Thr Ala Gly Pro Ala Arg Arg Leu Gly Ile Arg Arg
    530                 535                 540

Ser
545
```

<210> SEQ ID NO 4
<211> LENGTH: 544
<212> TYPE: PRT
<213> ORGANISM: Norovirus

<400> SEQUENCE: 4

Met Met Met Ala Ser Lys Asp Ala Thr Pro Ser Ala Asp Gly Ala Thr
1 5 10 15

Gly Ala Gly Gln Leu Val Pro Glu Val Asn Thr Ala Asp Pro Ile Pro
20 25 30

Ile Asp Pro Val Ala Gly Ser Ser Thr Ala Leu Ala Thr Ala Gly Gln
35 40 45

Val Asn Leu Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Gln Leu Gly Pro His Leu Asn Pro Phe Leu Ser His Leu
85 90 95

Ser Gln Met Tyr Asn Gly Trp Val Gly Asn Met Arg Val Arg Val Val
100 105 110

Leu Ala Gly Asn Ala Phe Thr Ala Gly Lys Val Ile Ile Cys Cys Val
115 120 125

Pro Pro Gly Phe Gln Ser Arg Thr Leu Ser Ile Ala Gln Ala Thr Leu
130 135 140

Phe Pro His Val Ile Ala Asp Val Arg Thr Leu Asp Pro Val Glu Val
145 150 155 160

Pro Leu Glu Asp Val Arg Asn Val Leu Tyr His Asn Asn Asp Thr Gln
165 170 175

Pro Thr Met Arg Leu Leu Cys Met Leu Tyr Thr Pro Leu Arg Thr Gly
180 185 190

Gly Ala Ser Gly Gly Thr Asp Ser Phe Val Val Ala Gly Arg Val Leu
195 200 205

Thr Cys Pro Gly Pro Asp Phe Asn Phe Leu Phe Leu Val Pro Pro Thr
210 215 220

Val Glu Gln Lys Thr Arg Pro Phe Thr Val Pro Asn Ile Pro Leu Lys
225 230 235 240

Tyr Leu Ser Asn Ser Arg Ile Pro Asn Pro Ile Glu Gly Met Ser Leu
245 250 255

Ser Pro Asp Gln Thr Gln Asn Val Gln Phe Gln Asn Gly Arg Cys Thr
260 265 270

Ile Asp Gly Gln Pro Leu Gly Thr Thr Pro Val Ser Val Ser Gln Leu
275 280 285

Cys Lys Phe Arg Gly Arg Ile Thr Ser Gly Gln Arg Val Leu Asn Leu
290 295 300

Thr Glu Leu Asp Gly Ser Pro Phe Met Ala Phe Ala Ala Pro Ala Pro
305 310 315 320

Ala Gly Phe Pro Asp Leu Gly Ser Cys Asp Trp His Ile Glu Met Ser
325 330 335

Lys Ile Pro Asn Ser Ser Thr Gln Asn Asn Pro Ile Val Val Asn Ser
340 345 350

Val Lys Pro Asn Ser Gln Gln Phe Val Pro His Leu Ser Ser Ile Thr
355 360 365

Leu Asp Asp Ile Val Ser Ser Gly Gly Asp Tyr Ile Gly Thr Ile Gln

```
    370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ser Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Glu Gln Ala
    450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Ser Ser Ser Thr Gly Pro Gln Gln Leu Pro Leu Asp
            500                 505                 510

Gly Val Phe Val Phe Ala Ser Trp Val Ser Arg Phe Tyr Gln Leu Lys
        515                 520                 525

Pro Val Gly Thr Ala Gly Pro Ala Arg Gly Arg Leu Gly Val Arg Arg
    530                 535                 540


<210> SEQ ID NO 5
<211> LENGTH: 539
<212> TYPE: PRT
<213> ORGANISM: Norovirus

<400> SEQUENCE: 5

Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Val Gly Ala Ala Thr Ala Ala Ala Thr Ala Gly Gln
        35                  40                  45

Val Asn Leu Ile Asp Pro Trp Ile Met Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu His Leu Gly Pro His Leu Asn Pro Phe Leu Gln His Leu
                85                  90                  95

Ser Gln Met Tyr Asn Gly Trp Val Gly Asn Met Arg Val Arg Val Met
            100                 105                 110

Leu Ala Gly Asn Ala Phe Thr Ala Gly Lys Ile Ile Ile Cys Cys Val
        115                 120                 125

Pro Pro Gly Phe Ala Ser Gln Asn Ile Ser Ile Gly Gln Ala Thr Met
    130                 135                 140

Phe Pro His Val Ile Ala Asp Val Arg Val Leu Glu Pro Ile Glu Ile
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205
```

```
Thr Cys Pro Ser Pro Asp Phe Asn Phe Leu Phe Leu Val Pro Pro Ser
    210                 215                 220

Val Glu Gln Lys Thr Arg Gln Leu Thr Val Pro Asn Ile Pro Leu Asn
225                 230                 235                 240

Asn Leu Ala Asn Ser Arg Val Pro Ala Met Ile Asn Lys Met Thr Val
                245                 250                 255

Ser Thr Asp Gln Asn Gln Val Val Gln Phe Gln Asn Gly Arg Cys Thr
            260                 265                 270

Leu Glu Gly Gln Leu Leu Gly Thr Thr Pro Val Ser Ala Ser Gln Val
        275                 280                 285

Ala Arg Ile Arg Gly Lys Val Phe Ser Thr Ala Ser Gly Lys Gly Leu
    290                 295                 300

Asn Leu Thr Glu Leu Asp Gly Thr Pro Tyr His Ala Phe Glu Ser Pro
305                 310                 315                 320

Ala Pro Leu Gly Phe Pro Asp Ile Gly Ala Cys Asp Trp His Val Ser
                325                 330                 335

Thr Phe Lys Val Asp Gln Asn Leu Ser Gly Asp Pro Met Ser Arg Leu
            340                 345                 350

Asp Val Lys Gln Asn Ala Pro Phe Ala Pro His Leu Gly Ser Ile Glu
        355                 360                 365

Phe Thr Ser Asp Gln Asp Pro Thr Gly Asp Gln Leu Gly Thr Leu Ala
    370                 375                 380

Trp Val Ser Pro Ser Thr Ser Gly Ala Arg Val Asp Pro Trp Lys Ile
385                 390                 395                 400

Pro Ser Tyr Gly Ser Thr Val Thr Glu Ser Thr His Leu Ala Pro Pro
                405                 410                 415

Ile Phe Pro Pro Gly Phe Gly Glu Ala Ile Val Tyr Phe Met Ser Asp
            420                 425                 430

Phe Pro Ile Val Ser Gly Asn Thr Ala Gln Val Pro Cys Thr Leu Pro
        435                 440                 445

Gln Glu Phe Val Ser His Phe Val Glu Gln Gln Ala Pro Val Arg Gly
    450                 455                 460

Glu Ala Ala Leu Leu His Tyr Val Asp Pro Asp Thr His Arg Asn Leu
465                 470                 475                 480

Gly Glu Phe Lys Leu Tyr Pro Asp Gly Phe Ile Thr Cys Val Pro Asn
                485                 490                 495

Thr Gly Gly Gly Pro Gln Asn Leu Pro Thr Asn Gly Val Phe Val Phe
            500                 505                 510

Ser Ser Trp Val Ser Arg Tyr Tyr Gln Leu Lys Pro Val Gly Thr Ala
        515                 520                 525

Gly Pro Ala Arg Arg Leu Gly Val Arg Arg Val
    530                 535
```

<210> SEQ ID NO 6
<211> LENGTH: 540
<212> TYPE: PRT
<213> ORGANISM: Norovirus

<400> SEQUENCE: 6

```
Met Met Met Ala Ser Lys Asp Ala Pro Thr Ser Pro Asp Gly Ala Ser
1               5                   10                  15

Gly Ala Gly Gln Leu Val Pro Glu Ala Asn Thr Ala Glu Gln Ile Ser
            20                  25                  30

Met Asp Pro Val Ala Gly Ala Ser Thr Ala Val Ala Thr Ala Gly Gln
        35                  40                  45
```

```
Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Ile Leu
            100                 105                 110

Leu Ala Gly Asn Ala Phe Thr Ala Gly Lys Ile Ile Ile Cys Cys Val
        115                 120                 125

Pro Pro Gly Phe Asp Ala Arg Ile Leu Thr Ile Ala Gln Ala Thr Leu
    130                 135                 140

Phe Pro His Leu Ile Ala Asp Val Arg Thr Leu Glu Pro Val Glu Leu
145                 150                 155                 160

Pro Leu Glu Asp Val Arg Asn Val Leu Tyr His Asn Ser Ser Gln Pro
                165                 170                 175

Gln Pro Thr Met Arg Leu Val Ala Met Leu Tyr Thr Pro Leu Arg Thr
            180                 185                 190

Gly Gly Gly Ser Gly Gly Thr Asp Ala Phe Val Val Ala Gly Arg Val
        195                 200                 205

Leu Thr Cys Pro Ala Pro Asp Phe Ser Phe Leu Phe Leu Val Pro Pro
    210                 215                 220

Ser Val Glu Gln Lys Thr Arg Val Phe Ser Val Pro Asn Ile Pro Leu
225                 230                 235                 240

Lys Asp Leu Ser Asn Ser Arg Val Pro Val Pro Ile Gln Gly Met Phe
                245                 250                 255

Met Ser Pro Asp Val Asn Gln Ser Val Gln Phe Gln Asn Gly Arg Cys
            260                 265                 270

Gln Ile Asp Gly Gln Leu Gln Gly Thr Thr Pro Val Ser Leu Ser Gln
        275                 280                 285

Leu Cys Lys Ile Arg Gly Lys Thr Ser Ser Asn Ala Arg Val Leu Asn
    290                 295                 300

Leu Ser Glu Val Asp Gly Thr Pro Phe Ile Pro Leu Glu Ser Pro Ala
305                 310                 315                 320

Pro Val Gly Phe Pro Asp Leu Gly Gly Cys Asp Trp His Val Asn Phe
                325                 330                 335

Thr Phe Gln Ala Gln Asn Gln Asp Pro Ser Gln Ser Val Thr Phe Ala
            340                 345                 350

Thr Asn Asp Ala Ser Phe Val Pro Tyr Leu Gly Ser Ile Ser Pro His
        355                 360                 365

Asn Gly Gly Asp Phe His Ala Gly Asp Ile Ile Gly Ser Leu Gly Trp
    370                 375                 380

Ile Ser Ala Pro Ser Asp Asn Thr Gln Leu Asn Val Trp Thr Ile Pro
385                 390                 395                 400

Lys Tyr Gly Ser Ser Leu Pro Asp Val Thr His Leu Ala Pro Ala Val
                405                 410                 415

Phe Pro Pro Gly Phe Gly Glu Val Ile Leu Tyr Phe Tyr Ser Thr Phe
            420                 425                 430

Pro Gly Ser Gly Gln Pro Ser Gln Leu Gln Val Pro Cys Leu Leu Pro
        435                 440                 445

Gln Glu Phe Ile Thr His Phe Cys Asn Glu Gln Ala Pro Ile Ala Gly
    450                 455                 460
```

```
Glu Ala Ala Leu Leu His Tyr Val Asp Pro Asp Thr Gly Arg Asn Leu
465                 470                 475                 480

Gly Glu Phe Lys Leu Tyr Pro Asp Gly Phe Met Thr Cys Val Pro Asn
                485                 490                 495

Ser Val Ser Ser Gly Pro Gln Thr Leu Pro Ile Asn Gly Val Phe Val
            500                 505                 510

Phe Val Ser Trp Val Ser Arg Phe Tyr Gln Leu Lys Pro Val Gly Thr
        515                 520                 525

Ala Ser Ala Ala Arg Arg Leu Gly Leu Arg Arg Ile
    530                 535                 540


<210> SEQ ID NO 7
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 7

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Cys Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Cys Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285
```

```
Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 8
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 8

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110
```

-continued

```
Leu Ala Gly Asn Ala Cys Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Cys Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
```

530

<210> SEQ ID NO 9
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 9

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Cys Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Cys Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
```

```
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 10
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 10

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Cys Gly Ser Ser Thr Ala Val Cys Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
```

```
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 11
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 11

Met Met Met Ala Ser Lys Asp Ala Thr Ser Ser Val Asp Gly Ala Ser
```

-continued

```
1               5                   10                  15

Gly Ala Gly Gln Leu Val Pro Glu Val Asn Ala Ser Asp Pro Leu Ala
            20                  25                  30

Met Asp Pro Val Ile Gly Ser Ser Thr Ala Val Leu Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430
```

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530

<210> SEQ ID NO 12
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 12

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Val Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Leu Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
260 265 270

Asp Gly Arg Leu Val Gly Thr Thr Pro Val Ser Leu Ser His Val Ala
275 280 285

Lys Ile Arg Gly Thr Ser Asn Gly Thr Val Ile Asn Leu Thr Glu Leu
290 295 300

Asp Gly Thr Pro Phe His Pro Phe Glu Gly Pro Ala Pro Ile Gly Phe
305 310 315 320

Pro Asp Leu Gly Gly Cys Asp Trp His Ile Asn Met Thr Gln Phe Gly
325 330 335

His Ser Ser Gln Thr Gln Tyr Asp Val Asp Thr Thr Pro Asp Thr Phe
340 345 350

Val Pro His Leu Gly Ser Ile Gln Ala Asn Gly Ile Gly Ser Gly Asn
355 360 365

Tyr Val Gly Val Leu Ser Trp Ile Ser Pro Pro Ser His Pro Ser Gly
370 375 380

Ser Gln Val Asp Leu Trp Lys Ile Pro Asn Tyr Gly Ser Ser Ile Thr
385 390 395 400

Glu Ala Thr His Leu Ala Pro Ser Val Tyr Pro Pro Gly Phe Gly Glu
405 410 415

Val Leu Val Phe Phe Met Ser Lys Met Pro Gly Pro Gly Ala Tyr Asn
420 425 430

Leu Pro Cys Leu Leu Pro Gln Glu Tyr Ile Ser His Leu Ala Ser Glu
435 440 445

Gln Ala Pro Thr Val Gly Glu Ala Ala Leu Leu His Tyr Val Asp Pro
450 455 460

Asp Thr Gly Arg Asn Leu Gly Glu Phe Lys Ala Tyr Pro Asp Gly Phe
465 470 475 480

Leu Thr Cys Val Pro Asn Gly Ala Ser Ser Gly Pro Gln Gln Leu Pro
485 490 495

Ile Asn Gly Val Phe Val Phe Val Ser Trp Val Ser Arg Phe Tyr Gln
500 505 510

Leu Lys Pro Val Gly Thr Ala Ser Ser Ala Arg Gly Arg Leu Gly Leu
515 520 525

Arg Arg
530

<210> SEQ ID NO 13
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 13

Met Met Met Ala Ser Lys Asp Ala Thr Ser Ser Val Asp Gly Ala Ser
1 5 10 15

Gly Ala Gly Gln Leu Val Pro Glu Val Asn Ala Ser Asp Pro Leu Ala
20 25 30

Met Asp Pro Val Ala Gly Ser Ser Thr Ala Val Ala Thr Ala Gly Gln
35 40 45

Val Asn Pro Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

```
Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Cys
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Cys Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495
```

Ile Asn Gly Val Phe Val Phe Val Ser Trp Val Ser Arg Phe Tyr Gln
500 505 510

Leu Lys Pro Val Gly Thr Ala Ser Ser Ala Arg Gly Arg Leu Gly Leu
515 520 525

Arg Arg
530

<210> SEQ ID NO 14
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 14

Met Met Met Ala Ser Lys Asp Ala Thr Ser Ser Val Asp Gly Ala Ser
1 5 10 15

Gly Ala Gly Gln Leu Val Pro Glu Val Asn Ala Ser Asp Pro Leu Ala
20 25 30

Met Asp Pro Val Ala Gly Ser Ser Thr Ala Val Ala Thr Ala Gly Gln
35 40 45

Val Asn Pro Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Ser Leu Gly Pro His Leu Asn Pro Phe Leu Leu His Leu
85 90 95

Ser Gln Met Tyr Asn Gly Trp Val Gly Asn Met Arg Val Arg Ile Met
100 105 110

Leu Ala Gly Asn Ala Phe Thr Ala Gly Lys Ile Ile Val Ser Cys Ile
115 120 125

Pro Pro Cys Phe Gly Ser His Asn Leu Thr Ile Ala Gln Ala Thr Leu
130 135 140

Phe Pro His Val Ile Ala Asp Val Arg Thr Leu Asp Pro Ile Glu Val
145 150 155 160

Pro Leu Glu Asp Val Arg Asn Val Leu Phe His Cys Asn Asp Arg Asn
165 170 175

Gln Gln Thr Met Arg Leu Val Cys Met Leu Tyr Thr Pro Leu Arg Thr
180 185 190

Gly Gly Gly Thr Gly Asp Ser Phe Val Val Ala Gly Arg Val Met Thr
195 200 205

Cys Pro Ser Pro Asp Phe Asn Phe Leu Phe Leu Val Pro Pro Thr Val
210 215 220

Glu Gln Lys Thr Arg Pro Phe Thr Leu Pro Asn Leu Pro Leu Ser Ser
225 230 235 240

Leu Ser Asn Ser Arg Ala Pro Leu Pro Ile Ser Ser Met Gly Ile Ser
245 250 255

Pro Asp Asn Val Gln Ser Val Gln Phe Gln Asn Gly Arg Cys Thr Leu
260 265 270

Asp Gly Arg Leu Val Gly Thr Thr Pro Val Ser Leu Ser His Val Ala
275 280 285

Lys Ile Arg Gly Thr Ser Asn Gly Thr Val Ile Asn Leu Thr Glu Leu
290 295 300

Asp Gly Thr Pro Phe His Pro Phe Glu Gly Pro Ala Pro Ile Gly Phe
305 310 315 320

Pro Asp Leu Gly Gly Cys Asp Trp His Ile Asn Met Thr Gln Phe Gly
325 330 335

His Ser Ser Gln Thr Gln Tyr Asp Val Asp Thr Thr Pro Asp Thr Phe
340 345 350

Val Pro His Leu Gly Ser Ile Gln Ala Asn Gly Ile Gly Ser Gly Asn
355 360 365

Tyr Val Gly Val Leu Ser Trp Ile Ser Pro Pro Ser His Pro Ser Gly
370 375 380

Ser Gln Val Asp Leu Trp Lys Ile Pro Asn Tyr Gly Ser Ser Ile Thr
385 390 395 400

Glu Ala Thr His Leu Ala Pro Ser Val Tyr Pro Pro Gly Phe Gly Glu
405 410 415

Val Leu Val Phe Phe Met Ser Lys Met Pro Gly Pro Gly Ala Tyr Asn
420 425 430

Leu Pro Cys Leu Leu Pro Gln Glu Tyr Ile Ser His Leu Ala Ser Glu
435 440 445

Gln Ala Pro Thr Val Gly Glu Ala Ala Leu Leu His Tyr Val Asp Pro
450 455 460

Asp Thr Gly Arg Asn Leu Gly Glu Phe Lys Ala Tyr Pro Asp Gly Phe
465 470 475 480

Leu Thr Cys Val Pro Asn Gly Ala Ser Ser Gly Pro Gln Gln Leu Pro
485 490 495

Ile Asn Gly Val Phe Val Phe Val Ser Trp Val Ser Arg Phe Tyr Gln
500 505 510

Leu Lys Pro Val Gly Thr Ala Ser Ser Ala Arg Gly Arg Leu Gly Leu
515 520 525

Arg Arg
530

<210> SEQ ID NO 15
<211> LENGTH: 530
<212> TYPE: PRT
<213> ORGANISM: Artificial Sequence
<220> FEATURE:
<223> OTHER INFORMATION: Recombinant Norovirus Protein

<400> SEQUENCE: 15

Met Met Met Ala Ser Lys Asp Ala Thr Ser Ser Val Asp Gly Ala Ser
1 5 10 15

Gly Ala Gly Gln Leu Val Pro Glu Val Asn Ala Ser Asp Pro Leu Ala
20 25 30

Met Asp Pro Val Ala Gly Ser Ser Thr Ala Val Ala Thr Ala Gly Gln
35 40 45

Val Asn Pro Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Ser Leu Gly Pro His Leu Asn Pro Phe Leu Leu His Leu
85 90 95

Ser Gln Met Tyr Asn Gly Trp Val Gly Asn Met Arg Val Arg Ile Met
100 105 110

Leu Ala Gly Asn Ala Phe Thr Ala Gly Lys Ile Ile Val Ser Cys Ile
115 120 125

Pro Pro Gly Phe Gly Ser His Asn Leu Thr Ile Ala Gln Ala Thr Leu
130 135 140

```
Phe Pro His Val Ile Ala Asp Val Arg Thr Leu Asp Pro Ile Glu Val
145                 150                 155                 160

Pro Leu Glu Asp Val Arg Cys Val Cys Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530
```

<210> SEQ ID NO 16
<211> LENGTH: 546
<212> TYPE: PRT

<213> ORGANISM: Artificial Sequence
<220> FEATURE:
<223> OTHER INFORMATION: Recombinant Norovirus Protein

<400> SEQUENCE: 16

```
Met Met Met Ala Ser Lys Asp Ala Ser Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Cys Gly Pro Thr Thr Ala Val Cys Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
```

385 390 395 400

Trp Glu Ile Pro Asp Tyr Gly Ser Ser Leu Ser Gln Ala Ala Asn Leu
405 410 415

Ala Pro Pro Val Phe Pro Pro Gly Phe Gly Glu Ala Leu Val Tyr Phe
420 425 430

Val Ser Ala Phe Pro Gly Pro Asn Asn Arg Ser Ala Pro Asn Asp Val
435 440 445

Pro Cys Leu Leu Pro Gln Glu Tyr Ile Thr His Phe Val Ser Glu Gln
450 455 460

Ala Pro Thr Met Gly Asp Ala Ala Leu Leu His Tyr Val Asp Pro Asp
465 470 475 480

Thr Asn Arg Asn Leu Gly Glu Phe Lys Leu Tyr Pro Gly Gly Tyr Leu
485 490 495

Thr Cys Val Pro Asn Gly Val Gly Ala Gly Pro Gln Gln Leu Pro Leu
500 505 510

Asn Gly Val Phe Leu Phe Val Ser Trp Val Ser Arg Phe Tyr Gln Leu
515 520 525

Lys Pro Val Gly Thr Ala Ser Thr Ala Arg Gly Arg Leu Gly Val Arg
530 535 540

Arg Ile
545

<210> SEQ ID NO 17
<211> LENGTH: 546
<212> TYPE: PRT
<213> ORGANISM: Artificial Sequence
<220> FEATURE:
<223> OTHER INFORMATION: Recombinant Norovirus Protein

<400> SEQUENCE: 17

Met Met Met Ala Ser Lys Asp Ala Ser Gln Ser Ala Asp Gly Ala Ser
1 5 10 15

Gly Ala Gly Gln Leu Val Pro Glu Val Asn Thr Ala Asp Pro Leu Pro
20 25 30

Met Glu Pro Val Ala Gly Pro Thr Thr Ala Val Ala Thr Ala Gly Gln
35 40 45

Val Asn Met Ile Asp Pro Trp Ile Val Asn Asn Phe Val Gln Ser Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Ser His Leu
85 90 95

Ser Gln Met Tyr Asn Gly Trp Val Gly Asn Met Arg Val Arg Ile Leu
100 105 110

Leu Ala Gly Cys Ala Phe Ser Ala Gly Lys Ile Ile Val Cys Cys Val
115 120 125

Pro Pro Gly Phe Thr Ser Ser Ser Leu Thr Ile Ala Gln Ala Thr Leu
130 135 140

Phe Pro His Val Ile Ala Asp Val Arg Thr Leu Glu Pro Ile Glu Met
145 150 155 160

Pro Leu Glu Asp Val Arg Asn Val Leu Tyr His Thr Asn Asp Asn Gln
165 170 175

Pro Thr Met Arg Leu Val Cys Met Leu Tyr Thr Pro Leu Arg Thr Cys
180 185 190

Gly Gly Ser Gly Asn Ser Asp Ser Phe Val Val Ala Gly Arg Val Leu

```
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Ile Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Gly Arg Leu Gly Val Arg
    530                 535                 540

Arg Ile
545


<210> SEQ ID NO 18
<211> LENGTH: 545
<212> TYPE: PRT
<213> ORGANISM: Artificial Sequence
<220> FEATURE:
<223> OTHER INFORMATION: Recombinant Norovirus Protein

<400> SEQUENCE: 18

Met Met Met Ala Ser Lys Asp Ala Pro Pro Asn Met Asp Gly Thr Ser
```

-continued

```
1               5                   10                  15

Gly Ala Gly Gln Leu Val Pro Glu Ala Asn Thr Ala Glu Pro Ile Ser
            20                  25                  30

Met Glu Pro Val Cys Gly Ala Ala Thr Ala Ala Cys Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ala Gln Asn Ile Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Thr
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Thr Leu Ser Asn Ser Arg Val Pro Ser Leu Ile Arg Ser Met Met Val
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Ser Val Phe His Ala Asn Gly Gly Asn Gly Tyr
    290                 295                 300

Asn Leu Thr Glu Leu Asp Gly Ser Pro Tyr His Ala Phe Glu Ser Pro
305                 310                 315                 320

Ala Pro Ile Gly Phe Pro Asp Leu Gly Glu Cys Asp Trp His Met Glu
                325                 330                 335

Ala Ser Pro Thr Thr Gln Phe Asp Thr Gly Asp Val Ile Lys Gln Ile
            340                 345                 350

Asn Val Lys Gln Glu Ala Ala Phe Ala Pro His Leu Gly Thr Ile Gln
        355                 360                 365

Ala Asp Gly Leu Ser Asp Val Ser Val Asn Thr Asn Met Ile Ala Lys
    370                 375                 380

Leu Gly Trp Val Ser Pro Val Ser Asp Gly His Arg Gly Ser Val Asp
385                 390                 395                 400

Pro Trp Val Ile Pro Arg Tyr Gly Ser Thr Leu Thr Glu Ala Ala Gln
                405                 410                 415

Leu Ala Pro Pro Ile Tyr Pro Pro Gly Phe Gly Glu Ala Ile Val Phe
            420                 425                 430
```

Phe Met Ser Asp Phe Pro Ile Ala His Gly Ala Asn Gly Leu Ser Val
435 440 445

Pro Cys Thr Ile Pro Gln Glu Phe Val Thr His Phe Val Asn Glu Gln
450 455 460

Ala Pro Thr Arg Gly Glu Ala Ala Leu Leu His Tyr Leu Asp Pro Asp
465 470 475 480

Thr His Arg Asn Leu Gly Glu Phe Lys Leu Tyr Pro Glu Gly Phe Met
485 490 495

Thr Cys Val Pro Asn Ser Ser Gly Thr Gly Pro Gln Thr Leu Pro Ile
500 505 510

Asn Gly Val Phe Ala Phe Val Ser Trp Val Ser Arg Phe Tyr Gln Leu
515 520 525

Lys Pro Val Gly Thr Ala Gly Pro Ala Arg Arg Leu Gly Ile Arg Arg
530 535 540

Ser
545

<210> SEQ ID NO 19
<211> LENGTH: 545
<212> TYPE: PRT
<213> ORGANISM: Artificial Sequence
<220> FEATURE:
<223> OTHER INFORMATION: Recombinant Norovirus Protein

<400> SEQUENCE: 19

Met Met Met Ala Ser Lys Asp Ala Pro Pro Asn Met Asp Gly Thr Ser
1 5 10 15

Gly Ala Gly Gln Leu Val Pro Glu Ala Asn Thr Ala Glu Pro Ile Ser
20 25 30

Met Glu Pro Val Ala Gly Ala Ala Thr Ala Ala Ala Thr Ala Gly Gln
35 40 45

Val Asn Met Ile Asp Pro Trp Ile Met Asn Asn Tyr Val Gln Ala Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Ser His Leu
85 90 95

Ala Gln Met Tyr Asn Gly Trp Val Gly Asn Met Lys Val Lys Val Leu
100 105 110

Leu Ala Gly Cys Ala Phe Thr Ala Gly Lys Ile Ile Ile Ser Cys Ile
115 120 125

Pro Pro Gly Phe Ala Ala Gln Asn Ile Ser Ile Ala Gln Ala Thr Met
130 135 140

Phe Pro His Val Ile Ala Asp Val Arg Val Leu Glu Pro Ile Glu Val
145 150 155 160

Pro Leu Glu Asp Val Arg Asn Val Leu Phe His Asn Asn Asp Asn Thr
165 170 175

Pro Thr Met Arg Leu Val Cys Met Leu Tyr Thr Pro Leu Arg Ala Cys
180 185 190

Gly Ser Ser Ser Gly Thr Asp Pro Phe Val Ile Ala Gly Arg Val Leu
195 200 205

Thr Cys Pro Ser Pro Asp Phe Ser Phe Leu Phe Leu Val Pro Pro Asn
210 215 220

Val Glu Gln Lys Thr Lys Pro Phe Ser Val Pro Asn Leu Pro Leu Asn
225 230 235 240

Thr Leu Ser Asn Ser Arg Val Pro Ser Leu Ile Arg Ser Met Met Val
245 250 255

Ser Arg Asp His Gly Gln Met Val Gln Phe Gln Asn Gly Arg Val Thr
260 265 270

Leu Asp Gly Gln Leu Gln Gly Thr Thr Pro Thr Ser Ala Ser Gln Leu
275 280 285

Cys Lys Ile Arg Gly Ser Val Phe His Ala Asn Gly Gly Asn Gly Tyr
290 295 300

Asn Leu Thr Glu Leu Asp Gly Ser Pro Tyr His Ala Phe Glu Ser Pro
305 310 315 320

Ala Pro Ile Gly Phe Pro Asp Leu Gly Glu Cys Asp Trp His Met Glu
325 330 335

Ala Ser Pro Thr Thr Gln Phe Asp Thr Gly Asp Val Ile Lys Gln Ile
340 345 350

Asn Val Lys Gln Glu Ala Ala Phe Ala Pro His Leu Gly Thr Ile Gln
355 360 365

Ala Asp Gly Leu Ser Asp Val Ser Val Asn Thr Asn Met Ile Ala Lys
370 375 380

Leu Gly Trp Val Ser Pro Val Ser Asp Gly His Arg Gly Ser Val Asp
385 390 395 400

Pro Trp Val Ile Pro Arg Tyr Gly Ser Thr Leu Thr Glu Ala Ala Gln
405 410 415

Leu Ala Pro Pro Ile Tyr Pro Pro Gly Phe Gly Glu Ala Ile Val Phe
420 425 430

Phe Met Ser Asp Phe Pro Ile Ala His Gly Ala Asn Gly Leu Ser Val
435 440 445

Pro Cys Thr Ile Pro Gln Glu Phe Val Thr His Phe Val Asn Glu Gln
450 455 460

Ala Pro Thr Arg Gly Glu Ala Ala Leu Leu His Tyr Leu Asp Pro Asp
465 470 475 480

Thr His Arg Asn Leu Gly Glu Phe Lys Leu Tyr Pro Glu Gly Phe Met
485 490 495

Thr Cys Val Pro Asn Ser Ser Gly Thr Gly Pro Gln Thr Leu Pro Ile
500 505 510

Asn Gly Val Phe Ala Phe Val Ser Trp Val Ser Arg Phe Tyr Gln Leu
515 520 525

Lys Pro Val Gly Thr Ala Gly Pro Ala Arg Arg Leu Gly Ile Arg Arg
530 535 540

Ser
545

<210> SEQ ID NO 20
<211> LENGTH: 544
<212> TYPE: PRT
<213> ORGANISM: Artificial Sequence
<220> FEATURE:
<223> OTHER INFORMATION: Recombinant Norovirus Protein

<400> SEQUENCE: 20

Met Met Met Ala Ser Lys Asp Ala Thr Pro Ser Ala Asp Gly Ala Thr
1 5 10 15

Gly Ala Gly Gln Leu Val Pro Glu Val Asn Thr Ala Asp Pro Ile Pro
20 25 30

Ile Asp Pro Val Cys Gly Ser Ser Thr Ala Leu Cys Thr Ala Gly Gln
35 40 45

```
Val Asn Leu Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Val Val
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Val Ile Ala Asp Val Arg Thr Leu Asp Pro Val Glu Val
145                 150                 155                 160

Pro Leu Glu Asp Val Arg Asn Val Leu Tyr His Asn Asn Asp Thr Gln
                165                 170                 175

Pro Thr Met Arg Leu Leu Cys Met Leu Tyr Thr Pro Leu Arg Thr Gly
            180                 185                 190

Gly Ala Ser Gly Gly Thr Asp Ser Phe Val Val Ala Gly Arg Val Leu
        195                 200                 205

Thr Cys Pro Gly Pro Asp Phe Asn Phe Leu Phe Leu Val Pro Pro Thr
    210                 215                 220

Val Glu Gln Lys Thr Arg Pro Phe Thr Val Pro Asn Ile Pro Leu Lys
225                 230                 235                 240

Tyr Leu Ser Asn Ser Arg Ile Pro Asn Pro Ile Glu Gly Met Ser Leu
                245                 250                 255

Ser Pro Asp Gln Thr Gln Asn Val Gln Phe Gln Asn Gly Arg Cys Thr
            260                 265                 270

Ile Asp Gly Gln Pro Leu Gly Thr Thr Pro Val Ser Val Ser Gln Leu
        275                 280                 285

Cys Lys Phe Arg Gly Arg Ile Thr Ser Gly Gln Arg Val Leu Asn Leu
    290                 295                 300

Thr Glu Leu Asp Gly Ser Pro Phe Met Ala Phe Ala Ala Pro Ala Pro
305                 310                 315                 320

Ala Gly Phe Pro Asp Leu Gly Ser Cys Asp Trp His Ile Glu Met Ser
                325                 330                 335

Lys Ile Pro Asn Ser Ser Thr Gln Asn Asn Pro Ile Val Val Asn Ser
            340                 345                 350

Val Lys Pro Asn Ser Gln Gln Phe Val Pro His Leu Ser Ser Ile Thr
        355                 360                 365

Leu Asp Asp Ile Val Ser Ser Gly Gly Asp Tyr Ile Gly Thr Ile Gln
    370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ser Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Glu Gln Ala
    450                 455                 460
```

Pro Ile Gln Gly Glu Ala Ala Leu Leu His Tyr Val Asp Pro Asp Thr
465 470 475 480

Asn Arg Asn Leu Gly Glu Phe Lys Leu Tyr Pro Gly Gly Tyr Leu Thr
485 490 495

Cys Val Pro Asn Ser Ser Ser Thr Gly Pro Gln Gln Leu Pro Leu Asp
500 505 510

Gly Val Phe Val Phe Ala Ser Trp Val Ser Arg Phe Tyr Gln Leu Lys
515 520 525

Pro Val Gly Thr Ala Gly Pro Ala Arg Gly Arg Leu Gly Val Arg Arg
530 535 540

<210> SEQ ID NO 21
<211> LENGTH: 544
<212> TYPE: PRT
<213> ORGANISM: Artificial Sequence
<220> FEATURE:
<223> OTHER INFORMATION: Recombinant Norovirus Protein

<400> SEQUENCE: 21

Met Met Met Ala Ser Lys Asp Ala Thr Pro Ser Ala Asp Gly Ala Thr
1 5 10 15

Gly Ala Gly Gln Leu Val Pro Glu Val Asn Thr Ala Asp Pro Ile Pro
20 25 30

Ile Asp Pro Val Ala Gly Ser Ser Thr Ala Leu Ala Thr Ala Gly Gln
35 40 45

Val Asn Leu Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Gln Leu Gly Pro His Leu Asn Pro Phe Leu Ser His Leu
85 90 95

Ser Gln Met Tyr Asn Gly Trp Val Gly Asn Met Arg Val Arg Val Val
100 105 110

Leu Ala Gly Cys Ala Phe Thr Ala Gly Lys Val Ile Ile Cys Cys Val
115 120 125

Pro Pro Gly Phe Gln Ser Arg Thr Leu Ser Ile Ala Gln Ala Thr Leu
130 135 140

Phe Pro His Val Ile Ala Asp Val Arg Thr Leu Asp Pro Val Glu Val
145 150 155 160

Pro Leu Glu Asp Val Arg Asn Val Leu Tyr His Asn Asn Asp Thr Gln
165 170 175

Pro Thr Met Arg Leu Leu Cys Met Leu Tyr Thr Pro Leu Arg Thr Cys
180 185 190

Gly Ala Ser Gly Gly Thr Asp Ser Phe Val Val Ala Gly Arg Val Leu
195 200 205

Thr Cys Pro Gly Pro Asp Phe Asn Phe Leu Phe Leu Val Pro Pro Thr
210 215 220

Val Glu Gln Lys Thr Arg Pro Phe Thr Val Pro Asn Ile Pro Leu Lys
225 230 235 240

Tyr Leu Ser Asn Ser Arg Ile Pro Asn Pro Ile Glu Gly Met Ser Leu
245 250 255

Ser Pro Asp Gln Thr Gln Asn Val Gln Phe Gln Asn Gly Arg Cys Thr
260 265 270

Ile Asp Gly Gln Pro Leu Gly Thr Thr Pro Val Ser Val Ser Gln Leu
275 280 285

```
Cys Lys Phe Arg Gly Arg Ile Thr Ser Gly Gln Arg Val Leu Asn Leu
    290                 295                 300

Thr Glu Leu Asp Gly Ser Pro Phe Met Ala Phe Ala Ala Pro Ala Pro
305                 310                 315                 320

Ala Gly Phe Pro Asp Leu Gly Ser Cys Asp Trp His Ile Glu Met Ser
                325                 330                 335

Lys Ile Pro Asn Ser Ser Thr Gln Asn Asn Pro Ile Val Val Asn Ser
            340                 345                 350

Val Lys Pro Asn Ser Gln Gln Phe Val Pro His Leu Ser Ser Ile Thr
        355                 360                 365

Leu Asp Asp Ile Val Ser Ser Gly Gly Asp Tyr Ile Gly Thr Ile Gln
    370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ser Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Glu Gln Ala
    450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Ser Ser Ser Thr Gly Pro Gln Gln Leu Pro Leu Asp
            500                 505                 510

Gly Val Phe Val Phe Ala Ser Trp Val Ser Arg Phe Tyr Gln Leu Lys
        515                 520                 525

Pro Val Gly Thr Ala Gly Pro Ala Arg Gly Arg Leu Gly Val Arg Arg
    530                 535                 540


<210> SEQ ID NO 22
<211> LENGTH: 539
<212> TYPE: PRT
<213> ORGANISM: Artificial Sequence
<220> FEATURE:
<223> OTHER INFORMATION: Recombinant Norovirus Protein

<400> SEQUENCE: 22

Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Cys Gly Ala Ala Thr Ala Ala Cys Thr Ala Gly Gln
        35                  40                  45

Val Asn Leu Ile Asp Pro Trp Ile Met Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu His Leu Gly Pro His Leu Asn Pro Phe Leu Gln His Leu
                85                  90                  95

Ser Gln Met Tyr Asn Gly Trp Val Gly Asn Met Arg Val Arg Val Met
            100                 105                 110
```

```
Leu Ala Gly Asn Ala Phe Thr Ala Gly Lys Ile Ile Ile Cys Cys Val
        115                 120                 125

Pro Pro Gly Phe Ala Ser Gln Asn Ile Ser Ile Gly Gln Ala Thr Met
    130                 135                 140

Phe Pro His Val Ile Ala Asp Val Arg Val Leu Glu Pro Ile Glu Ile
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Ser
    210                 215                 220

Val Glu Gln Lys Thr Arg Gln Leu Thr Val Pro Asn Ile Pro Leu Asn
225                 230                 235                 240

Asn Leu Ala Asn Ser Arg Val Pro Ala Met Ile Asn Lys Met Thr Val
                245                 250                 255

Ser Thr Asp Gln Asn Gln Val Val Gln Phe Gln Asn Gly Arg Cys Thr
            260                 265                 270

Leu Glu Gly Gln Leu Leu Gly Thr Thr Pro Val Ser Ala Ser Gln Val
        275                 280                 285

Ala Arg Ile Arg Gly Lys Val Phe Ser Thr Ala Ser Gly Lys Gly Leu
    290                 295                 300

Asn Leu Thr Glu Leu Asp Gly Thr Pro Tyr His Ala Phe Glu Ser Pro
305                 310                 315                 320

Ala Pro Leu Gly Phe Pro Asp Ile Gly Ala Cys Asp Trp His Val Ser
                325                 330                 335

Thr Phe Lys Val Asp Gln Asn Leu Ser Gly Asp Pro Met Ser Arg Leu
            340                 345                 350

Asp Val Lys Gln Asn Ala Pro Phe Ala Pro His Leu Gly Ser Ile Glu
        355                 360                 365

Phe Thr Ser Asp Gln Asp Pro Thr Gly Asp Gln Leu Gly Thr Leu Ala
    370                 375                 380

Trp Val Ser Pro Ser Thr Ser Gly Ala Arg Val Asp Pro Trp Lys Ile
385                 390                 395                 400

Pro Ser Tyr Gly Ser Thr Val Thr Glu Ser Thr His Leu Ala Pro Pro
                405                 410                 415

Ile Phe Pro Pro Gly Phe Gly Glu Ala Ile Val Tyr Phe Met Ser Asp
            420                 425                 430

Phe Pro Ile Val Ser Gly Asn Thr Ala Gln Val Pro Cys Thr Leu Pro
        435                 440                 445

Gln Glu Phe Val Ser His Phe Val Glu Gln Gln Ala Pro Val Arg Gly
    450                 455                 460

Glu Ala Ala Leu Leu His Tyr Val Asp Pro Asp Thr His Arg Asn Leu
465                 470                 475                 480

Gly Glu Phe Lys Leu Tyr Pro Asp Gly Phe Ile Thr Cys Val Pro Asn
                485                 490                 495

Thr Gly Gly Gly Pro Gln Asn Leu Pro Thr Asn Gly Val Phe Val Phe
            500                 505                 510

Ser Ser Trp Val Ser Arg Tyr Tyr Gln Leu Lys Pro Val Gly Thr Ala
        515                 520                 525

Gly Pro Ala Arg Arg Leu Gly Val Arg Arg Val
```

530 535

<210> SEQ ID NO 23
<211> LENGTH: 539
<212> TYPE: PRT
<213> ORGANISM: Artificial Sequence
<220> FEATURE:
<223> OTHER INFORMATION: Recombinant Norovirus Protein

<400> SEQUENCE: 23

Met Met Met Ala Ser Lys Asp Ala Pro Ser Asn Met Asp Gly Thr Ser
1 5 10 15

Gly Ala Gly Gln Leu Val Pro Glu Val Asn Ala Ala Glu Pro Leu Pro
20 25 30

Leu Glu Pro Val Val Gly Ala Ala Thr Ala Ala Ala Thr Ala Gly Gln
35 40 45

Val Asn Leu Ile Asp Pro Trp Ile Met Asn Asn Phe Val Gln Ala Pro
50 55 60

Glu Gly Glu Phe Thr Ile Ser Pro Asn Asn Thr Pro Gly Asp Ile Leu
65 70 75 80

Phe Asp Leu His Leu Gly Pro His Leu Asn Pro Phe Leu Gln His Leu
85 90 95

Ser Gln Met Tyr Asn Gly Trp Val Gly Asn Met Arg Val Arg Val Met
100 105 110

Leu Ala Gly Cys Ala Phe Thr Ala Gly Lys Ile Ile Ile Cys Cys Val
115 120 125

Pro Pro Gly Phe Ala Ser Gln Asn Ile Ser Ile Gly Gln Ala Thr Met
130 135 140

Phe Pro His Val Ile Ala Asp Val Arg Val Leu Glu Pro Ile Glu Ile
145 150 155 160

Pro Leu Asp Asp Val Arg Asn Val Leu Phe His Thr Asn Glu Asn Arg
165 170 175

Pro Thr Met Arg Leu Leu Cys Met Leu Tyr Thr Pro Leu Arg Ala Cys
180 185 190

Gly Ala Ser Ser Gly Thr Asp Pro Phe Val Ile Ala Gly Arg Val Leu
195 200 205

Thr Cys Pro Ser Pro Asp Phe Asn Phe Leu Phe Leu Val Pro Pro Ser
210 215 220

Val Glu Gln Lys Thr Arg Gln Leu Thr Val Pro Asn Ile Pro Leu Asn
225 230 235 240

Asn Leu Ala Asn Ser Arg Val Pro Ala Met Ile Asn Lys Met Thr Val
245 250 255

Ser Thr Asp Gln Asn Gln Val Val Gln Phe Gln Asn Gly Arg Cys Thr
260 265 270

Leu Glu Gly Gln Leu Leu Gly Thr Thr Pro Val Ser Ala Ser Gln Val
275 280 285

Ala Arg Ile Arg Gly Lys Val Phe Ser Thr Ala Ser Gly Lys Gly Leu
290 295 300

Asn Leu Thr Glu Leu Asp Gly Thr Pro Tyr His Ala Phe Glu Ser Pro
305 310 315 320

Ala Pro Leu Gly Phe Pro Asp Ile Gly Ala Cys Asp Trp His Val Ser
325 330 335

Thr Phe Lys Val Asp Gln Asn Leu Ser Gly Asp Pro Met Ser Arg Leu
340 345 350

Asp Val Lys Gln Asn Ala Pro Phe Ala Pro His Leu Gly Ser Ile Glu

```
        355                 360                 365

Phe Thr Ser Asp Gln Asp Pro Thr Gly Asp Gln Leu Gly Thr Leu Ala
    370                 375                 380

Trp Val Ser Pro Ser Thr Ser Gly Ala Arg Val Asp Pro Trp Lys Ile
385                 390                 395                 400

Pro Ser Tyr Gly Ser Thr Val Thr Glu Ser Thr His Leu Ala Pro Pro
            405                 410                 415

Ile Phe Pro Pro Gly Phe Gly Glu Ala Ile Val Tyr Phe Met Ser Asp
            420                 425                 430

Phe Pro Ile Val Ser Gly Asn Thr Ala Gln Val Pro Cys Thr Leu Pro
        435                 440                 445

Gln Glu Phe Val Ser His Phe Val Glu Gln Gln Ala Pro Val Arg Gly
    450                 455                 460

Glu Ala Ala Leu Leu His Tyr Val Asp Pro Asp Thr His Arg Asn Leu
465                 470                 475                 480

Gly Glu Phe Lys Leu Tyr Pro Asp Gly Phe Ile Thr Cys Val Pro Asn
            485                 490                 495

Thr Gly Gly Gly Pro Gln Asn Leu Pro Thr Asn Gly Val Phe Val Phe
            500                 505                 510

Ser Ser Trp Val Ser Arg Tyr Tyr Gln Leu Lys Pro Val Gly Thr Ala
        515                 520                 525

Gly Pro Ala Arg Arg Leu Gly Val Arg Arg Val
    530                 535


<210> SEQ ID NO 24
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 24

Met Met Met Ala Ser Lys Asp Ala Pro Thr Ser Pro Asp Gly Ala Ser
1               5                   10                  15

Gly Ala Gly Gln Leu Val Pro Glu Ala Asn Thr Ala Glu Gln Ile Ser
            20                  25                  30

Met Asp Pro Val Cys Gly Ala Ser Thr Ala Val Cys Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
            85                  90                  95

Ser Gln Met Tyr Asn Gly Trp Val Gly Asn Met Arg Val Arg Ile Leu
            100                 105                 110

Leu Ala Gly Asn Ala Phe Thr Ala Gly Lys Ile Ile Ile Cys Cys Val
        115                 120                 125

Pro Pro Gly Phe Asp Ala Arg Ile Leu Thr Ile Ala Gln Ala Thr Leu
    130                 135                 140

Phe Pro His Leu Ile Ala Asp Val Arg Thr Leu Glu Pro Val Glu Leu
145                 150                 155                 160

Pro Leu Glu Asp Val Arg Asn Val Leu Tyr His Asn Ser Ser Gln Pro
            165                 170                 175

Gln Pro Thr Met Arg Leu Val Ala Met Leu Tyr Thr Pro Leu Arg Thr
```

```
            180                 185                 190

Gly Gly Gly Ser Gly Gly Thr Asp Ala Phe Val Val Ala Gly Arg Val
        195                 200                 205

Leu Thr Cys Pro Ala Pro Asp Phe Ser Phe Leu Phe Leu Val Pro Pro
    210                 215                 220

Ser Val Glu Gln Lys Thr Arg Val Phe Ser Val Pro Asn Ile Pro Leu
225                 230                 235                 240

Lys Asp Leu Ser Asn Ser Arg Val Pro Val Pro Ile Gln Gly Met Phe
                245                 250                 255

Met Ser Pro Asp Val Asn Gln Ser Val Gln Phe Gln Asn Gly Arg Cys
            260                 265                 270

Gln Ile Asp Gly Gln Leu Gln Gly Thr Thr Pro Val Ser Leu Ser Gln
        275                 280                 285

Leu Cys Lys Ile Arg Gly Lys Thr Ser Ser Asn Ala Arg Val Leu Asn
    290                 295                 300

Leu Ser Glu Val Asp Gly Thr Pro Phe Ile Pro Leu Glu Ser Pro Ala
305                 310                 315                 320

Pro Val Gly Phe Pro Asp Leu Gly Gly Cys Asp Trp His Val Asn Phe
                325                 330                 335

Thr Phe Gln Ala Gln Asn Gln Asp Pro Ser Gln Ser Val Thr Phe Ala
            340                 345                 350

Thr Asn Asp Ala Ser Phe Val Pro Tyr Leu Gly Ser Ile Ser Pro His
        355                 360                 365

Asn Gly Gly Asp Phe His Ala Gly Asp Ile Ile Gly Ser Leu Gly Trp
    370                 375                 380

Ile Ser Ala Pro Ser Asp Asn Thr Gln Leu Asn Val Trp Thr Ile Pro
385                 390                 395                 400

Lys Tyr Gly Ser Ser Leu Pro Asp Val Thr His Leu Ala Pro Ala Val
                405                 410                 415

Phe Pro Pro Gly Phe Gly Glu Val Ile Leu Tyr Phe Tyr Ser Thr Phe
            420                 425                 430

Pro Gly Ser Gly Gln Pro Ser Gln Leu Gln Val Pro Cys Leu Leu Pro
        435                 440                 445

Gln Glu Phe Ile Thr His Phe Cys Asn Glu Gln Ala Pro Ile Ala Gly
    450                 455                 460

Glu Ala Ala Leu Leu His Tyr Val Asp Pro Asp Thr Gly Arg Asn Leu
465                 470                 475                 480

Gly Glu Phe Lys Leu Tyr Pro Asp Gly Phe Met Thr Cys Val Pro Asn
                485                 490                 495

Ser Val Ser Ser Gly Pro Gln Thr Leu Pro Ile Asn Gly Val Phe Val
            500                 505                 510

Phe Val Ser Trp Val Ser Arg Phe Tyr Gln Leu Lys Pro Val Gly Thr
        515                 520                 525

Ala Ser Ala Ala Arg Arg Leu Gly Leu Arg Arg Ile
    530                 535                 540
```

<210> SEQ ID NO 25
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 25

```
Met Met Met Ala Ser Lys Asp Ala Pro Thr Ser Pro Asp Gly Ala Ser
```

```
1               5                   10                  15

Gly Ala Gly Gln Leu Val Pro Glu Ala Asn Thr Ala Glu Gln Ile Ser
            20                  25                  30

Met Asp Pro Val Ala Gly Ala Ser Thr Ala Val Ala Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Ile Leu
            100                 105                 110

Leu Ala Gly Cys Ala Phe Thr Ala Gly Lys Ile Ile Ile Cys Cys Val
        115                 120                 125

Pro Pro Gly Phe Asp Ala Arg Ile Leu Thr Ile Ala Gln Ala Thr Leu
    130                 135                 140

Phe Pro His Leu Ile Ala Asp Val Arg Thr Leu Glu Pro Val Glu Leu
145                 150                 155                 160

Pro Leu Glu Asp Val Arg Asn Val Leu Tyr His Asn Ser Ser Gln Pro
                165                 170                 175

Gln Pro Thr Met Arg Leu Val Ala Met Leu Tyr Thr Pro Leu Arg Thr
            180                 185                 190

Cys Gly Gly Ser Gly Gly Thr Asp Ala Phe Val Val Ala Gly Arg Val
        195                 200                 205

Leu Thr Cys Pro Ala Pro Asp Phe Ser Phe Leu Phe Leu Val Pro Pro
    210                 215                 220

Ser Val Glu Gln Lys Thr Arg Val Phe Ser Val Pro Asn Ile Pro Leu
225                 230                 235                 240

Lys Asp Leu Ser Asn Ser Arg Val Pro Val Pro Ile Gln Gly Met Phe
                245                 250                 255

Met Ser Pro Asp Val Asn Gln Ser Val Gln Phe Gln Asn Gly Arg Cys
            260                 265                 270

Gln Ile Asp Gly Gln Leu Gln Gly Thr Thr Pro Val Ser Leu Ser Gln
        275                 280                 285

Leu Cys Lys Ile Arg Gly Lys Thr Ser Ser Asn Ala Arg Val Leu Asn
    290                 295                 300

Leu Ser Glu Val Asp Gly Thr Pro Phe Ile Pro Leu Glu Ser Pro Ala
305                 310                 315                 320

Pro Val Gly Phe Pro Asp Leu Gly Gly Cys Asp Trp His Val Asn Phe
                325                 330                 335

Thr Phe Gln Ala Gln Asn Gln Asp Pro Ser Gln Ser Val Thr Phe Ala
            340                 345                 350

Thr Asn Asp Ala Ser Phe Val Pro Tyr Leu Gly Ser Ile Ser Pro His
        355                 360                 365

Asn Gly Gly Asp Phe His Ala Gly Asp Ile Ile Gly Ser Leu Gly Trp
    370                 375                 380

Ile Ser Ala Pro Ser Asp Asn Thr Gln Leu Asn Val Trp Thr Ile Pro
385                 390                 395                 400

Lys Tyr Gly Ser Ser Leu Pro Asp Val Thr His Leu Ala Pro Ala Val
                405                 410                 415

Phe Pro Pro Gly Phe Gly Glu Val Ile Leu Tyr Phe Tyr Ser Thr Phe
            420                 425                 430
```

Pro Gly Ser Gly Gln Pro Ser Gln Leu Gln Val Pro Cys Leu Leu Pro
435 440 445

Gln Glu Phe Ile Thr His Phe Cys Asn Glu Gln Ala Pro Ile Ala Gly
450 455 460

Glu Ala Ala Leu Leu His Tyr Val Asp Pro Asp Thr Gly Arg Asn Leu
465 470 475 480

Gly Glu Phe Lys Leu Tyr Pro Asp Gly Phe Met Thr Cys Val Pro Asn
485 490 495

Ser Val Ser Ser Gly Pro Gln Thr Leu Pro Ile Asn Gly Val Phe Val
500 505 510

Phe Val Ser Trp Val Ser Arg Phe Tyr Gln Leu Lys Pro Val Gly Thr
515 520 525

Ala Ser Ala Ala Arg Arg Leu Gly Leu Arg Arg Ile
530 535 540

<210> SEQ ID NO 26
<211> LENGTH: 535
<212> TYPE: PRT
<213> ORGANISM: Norovirus
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 26

Met Lys Met Ala Ser Asn Asp Ala Ala Pro Ser Asn Asp Gly Ala Ala
1 5 10 15

Gly Leu Val Pro Xaa Val Asn Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Met Asn Phe Val Gln Ala Pro Asn Gly Glu Phe
50 55 60

Thr Val Ser Pro Arg Asn Ser Pro Gly Glu Ile Leu Leu Asn Leu Glu
65 70 75 80

Leu Gly Pro Glu Leu Asn Pro Phe Leu Ala His Leu Ser Arg Met Xaa
85 90 95

Asn Gly Tyr Ala Gly Gly Val Glu Met Gln Val Leu Leu Ala Gly Asn
100 105 110

Ala Phe Thr Ala Gly Lys Leu Leu Phe Ala Ala Ile Pro Pro His Phe
115 120 125

Pro Ile Glu Asn Leu Ser Pro Gly Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Glu Pro Glu Pro Arg Met
165 170 175

Trp Leu Val Ala Met Leu Tyr Thr Pro Leu Arg Ser Asn Gly Ser Gly
180 185 190

Asp Asp Val Phe Thr Val Ser Cys Arg Val Pro Thr Arg Pro Ser Pro
195 200 205

Asp Phe Asp Phe Asn Tyr Leu Val Pro Pro Thr Val Glu Ser Lys Thr
210 215 220

```
Lys Pro Phe Thr Leu Pro Ile Leu Thr Ile Gly Glu Leu Ser Asn Ser
225                 230                 235                 240

Arg Phe Pro Ala Pro Ile Asp Glu Leu Tyr Thr Ser Pro Asn Glu Gly
                245                 250                 255

Leu Val Val Gln Pro Gln Asn Gly Arg Thr Thr Leu Asp Gly Glu Leu
            260                 265                 270

Leu Gly Thr Thr Gln Leu Val Pro Ser Asn Ile Cys Ser Leu Arg Gly
        275                 280                 285

Arg Ile Asn Ala His Leu Ser Asp Asn Gln His Arg Trp Asn Met Gln
    290                 295                 300

Val Thr Asn Ala Asn Gly Thr Pro Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Ile Leu
            340                 345                 350

Ala Thr Trp Ser Pro Lys Phe Thr Pro Lys Leu Gly Ser Val Val Leu
        355                 360                 365

Gly Thr Trp Glu Asp Arg Asp Phe Asp Ile Asn Gln Pro Thr Arg Phe
    370                 375                 380

Thr Pro Val Gly Leu Tyr Asp Thr Asp His Phe Asn Gln Trp Ala Leu
385                 390                 395                 400

Pro Asn Tyr Ser Gly Ala Leu Thr Leu Asn Met Asn Leu Ala Pro Ser
                405                 410                 415

Val Ala Pro Leu Phe Pro Gly Glu Gln Leu Leu Phe Phe Arg Ser His
            420                 425                 430

Ile Pro Leu Lys Gly Gly Thr Ser Asn Gly Ala Ile Asp Cys Leu Leu
        435                 440                 445

Pro Gln Glu Trp Val Gln His Phe Tyr Gln Glu Ser Ala Pro Ser Ser
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Thr Gly Ser Arg Pro Ile Val Val Pro Pro Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 27
<211> LENGTH: 542
<212> TYPE: PRT
<213> ORGANISM: Norovirus

<400> SEQUENCE: 27

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
```

```
    50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu Gln Asp Asn Asp His Leu Tyr Asn Ile Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Thr Gln Arg Asp Lys Gln Asn Ala Ala Gly Gln Ser Gln Pro Ala Asn
            340                 345                 350

Arg Gly His Asp Ala Val Val Pro Thr Tyr Thr Ala Gln Tyr Thr Pro
        355                 360                 365

Lys Leu Gly Gln Val Gln Ile Gly Thr Trp Gln Thr Asp Asp Leu Lys
    370                 375                 380

Val Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Leu Pro Leu Lys Gly Gly Tyr Gly Asn
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480
```

Asn Pro Asp Thr Gly Arg Ala Leu Phe Glu Ala Lys Leu His Arg Ala
485 490 495

Gly Phe Met Thr Val Ser Ser Asn Thr Ser Ala Pro Val Val Val Pro
500 505 510

Ala Asn Gly Tyr Phe Arg Phe Asp Ser Trp Val Asn Gln Phe Tyr Ser
515 520 525

Leu Ala Pro Met Gly Thr Gly Asn Gly Arg Arg Arg Ile Gln
530 535 540

<210> SEQ ID NO 28
<211> LENGTH: 548
<212> TYPE: PRT
<213> ORGANISM: Norovirus

<400> SEQUENCE: 28

Met Lys Met Ala Ser Asn Asp Ala Thr Pro Ser Asn Asp Gly Ala Ala
1 5 10 15

Gly Leu Val Pro Glu Ile Asn Asn Glu Ala Met Ala Leu Asp Pro Val
20 25 30

Ala Gly Ala Ala Ile Ala Ala Pro Leu Thr Gly Gln Gln Asn Ile Ile
35 40 45

Asp Pro Trp Ile Met Asn Asn Phe Val Gln Ala Pro Gly Gly Glu Phe
50 55 60

Thr Val Ser Pro Arg Asn Ser Pro Gly Glu Val Leu Leu Asn Leu Glu
65 70 75 80

Leu Gly Pro Glu Ile Asn Pro Tyr Leu Ala His Leu Ala Arg Met Tyr
85 90 95

Asn Gly Tyr Ala Gly Gly Phe Glu Val Gln Val Val Leu Ala Gly Asn
100 105 110

Ala Phe Thr Ala Gly Lys Ile Ile Phe Ala Ala Ile Pro Pro Tyr Phe
115 120 125

Pro Ile Asp Asn Leu Ser Ala Ala Gln Ile Thr Met Cys Pro His Val
130 135 140

Ile Val Asp Val Arg Gln Leu Glu Pro Val Asn Leu Pro Met Pro Asp
145 150 155 160

Val Arg Asn Asn Phe Phe His Tyr Asn Gln Gly Ser Asp Ser Arg Leu
165 170 175

Arg Leu Val Ala Met Leu Tyr Thr Pro Leu Arg Ala Asn Asn Ser Gly
180 185 190

Asp Asp Val Phe Thr Val Ser Leu Arg Val Leu Thr Arg Pro Ser Pro
195 200 205

Asp Phe Ser Phe Asn Phe Leu Val Pro Pro Thr Val Glu Ser Lys Thr
210 215 220

Lys Pro Phe Thr Leu Pro Ile Leu Thr Ile Ser Glu Met Ser Asn Ser
225 230 235 240

Arg Phe Pro Val Pro Ile Asp Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Ala Phe Arg Gly
275 280 285

Val Leu Thr Arg Ser Thr Ser Arg Ala Ser Asp Gln Ala Asp Thr Ala
290 295 300

Thr Pro Arg Leu Phe Asn Tyr Tyr Trp His Ile Gln Leu Asp Asn Leu

```
305                 310                 315                 320

Asn Gly Thr Pro Tyr Asp Pro Ala Glu Asp Ile Pro Gly Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ala
        355                 360                 365

Gly Arg Phe Thr Pro Lys Leu Gly Ser Leu Glu Ile Ser Thr Glu Ser
    370                 375                 380

Asp Asp Phe Asp Gln Asn Gln Pro Thr Arg Phe Thr Pro Val Gly Ile
385                 390                 395                 400

Gly Val Asp His Glu Ala Asp Phe Gln Gln Trp Ser Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545


<210> SEQ ID NO 29
<211> LENGTH: 540
<212> TYPE: PRT
<213> ORGANISM: Norovirus

<400> SEQUENCE: 29

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125
```

```
Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 30
<211> LENGTH: 538
<212> TYPE: PRT
<213> ORGANISM: Norovirus

<400> SEQUENCE: 30

```
Met Ala Ser Asn Asp Ala Thr Pro Ser Asn Asp Gly Ala Ala Gly Leu
1               5                   10                  15

Val Pro Glu Ser Asn Asn Glu Ala Met Ala Leu Glu Pro Val Val Gly
            20                  25                  30

Ala Ser Leu Ala Ala Pro Val Thr Gly Gln Thr Asn Ile Ile Asp Pro
        35                  40                  45

Trp Ile Arg Thr Asn Phe Val Gln Ala Pro Asn Gly Glu Phe Thr Val
    50                  55                  60

Ser Pro Arg Asn Ser Pro Gly Glu Ile Leu Val Asn Leu Glu Leu Gly
65                  70                  75                  80

Pro Glu Leu Asn Pro Tyr Leu Ala His Leu Ala Arg Met Tyr Asn Gly
                85                  90                  95

Tyr Ala Gly Gly Met Glu Val Gln Val Met Leu Ala Gly Asn Ala Phe
            100                 105                 110

Thr Ala Gly Lys Ile Ile Phe Ala Ala Val Pro Pro Tyr Phe Pro Val
        115                 120                 125

Glu Asn Leu Ser Pro Ser Gln Ile Thr Met Phe Pro His Val Ile Ile
    130                 135                 140

Asp Val Arg Thr Leu Glu Pro Val Leu Leu Pro Met Pro Asp Val Arg
145                 150                 155                 160

Ser Thr Leu Phe His Phe Asn Gln Lys Asp Glu Pro Lys Met Arg Leu
                165                 170                 175

Val Ala Met Leu Tyr Thr Pro Leu Arg Ser Asn Gly Ser Gly Asp Asp
            180                 185                 190

Val Phe Thr Val Ser Cys Arg Ile Leu Thr Arg Pro Ser Pro Glu Phe
        195                 200                 205

Asp Phe Thr Tyr Leu Val Pro Pro Thr Val Glu Ser Lys Thr Lys Pro
    210                 215                 220

Phe Thr Leu Pro Val Leu Thr Leu Gly Glu Leu Ser Asn Ser Arg Phe
225                 230                 235                 240

Pro Leu Ser Ile Asp Glu Met Val Thr Ser Pro Asn Glu Ser Ile Val
                245                 250                 255

Val Gln Pro Gln Asn Gly Arg Val Thr Leu Asp Gly Glu Leu Leu Gly
            260                 265                 270

Thr Thr Gln Leu Gln Ala Cys Asn Ile Cys Ser Ile Arg Gly Lys Val
        275                 280                 285

Thr Gly Gln Val Pro Asn Glu Gln His Met Trp Asn Leu Glu Ile Thr
    290                 295                 300

Asn Leu Asn Gly Thr Gln Phe Asp Pro Thr Asp Asp Val Pro Ala Pro
305                 310                 315                 320

Leu Gly Val Pro Asp Phe Ala Gly Glu Val Phe Gly Val Leu Ser Gln
                325                 330                 335

Arg Asn Arg Gly Glu Ser Asn Pro Ala Asn Arg Ala His Asp Ala Val
            340                 345                 350

Val Ala Thr Tyr Ser Asp Lys Tyr Thr Pro Lys Leu Gly Leu Val Gln
        355                 360                 365

Ile Gly Thr Trp Asn Thr Asn Asp Val Glu Asn Gln Pro Thr Lys Phe
    370                 375                 380
```

```
Thr Pro Ile Gly Leu Asn Glu Val Ala Asn Gly His Arg Phe Glu Gln
385                 390                 395                 400

Trp Thr Leu Pro Arg Tyr Ser Gly Ala Leu Thr Leu Asn Met Asn Leu
                405                 410                 415

Ala Pro Ala Val Ala Pro Leu Phe Pro Gly Glu Arg Leu Leu Phe Phe
            420                 425                 430

Arg Ser Tyr Val Pro Leu Lys Gly Gly Phe Gly Asn Pro Ala Ile Asp
        435                 440                 445

Cys Leu Val Pro Gln Glu Trp Val Gln His Phe Tyr Gln Glu Ser Ala
    450                 455                 460

Pro Ser Leu Gly Asp Val Ala Leu Val Arg Tyr Val Asn Pro Asp Thr
465                 470                 475                 480

Gly Arg Val Leu Phe Glu Ala Lys Leu His Lys Gly Gly Phe Leu Thr
                485                 490                 495

Val Ser Ser Thr Ser Thr Gly Pro Val Val Val Pro Ala Asn Gly Tyr
            500                 505                 510

Phe Arg Phe Asp Pro Trp Gly Asn Gln Phe Tyr Ser Leu Ala Pro Met
        515                 520                 525

Gly Thr Gly Asn Gly Arg Arg Arg Phe Gln
    530                 535


<210> SEQ ID NO 31
<211> LENGTH: 547
<212> TYPE: PRT
<213> ORGANISM: Norovirus

<400> SEQUENCE: 31

Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asp Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220
```

Pro Phe Thr Leu Pro Ile Leu Thr Leu Gly Glu Leu Ser Asn Ser Arg
225 230 235 240

Phe Pro Ala Pro Ile Asp Met Leu Tyr Thr Asp Pro Asn Glu Thr Ile
245 250 255

Val Val Gln Pro Gln Asn Gly Arg Cys Thr Leu Asp Gly Thr Leu Gln
260 265 270

Gly Thr Thr Gln Leu Val Pro Thr Gln Ile Cys Ser Phe Arg Gly Thr
275 280 285

Leu Ile Ser Gln Thr Ser Arg Ser Ala Asp Ser Thr Asp Ser Ala Pro
290 295 300

Arg Val Arg Asn His Pro Leu His Val Gln Leu Lys Asn Leu Asp Gly
305 310 315 320

Thr Pro Tyr Asp Pro Thr Asp Glu Val Pro Ala Val Leu Gly Ala Ile
325 330 335

Asp Phe Lys Gly Thr Val Phe Gly Val Ala Ser Gln Arg Asn Thr Thr
340 345 350

Gly Ser Ser Val Gly Ala Thr Arg Ala His Glu Val His Ile Asp Thr
355 360 365

Thr Asn Pro Arg Tyr Thr Pro Lys Leu Gly Ser Val Leu Met Tyr Ser
370 375 380

Glu Ser Ser Asp Phe Asp Asp Gly Gln Pro Thr Arg Phe Thr Pro Ile
385 390 395 400

Gly Met Gly Ala Asp Asp Trp His Gln Trp Glu Leu Pro Glu Tyr Ser
405 410 415

Gly His Leu Thr Leu Asn Met Asn Leu Ala Pro Ala Val Ala Pro Ala
420 425 430

Phe Pro Gly Glu Arg Ile Leu Phe Phe Arg Ser Val Val Pro Ser Ala
435 440 445

Gly Gly Tyr Gly Ser Gly Gln Ile Asp Cys Leu Ile Pro Gln Glu Trp
450 455 460

Val Gln His Phe Tyr Gln Glu Ala Ala Pro Ser Gln Ser Ala Val Ala
465 470 475 480

Leu Ile Arg Tyr Val Asn Pro Asp Thr Gly Arg Asn Ile Phe Glu Ala
485 490 495

Lys Leu His Arg Glu Gly Phe Ile Thr Val Ala Asn Ser Gly Asn Asn
500 505 510

Pro Ile Val Val Pro Pro Asn Gly Tyr Phe Arg Phe Glu Ala Trp Val
515 520 525

Asn Gln Phe Tyr Thr Leu Thr Pro Met Gly Thr Gly Gln Gly Arg Arg
530 535 540

Arg Val Gln
545

<210> SEQ ID NO 32
<211> LENGTH: 540
<212> TYPE: PRT
<213> ORGANISM: Norovirus

<400> SEQUENCE: 32

Met Lys Met Ala Ser Asn Asp Ala Ala Pro Ser Asn Asp Gly Ala Ala
1 5 10 15

Gly Leu Val Pro Glu Ile Asn Asn Glu Val Met Pro Leu Glu Pro Val
20 25 30

Ala Gly Ala Ser Leu Ala Thr Pro Val Val Gly Gln Gln Asn Ile Ile

-continued

```
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Ile Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Ile Phe Ala Ala Ile Pro Pro Gly Phe
        115                 120                 125

Pro Tyr Glu Asn Leu Ser Pro Ser Gln Ile Thr Met Cys Pro His Val
    130                 135                 140

Ile Ile Asp Val Arg Gln Leu Glu Pro Val Leu Leu Pro Met Pro Asp
145                 150                 155                 160

Ile Arg Asn Asn Phe Phe His Tyr Asn Gln Gly Asn Asp Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Lys Pro Ser Pro
        195                 200                 205

Asp Phe Glu Phe Thr Phe Leu Val Pro Pro Thr Val Glu Ser Lys Thr
    210                 215                 220

Lys Gln Phe Thr Leu Pro Ile Leu Lys Ile Ser Glu Met Thr Asn Ser
225                 230                 235                 240

Arg Phe Pro Val Pro Val Glu Met Met Tyr Thr Ser Arg Asn Glu Asn
                245                 250                 255

Gln Val Val Gln Pro Gln Asn Gly Arg Val Thr Leu Asp Gly Glu Leu
            260                 265                 270

Leu Gly Thr Thr Pro Leu Leu Ala Val Asn Ile Cys Lys Phe Lys Gly
        275                 280                 285

Glu Val Ile Ala Lys Asn Gly Asp Val Arg Ser Tyr Arg Met Asp Met
    290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
                325                 330                 335

Ala Ser Gln Arg Asn Lys Asn Glu Gln Asn Pro Ala Thr Arg Ser His
            340                 345                 350

Glu Ala Asn Ile Asn Thr Gly Gly Asp Gln Tyr Ala Pro Lys Leu Ala
        355                 360                 365

Gln Val Lys Ile Phe Ser Gln Ser Gln Asp Phe Glu Val His Gln Pro
    370                 375                 380

Thr Val Phe Thr Pro Val Gly Val Ala Gly Asp Thr Ser His Pro Phe
385                 390                 395                 400

Arg Gln Trp Thr Leu Pro Arg Tyr Gly Gly His Leu Thr Asn Asn Thr
                405                 410                 415

His Leu Ala Pro Ala Val Ala Pro Leu Phe Pro Gly Glu Gln Ile Leu
            420                 425                 430

Phe Phe Arg Ser Gln Ile Pro Ser Ser Gly Gly His Glu Leu Gly Tyr
        435                 440                 445

Met Asp Cys Leu Val Pro Gln Glu Trp Val Gln His Phe Tyr Gln Glu
    450                 455                 460
```

Ala Ala Thr Ala Gln Ser Glu Val Ala Leu Ile Arg Phe Ile Asn Pro
465 470 475 480

Asp Thr Gly Arg Val Leu Phe Glu Ala Lys Leu His Lys Gln Gly Phe
485 490 495

Ile Thr Val Ala His Thr Gly Asp Asn Pro Ile Val Met Pro Pro Asn
500 505 510

Gly Tyr Phe Arg Phe Glu Ala Trp Val Asn Gln Phe Tyr Ser Leu Ala
515 520 525

Pro Val Gly Thr Gly Asn Gly Arg Arg Arg Ile Gln
530 535 540

<210> SEQ ID NO 33
<211> LENGTH: 537
<212> TYPE: PRT
<213> ORGANISM: Norovirus

<400> SEQUENCE: 33

Met Lys Met Ala Ser Asn Asp Ala Ala Pro Ser Asn Asp Gly Ala Ala
1 5 10 15

Gly Leu Val Pro Glu Ile Asn His Glu Val Met Ala Ile Glu Pro Val
20 25 30

Ala Gly Ala Ser Leu Ala Ala Pro Val Val Gly Gln Leu Asn Ile Ile
35 40 45

Asp Pro Trp Ile Arg Asn Asn Phe Val Gln Ala Pro Ala Gly Glu Phe
50 55 60

Thr Val Ser Pro Arg Asn Ala Pro Gly Glu Phe Leu Leu Asp Leu Glu
65 70 75 80

Leu Gly Pro Glu Leu Asn Pro Tyr Leu Ala His Leu Ala Arg Met Tyr
85 90 95

Asn Gly His Ala Gly Gly Met Glu Val Gln Ile Val Leu Ala Gly Asn
100 105 110

Ala Phe Thr Ala Gly Lys Ile Leu Phe Ala Val Ile Pro Pro Gly Phe
115 120 125

Pro Tyr Glu Asn Leu Ser Pro Ala Gln Leu Thr Met Cys Pro His Val
130 135 140

Val Val Asp Val Arg Gln Leu Glu Pro Ile Leu Leu Pro Met Pro Asp
145 150 155 160

Ile Arg Asn Thr Phe Phe His Tyr Asn Gln Ser Asn Gly Pro Lys Leu
165 170 175

Arg Leu Val Ala Met Leu Tyr Thr Pro Leu Arg Ala Asn Asn Ala Gly
180 185 190

Glu Asp Val Phe Thr Val Ser Cys Arg Val Leu Thr Arg Pro Ser Pro
195 200 205

Asp Phe Glu Phe Asn Phe Leu Val Pro Pro Ser Val Glu Ser Lys Thr
210 215 220

Lys Ala Phe Thr Leu Pro Ile Leu Lys Ile Ser Glu Met Thr Asn Ser
225 230 235 240

Arg Phe Pro Ile Pro Val Asp Gln Met Tyr Thr Ser Arg Asn Glu Asn
245 250 255

Ile Val Val Gln Pro Gln Asn Gly Arg Val Thr Leu Asp Gly Glu Leu
260 265 270

Gln Gly Thr Thr Thr Leu Gln Pro Val Ser Ile Cys Gly Phe Arg Gly
275 280 285

Thr Leu Gln Thr Arg Leu Ala Asp Gln Pro Asn Tyr Thr Tyr Gln Val

```
    290                 295                 300

His Leu Glu Asn Leu Asp Gly Ser Pro Val Asp Pro Thr Asp Glu Val
305                 310                 315                 320

Pro Ala Pro Leu Gly Thr Pro Asp Phe Gln Ala Gln Leu Phe Gly Val
                325                 330                 335

Ile Ser Gln Arg Ser Ser Asp Asn Ala Thr Arg Ala His Glu Ala Arg
            340                 345                 350

Val Asn Thr Asn Asp Pro Thr Phe Ala Pro Gln Ile Ala Gln Val Arg
        355                 360                 365

Phe Lys Ser Pro Ser Asn Asp Phe Phe Asp Asn Glu Pro Ile Lys Phe
    370                 375                 380

Thr Pro Val Gly Ile Ser Val Asp Ser Gln Asn Ser Tyr Asn Gln Trp
385                 390                 395                 400

Leu Leu Pro Arg Tyr Gly Gly His Leu Thr Asn Asn Thr His Leu Ala
                405                 410                 415

Pro Ser Val Ser Pro Met Phe Pro Gly Glu Gln Ile Leu Phe Phe Arg
            420                 425                 430

Ser Phe Met Pro Gly Ala Ser Gly His Thr Asp Gly Ala Ile Asp Cys
        435                 440                 445

Leu Leu Pro Gln Glu Trp Val Ala His Phe Tyr Gln Glu Ala Ala Thr
    450                 455                 460

Ala Gln Thr Asp Val Ala Leu Ile Arg Phe Val Asn Pro Asp Thr Gly
465                 470                 475                 480

Arg Val Leu Phe Glu Gly Lys Leu His Lys Gln Gly Phe Ile Thr Ile
                485                 490                 495

Ser Asn Ser Gly Asp His Pro Ile Val Met Pro Ala Asn Gly Tyr Phe
            500                 505                 510

Arg Phe Glu Ala Trp Val Asn Gln Phe Tyr Ser Leu Ala Pro Val Gly
        515                 520                 525

Thr Gly Ser Gly Arg Arg Arg Ile Gln
    530                 535


<210> SEQ ID NO 34
<211> LENGTH: 537
<212> TYPE: PRT
<213> ORGANISM: Norovirus

<400> SEQUENCE: 34

Met Lys Met Ala Ser Asn Asp Ala Ala Pro Ser Ser Asp Gly Ala Ala
1               5                   10                  15

Gly Val Val Pro Glu Ile Asn His Glu Val Met Ala Ile Glu Pro Val
            20                  25                  30

Ala Gly Ala Ser Ile Ala Ala Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ala Pro Gly Glu Phe Leu Leu Asp Leu Glu
65                  70                  75                  80

Leu Gly Pro Asp Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Leu Phe Ala Val Ile Pro Pro Gly Phe
        115                 120                 125
```

```
Pro Tyr Glu Asn Leu Cys Pro Ala Gln Leu Thr Met Cys Pro His Val
    130                 135                 140

Val Val Asp Val Arg Gln Leu Glu Pro Val Met Leu Pro Met Pro Asp
145                 150                 155                 160

Ile Arg Asn Thr Phe Phe His Tyr Asn Gln Asp Gly Gly Pro Lys Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ala Pro
        195                 200                 205

Asp Phe Glu Phe Thr Phe Leu Val Pro Pro Ser Ile Glu Ser Lys Thr
    210                 215                 220

Lys Ala Phe Thr Ile Pro Val Leu Lys Ile Ser Glu Met Thr Asn Ser
225                 230                 235                 240

Arg Phe Pro Val Pro Val Asp Gln Met Tyr Thr Ser Arg Ser Glu Gly
                245                 250                 255

Ile Val Val Gln Pro Gln Asn Gly Arg Ala Thr Ile Asp Gly Glu Leu
            260                 265                 270

Leu Gly Thr Thr Leu Val Ser Pro Val Ser Val Cys Asn Phe Lys Gly
        275                 280                 285

Asn Leu Gln Ala Glu Val Pro Gly Gln His Gln Leu Tyr Gln Leu Gln
    290                 295                 300

Leu Thr Asn Leu Asp Gly Ser Pro Ile Asp Pro Thr Asp Asp Thr Pro
305                 310                 315                 320

Gly Pro Leu Gly Cys Pro Asp Phe Thr Gly Leu Leu Tyr Gly Val Ala
                325                 330                 335

Ser Gln Arg Gly Pro Gly Asp Ala Thr Arg Ala His Glu Ala Arg Ile
            340                 345                 350

Asp Thr Gly Ser Asp Thr Phe Ala Pro Lys Ile Gly Gln Val Arg Phe
        355                 360                 365

Tyr Ser Thr Ser Ser Asp Phe Glu Thr Asn Gln Pro Thr His Phe Thr
    370                 375                 380

Pro Ile Gly Ile Tyr Ile Glu Gly Asn Ser Ser Asp Phe Asn Gln Trp
385                 390                 395                 400

Gln Leu Pro Arg Tyr Gly Gly His Leu Ala Asn Asn Asn His Leu Ala
                405                 410                 415

Pro Ala Val Ser Pro Leu Phe Pro Gly Glu Gln Ile Leu Phe Phe Arg
            420                 425                 430

Ser Phe Ile Pro Gly Ala Ser Gly His Thr Asn Gly Glu Met Asp Cys
        435                 440                 445

Leu Leu Pro Gln Glu Phe Val Gln His Phe Tyr Gln Glu Ala Ala Thr
    450                 455                 460

Ala Arg Ser Glu Val Ala Leu Leu Arg Phe Val Asn Pro Asp Thr Gly
465                 470                 475                 480

Arg Ala Leu Phe Glu Ser Lys Leu His Lys Gln Gly Phe Met Thr Ile
                485                 490                 495

Ala Ser Ser Gly Asp His Pro Ile Ile Met Pro Thr Asn Gly Tyr Phe
            500                 505                 510

Arg Phe Glu Ala Trp Val Asn Gln Phe Tyr Ser Leu Ala Pro Val Gly
        515                 520                 525

Thr Gly Ser Gly Arg Arg Arg Ile Gln
    530                 535
```

<210> SEQ ID NO 35
<211> LENGTH: 548
<212> TYPE: PRT
<213> ORGANISM: Norovirus

<400> SEQUENCE: 35

```
Met Lys Met Ala Ser Asn Asp Ala Ala Pro Ser Ser Asp Gly Ala Ala
1               5                   10                  15

Gly Leu Val Pro Glu Ser Asn Asn Glu Val Met Ala Leu Glu Pro Val
            20                  25                  30

Ala Gly Ala Ser Leu Ala Ala Pro Val Thr Gly Gln Thr Asn Ile Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Met Glu Val Gln Ile Met Leu Ala Gly Asn
            100                 105                 110

Ala Phe Thr Ala Gly Lys Leu Ile Phe Ala Ala Val Pro Pro His Phe
        115                 120                 125

Pro Ile Glu Asn Leu Ser Pro Pro Gln Ile Thr Met Phe Pro His Val
    130                 135                 140

Ile Ile Asp Val Arg Thr Leu Glu Pro Val Leu Leu Pro Met Pro Asp
145                 150                 155                 160

Ile Arg Asn Ser Phe Phe His Phe Ile Gln Arg Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Asp Phe Thr Tyr Leu Val Pro Pro Thr Val Glu Ser Lys Ser
    210                 215                 220

Lys Pro Phe Thr Leu Pro Ile Leu Thr Leu Gly Glu Leu Thr Asn Ser
225                 230                 235                 240

Arg Phe Pro Leu Pro Ile Asp Val Leu Tyr Thr Asn Pro Asn Glu Ser
                245                 250                 255

Ala Ile Val Gln Cys Gln Asn Gly Arg Cys Thr Leu Asp Gly Glu Leu
            260                 265                 270

Gln Gly Thr Thr Gln Leu Leu Pro Thr Gly Ile Cys Ala Phe Arg Gly
        275                 280                 285

Lys Val Thr Gln Gln Val Gln Asp Glu His Arg Gly Thr His Trp Asn
    290                 295                 300

Met Thr Val Thr Asn Leu Asn Gly Thr Pro Phe Asp Pro Thr Glu Asp
305                 310                 315                 320

Val Pro Ala Pro Leu Gly Thr Pro Asp Phe Ser Gly Gln Ile Tyr Gly
                325                 330                 335

Val Ile Ser Gln Arg Asn Thr Asn Thr Val Pro Gly Glu Gly Asp Leu
            340                 345                 350

Pro Ala Asn Arg Ala His Glu Ala Val Ile Ala Thr Tyr Ser Pro Lys
        355                 360                 365

Phe Thr Pro Lys Leu Gly Asn Ile Gln Phe Ser Thr Trp Glu Thr Gln
    370                 375                 380
```

```
Asp Val Ser Ser Gly Gln Pro Thr Lys Phe Thr Pro Val Gly Leu Ala
385                 390                 395                 400

Ser Val Asp Ala Asn Ser His Phe Asp Gln Trp Thr Leu Pro Ser Tyr
                405                 410                 415

Ser Gly Ala Leu Thr Leu Asn Met Asn Leu Ala Pro Ser Val Ala Pro
            420                 425                 430

Val Phe Pro Gly Glu Cys Leu Leu Phe Phe Arg Ser Phe Ile Pro Leu
        435                 440                 445

Lys Gly Gly Tyr Gly Asn Pro Ala Ile Asp Cys Leu Met Pro Gln Glu
    450                 455                 460

Trp Val Gln His Leu Tyr Gln Glu Ser Ala Pro Ser Leu Ser Asp Val
465                 470                 475                 480

Ala Leu Val Arg Tyr Val Asn Pro Glu Thr Gly Arg Thr Leu Phe Glu
                485                 490                 495

Ala Lys Leu His Arg Asn Gly Phe Leu Thr Val Ala Arg Asn Ser Ala
            500                 505                 510

Gly Pro Val Val Ala Pro Thr Asn Gly Tyr Phe Arg Phe Asp Ser Trp
        515                 520                 525

Val Asn Gln Phe Tyr Thr Leu Ala Pro Met Gly Asn Gly Ser Gly Arg
    530                 535                 540

Arg Arg Met Gln
545
```

<210> SEQ ID NO 36
<211> LENGTH: 547
<212> TYPE: PRT
<213> ORGANISM: Norovirus

<400> SEQUENCE: 36

```
Met Lys Met Ala Ser Ser Asp Ala Pro Pro Ser Thr Asp Gly Ser Ala
1               5                   10                  15

Gly Leu Val Pro Glu Val Asn Asn Glu Thr Met Ala Leu Glu Pro Val
            20                  25                  30

Val Gly Ala Pro Leu Ala Ala Pro Val Ala Gly Gln His Asn Ile Ile
        35                  40                  45

Asp Pro Trp Ile Lys Met Asn Phe Val Gln Ala Pro Asn Gly Glu Phe
    50                  55                  60

Thr Val Ser Pro Arg Asn Ala Pro Gly Glu Ile Leu Leu Asp Leu Glu
65                  70                  75                  80

Leu Gly Pro Asp Leu Asn Pro Tyr Leu Ser His Leu Ala Arg Met Tyr
                85                  90                  95

Asn Gly Tyr Ala Gly Gly Met Glu Val Gln Val Val Leu Ala Gly Asn
            100                 105                 110

Ala Phe Thr Ala Gly Lys Ile Ile Phe Ala Ala Val Pro Pro Asn Phe
        115                 120                 125

Pro Ala Glu Asn Leu Ser Ala Ala Gln Val Thr Met Cys Pro His Val
    130                 135                 140

Ile Val Asp Val Arg Gln Leu Glu Pro Val Met Leu Pro Met Pro Asp
145                 150                 155                 160

Ile Arg Asn Lys Leu Phe His Tyr Asn Gln Val Asp Asp Pro Lys Leu
                165                 170                 175

Arg Leu Leu Ala Tyr Leu Tyr Thr Pro Leu Arg Ala Asn Asn Ala Gly
            180                 185                 190

Asp Asp Val Phe Thr Val Ser Cys Arg Val Leu Thr Arg Pro Thr Pro
        195                 200                 205
```

Asp Phe Glu Phe Met Phe Leu Val Pro Pro Thr Val Glu Ser Lys Thr
210 215 220

Lys Pro Phe Ser Leu Pro Gly Leu Thr Leu Asp Glu Leu Ser Asn Ser
225 230 235 240

Arg Phe Pro Ala Pro Ile Val Gln Leu Tyr Thr Asn Pro His Asp Asn
245 250 255

Leu Ile Val Gln Pro Gln Asn Gly Arg Cys Thr Ile Asp Gly Leu Leu
260 265 270

Gln Gly Thr Thr Gln Leu Val Ser Cys Asn Val Cys Ser Phe Arg Gly
275 280 285

Thr Met Gly Glu Gly Gln Pro Ala Ala His Ser Glu Asp Glu Ile Met
290 295 300

Pro Met Ala Phe Asn Val Gln Arg Glu Ile Met Leu Glu Asn Leu Asp
305 310 315 320

Gly Ser Pro Tyr Asp Pro Thr Asp Asp Ile Pro Ala Val Leu Gly Ser
325 330 335

Pro Asp Phe Gln Gly Val Met Phe Gly Ile Leu Ser Gln Arg Asn Thr
340 345 350

Asp Gly Gln Thr Arg Ala His Glu Ala Lys Val Asp Thr Arg Ala Ala
355 360 365

Arg Phe Ala Pro Lys Leu Gly Phe Val Val Ala Thr Val Glu Ser Thr
370 375 380

Asp Phe His Ala Asn Gln Pro Ser Arg Phe Thr Pro Val Gly Leu Gly
385 390 395 400

Gly Asp Thr Asn Arg Asp Phe Asn Gln Trp Gln Leu Pro Ala Tyr Gly
405 410 415

Gly Ala Leu Thr Asn Asn Thr Asn Leu Ala Pro Pro Val Met Pro Val
420 425 430

Tyr Pro Gly Glu Gln Leu Leu Phe Phe Arg Ser Gln Leu Pro Ser Ser
435 440 445

Gly Gly Val Val Ala Gly Trp Leu Asp Cys Leu Leu Pro Gln Glu Trp
450 455 460

Val Gln His Phe Phe Gln Glu Ser Ala Thr Ser Gln Ser Asp Val Ala
465 470 475 480

Leu Val Arg Tyr Val Asn Pro Thr Thr Gly Arg Val Leu Phe Glu Ala
485 490 495

Lys Leu His Lys Gln Gly Phe Leu Thr Val Ala Ala Ser Gly Ser Tyr
500 505 510

Pro Leu Val Val Pro Ala Asp Gly Tyr Phe Arg Phe Glu Ser Trp Val
515 520 525

Asn Gln Phe Tyr Thr Leu Ala Pro Met Gly Asn Gly Ser Gly Arg Arg
530 535 540

Arg Ala Arg
545

<210> SEQ ID NO 37
<211> LENGTH: 535
<212> TYPE: PRT
<213> ORGANISM: Norovirus

<400> SEQUENCE: 37

Met Lys Met Ala Ser Asn Asp Ala Ala Pro Ser Asn Asp Gly Ala Ala
1 5 10 15

Gly Leu Val Pro Glu Ala Asn Asn Glu Thr Met Ala Leu Glu Pro Val

```
            20                  25                  30

Ala Gly Ala Ser Ile Ala Ala Pro Leu Thr Gly Gln Asn Asn Ile Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Leu Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asn Gly Thr Pro Phe Asp Pro Thr Gly Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Glu Asp Asp Val His Ile Asn Gln Pro Thr Lys Phe
    370                 375                 380

Thr Pro Val Gly Leu Phe Glu Asn Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445
```

Pro Gln Glu Trp Ile Gln His Leu Tyr Gln Glu Ser Ala Pro Ser Gln
450 455 460

Ser Asp Val Ala Leu Ile Arg Phe Thr Asn Pro Asp Thr Gly Arg Val
465 470 475 480

Leu Phe Glu Ala Lys Leu His Arg Ser Gly Tyr Ile Thr Val Ala Asn
485 490 495

Thr Gly Ser Arg Pro Ile Val Val Pro Ala Asn Gly Tyr Phe Arg Phe
500 505 510

Asp Thr Trp Val Asn Gln Phe Tyr Ser Leu Ala Pro Met Gly Thr Gly
515 520 525

Asn Gly Arg Arg Arg Val Gln
530 535

<210> SEQ ID NO 38
<211> LENGTH: 542
<212> TYPE: PRT
<213> ORGANISM: Norovirus

<400> SEQUENCE: 38

Met Lys Met Ala Ser Asn Asp Ala Ala Pro Ser Asn Asp Gly Ala Ala
1 5 10 15

Ser Leu Val Pro Glu Gly Ile Asn Glu Thr Met Pro Leu Glu Pro Val
20 25 30

Ala Gly Ala Ser Ile Ala Ala Pro Val Ala Gly Gln Thr Asn Ile Ile
35 40 45

Asp Pro Trp Ile Arg Thr Asn Phe Val Gln Ala Pro Asn Gly Glu Phe
50 55 60

Thr Val Ser Pro Arg Asn Ser Pro Gly Glu Ile Leu Leu Asn Leu Glu
65 70 75 80

Leu Gly Pro Asp Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Ile Leu Phe Ala Ala Ile Pro Pro Asn Phe
115 120 125

Leu Val Asp Met Ile Ser Pro Ala Gln Ile Thr Met Leu Pro His Leu
130 135 140

Ile Val Asp Val Arg Thr Leu Glu Pro Ile Met Thr Pro Leu Pro Asp
145 150 155 160

Val Arg Asn Val Phe Tyr His Phe Asn Asn Gln Pro Gln Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Thr Pro
195 200 205

Asp Phe Glu Phe Ile Tyr Leu Val Pro Pro Ser Val Glu Ser Lys Thr
210 215 220

Lys Pro Phe Thr Leu Pro Ile Leu Thr Ile Ser Glu Leu Thr Asn Ser
225 230 235 240

Arg Phe Pro Ile Pro Ile Glu Gln Leu Tyr Thr Ala Pro Asn Glu Thr
245 250 255

Asn Val Val Gln Cys Gln Asn Gly Arg Cys Thr Leu Asp Gly Glu Leu
260 265 270

Gln Gly Thr Thr Gln Leu Leu Ser Ser Ala Val Cys Phe Leu Gln Gly

```
        275                 280                 285

Arg Thr Val Ala Asp Asn Gly Asp Asn Trp Asp Gln Asn Leu Leu Gln
    290                 295                 300

Leu Thr Tyr Pro Asn Gly Ala Ser Tyr Asp Pro Thr Asp Glu Val Pro
305                 310                 315                 320

Ala Pro Leu Gly Thr Gln Asp Phe Ser Gly Met Leu Tyr Gly Val Leu
                325                 330                 335

Thr Gln Asp Asn Val Asn Val Ser Thr Gly Glu Ala Lys Asn Ala Lys
            340                 345                 350

Gly Ile Tyr Ile Ser Thr Thr Ser Gly Lys Phe Thr Pro Lys Ile Gly
        355                 360                 365

Ser Ile Gly Leu His Ser Ile Thr Glu His Val His Pro Asn Gln Gln
    370                 375                 380

Ser Arg Phe Thr Pro Val Gly Val Ala Val Asp Glu Asn Thr Pro Phe
385                 390                 395                 400

Gln Gln Trp Val Leu Pro His Tyr Ala Gly Ser Leu Ala Leu Asn Thr
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
                485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540


<210> SEQ ID NO 39
<211> LENGTH: 536
<212> TYPE: PRT
<213> ORGANISM: Norovirus

<400> SEQUENCE: 39

Met Lys Met Ala Ser Asn Asp Ala Thr Pro Ser Asp Asp Gly Ala Ala
1               5                   10                  15

Gly Leu Val Pro Glu Ile Asn Asn Glu Val Met Ala Leu Glu Pro Val
            20                  25                  30

Ala Gly Ala Ser Ile Ala Ala Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Leu Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110
```

```
Ala Phe Thr Ala Gly Lys Ile Leu Phe Ala Ala Ile Pro Pro Ser Phe
        115                 120                 125

Pro Tyr Glu Asn Leu Ser Pro Ala Gln Leu Thr Met Cys Pro His Val
    130                 135                 140

Ile Val Asp Val Arg Gln Leu Glu Pro Val Leu Leu Pro Met Pro Asp
145                 150                 155                 160

Ile Arg Asn Val Phe Tyr His Tyr Asn Gln Asn Asn Ser Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Gln Phe Thr Phe Leu Val Pro Pro Thr Val Glu Ser Lys Thr
    210                 215                 220

Lys Asn Phe Thr Leu Pro Val Leu Arg Val Ser Glu Met Thr Asn Ser
225                 230                 235                 240

Arg Phe Pro Val Val Leu Asp Gln Met Tyr Thr Ser Arg Asn Glu Asn
                245                 250                 255

Ile Ile Val Gln Pro Gln Asn Gly Arg Cys Thr Thr Asp Gly Glu Leu
            260                 265                 270

Leu Gly Thr Thr Thr Leu Gln Ser Val Ser Ile Cys Asn Phe Arg Gly
        275                 280                 285

Thr Met Gln Ala Lys Leu Asn Glu Gln Pro Arg Tyr Gln Leu Gln Leu
    290                 295                 300

Thr Asn Leu Asp Gly Ser Pro Ile Asp Pro Thr Asp Asp Met Pro Ala
305                 310                 315                 320

Pro Leu Gly Thr Pro Asp Phe Gln Ala Met Leu Tyr Gly Val Ala Ser
                325                 330                 335

Gln Arg Ser Ser Arg Asp Asn Ala Thr Arg Ala His Asp Ala Gln Ile
            340                 345                 350

Asp Thr Ala Gly Asp Thr Phe Ala Pro Lys Ile Gly Gln Val Arg Phe
        355                 360                 365

Lys Ser Ser Ser Asp Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

His Ile Pro Ser Ala Gly Gly His Thr Asp Gly Ala Ile Asp Cys Leu
        435                 440                 445

Leu Pro Gln Glu Trp Ile Glu His Phe Tyr Gln Glu Ala Ala Pro Ser
    450                 455                 460

Gln Ser Asp Ile Ala Leu Val Arg Phe Ile Asn Pro Asp Thr Gly Arg
465                 470                 475                 480

Val Leu Leu Glu Ala Lys Leu His Lys Gln Gly Phe Leu Thr Val Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525

Gly Ser Gly Arg Arg Arg Ile Gln
```

530 535

<210> SEQ ID NO 40
<211> LENGTH: 536
<212> TYPE: PRT
<213> ORGANISM: Norovirus

<400> SEQUENCE: 40

Met Lys Met Ala Ser Asn Asp Ala Thr Pro Ser Asp Asp Gly Ala Ala
1 5 10 15

Gly Leu Val Pro Glu Ile Asn Asn Glu Val Met Ala Leu Glu Pro Val
20 25 30

Ala Gly Ala Ser Ile Ala Ala Pro Val Val Gly Gln Gln Asn Ile Ile
35 40 45

Asp Pro Trp Ile Arg Asn Asn Phe Val Gln Ala Pro Ala Gly Glu Phe
50 55 60

Thr Val Ser Pro Arg Asn Ser Pro Gly Glu Leu Leu Leu Asp Leu Glu
65 70 75 80

Leu Gly Pro Glu Leu Asn Pro Tyr Leu Ala His Leu Ala Arg Met Tyr
85 90 95

Asn Gly His Ala Gly Gly Met Glu Val Gln Ile Val Leu Ala Gly Asn
100 105 110

Ala Phe Thr Ala Gly Lys Ile Leu Phe Ala Ala Ile Pro Pro Ser Phe
115 120 125

Pro Tyr Glu Asn Leu Ser Pro Ala Gln Leu Thr Met Cys Pro His Val
130 135 140

Ile Val Asp Val Arg Gln Leu Glu Pro Val Leu Leu Pro Met Pro Asp
145 150 155 160

Ile Arg Asn Val Phe Tyr His Tyr Asn Gln Asn Asn Ser Pro Lys Leu
165 170 175

Arg Leu Val Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Gln Phe Thr Phe Leu Val Pro Pro Thr Val Glu Ser Lys Thr
210 215 220

Lys Asn Phe Thr Leu Pro Val Leu Arg Val Ser Glu Met Thr Asn Ser
225 230 235 240

Arg Phe Pro Val Val Leu Asp Gln Met Tyr Thr Ser Arg Asn Glu Asn
245 250 255

Ile Ile Val Gln Pro Gln Asn Gly Arg Cys Thr Thr Asp Gly Glu Leu
260 265 270

Leu Gly Thr Thr Thr Leu Gln Ser Val Ser Ile Cys Asn Phe Arg Gly
275 280 285

Thr Met Gln Ala Lys Leu Asn Glu Gln Pro Arg Tyr Gln Leu Gln Leu
290 295 300

Thr Asn Leu Asp Gly Ser Pro Ile Asp Pro Thr Asp Asp Met Pro Ala
305 310 315 320

Pro Leu Gly Thr Pro Asp Phe Gln Ala Met Leu Tyr Gly Val Ala Ser
325 330 335

Gln Arg Ser Ser Arg Asp Asn Ala Thr Arg Ala His Asp Ala Gln Ile
340 345 350

Asp Thr Ala Gly Asp Thr Phe Ala Pro Lys Ile Gly Gln Val Arg Phe
355 360 365

Lys Ser Ser Ser Asp Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

His Ile Pro Ser Ala Gly Gly His Thr Asp Gly Ala Ile Asp Cys Leu
        435                 440                 445

Leu Pro Gln Glu Trp Ile Glu His Phe Tyr Gln Glu Ala Ala Pro Ser
    450                 455                 460

Gln Ser Asp Ile Ala Leu Val Arg Phe Ile Asn Pro Asp Thr Gly Arg
465                 470                 475                 480

Val Leu Leu Glu Ala Lys Leu His Lys Gln Gly Phe Leu Thr Val Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525

Gly Ser Gly Arg Arg Arg Ile Gln
    530                 535

<210> SEQ ID NO 41
<211> LENGTH: 540
<212> TYPE: PRT
<213> ORGANISM: Norovirus

<400> SEQUENCE: 41

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Val Asp Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Ser Asp Gln Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Ser Val Pro Val Leu Thr Leu Asn Glu Leu Thr Asn Ser
225                 230                 235                 240

Arg Phe Pro Val Pro Ile Asp Ala Met Tyr Thr Ser Pro Asn Asp Ser
                245                 250                 255

Ile Val Val Gln Pro Gln Asn Gly Arg Ala Thr Ile Asp Gly Glu Leu
            260                 265                 270

Leu Gly Thr Thr Gln Leu Ile Pro Ser Gly Ile Cys Ser Phe Arg Gly
        275                 280                 285

Lys Ile Thr Thr His Leu Ser Asp Asp Arg His Leu Trp Asn Ile Gln
    290                 295                 300

Val Ser Asn Leu Asn Gly Thr Pro Phe Asp Pro Thr Asp Asp Val Pro
305                 310                 315                 320

Ala Pro Leu Gly Met Pro Asp Phe Ser Gly Gln Ile Phe Gly Val Val
                325                 330                 335

Ser Gln Arg Asp Thr Gly Thr Asn Pro Ala Asn Arg Ala His Asp Ala
            340                 345                 350

Val Leu Ala Thr Tyr Ser Ala Lys Tyr Thr Pro Lys Leu Gly Ser Val
        355                 360                 365

Gln Ile Gly Thr Trp Asp Thr Glu Asp Leu Leu Glu Arg Gln Pro Val
    370                 375                 380

Lys Phe Thr Pro Val Gly Leu Asn Glu Ile Gly Gln Asp Lys His Phe
385                 390                 395                 400

Asp Gln Trp Val Leu Pro Asn Tyr Ser Gly Ala Leu Gly Leu Asn Met
                405                 410                 415

His Leu Ala Pro Ala Val Ser Pro Leu Phe Pro Gly Glu Arg Leu Leu
            420                 425                 430

Phe Phe Arg Ser Tyr Ile Pro Leu Lys Gly Gly His Gly Asp Pro Phe
        435                 440                 445

Ile Asp Cys Leu Val Pro Gln Glu Trp Ile Gln His Phe Tyr Gln Glu
    450                 455                 460

Ser Ala Pro Ala Gln Ser Ser Val Ala Leu Leu Arg Tyr Val Asn Pro
465                 470                 475                 480

Asp Thr Gly Arg Thr Leu Phe Glu Ala Lys Leu His Lys Glu Gly Phe
                485                 490                 495

Ile Thr Val Ser Ser Thr Glu Asn Arg Pro Val Ile Val Pro Pro Asn
            500                 505                 510

Gly Tyr Phe Arg Phe Asp Ser Trp Val Asn Gln Phe Tyr Ser Leu Ala
        515                 520                 525

Pro Met Gly Thr Gly Asn Gly Arg Arg Arg Met Gln
    530                 535                 540

<210> SEQ ID NO 42
<211> LENGTH: 540
<212> TYPE: PRT
<213> ORGANISM: Norovirus

<400> SEQUENCE: 42

Met Lys Met Ala Ser Asn Asp Ala Ala Pro Ser Asn Asp Gly Ala Thr
1               5                   10                  15

Gly Leu Val Pro Glu Ile Asn Asn Glu Thr Leu Pro Leu Glu Pro Val
            20                  25                  30

Ala Gly Ala Ala Ile Ala Ala Pro Val Thr Gly Gln Asn Asn Ile Ile

```
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Ala Asn Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Ile Ser Glu Leu Thr Asn Ser
225                 230                 235                 240

Arg Phe Pro Ala Pro Ile Asp Ser Leu Phe Thr Ala Gln Asn Asn Asn
                245                 250                 255

Leu Asn Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Leu Thr Ala Asp Val Asp Gly Ser His Asp Asp Arg Trp His Met
    290                 295                 300

Gln Leu Thr Asn Leu Asn Gly Thr Pro Phe Asp Pro Thr Glu Asp Val
305                 310                 315                 320

Pro Ala Pro Leu Gly Thr Pro Asp Phe Thr Gly Leu Leu Phe Gly Val
                325                 330                 335

Ala Ser Gln Arg Asn Val Gly Ser Asn Pro Asn Thr Thr Arg Ala His
            340                 345                 350

Glu Ala Val Val Ser Thr Thr Ser Ser Gln Phe Val Pro Lys Leu Gly
        355                 360                 365

Ser Val Asn Phe Gly Ser Thr Ser Thr Asp Phe Gln Leu Gln Gln Pro
    370                 375                 380

Thr Lys Phe Thr Pro Val Gly Ile Lys Ile Glu Ser Gly His Glu Phe
385                 390                 395                 400

Asp Gln Trp Ala Leu Pro Arg Tyr Ser Gly His Leu Thr Leu Asn Met
                405                 410                 415

Asn Leu Ala Pro Pro Ile Ala Pro Asn Phe Pro Gly Glu Gln Leu Leu
            420                 425                 430

Phe Phe Arg Ser Asn Val Pro Cys Ala Gly Gly Val Ser Asp Gly Val
        435                 440                 445

Ile Asp Cys Leu Leu Pro Gln Glu Trp Ile Gln His Phe Tyr Gln Glu
    450                 455                 460
```

```
Ser Ala Pro Ser Gln Ser Asp Val Ala Leu Ile Arg Tyr Val Asn Pro
465                 470                 475                 480

Asp Thr Gly Arg Thr Leu Phe Glu Ala Lys Leu His Arg Thr Gly Tyr
                485                 490                 495

Ile Thr Val Ala His Ser Gly Asp Tyr Pro Leu Val Val Pro Ser Asn
            500                 505                 510

Gly Tyr Phe Arg Phe Asp Ser Trp Val Asn Gln Phe Tyr Ser Leu Ala
        515                 520                 525

Pro Met Gly Thr Gly Asn Gly Arg Arg Arg Val Gln
    530                 535                 540


<210> SEQ ID NO 43
<211> LENGTH: 538
<212> TYPE: PRT
<213> ORGANISM: Norovirus

<400> SEQUENCE: 43

Met Lys Met Ala Ser Asn Asp Ala Ala Pro Ser Asn Asp Gly Ala Ala
1               5                   10                  15

Gly Leu Val Pro Glu Gly Asn Asn Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
```

290 295 300

Gln Asn Leu Asn Gly Thr Thr Tyr Asp Pro Thr Asp Asp Val Pro Ala
305 310 315 320

Pro Leu Gly Thr Pro Asp Phe Lys Gly Val Val Phe Gly Val Ala Ser
325 330 335

Gln Arg Asn Val Gly Asn Asp Ala Pro Gly Ser Thr Arg Ala His Glu
340 345 350

Ala Val Ile Ser Thr Tyr Ser Pro Gln Phe Val Pro Lys Leu Gly Ser
355 360 365

Val Asn Phe Arg Ser Asn Asp Asn Asp Phe Gln Leu Gln Pro Thr Lys
370 375 380

Phe Thr Pro Val Gly Ile Asn Asp Asp Gly Asp His Pro Phe Arg Gln
385 390 395 400

Trp Glu Leu Pro Asp Tyr Ser Gly Leu Leu Thr Leu Asn Met Asn Leu
405 410 415

Ala Pro Pro Val Ala Pro Asn Phe Pro Gly Glu Gln Leu Leu Phe Phe
420 425 430

Arg Ser Phe Val Pro Cys Ser Gly Gly Tyr Asn Gln Gly Ile Val Asp
435 440 445

Cys Leu Ile Pro Gln Glu Trp Ile Gln His Phe Tyr Gln Glu Ser Ala
450 455 460

Pro Ser Gln Ser Asp Val Ala Leu Ile Arg Tyr Val Asn Pro Asp Thr
465 470 475 480

Gly Arg Thr Leu Phe Glu Ala Lys Leu His Arg Ser Gly Tyr Ile Thr
485 490 495

Val Ala His Ser Gly Asp Tyr Pro Leu Val Val Pro Ala Asn Gly Tyr
500 505 510

Phe Arg Phe Asp Ser Trp Val Asn Gln Phe Tyr Ser Leu Ala Pro Met
515 520 525

Gly Thr Gly Asn Gly Arg Arg Arg Ala Gln
530 535

<210> SEQ ID NO 44
<211> LENGTH: 557
<212> TYPE: PRT
<213> ORGANISM: Norovirus

<400> SEQUENCE: 44

Met Met Met Ala Ser Asn Asp Ala Thr Ala Pro Thr Asp Gly Ala Ala
1 5 10 15

Gly Leu Val Pro Glu Val Thr Asn Glu Thr Met Ala Leu Glu Pro Val
20 25 30

Ala Gly Ala Ala Leu Ala Ala Pro Val Val Gly Gln His Asn Val Ile
35 40 45

Asp Pro Trp Ile Arg Gly Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ala Arg Met Tyr
85 90 95

Asn Gly Tyr Ala Gly Gly Met Glu Val Gln Val Val Leu Ala Gly Asn
100 105 110

Ala Phe Ala Ala Gly Lys Ile Ile Phe Ala Ala Val Pro Pro Ser Phe
115 120 125

```
Pro Val Asp Ala Leu Ser Ala Pro Thr Ile Thr Met Cys Pro His Val
    130                 135                 140

Ile Val Asp Val Arg Gln Leu Glu Pro Val Leu Leu Pro Met Pro Asp
145                 150                 155                 160

Val Arg Asn Asn Phe Phe His Tyr Asn Gln Ser Ser Asp Pro Lys Leu
                165                 170                 175

Arg Leu Val Ala Met Leu Tyr Thr Pro Leu Arg Ala Asn Ser Pro Thr
            180                 185                 190

Asp Asp Val Phe Thr Val Ser Cys Arg Val Leu Thr Arg Pro Ser Pro
        195                 200                 205

Asp Phe Glu Phe Thr Phe Leu Ile Pro Pro Thr Val Glu Ser Lys Ser
    210                 215                 220

Lys Pro Phe Thr Ile Pro Gln Leu Thr Leu Ser Glu Leu Ser Asn Ser
225                 230                 235                 240

Arg Phe Pro Ala Pro Ile Asp Met Leu Tyr Thr Ser Pro Asn Asp Asn
                245                 250                 255

Ile Val Val Gln Pro Gln Asn Gly Arg Cys Thr Leu Asp Gly Glu Leu
            260                 265                 270

Gln Gly Thr Thr Gln Leu Gln Pro Ser Leu Ile Cys Ser Phe Arg Gly
        275                 280                 285

Val Thr Leu Asn Glu Thr Ser Arg Met Leu Val Asp Gln Glu Glu Glu
    290                 295                 300

Glu Glu Gly Glu Val Gln Arg Pro Gln Ala Arg Ala Phe Asn His Glu
305                 310                 315                 320

Tyr His Leu Gln Leu Gln Asn Leu Asp Gly Thr Asp Tyr Asp Pro Ala
                325                 330                 335

Gly Asp Leu Pro Ala Thr Leu Gly Ala Pro Asp Phe Ile Gly Thr Val
            340                 345                 350

Tyr Gly Val Val Ser Gln Arg Thr Thr Arg Asp Ser Ala Ala Arg Ala
        355                 360                 365

His Glu Ala Lys Ile Thr Thr Ser Asp Pro Arg Tyr Ala Pro Lys Leu
    370                 375                 380

Gly Ser Val Glu Phe Val Thr Glu Ser Thr Asp Ile Val Leu Asn Asp
385                 390                 395                 400

Gln Thr Lys Phe Thr Pro Val Gly Leu Ala His Asn Arg Ala Val Asp
                405                 410                 415

Tyr Lys Gln Trp Glu Leu Pro His Tyr Ala Gly Glu Leu Thr Ala Asn
            420                 425                 430

Thr Asn Leu Ala Pro Pro Val Ala Pro Val Tyr Pro Gly Glu Gln Leu
        435                 440                 445

Leu Phe Phe Arg Ser Asn Leu Pro Leu Ala Gly Gly Thr Ala Ala Ser
    450                 455                 460

Val Leu Asp Cys Leu Leu Pro Gln Glu Trp Ile Gln His Phe Tyr Gln
465                 470                 475                 480

Glu Ser Phe Ala Pro Gln Ser Asp Ile Ala Leu Leu Arg Tyr Val Asn
                485                 490                 495

Pro Asp Thr Gly Arg Val Leu Phe Glu Ala Lys Leu His Arg Gln Gly
            500                 505                 510

Tyr Ile Thr Val Ala Gly Ala Gly Thr Ser Pro Val Ala Val Pro Pro
        515                 520                 525

Asn Gly Tyr Phe Arg Phe Glu Ser Trp Val Ser Gln Phe Tyr Thr Leu
    530                 535                 540

Ala Pro Met Gly Ser Gly Thr Gly Arg Arg Arg Asn Gln
```

545 550 555

<210> SEQ ID NO 45
<211> LENGTH: 548
<212> TYPE: PRT
<213> ORGANISM: Norovirus

<400> SEQUENCE: 45

Met Lys Met Ala Ser Ser Asp Ala Ala Pro Ser Ser Asp Gly Ser Ala
1 5 10 15

Gly Leu Val Pro Glu Val Asn Ser Glu Thr Met Ala Leu Glu Pro Val
20 25 30

Val Gly Ala Pro Leu Ala Ala Pro Val Ala Gly Gln His Asn Ile Ile
35 40 45

Asp Pro Trp Ile Lys Leu Asn Phe Val Gln Ala Pro Asn Gly Glu Phe
50 55 60

Thr Val Ser Pro Arg Asn Ala Pro Gly Glu Ile Leu Leu Asp Leu Glu
65 70 75 80

Leu Gly Pro Asp Leu Asn Pro Tyr Leu Ala His Leu Ser Arg Met Tyr
85 90 95

Asn Ala Tyr Ala Gly Gly Met Glu Val Gln Val Ile Leu Ala Gly Asn
100 105 110

Ala Phe Thr Ala Gly Lys Ile Ile Phe Ala Ala Val Pro Pro Asn Phe
115 120 125

Pro Leu Glu Asn Leu Ser Ala Ala Gln Ile Thr Met Cys Pro His Ile
130 135 140

Ile Val Asp Val Arg Gln Leu Glu Pro Val Met Leu Pro Met Pro Asp
145 150 155 160

Val Arg Asn Arg Leu Phe His Tyr Asn Gln Val Arg Glu Pro Arg Leu
165 170 175

Arg Leu Val Ala Tyr Leu Tyr Thr Pro Leu Arg Ala Asn Asn Ala Gly
180 185 190

Asp Asp Val Phe Thr Val Ser Cys Arg Val Leu Thr Arg Pro Ser Gln
195 200 205

Asp Phe Glu Phe Met Phe Leu Val Pro Pro Ser Val Glu Ser Lys Thr
210 215 220

Lys Pro Phe Ser Leu Pro Asn Leu Thr Leu Ala Glu Leu Ser Asn Ser
225 230 235 240

Arg Phe Pro Leu Pro Ile Glu Gln Leu Tyr Thr Asn Pro Leu Asp Asn
245 250 255

Leu Val Val Gln Pro Gln Asn Gly Arg Cys Thr Ile Asp Gly Ile Leu
260 265 270

Leu Gly Thr Thr Gln Leu Val Pro Ser Leu Ile Cys Ser Met Arg Gly
275 280 285

Thr Leu Glu Ala Asp Gln Ala Ser Gly His Thr Asp Asp Glu Ser Val
290 295 300

Gln Ser Arg Ala Phe Asn Arg Gln Arg Ser Leu Met Leu Glu Asn Pro
305 310 315 320

Asp Gly Ser Ala Phe Asp Pro Ser Asp Glu Val Pro Ala Val Leu Gly
325 330 335

Val Pro Asp Phe Arg Gly Val Val Phe Gly Val Leu Ser Gln Arg Asn
340 345 350

Asn Gly Asp Thr Thr Arg Ser His Glu Ala Lys Ile Asp Thr Arg Arg
355 360 365

```
Pro Arg Tyr Ala Pro Lys Leu Gly Phe Val Glu Val Leu Thr Glu Ser
    370                 375                 380

Asp Asp Phe Gln Asn Gly Pro Pro Thr Lys Phe Thr Pro Val Gly Leu
385                 390                 395                 400

Gly Gly Asp Gly Asn Pro Asp Phe Gln Gln Trp Ala Leu Pro Asp Tyr
                405                 410                 415

Gly Gly Ala Leu Thr Asn Asn Thr Asn Leu Ala Pro Pro Val Val Pro
            420                 425                 430

Val Tyr Pro Gly Glu Gln Ile Leu Phe Phe Arg Ser Gln Leu Pro Ser
        435                 440                 445

Ser Gly Gly Thr Val Ala Gly Trp Leu Asp Cys Leu Leu Pro Gln Glu
    450                 455                 460

Trp Ile Gln His Phe Tyr Gln Asp Ser Ala Ala Ala Gln Ser Asp Val
465                 470                 475                 480

Ala Leu Val Arg Tyr Ile Asn Pro Ala Thr Gly Arg Val Leu Phe Glu
                485                 490                 495

Ala Lys Leu His Arg Gln Gly Phe Leu Thr Val Ser Ala Ala Gly Pro
            500                 505                 510

His Pro Val Val Ala Pro Ala Asp Gly Tyr Phe Arg Phe Glu Ser Trp
        515                 520                 525

Val Asn Gln Phe Tyr Thr Leu Ala Pro Met Gly Asn Gly Ser Gly Arg
    530                 535                 540

Arg Arg Val Tyr
545


<210> SEQ ID NO 46
<211> LENGTH: 535
<212> TYPE: PRT
<213> ORGANISM: Norovirus

<400> SEQUENCE: 46

Met Lys Met Ala Ser Asn Asp Ala Asn Pro Ser Ser Asp Gly Ser Ala
1               5                   10                  15

Asn Leu Val Pro Glu Ile Ser Asn Glu Val Met Ala Leu Glu Pro Val
            20                  25                  30

Ala Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Val Leu Leu Asn Leu Pro
65                  70                  75                  80

Leu Ser Pro Asp Ile Asn Pro Tyr Leu Ala His Leu Ser Arg Met Tyr
                85                  90                  95

Asn Gly Tyr Ala Gly Gly Val Glu Val Glu Val Val Leu Ala Gly Asn
            100                 105                 110

Ala Phe Thr Ala Gly Lys Ile Ile Phe Ala Ala Val Pro Pro Asn Phe
        115                 120                 125

Pro Pro Glu Asn Leu Ser Pro Ser Gln Ile Thr Met Leu Pro His Ile
    130                 135                 140

Ile Val Asp Val Arg Gln Leu Glu Pro Val Arg Ile Pro Leu Pro Asp
145                 150                 155                 160

Val Arg Asn Asn Phe Tyr His Tyr Ser Arg Glu Asn Asp Ser Thr Leu
                165                 170                 175

Arg Leu Ile Ala Met Leu Tyr Thr Pro Leu Arg Ala Asn Asn Ala Gly
            180                 185                 190
```

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Lys Ser
210 215 220

Lys Pro Phe Thr Ile Pro Met Leu Thr Ile Glu Glu Met Thr Asn Ser
225 230 235 240

Arg Phe Pro Ala Pro Leu Glu Leu Met Thr Thr Gly Pro Ser His Asp
245 250 255

Ile Val Val Gln Pro Gln Asn Gly Arg Cys Thr Ile Asp Gly Val Leu
260 265 270

Leu Gly Thr Thr Gln Leu Ser Pro Val Asn Ile Cys Ser Leu Arg Gly
275 280 285

Val Pro Thr Lys Arg Thr Asn Gly Asn Asp Asn Cys Phe Val Gln Leu
290 295 300

Glu Asn Pro Asn Gly Ser Ala Tyr Asp Pro Thr Glu Asp Ile Pro Ala
305 310 315 320

Val Leu Gly Ser Pro Asp Phe Val Gly Glu Leu Tyr Gly Thr Ile Thr
325 330 335

Gln Arg Ser Ser Asp Asn Ser Thr Arg Ala His Pro Phe Thr Leu Asn
340 345 350

Thr Gly Ser Pro Arg Tyr Thr Pro Lys Ile Gly Ser Val Asp Ile Arg
355 360 365

Val Thr Asp Val Ser Asp Leu Gln Asp His Asp Pro Val Lys Leu Thr
370 375 380

Pro Val Gly Leu Ser Gly Asp Arg Gly Ser Ile His Gln Trp Gln Leu
385 390 395 400

Pro Asn Tyr Ser Gly Val Ala Thr His Asn Met His Leu Ala Pro Ser
405 410 415

Val Ala Pro Leu Phe Pro Gly Glu Gln Ile Leu Phe Phe Arg Ser Thr
420 425 430

Val Pro Gly Cys Gly Gly Tyr Pro Asn Ser Asn Ile Asp Cys Leu Ile
435 440 445

Pro Gln Glu Trp Val Gln His Phe Tyr Gln Glu Gly Ala Pro Ala Arg
450 455 460

Thr Asp Val Ala Leu Leu Arg Phe Ile Asn Pro Asp Thr Gly Arg Val
465 470 475 480

Leu Phe Glu Cys Lys Leu His Lys His Gly Phe Ile Thr Val Ala Tyr
485 490 495

Ser Gly Asn His Asp Leu Val Met Pro Pro Asn Gly Tyr Phe Arg Phe
500 505 510

Glu Ser Trp Val Asn Gln Phe His Thr Leu Ala Pro Met Gly Thr Gly
515 520 525

Ser Gly Arg Arg Arg Ile Gln
530 535

<210> SEQ ID NO 47
<211> LENGTH: 535
<212> TYPE: PRT
<213> ORGANISM: Norovirus

<400> SEQUENCE: 47

Met Lys Met Ala Ser Asn Asp Ala Asn Pro Ser Ser Asp Gly Ser Ala
1 5 10 15

Asn Leu Val Pro Glu Ile Ser Asn Glu Val Met Ala Leu Glu Pro Val

```
            20                  25                  30

Ala Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Val Leu Leu Asn Leu Pro
65                  70                  75                  80

Leu Ser Pro Asp Ile Asn Pro Tyr Leu Ala His Leu Ser Arg Met Tyr
                85                  90                  95

Asn Gly Tyr Ala Gly Gly Val Glu Val Glu Val Val Leu Ala Gly Asn
            100                 105                 110

Ala Phe Thr Ala Gly Lys Ile Ile Phe Ala Ala Val Pro Pro Asn Phe
        115                 120                 125

Pro Pro Glu Asn Leu Ser Pro Ser Gln Ile Thr Met Leu Pro His Ile
    130                 135                 140

Ile Val Asp Val Arg Gln Leu Glu Pro Val Arg Ile Pro Leu Pro Asp
145                 150                 155                 160

Val Arg Asn Asn Phe Tyr His Tyr Ser Arg Glu Asn Asp Ser Thr Leu
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Lys Ser
    210                 215                 220

Lys Pro Phe Thr Ile Pro Met Leu Thr Ile Glu Glu Met Thr Asn Ser
225                 230                 235                 240

Arg Phe Pro Ala Pro Leu Glu Leu Met Thr Thr Gly Pro Ser His Asp
                245                 250                 255

Ile Val Val Gln Pro Gln Asn Gly Arg Cys Thr Ile Asp Gly Val Leu
            260                 265                 270

Leu Gly Thr Thr Gln Leu Ser Pro Val Asn Ile Cys Ser Leu Arg Gly
        275                 280                 285

Val Pro Thr Lys Arg Thr Asn Gly Asn Asp Asn Cys Phe Val Gln Leu
    290                 295                 300

Glu Asn Pro Asn Gly Ser Ala Tyr Asp Pro Thr Glu Asp Ile Pro Ala
305                 310                 315                 320

Val Leu Gly Ser Pro Asp Phe Val Gly Glu Leu Tyr Gly Thr Ile Thr
                325                 330                 335

Gln Arg Ser Ser Asp Asn Ser Thr Arg Ala His Pro Phe Thr Leu Asn
            340                 345                 350

Thr Gly Ser Pro Arg Tyr Thr Pro Lys Ile Gly Ser Val Asp Ile Arg
        355                 360                 365

Val Thr Asp Val Ser Asp Leu Gln Asp His Asp Pro Val Lys Leu Thr
    370                 375                 380

Pro Val Gly Leu Ser Gly Asp Arg Gly Ser Ile His Gln Trp Gln Leu
385                 390                 395                 400

Pro Asn Tyr Ser Gly Val Ala Thr His Asn Met His Leu Ala Pro Ser
                405                 410                 415

Val Ala Pro Leu Phe Pro Gly Glu Gln Ile Leu Phe Phe Arg Ser Thr
            420                 425                 430

Val Pro Gly Cys Gly Gly Tyr Pro Asn Ser Asn Ile Asp Cys Leu Ile
        435                 440                 445
```

```
Pro Gln Glu Trp Val Gln His Phe Tyr Gln Glu Gly Ala Pro Ala Arg
    450                 455                 460

Thr Asp Val Ala Leu Leu Arg Phe Ile Asn Pro Asp Thr Gly Arg Val
465                 470                 475                 480

Leu Phe Glu Cys Lys Leu His Lys His Gly Phe Ile Thr Val Ala Tyr
                485                 490                 495

Ser Gly Asn His Asp Leu Val Met Pro Pro Asn Gly Tyr Phe Arg Phe
            500                 505                 510

Glu Ser Trp Val Asn Gln Phe His Thr Leu Ala Pro Met Gly Thr Gly
        515                 520                 525

Ser Gly Arg Arg Arg Ile Gln
    530                 535


<210> SEQ ID NO 48
<211> LENGTH: 555
<212> TYPE: PRT
<213> ORGANISM: Norovirus

<400> SEQUENCE: 48

Met Lys Met Ala Ser Lys Asp Ala Ser Pro Ser Thr Asp Gly Ala Ala
1               5                   10                  15

Asn Leu Val Pro Glu Ser Gln Gln Glu Val Leu Ala Leu Gln Pro Val
            20                  25                  30

Ala Gly Ala Gln Ile Ala Ala Pro Val Ala Gly Gln Phe Asn Val Ile
        35                  40                  45

Asp Pro Trp Ile Tyr Gln Asn Phe Val Gln Ala Pro Glu Gly Glu Phe
    50                  55                  60

Thr Val Ser Pro Arg Asn Ser Thr Gly Glu Ile Leu Met Asn Leu Glu
65                  70                  75                  80

Leu Gly Pro Gln Leu Asn Pro Tyr Leu Ala His Leu Ala Arg Met Tyr
                85                  90                  95

Asn Ala Tyr Ala Gly Gly Phe Glu Val Gln Val Leu Leu Ala Gly Asn
            100                 105                 110

Ala Phe Thr Ala Gly Lys Ile Ile Val Cys Ala Val Pro Pro Asn Phe
        115                 120                 125

Pro Leu Gln Asn Ile Ser Ala Ala Gln Ala Thr Gln Leu Pro His Val
    130                 135                 140

Val Val Asp Val Arg Gln Leu Glu Pro Val Val Leu Pro Leu Pro Asp
145                 150                 155                 160

Val Arg Ala Gly Phe Tyr His Tyr Asn Gln Val Glu Glu Ser Arg Met
                165                 170                 175

Arg Leu Val Ala Ile Leu Tyr Thr Pro Leu Arg Thr Asn Ser Ala Gly
            180                 185                 190

Asp Asp Ala Phe Thr Val Ser Cys Arg Ile Leu Thr Arg Pro Ala Pro
        195                 200                 205

Asp Phe Ser Phe Phe Phe Leu Ile Pro Pro Thr Ile Glu Ser Lys Thr
    210                 215                 220

Thr Pro Phe Thr Leu Pro Arg Leu Pro Ile Ser Glu Met Thr Asn Ser
225                 230                 235                 240

Arg Phe Pro Leu Val Ile Lys Gly Met Val Val Asp Pro Asn Leu Pro
                245                 250                 255

Leu Gln Ala Asn Phe Gln Asn Gly Arg Ile Thr Leu Asp Gly Glu Leu
            260                 265                 270

Gln Gly Thr Thr Leu Pro Thr Ser Thr Ser Ile Gly Arg Ile Ser Gly
```

```
        275                 280                 285

Thr Tyr Met Ser Ser Thr Pro Ser Arg Ile Ile Gln His Glu Asp Ser
    290                 295                 300

Gly Asp Ser Thr Gln Pro Arg Val Phe Asn Pro Val Trp Met Asp Leu
305                 310                 315                 320

Thr Glu Asn Asn Trp Thr Glu Phe Gln Pro Phe Asn Asp Gln Pro Ala
                325                 330                 335

Pro Leu Gly Cys Pro Asp Phe Lys Ala Lys Ile Leu Gly Thr Leu Ile
            340                 345                 350

Arg Gln Pro Asn Asn Gly Ser Tyr Tyr Phe Asp Ala Tyr Leu Asp Thr
        355                 360                 365

Arg Gln His Gly Thr Phe Ala Pro Tyr Thr Gly His Ala Ala Val His
    370                 375                 380

Ser Asp Gln Gln Ala Gly His Leu Ala Gln Gly Tyr Lys Ile Gln Phe
385                 390                 395                 400

Ser Pro Thr Gly Ile Glu Ser Asp Gln Asn Thr Asp Leu Asn Gln Leu
                405                 410                 415

Pro Asp Tyr Gly Gly Ala Met Thr Val Ser Lys Gly Leu Ala Pro Ala
            420                 425                 430

Ala Ala Pro Asp Phe Pro Gly Glu Met Ile Leu Tyr Phe Val Ser Asp
        435                 440                 445

Met Pro Val Arg Asn Pro Asn Gly Glu Arg Arg Asp Thr Glu Ile Leu
    450                 455                 460

Cys Leu Leu Pro Gln Glu Met Val Thr His Phe Tyr Glu Gln Gln Ala
465                 470                 475                 480

Pro Ser Gln Gly Asp Val Ala Leu Val Arg Tyr Ile Asn Ala Glu Thr
                485                 490                 495

Gly Arg Val Met Phe Glu Gly Lys Leu His Arg Asn Gly Phe Phe Thr
            500                 505                 510

Val Ser Ala Thr Ala Arg Thr Leu Ile Val Pro Asp Gly Tyr Phe Arg
        515                 520                 525

Phe Asp Ser Trp Val Asn Arg Phe Tyr Thr Leu Ser Pro Met Gly Thr
    530                 535                 540

Gly Asn Gly Arg Arg Arg Ala Arg Met Leu Glu
545                 550                 555


<210> SEQ ID NO 49
<211> LENGTH: 542
<212> TYPE: PRT
<213> ORGANISM: Norovirus

<400> SEQUENCE: 49

Met Lys Met Ala Ser Asn Asp Ala Ala Pro Ser Asn Asp Gly Ala Ser
1               5                   10                  15

Ser Leu Val Pro Glu Ile Asn Asn Glu Thr Met Ala Leu Glu Pro Val
            20                  25                  30

Ala Gly Gly Ala Ile Ala Ala Pro Leu Thr Gly Gln Thr Asn Phe Ile
        35                  40                  45

Asp Pro Trp Ile Arg Asn Asn Tyr Val Gln Ala Pro Asn Gly Glu Phe
    50                  55                  60

Thr Ile Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ala Arg Met Tyr
                85                  90                  95
```

```
Asn Gly Tyr Ala Gly Gly Val Asp Val Gln Val Ile Met Ala Gly Asn
            100                 105                 110

Ala Phe Thr Ala Gly Lys Val Ile Phe Ala Ala Val Pro Pro His Phe
        115                 120                 125

Pro Val Glu Ser Leu Ser Pro Pro Gln Ile Thr Met Phe Pro His Ile
    130                 135                 140

Ile Val Asp Val Arg Thr Leu Glu Pro Ile Asn Ile Pro Ile Pro Asp
145                 150                 155                 160

Val Arg Asn Asn Phe Phe His Tyr Asn Gln Asn Asn Glu Pro Arg Met
                165                 170                 175

Arg Leu Val Ala Met Leu Tyr Thr Pro Leu Arg Ser Asn Gly Ser Ala
            180                 185                 190

Asp Asp Val Phe Thr Val Ser Cys Arg Val Leu Thr Lys Pro Ser Ala
        195                 200                 205

Asp Phe Glu Phe Asn Tyr Leu Val Pro Pro Thr Val Glu Ser Arg Thr
    210                 215                 220

Lys Pro Phe Thr Ile Pro Ile Leu Thr Ile Gly Glu Met Thr Asn Ser
225                 230                 235                 240

Arg Phe Pro Val Ala Ile Asp Met Leu Tyr Thr Ser Pro Thr Glu Asn
                245                 250                 255

Leu Val Val Gln Pro Gln Asn Gly Arg Cys Thr Leu Glu Gly Glu Leu
            260                 265                 270

Leu Gly Thr Thr Gln Leu Val Thr Pro Asn Ile Cys Ser Leu Arg Gly
        275                 280                 285

Ala Ile Thr Gly His Glu Gly Asn Asp Asp Asn His Lys Trp His Met
    290                 295                 300

Thr Val Thr Asn Pro Asn Gly Ser Ala Phe Asp Pro Thr Glu Asp Val
305                 310                 315                 320

Pro Ala Pro Leu Gly Thr Pro Asp Phe Ile Gly Asp Val Tyr Gly Val
                325                 330                 335

Leu Ser Gln Arg Asn Arg Asn Ile Glu Ser Gly Gln Thr Ala Pro Ala
            340                 345                 350

Asn Arg Ser His Glu Ala Val Ile Ser Thr Arg Ser Asn Lys Phe Thr
        355                 360                 365

Pro Lys Leu Gly Ser Val Met Ile Ala Thr Trp Asn Thr Asn Asp Val
    370                 375                 380

Glu Asn Gln Pro Thr Lys Phe Thr Pro Val Gly Leu Glu Asn Pro Gly
385                 390                 395                 400

Ser Phe His Gln Trp Glu Leu Pro Asn Tyr Ser Gly Ala Leu Thr Leu
                405                 410                 415

Asn Met Gly Leu Ala Pro Pro Val Phe Pro Thr Tyr Pro Gly Glu Gln
            420                 425                 430

Leu Leu Phe Phe Arg Ser Tyr Ile Pro Leu Lys Gly Gly Phe Gly Asn
        435                 440                 445

Ser Ile Ile Asp Cys Leu Val Pro Gln Glu Trp Ile Gln His Phe Tyr
    450                 455                 460

Gln Glu Ser Ala Pro Ser Gln Thr Asp Val Ala Leu Ile Arg Tyr Val
465                 470                 475                 480

Asn Pro Glu Thr Gly Arg Val Leu Phe Glu Ala Lys Leu His Arg Gln
                485                 490                 495

Gly Phe Ile Thr Val Ala Lys Thr Gly Asp Ser Pro Ile Asn Val Pro
            500                 505                 510

Ala Asn Gly Tyr Phe Arg Phe Asp Ser Trp Val Asn Ser Phe Tyr Ser
```

515 520 525

Leu Ala Pro Met Gly Thr Gly Asn Gly Arg Arg Arg Ile Gln
530 535 540

<210> SEQ ID NO 50
<211> LENGTH: 542
<212> TYPE: PRT
<213> ORGANISM: Norovirus

<400> SEQUENCE: 50

Met Lys Met Ala Ser Asn Asp Ala Ala Pro Ser Asn Asp Gly Ala Ala
1 5 10 15

Asn Leu Val Pro Glu Ala Asn Lys Glu Val Met Ala Leu Glu Pro Val
20 25 30

Ala Gly Gly Ala Ile Ala Ala Pro Leu Thr Gly Gln Thr Asn Ile Ile
35 40 45

Asp Pro Trp Ile Met Asn Asn Phe Val Gln Ala Pro Asn Gly Glu Phe
50 55 60

Thr Ile Ser Pro Arg Asn Ser Pro Gly Glu Val Leu Leu Asn Leu Glu
65 70 75 80

Leu Gly Pro Asp Leu Asn Pro Phe Leu Ala His Leu Ser Arg Met Tyr
85 90 95

Asn Gly Tyr Ala Gly Gly Val Glu Val Gln Val Ile Met Ala Gly Asn
100 105 110

Ala Phe Thr Ala Gly Lys Val Ile Phe Ala Ala Val Pro Pro His Phe
115 120 125

Pro Val Asp Asn Leu Ser Pro Pro Gln Val Thr Met Phe Pro His Val
130 135 140

Ile Val Asp Val Arg Thr Phe Glu Pro Ile Leu Leu Pro Leu Pro Asp
145 150 155 160

Val Arg Asn Ser Phe Tyr His Tyr Asn Gln Val Asn Asp Ser Arg Met
165 170 175

Arg Leu Ile Ala Met Leu Tyr Thr Pro Leu Arg Ser Asn Gly Ser Ser
180 185 190

Asp Asp Val Phe Thr Val Ser Cys Arg Val Leu Thr Arg Pro Thr Pro
195 200 205

Asp Phe Glu Phe Asn Tyr Leu Val Pro Pro Thr Val Glu Ser Arg Thr
210 215 220

Lys Pro Phe Ser Val Pro Ile Leu Thr Ile Gly Glu Met Thr Asn Ser
225 230 235 240

Arg Phe Pro Leu Pro Ile Asp Met Leu Tyr Thr Ser Pro Thr Glu Asn
245 250 255

Ile Val Val Gln Pro Gln Asn Gly Arg Cys Thr Leu Glu Gly Glu Leu
260 265 270

Leu Gly Thr Thr Gln Leu Val Thr Pro Asn Ile Cys Ala Leu Arg Gly
275 280 285

Glu Ile Arg Gly His Glu Gly Ser Gly Asp Asn His Lys Trp His Phe
290 295 300

Met Val Arg Ser Pro Asn Gly Ala Ala Phe Asp Pro Thr Glu Asp Val
305 310 315 320

Pro Ala Pro Leu Gly Thr Pro Asp Phe Ile Gly Asp Val Phe Gly Val
325 330 335

Leu Ser Gln Arg Asn Arg Asn Thr Asp Ser Gly Gln Ser Gly Pro Ala
340 345 350

```
Asn Arg Ser His Asp Ala Val Val Ser Thr Arg Asp Ser Arg Phe Thr
        355                 360                 365

Pro Lys Leu Gly Ser Val Met Ile Ala Thr Trp Glu Thr Ser Asp Ile
    370                 375                 380

Gln Asp Gln Pro Thr Arg Phe Thr Pro Val Gly Leu Glu Asn Pro Asp
385                 390                 395                 400

His Tyr Asn Gln Trp Gln Leu Pro Asn Tyr Ser Gly Ala Leu Thr Leu
                405                 410                 415

Asn Met Gly Leu Ala Pro Ser Val Phe Pro Thr Tyr Pro Gly Glu Gln
            420                 425                 430

Ile Leu Phe Phe Arg Ser Tyr Ile Pro Leu Lys Gly Gly Tyr Gly Asp
        435                 440                 445

Ser His Ile Asp Cys Leu Val Pro Gln Glu Trp Ile Gln His Phe Tyr
    450                 455                 460

Gln Glu Ser Ala Pro Ser Gln Thr Asp Val Ala Leu Ile Arg Tyr Val
465                 470                 475                 480

Asn Pro Glu Thr Gly Arg Val Leu Phe Glu Ala Lys Leu His Arg Gln
                485                 490                 495

Gly Tyr Ile Thr Val Ala Arg Ser Gly Ser Ser Pro Ile Asn Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540


<210> SEQ ID NO 51
<211> LENGTH: 540
<212> TYPE: PRT
<213> ORGANISM: Norovirus

<400> SEQUENCE: 51

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190
```

```
Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 52
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 52

Met Lys Met Ala Ser Asn Asp Ala Asn Pro Ser Asp Gly Ser Thr Ala
1               5                   10                  15
```

```
Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Cys
            100                 105                 110

Ala Phe Thr Cys Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430
```

```
Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 53
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 53

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Cys Asn Ala Gly
            180                 185                 190

Asp Cys Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255
```

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Ala Gly Thr Gln Glu Tyr Thr Met Asn Leu Ala
290 295 300

Ser Gln Asn Trp Asn Asn Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Gly Asp Gly Ser Thr Arg Gly His Lys Ala Thr Val Ser
340 345 350

Thr Gly Ser Val His Phe Thr Pro Lys Leu Gly Ser Val Gln Phe Ser
355 360 365

Thr Asp Thr Ser Asn Asp Phe Glu Thr Gly Gln Asn Thr Lys Phe Thr
370 375 380

Pro Val Gly Val Val Gln Asp Gly Ser Thr Thr His Gln Asn Glu Pro
385 390 395 400

Gln Gln Trp Val Leu Pro Asp Tyr Ser Gly Arg Asp Ser His Asn Val
405 410 415

His Leu Ala Pro Ala Val Ala Pro Thr Phe Pro Gly Glu Gln Leu Leu
420 425 430

Phe Phe Arg Ser Thr Met Pro Gly Cys Ser Gly Tyr Pro Asn Met Asn
435 440 445

Leu Asp Cys Leu Leu Pro Gln Glu Trp Val Gln His Phe Tyr Gln Glu
450 455 460

Ala Ala Pro Ala Gln Ser Asp Val Ala Leu Leu Arg Phe Val Asn Pro
465 470 475 480

Asp Thr Gly Arg Val Leu Phe Glu Cys Lys Leu His Lys Ser Gly Tyr
485 490 495

Val Thr Val Ala His Thr Gly Gln His Asp Leu Val Ile Pro Pro Asn
500 505 510

Gly Tyr Phe Arg Phe Asp Ser Trp Val Asn Gln Phe Tyr Thr Leu Ala
515 520 525

Pro Met Gly Asn Gly Thr Gly Arg Arg Arg Ala Leu
530 535 540

<210> SEQ ID NO 54
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 54

Met Lys Met Ala Ser Asn Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Cys Gly Gly Glu Phe
50 55 60

Thr Val Ser Pro Arg Asn Ala Pro Gly Glu Ile Leu Trp Ser Ala Pro
65 70 75 80

-continued

```
Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Cys Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
```

500 505 510

Gly Tyr Phe Arg Phe Asp Ser Trp Val Asn Gln Phe Tyr Thr Leu Ala
515 520 525

Pro Met Gly Asn Gly Thr Gly Arg Arg Arg Ala Leu
530 535 540

<210> SEQ ID NO 55
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 55

Met Lys Met Ala Ser Asn Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Ile Ile Phe Ala Ala Val Pro Pro Asn Phe
115 120 125

Pro Thr Glu Gly Leu Ser Pro Ser Gln Val Thr Cys Phe Pro His Ile
130 135 140

Ile Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Cys Pro Thr Val Glu Ser Arg Thr
210 215 220

Lys Pro Phe Thr Val Pro Ile Leu Thr Val Glu Glu Met Thr Asn Ser
225 230 235 240

Arg Phe Pro Ile Pro Leu Glu Lys Leu Phe Thr Gly Pro Ser Gly Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Ala Gly Thr Gln Glu Tyr Thr Met Asn Leu Ala
290 295 300

Ser Gln Asn Trp Asn Asn Tyr Asp Pro Thr Glu Glu Ile Pro Ala Pro
305 310 315 320

Leu Gly Thr Pro Asp Phe Val Gly Lys Ile Gln Gly Val Leu Thr Gln

```
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 56
<211> LENGTH: 540
<212> TYPE: PRT
<213> ORGANISM: Artificial Sequence
<220> FEATURE:
<223> OTHER INFORMATION: Recombinant Norovirus Protein

<400> SEQUENCE: 56

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Cys Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
```

-continued

```
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Cys Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```

STABILIZED NOROVIRUS VIRUS-LIKE PARTICLES AS VACCINE IMMUNOGENS

CROSS REFERENCE TO RELATED APPLICATIONS

This is the U.S. National Stage of International Application No. PCT/US2021/055018, filed on Oct. 14, 2021, which was published in English under PCT Article 21(2), which in turn claims priority to U.S. Provisional Application No. 63/091,824, filed on Oct. 14, 2020. The provisional application, is incorporated herein by reference in its entirety.

ACKNOWLEDGMENT OF GOVERNMENT SUPPORT

This invention was made with government support under Grant Nos. AI109761 and AI148260 awarded by the National Institutes of Health. The government has certain rights in the invention.

FIELD

This disclosure relates to recombinant Norovirus Virus-Like Particles and their use.

BACKGROUND

Norovirus is a non-enveloped virus that belongs to the family Caliciviridae. It constitutes the major cause of epidemic gastroenteritis in close settings and since the introduction of rotavirus vaccines, Norovirus has become the leading cause of medically attended acute gastroenteritis in U.S. children, associated with nearly 1 million health care visits annually. A gastroenteritis episode due to Norovirus is incapacitating during the acute phase that usually lasts from 1 to 3 days and includes explosive vomiting, stomach cramps and diarrhea Immunocompetent patients usually recover completely from the illness, but the gastroenteritis may be severe in young children, the elderly and immunocompromised, increasing the risk for morbidity and mortality. It has been estimated that around 200,000 people die annually because of Norovirus gastroenteritis, mostly in developing countries. In immunocompromised patients, Norovirus is recognized as an important cause of chronic gastroenteritis, with long-term virus shedding and increased morbidity in this population. In immunocompetent patients the virus shedding after infection lasts for approximately days, while in immunocompromised patients virus shedding has been detected for up to 3 years. It has been proposed that long term virus shedding may contribute to the spread of the virus. Overall, the societal costs associated with Norovirus infection worldwide has been estimated to be upward of $60 billion.

The Norovirus genome is composed of a single-stranded positive-sense RNA molecule that contains three open reading frames. The genome is surrounded by a non-enveloped capsid composed of the major capsid protein, VP1, encoded by ORF2, and a minor structural protein, VP2, encoded by ORF3. Crystallographic cryoEM analyses have showed that the Norovirus capsid is formed by 180 molecules of VP1, organized into 90 dimers. Each VP1 monomer is divided into two domains designated shell (S) and protruding (P), linked by a flexible hinge. The P domain is further divided into P1 and P2 subdomains, with P2 as the outermost domain exposed on the surface.

Noroviruses are divided into six major genogroups designated Genogroup (G)I through GVI. GI and GII contain the majority of Norovirus strains associated with human disease. The Norovirus GI.1 was the first genotype described, and the GII.4 genotype has been associated with the majority of global outbreaks. Despite extensive effort, an approved vaccine for Norovirus infection remains elusive.

SUMMARY

Disclosed herein are recombinant Norovirus VLPs formed from self-assembled recombinant Norovirus VP1 proteins comprising one or more amino acid substitutions that increase stability of the recombinant Norovirus VLP compared to Norovirus VLPs formed from unmodified recombinant Norovirus VP1 proteins.

In some embodiments, the recombinant Norovirus VLP comprises a multimer of a recombinant Norovirus GI VP1 protein comprising amino acid substitutions set forth as one or more of the following pairs of cysteine substitutions that form a non-natural interprotomer disulfide bond: N116C/G193C, A37C/A44C, Q62C/A140C, L144C/P221C, G131C/N172C, and N167C/L169C, and/or one or more of the following pairs of hydrophobic amino acid substitutions: Q141V/P221L and A37I/A44L substitutions, wherein the amino acid positions are according to the reference GI VP1 protein sequence set forth as SEQ ID NO: 1.

In some embodiments, the recombinant Norovirus VLP comprises a multimer of a recombinant Norovirus GII VP1 protein comprising amino acid substitutions set forth as one or more of the following pairs of cysteine substitutions that form a non-natural interprotomer disulfide bond: N112C/A116C, N189C/D194C, P60C/S134C, M140C/P217C, P129C/R223C, wherein the amino acid positions are according to the reference GII VP1 protein sequence set forth as SEQ ID NO: 51.

In some embodiments, the recombinant VP1 protein further comprises one or more additional amino acid substitutions or deletions, such as amino acid substitutions that increase thermostability of the recombinant Norovirus VLP.

Immunogenic compositions including the recombinant Norovirus VLP that are suitable for administration to a subject are provided, and may also be contained in a unit dosage form. The compositions can further include an adjuvant.

Methods of inducing an immune response in a subject are disclosed, as are methods of treating, inhibiting or preventing a Norovirus infection in a subject, by administering to the subject an effective amount of a disclosed recombinant Norovirus VLP. Additionally, methods of identifying an antibody that specifically binds to a solvent-accessible epitope on a Norovirus VLP, as well as methods for identifying a sample from a subject with a neutralizing antibody response to Norovirus, are provided.

The foregoing and other features and advantages of this disclosure will become more apparent from the following detailed description of several embodiments which proceeds with reference to the accompanying figures.

BRIEF DESCRIPTION OF THE FIGURES

(FIG. 1A) Representative micrograph of negatively stained GI.1 WT VLPs. 2D class averages of small objects are shown in the bottom right corner and 2D class averages of intact VLPs in the top right corner. Notice the presence of dissociated VP1 dimers and larger oligomers. The shell and P domain are indicated by arrows. (FIG. 1B) Representative micrograph of GI.1 WT after incubation with A1227 Fab fragment. 2D class averages of small objects show 2 Fabs bound to each VP1 dimer. Intact particles do not show any A1227 Fab bound. (FIG. 1C) Representative micrograph of GI.1 WT after incubation with 512 Fab fragment. Class averages show VP1 dimers bound to two Fabs and intact VLPs decorated with a layer of 512 Fabs. (FIGS. 1D-1F) Analytical size-exclusion chromatography of (FIG. 1D) GI.1 WT, (1E) GI.1 WT+A1227 Fab and (FIG. 1F) GI.1 WT+512 Fab. In all cases, the peak at 8.5 mL elution volume corresponds to void volume. (1G) SDS-PAGE analysis of fractions from chromatogram in (FIG. 1D). (1H) SDS-PAGE analysis of fractions from chromatogram in (FIG. 1E). Fraction 4 contains equal amounts of VP1 and A1227 Fab, indicative of 1:1 complex (1 Fab: 1 VP1), while fraction 5 contains free A1227 Fab. (FIG. 1I) SDS-PAGE analysis of chromatogram in (FIG. 1F). 512 Fab is present in void peak (decorated VLPs) and in 1:1 complex with VP1 dimers (Fraction 3). Free 512 Fab is found in fractions 4 and 5. In all gels, the non-covalent VP1 dimer runs as a monomer (mVP1). Scale bars are 100 nm, 20 nm, and 10 nm for micrographs, 2D classes of VLPs, and 2D classes of small proteins, respectively.

(FIG. 2A) Two strategies can be used to form interprotomer contacts between adjacent VP1 protomers: 1) design of disulfides (or other intermolecular interactions) at the 5-fold and 3-fold symmetry axes (top panel) and 2) design of disulfides (or other interactions) within the icosahedral asymmetric unit (iASU) (bottom panel). One example of each strategy is shown on a portion of GI.1 VLP structure (P domain omitted for clarity). (FIG. 2B) Screening of 8 double-point mutants within GI.1 shell domain after oxidation in diamide. Top gel shows the expression levels of VP1 mutants in reducing conditions. Bottom gel shows same samples in non-reducing conditions. Asterisks indicate mutants that prevent VLP dissociation (intact VLPs fail to enter the separating gel due to their size). Notice the presence of other VP1 oligomers (dimers, tetramers, etc.). (FIG. 2C) Preparative-scale purification of diamide-treated mutant N116C-G193C (separation performed on Sephacryl 5500 column) (FIG. 2D) Stabilization of final product tested in reducing and non-reducing conditions. Notice that treatment with reducing agent alone does not completely dissociate particles into VP1 monomers (middle lane). (FIG. 2E) Differential scanning calorimetry thermogram of GI.1 WT and oxidized GI.1 DS1. The peak at 64° C. corresponds to the unfolding of the p domain, while the peak at 75° C. corresponds to the unfolding of the shell domain. (In all gels, mVP1 indicates monomeric VP1 protein).

(FIG. 3A) Overall electron density of GI.1-DS1 VLPs. Monomer A, B and C are indicated. (FIG. 3B,3C) Close up view of the region around (FIG. 3B) the 5-fold and (FIG. 3C) 3-fold symmetry axes of the icosahedron. (FIG. 3D,3E) Details of the electron density for one of the interprotomer disulfide bond between (FIG. 3D) A-A monomers and (FIG. 3E) B-C monomers.

(FIG. 4A) Representative micrograph of stabilized GI.1 VLPs (GI.1 DS1) in the absence of antibody. Particles appear to be intact and no disassembled components are visible. 2D class averaging yields very homogeneous particle classes with an approximate diameter 40 nm (top right panel) and no sign of dissociated molecule (bottom right panel). (FIG. 4B) Representative micrograph of stabilized VLPs after incubation with A1227 Fab. 2D class averages show two species: intact particles with no Fab bound (top right panel) and Fab fragments (bottom right panel). (FIG. 4C) Representative micrograph of stabilized VLPs after Incubation with 512 Fab. 2D class averages show two species: intact particles decorated with 512 Fabs (top right panel) and free Fab fragments (bottom right panel). Notice that the sizes of the intact particles increase by ~7 nm, consistent with the presence of a layer of Fabs bound to each particle. (FIG. 4D) The sample in (FIG. 4A) was separated by size-exclusion chromatography and (FIG. 4C) fractions analyzed by SDS-PAGE in reducing and non-reducing conditions. Only one peak is present at the void volume. Non-reducing gel show only bands at the top of the wells, consistent with the presence of intact stabilized particles. Notice that no dissociated component are detected. (FIG. 4E) Size-exclusion profile of stabilized VLPs incubated with 1A227 Fab and (FIG. 4F) corresponding fractions analyzed by SDS-PAGE. Only two peaks are present: one at the void volume (intact particles) and one corresponding to free Fabs. (FIG. 4H) Size-exclusion profile of stabilized particles incubated with 512 Fab and (FIG. 4I) corresponding fractions analyzed by SDS-PAGE. Only two peaks are present: one at the void volume (intact particles with bound 512 Fabs) and one corresponding to free 512 Fabs. In all gels, mVP1 indicates VP1 monomer. Scale bars are 50 nm, 20 nm, and 10 nm for micrographs, 2D classes of VLPs, and 2D classes of small proteins, respectively.

(FIG. 5A) Balb/c mice were immunized with 2 micrograms of either GI.1 WT or GI.1 DS1 VLPs intramuscularly at weeks 0, 3, 6, and 9. Blood draws were performed at week 3, 5, 8, and 11. To test durability of immune response, final bleed was performed 13 weeks after last immunization. For each blood draw, HBGA blockade titers were assessed. (FIG. 5B) Comparison of blockade antibody titers between GI.1 WT (light gray circles) and GI.1 DS1 (dark gray circles) in the absence of adjuvant. Disulfide stabilization of norovirus VLPs leads to fast development of blockade titers compared to wild-type VLPs (compare blockade titers after second immunization) (FIG. 5C) Comparison of blockade titers between GI.1 WT (light gray circles) and GI.1 DS1 (dark gray) in the presence of adjuvant (alum). No significant differences at any time point are observed, indicative of potentially stabilizing effect of GI.1 WT VLPs by alum. Limit of detection (titer=80) is indicated with a horizontal dotted line. Geometric mean titers±geometric SD are shown in scatter dot plot. P values were determined by two-tailed Mann-Whitney tests. * indicates $P \leq 0.05$,  indicates $P \leq 0.01$, * indicates $P \leq 0.001$. There were 8 mice per group for VLP immunizations and 6 mice pre group for controls (PBS and PBS+adjuvant).

(FIG. 6A) Ratio of blockade titers over total GI.1-reactive IgG titers at week 22. In the absence of alum, immunization with GI.1 DS1 leads to two-fold increase in blockade titers relative to total GI.1 reactive titers, compared to immunization with GI.1 WT. (FIG. 6B) Ability of serum antibodies at week 22 to compete with blockade antibody 512, relative to total GI.1 reactive titers.

For both non-adjuvanted and adjuvanted groups, sera from mice immunized with stabilized VLP can compete with 512 binding more than sera from mice immunized with wild type VLPs. (FIG. 6C) Ability of serum antibodies at week 22 to compete with occluded-site antibody A1227, relative to total GI.1 reactive titers. In the presence of alum, sera from mice immunized with wild type VLPs can compete with A1227 more than sera from immunization with stabilized VLPs. Mean±SD are shown in each box plot. P values were determined by two-tailed Mann-Whitney tests. * indicates P≤0.05, ** indicates P≤0.01.

FIG. 7. Cryo-EM Data Collection and Refinement Statistics.

(FIG. 9A) Fitting of the X-ray crystal structures of GII.4c P domain in complex with the Fab fragment of antibody A1227 (PDB ID: 6N81) into 3D-reconstruction from negatively stained samples of mixed GI.1 WT VLPs and A1227 Fab. (FIG. 9B) Fitting of the X-ray crystal structures of GI.1 P domain in complex with the Fab fragment of antibody 512 IgA (PDB ID: 5KW9) into 3D-reconstruction from negatively stained samples of mixed GI.1 WT VLPs and 512 Fab.

(FIG. 10A) Representative micrograph and CTF of the micrograph are shown. (FIG. 10B) Representative 2D class averages are shown. (FIG. 10C) The orientations of all particles used in the final refinement are shown as a heat-map. (FIG. 10D) The gold-standard Fourier shell correlation resulted in a resolution of 3.86 Å with I symmetry. The horizontal line indicates the 0.143 cut-off threshold (10E) The local resolution of the full map is shown generated through cryoSPARC using an FSC cutoff of 0.5.

(FIG. 11A) Shell domain sequence is shown in red (residues 1 to 225). Predicted disulfide bonds are shown with black lines connecting the cysteines in adjacent protomers. (FIG. 11B) Negative staining representative image of GI.1 DS2 in the absence of Fabs. All particles appear intact and with the correct size. (FIG. 11C) Addition of A1227 Fab did not lead to any changes to the appearance of the particles. (11D) Negative staining representative image of GI.1 DS3 in the absence of Fabs. All particles appear intact and with the correct size. (FIG. 11E) Addition of A1227 Fab did not lead to any changes to the appearance of the particles.

(FIG. 12A) Schematic of the HBGA (Hist blood group antigen) blockade assay used. (FIG. 12B) Blockade assay using 512 IgG and (FIG. 12C) 1227 IgG. As expected, 1227 is not able to block the binding of GI.1 wild-type or GI.1-DS1 to pig gastric mucin coated plates. 512 IgG was able to block both GI.1 wild-type and DS1 with similar potency. (FIG. 12D) Schematic of the VLP binding assay used. Binding of VLPs to monoclonal antibodies 512 IgA and 1227 IgG was tested by capturing GI.1 wild-type (12E) or GI.1-DS1 VLPs (FIG. 12F) onto pig gastric mucin coated plates and incubating the VLPs with 512 or A1227. Notice that A1227 only binds to GI.1 wild-type VLPs, but no detectable binding is measured to disulfide-stabilized particles. Conversely, 512 IgA can bind to GI.1 WT and GI.1-DS1 with similar affinities. (FIG. 12G) GI.1 WT captured on PGM coated plates were incubated with the neutralizing antibody NVB106 and cross-reactive non-neutralizing A401. Both antibodies can bind to the VLPs.

(FIG. 15A) Half-maximum binding titers for all groups. (FIG. 15B) Serum dilution that compete with 512 binding to GI.1 VLPs. (FIG. 15C) Serum dilution that compete with A1227 binding to GI.1 VLPs. In both cases, the 512 or A1227 IgGs were added at a concentration required to achieve 50% maximal binding [EC50]. All plots show box plots with mean±SD.

(FIG. 16A) Surface representation of a slice of GI.1 VLP with VP1 dimer shown in the dashed box. For this experiment, dissociated VP1 dimers were purified by size-exclusion chromatography. (FIG. 16B) Schematic of biolayer interferometry assay used to measure residual serum-antibody binding to VP1 dimers captured with 512-IgG or (FIG. 16C) A1227-IgG. Linearity of initial slope measurements was assessed by measuring binding of (FIG. 16D) A1227-IgG to VP1 dimer captured with 512-IgG or (FIG. 16E) 512-IgG to VP1 dimer captured with A1227-IgG. (FIG. 16F) Residual binding of sera at week 22 (50-fold dilution) from mice immunized with GI.1 WT or GI.1 DS1 to VP1 dimer captured with 512-IgG. (FIG. 16G) Same experiment as in (FIG. 16F), but using VP1 dimer captured with A1227-IgG.

17B) Cryo-electron density map of GI.1 (C116/C193, C37/C44). Introduction of second disulfide bond between C37 and C44 leads to increased electron densities for p domains, likely reflecting their increased homogeneity.

Figure 18A:
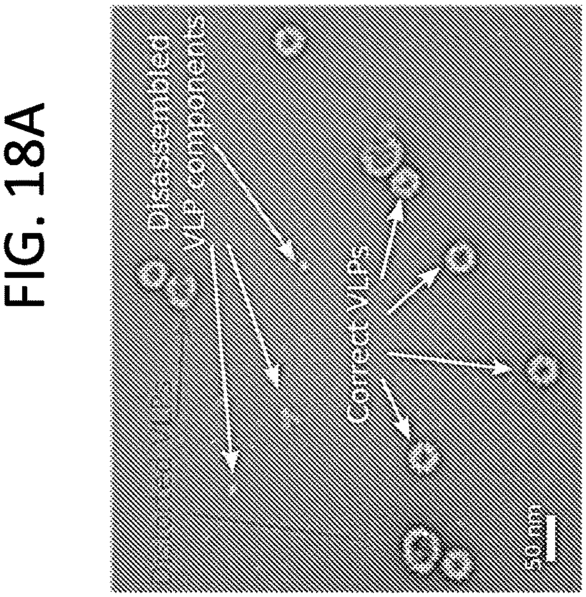
Figure 18B:
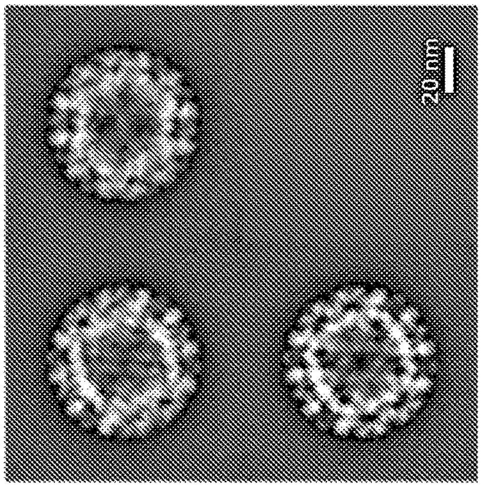
Figure 18C:
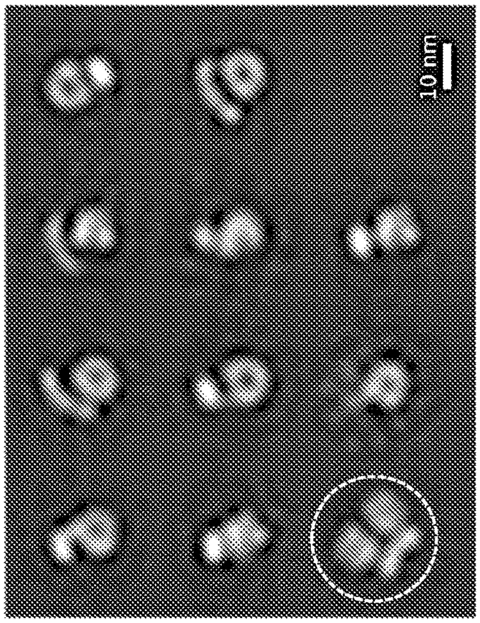

FIGS. 18A-18C. Norovirus VLPs are metastable and individual VLP components can be resolved by negative staining electron microscopy. (FIG. 18A) Representative image at 57,000× of GII4 VLP sample. Intact and broken VLPs as well as smaller objects are visible. (FIG. 18B) 2-D class averages of the intact VLPs show correct icosahedral symmetry and diameter. (FIG. 18C) 2-D class averages of smaller objects. Note in the lower left corner (dotted circle) two VP1 dimers connected by their shell domains are clearly visible.

Figure 19C:
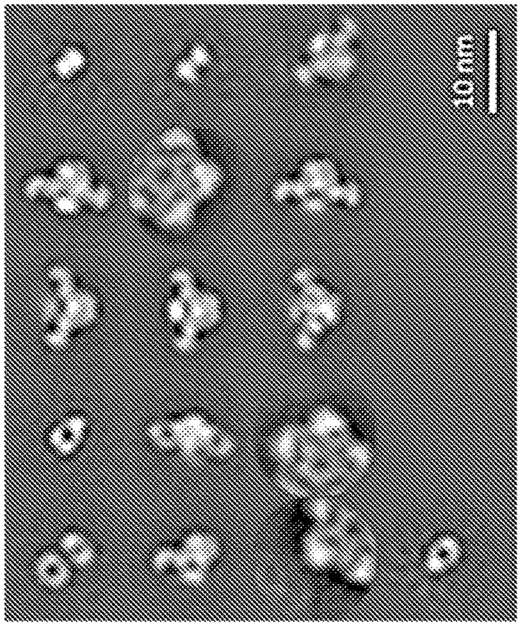
Figure 19B:
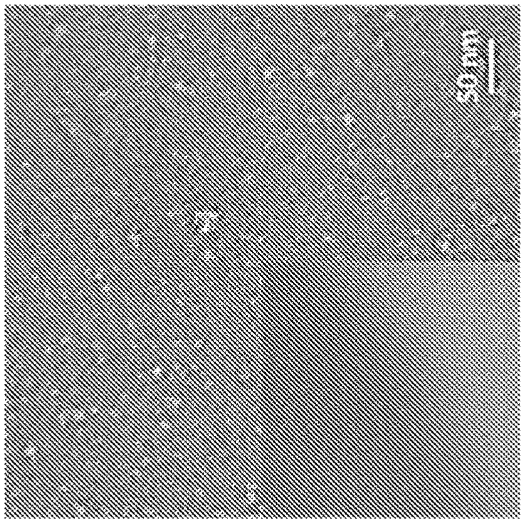
Figure 19A:
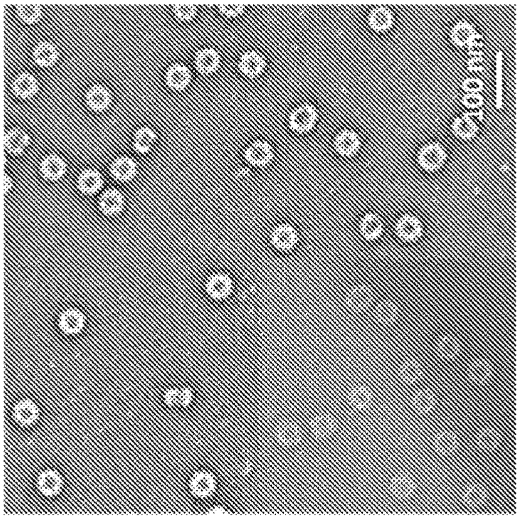

FIGS. 19A-19C. Norovirus VLPs disassembly after addition of norovirus specific Fab-1227. (FIG. 19A) Transmission electron micrograph at 57,000× magnification of GII.4.1997 VLPs before addition of Fab. (FIG. 19B) Same sample as in 19A, after incubation with 1227-Fab (at 1:2 VP1:Fab ratio) for 60 minutes at 4° C. at 100,000× magnification. (FIG. 19C) 2D-class averages for the sample in (FIG. 19B). Notice that most of the classes show one VP1 dimer in complex with two 1227-Fabs.

Figure 20:
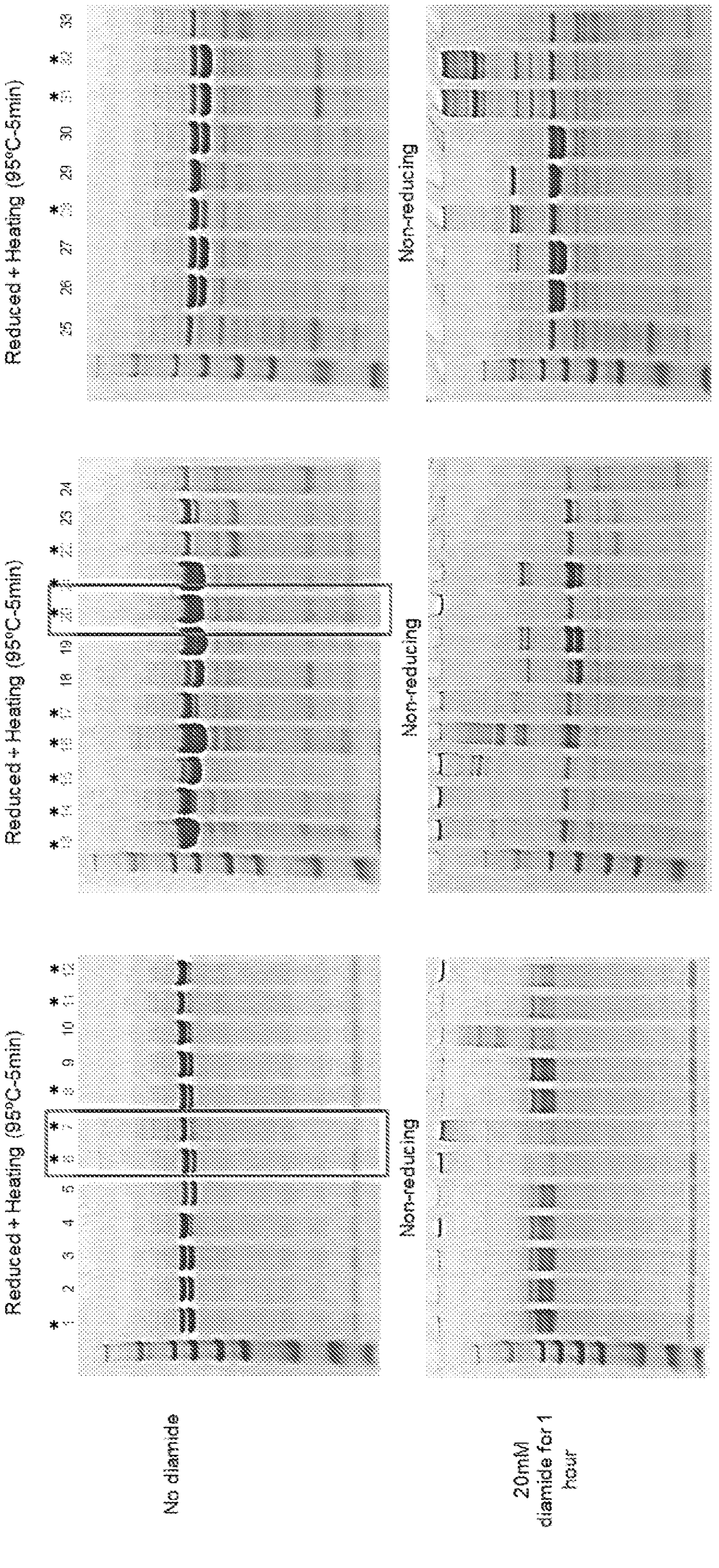

FIG. 20. Screening of GI14.4c stabilizing mutations. Baculoviruses harboring each clone were used to infect small-scale (50 mL) insect cell cultures for four days at 27C. Supernatants were collected and incubated with 20 mM diamide for 1 hour at room temp. Twenty microliters of each supernatant were run on SDS-PAGE gels. Thirty-three constructs were evaluated in reducing (top gels) and non-reducing (bottom-gels) conditions. Constructs containing cysteine mutations are marked with an asterisk. Boxes indicate promising candidates.

FIGS. 21A-21E. Purification and EM imaging of stabilized GII.4c v7 (N189C/D194C) VLP. (FIG. 21A) VLPs from 100 mL of Tni insect cells infected with baculorivurs carrying VP1 gene with N189C/D194C mutation were separated by size exclusion chromatography using Sephacryl S500 column. The peak was concentrated and incubated with 20 mM diamide for 1 hour at RT. (FIG. 21B) A second run on Sephacryl S500 was used to remove diamide from sample. The peak was collected, concentrated and used for characterization. (FIG. 21C) SDS-PAGE in reducing and non-reducing conditions and comparison with WT GII4c. Notice that most of the protein stays in the well in non-reducing conditions, indicative of stable VLP. (FIG. 21D) Dynamic light scattering of GII4c_v7 shows homogenous VLPs of ~40 nm diameter consistent with a T=3 assembly. (FIG. 21E) Negative stain EM of GII4c_v7. Notice that no dissociation of the VLP is visible. (FIG. 21F) Negative staining EM of GII4c_v7 after incubation with 1227 Fab at 1:2 molar ratio (VP1: Fab). The particles stay intact.

Figure 22:
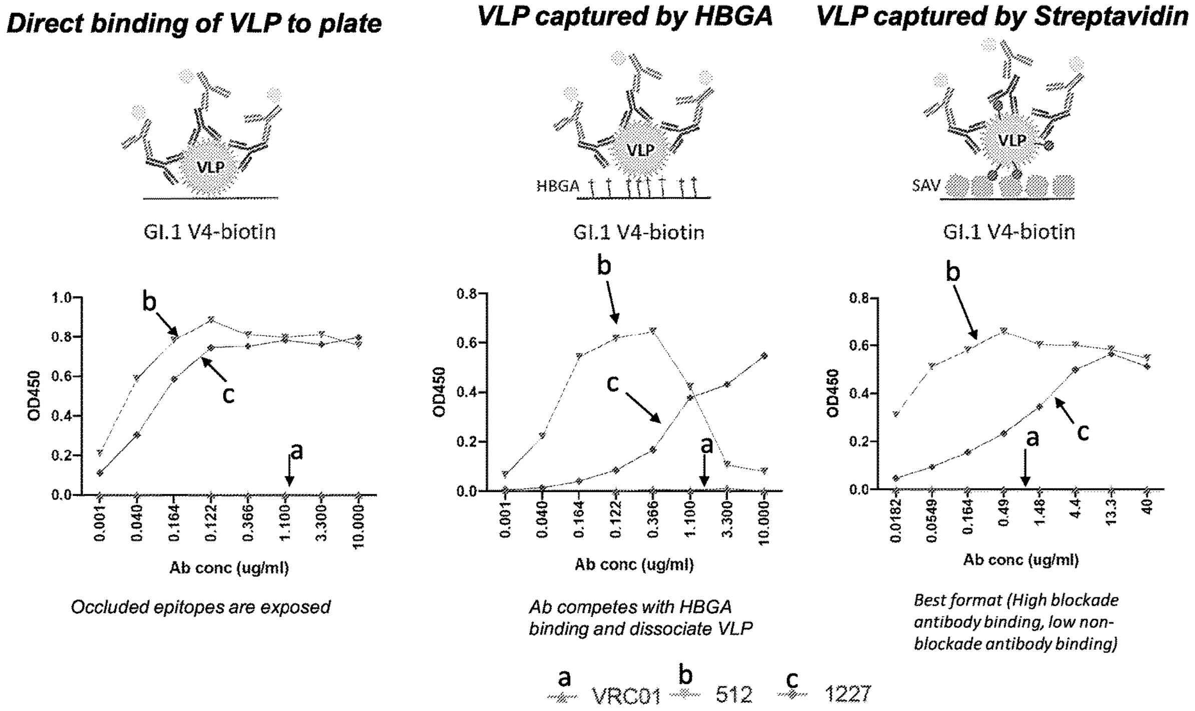

FIG. 22. Detection of blockade antibodies using stabilized GI.1 DS1 VLPs.

Figure 23:
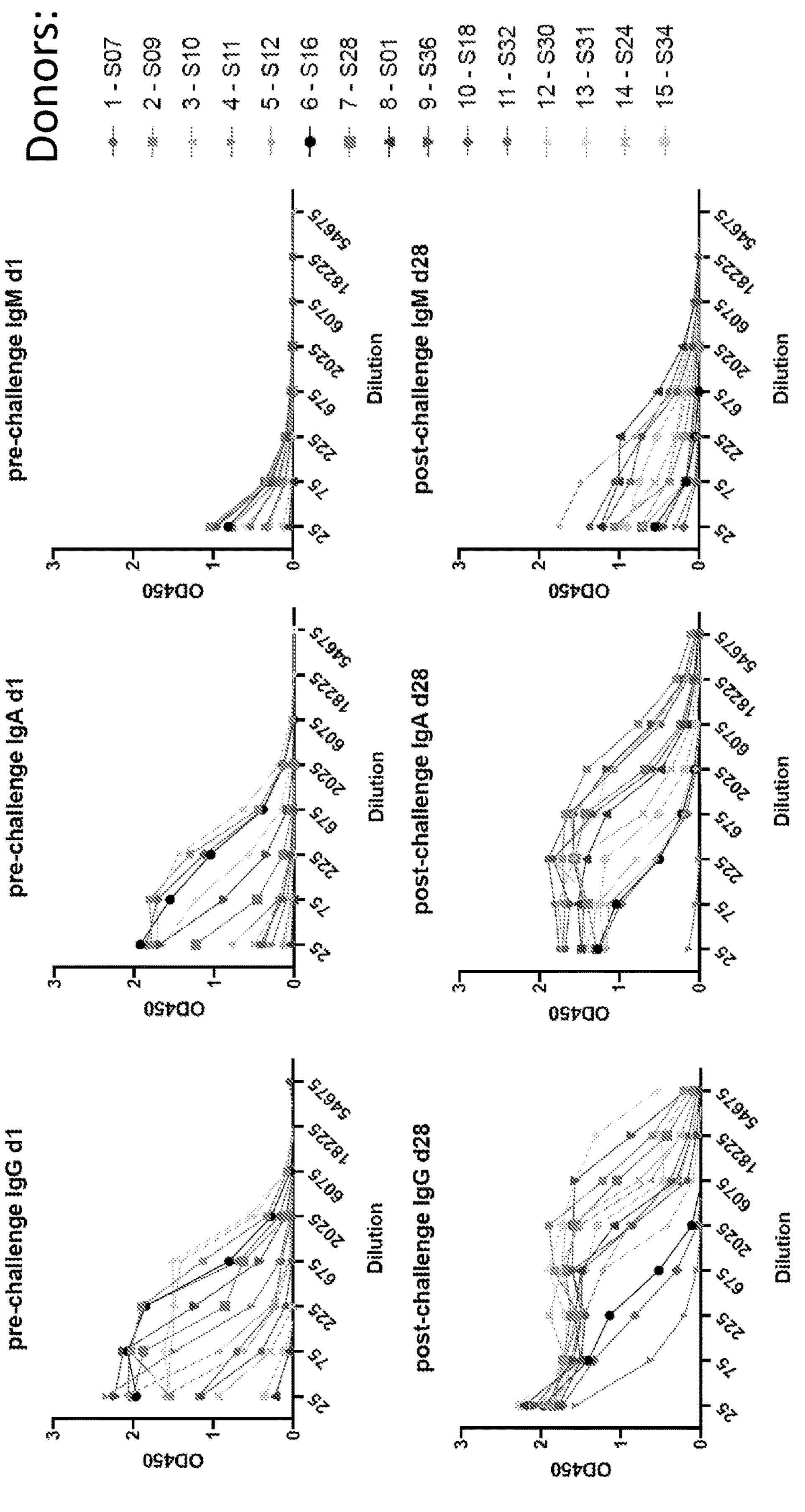

FIG. 23. IgG, IgA and IgM antibody titers against GI.1 DS1 before and after oral GI.1 challenge.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~260 kb), which was created on Apr. 5, 2023, which is incorporated by reference herein.

DETAILED DESCRIPTION

This disclosure provides recombinant Norovirus VLPs that include one or more amino acid substitutions that stabilize the VP1 assembly of the VLP and which are useful, for example, to elicit a neutralizing immune response to Norovirus in a subject.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine,* published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Plus or minus 5% relative to a reference value. For example, about 100 refers to from 95 to 105.

Adjuvant: A vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, AS01, MF59, and ALFQ adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. Additional description of adjuvants can be found, for example, in Singh (ed.) Vaccine Adjuvants and Delivery Systems. Wiley-Interscience, 2007). Adjuvants can be used in combination with the disclosed immunogens.

Administration: The introduction of an agent, such as a disclosed immunogen, into a subject by a chosen route. Administration can be local or systemic. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino Acid Substitution: The replacement of one amino acid in a polypeptide with a different amino acid.

Antibody: An immunoglobulin, antigen-binding fragment, or derivative thereof, that specifically binds and recognizes an analyte (antigen) such as a recombinant Norovirus VP1 protein or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2$^{nd}$ Ed., Springer Press, 2010).

A "neutralizing" antibody reduces the infectious titer of an infectious agent by binding to a specific antigen on the infectious agent. In some examples the infectious agent is a virus, such as a Norovirus, for example a Genogroup I or Genogroup II Norovirus, such as a Norwalk virus or MD2004 virus. In some examples, an antibody that is specific for a Norovirus polypeptide neutralizes the infectious titer of the virus. In some examples, an antibody specific for Norovirus VP1 neutralizes the infectious titer of the virus. In vitro assays for neutralization are known in the art. Thus, in some non-limiting examples, an assay for neutralization activity is blocking the binding of Norovirus-like particles (VLPs) to HBGA synthetic carbohydrates, for example H1 or H3 type HBGA, in a dose dependent manner In other non-limiting examples an assay for neutralization activity is blocking the binding of Norovirus VLPs to pig gastric mucin or saliva, in a dose dependent manner.

Biological Sample: A sample obtained from a subject. Biological samples include all clinical samples useful for detection of disease or infection (for example, Norovirus infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a Norovirus infection.

Carrier: An immunogenic molecule to which an antigen can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Greenfield (Ed.), *Antibodies: A Laboratory Manual,* 2$^{nd}$ ed. New York: Cold Spring Harbor Laboratory Press, 2014, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected, for example, through conventional methods such as immunohistochemistry (IHC), immunoprecipitation (IP), flow cytometry, immunofluorescence microscopy, ELISA, immunoblotting (for example, Western blot), magnetic resonance imaging (MRI), computed tomography (CT) scans, radiography, and affinity chromatography.

Conservative variants: "Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of a recombinant VP1 protein as described herein, such as the ability to self-assemble into a VLP. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a sample obtained from a healthy patient. In other embodiments, the control is a tissue sample obtained from a patient diagnosed with a Norovirus infection, such as a Norwalk virus infection that serves as a positive control. In still other embodiments, the control is a historical control or standard reference value or range of values (such as a previously tested control sample, such as a group of infected patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable Marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual,* $4^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

Effective Amount: An amount of agent, such as a recombinant Norovirus VLP as described herein, that is sufficient to elicit a desired response, such as an immune response in a subject. It is understood that to obtain a protective immune response against Norovirus infection can require multiple administrations of a disclosed recombinant Norovirus VLP, and/or administration of a disclosed recombinant Norovirus VLP as the "prime" in a prime boost protocol wherein the boost immunogen can be different from the prime immunogen. Accordingly, an effective amount of a disclosed recombinant Norovirus VLP can be the amount of the recombinant Norovirus VLP sufficient to elicit a priming immune response in a subject that can be subsequently boosted with the same or a different immunogen to elicit a protective immune response.

In one example, a desired response is to inhibit or reduce or prevent Norovirus infection. The Norovirus infection does not need to be completely eliminated or reduced or prevented for the method to be effective. For example, administration of an effective amount of the immunogen can induce an immune response that decreases the Norovirus infection (for example, as measured by infection of cells, or by number or percentage of subjects infected by the Norovirus) by a desired amount, for example by at least 50%, at least 60%, at least 70%, at least 80%, at least 90%, at least 95%, at least 98%, or even at least 100% (elimination or prevention of detectable 2 Norovirus infection), as compared to a suitable control.

Epitope: An antigenic determinant These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on a recombinant Norovirus VLP. Epitopes can be formed both from contiguous amino acids or noncontiguous amino acids juxtaposed by tertiary folding of a protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression Vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Host Cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny is included when the term "host cell" is used.

Immune Complex: The binding of antibody or antigen binding fragment to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance (for example, a recombinant Norovirus VLP) that can elicit an immune response in an animal, including compositions that are injected or absorbed into an animal. Administration of an immunogen to a subject can lead to protective immunity against a pathogen of interest.

Immunogenic Composition: A composition comprising a disclosed recombinant Norovirus VLP that induces a measurable CTL response, or induces a measurable B cell response (such as production of antibodies), against the genotype and strain of the Norovirus, when administered to a subject. For in vivo use, the immunogenic composition will typically include the recombinant Norovirus VLP in a pharmaceutically acceptable carrier and may also include other agents, such as an adjuvant.

Inhibiting or Treating a Disease: Inhibiting the full development of a disease or condition, for example, in a subject who is at risk for a disease such as a Norovirus infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Native Protein, Sequence, or disulfide Bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Norovirus (NoV): A non-enveloped virus that belongs to the family Caliciviridae. It constitutes the major cause of epidemic gastroenteritis in close settings and since the introduction of rotavirus vaccines, has become the leading cause of medically attended acute gastroenteritis in U.S. children, associated with nearly 1 million health care visits annually. A gastroenteritis episode due to Norovirus is incapacitating during the acute phase that usually lasts from 1 to 3 days and includes explosive vomiting, stomach cramps and diarrhea Immunocompetent patients usually recover completely from the illness, but the gastroenteritis may be severe in young children, the elderly and immunocompromised, increasing the risk for morbidity and mortality. It has been estimated that around 200,000 people die annually because of Norovirus gastroenteritis, especially in developing countries. In immunocompromised patients, Norovirus is recognized as an important cause of chronic gastroenteritis, with long-term virus shedding and increased morbidity in this population. In immunocompetent patients the virus shedding after infection lasts for approximately days, while in immunocompromised patients virus shedding has been detected for up to 3 years. It has been proposed that long term virus shedding may contribute to the spread of the virus.

The Norovirus genome is composed of a single-stranded positive-sense RNA molecule that contains three open reading frames. The genome is surrounded by a non-enveloped capsid composed of the major capsid protein, VP1, encoded by ORF2, and a minor structural protein, VP2, encoded by ORF3. Crystallographic analysis showed that the Norovirus capsid is formed by 180 molecules of VP1, organized into 90 dimers. Each VP1 monomer is divided into two domains designated shell (S) and protruding (P), linked by a flexible hinge. The P domain is further divided into P1 and P2 subdomains, with P2 as the outermost domain exposed on the surface (Prasad et al., Science 286(5438): 287-90, 1999).

Noroviruses are divided into six major genogroups designated Genogroup (G)I through GVI. GI and GII contain the majority of Norovirus strains associated with human disease and are further divided into 9 and 21 genotypes, respectively (Kroneman et al., Arch Virol 158(10): 2059-68, 2013). The Norovirus GI.1 was the first genotype described, the GII.4 genotype has been associated with the majority of global outbreaks since the mid-1990s, when active surveillance with molecular diagnostic techniques was initiated.

Non-limiting examples of Noroviruses include Norwalk virus (GI.1, GenBank M87661, NP_056821.2), Jingzhou virus (GI.2, GenBank KF306212.1), Desert Shield virus (GI.3, GenBank AAA16285.1), Chiba virus (G1.4, GenBank BAB18267.1), Musgrove (GI.5, GenBank AJ277614.1), Hawaii virus (GII.1, GenBank AAB97768.2), Snow Mountain virus (GII.2, GenBank AAB16915.1), Mexico virus (GII.3, GenBank AAB06271.1), and Sydney virus (GII.4, GenBank AAZ31411.2). The nucleic acid and corresponding amino acid sequences of each are all incorporated by reference in their entirety.

Standard methods for detecting viral infection may be used to detect Norovirus infection in a subject, including but not limited to, assessment of patient symptoms and background and genetic tests such as reverse transcription-polymerase chain reaction (rRT-PCR). The test can be done on patient samples such as stool, vomit, or blood samples.

Norovirus VP1 Protein: A capsid polypeptide that is encoded by open reading frame (ORF) 2 of the Norovirus genome. The VP1 proteins self-assemble under suitable conditions to form the Norovirus capsid. In the native virus, VP1 self assembles to form an icosahedral capsid with a T=3 symmetry, about 38 nm in diameter, and consisting of 180 VP1 proteins, organized into dimers. In the native virus, the capsid encapsulates the genomic RNA and VP2 proteins, and attaches virion to target cells by binding histo-blood group antigens present on gastroduodenal epithelial cells. Each VP1 monomer is divided into two domains designated shell (S) and protruding (P), linked by a flexible hinge. The P domain is further divided into P1 and P2 subdomains, with P2 as the outermost domain exposed on the surface (Prasad et al., Science 286(5438): 287-90, 1999).

An exemplary GI VP1 is provided in GenBank Accession No. M87661 (Norwalk virus), which is incorporated herein by reference and provided herein as SEQ ID NO: 1. The numbering used for the disclosed recombinant Norovirus GI VP1 proteins is relative to the Norovirus GI.1 VP1 protein sequence provided as SEQ ID NO: 1.

An exemplary GII VP1 is provided in GenBank Accession No. JX459908.1(GII.4 2012 Sydney strain), which is incorporated herein by reference and provided herein as SEQ ID NO: 29. The numbering used for the disclosed recombinant Norovirus GII VP1 proteins is relative to the Norovirus GII.4 VP1 protein sequence provided as SEQ ID NO: 29.

Norovirus Virus-Like Particle (VLP): A non-replicating genome-free viral shell formed from a self-assembly of Norovirus VP1 (capsid) proteins. The VP1 proteins in the VLP self assemble to form an icosahedral shaped structure including 180 VP1 proteins, organized into 90 dimers, and are about 38 nm in diameter. The icosahedral structure with T=3 symmetry, shows the characteristic 3-fold and 5-fold symmetry axes. The icosahedral asymmetric unit is made of three quasi-equivalent monomers termed A, B and C. (see FIG. 2). Human Norovirus VLPs can also self-assemble in T=1 and T=4 configuration. T=1 VLPs contain 60 VP1 monomers and are about 23 nm in diameter, while T=4 VLPs have 240 VP1 monomers and are about 55 nm in diameter.

Nucleic Acid Molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term “nucleic acid molecule” as used herein is synonymous with “nucleic acid” and “polynucleotide.” A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. “cDNA” refers to a DNA that is complementary or identical to an mRNA, in either single stranded or double stranded form. “Encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably Linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically Acceptable Carriers: The pharmaceutically acceptable carriers of use are conventional. *Remington's Pharmaceutical Sciences,* by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-Boost Vaccination: An immunotherapy including administration of a first immunogenic composition (the primary vaccine) followed by administration of a second immunogenic composition (the booster vaccine) to a subject to induce an immune response. The priming vaccine and/or the booster vaccine include a vector (such as a viral vector, RNA, or DNA vector) expressing the antigen to which the immune response is directed. The booster vaccine is administered to the subject after the priming vaccine; a suitable time interval between administration of the priming vaccine and the booster vaccine, and examples of such timeframes are disclosed herein. In some embodiments, the priming vaccine, the booster vaccine, or both primer vaccine and the booster vaccine additionally include an adjuvant. In one non-limiting example, the priming vaccine is a DNA-based vaccine (or other vaccine based on gene delivery), and the booster vaccine is a protein subunit or protein nanoparticle based vaccine.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant virus is one that includes a genome that includes a recombinant nucleic acid molecule. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence Identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Homologs and variants of a polypeptide (such as a Norovirus VP1 protein) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" or similar language refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals, such as non-human primates, pigs, camels, bats, sheep, cows, dogs, cats, rodents, and the like. In an example, a subject is a human. In a particular example, the subject is a human. In an additional example, a subject is selected that is in need of inhibiting a Norovirus infection. For example, the subject is either uninfected and at risk of the Norovirus infection or is infected and in need of treatment.

Vaccine: A pharmaceutical composition that induces a prophylactic or therapeutic immune response in a subject. In some cases, the immune response is a protective immune response. Typically, a vaccine induces an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed Norovirus VP1 VLP), a virus, a cell or one or more cellular constituents. In a non-limiting example, a vaccine induces an immune response that reduces the severity of the symptoms associated with a Norovirus infection (such as a GI.1 or GII.4 Norovirus infection) and/or decreases the viral load compared to a control. In another non-limiting example, a vaccine induces an immune response that reduces and/or prevents a Norovirus infection (such as a GI.1 or GII.4 Norovirus infection) compared to a control.

II. Recombinant Norovirus VLPs

Disclosed herein are embodiments of a recombinant Norovirus VLP comprising a multimer of a recombinant Norovirus VP1 proteins comprising one or more amino acid substitutions that stabilize the recombinant Norovirus VLP in its assembled form. The recombinant Norovirus VLPs provided herein elicit a superior immune response in an animal model compared to corresponding Norovirus VLPs that lack the stabilizing amino acid substitutions.

A. Recombinant GI VLPs

In some embodiments, the recombinant Norovirus VP1 VLP is composed of GI VP1 proteins as provided herein.

Non-limiting examples of native Norovirus GI VP1 proteins that can be modified as described herein by incorporation of one or more amino acid substitutions that stabilize the recombinant Norovirus VLP in its assembled form include:

GI.1 native VP1 sequence (GenBank Accession No. M87661)

(SEQ ID NO: 1)

MMMASKDATSSVDGASGAGQLVPEVNASDPLAMDPVAGSSTAVATAGQV

NPIDPWIINNFVQAPQGEFTISPNNTPGDVLFDLSLGPHLNPFLLHLSQ

MYNGWVGNMRVRIMLAGNAFTAGKIIVSCIPPGFGSHNLTIAQATLFPH

VIADVRTLDPIEVPLEDVRNVLFHNNDRNQQTMRLVCMLYTPLRTGGGT

GDSFVVAGRVMTCPSPDFNFLFLVPPTVEQKTRPFTLPNLPLSSLSNSR

APLPISSMGISPDNVQSVQFQNGRCTLDGRLVGTTPVSLSHVAKIRGTS

NGTVINLTELDGTPFHPFEGPAPIGFPDLGGCDWHINMTQFGHSSQTQY

DVDTTPDTFVPHLGSIQANGIGSGNYVGVLSWISPPSHPSGSQVDLWKI

PNYGSSITEATHLAPSVYPPGFGEVLVFFMSKMPGPGAYNLPCLLPQEY

ISHLASEQAPTVGEAALLHYVDPDTGRNLGEFKAYPDGFLTCVPNGASS

GPQQLPINGVFVFVSWVSRFYQLKPVGTASSARGRLGLRR

GI.2 native VP1 sequence (GenBank Accession No. JQ743332)

(SEQ ID NO: 2)

MMMASKDASQSADGASGAGQLVPEVNTADPLPMEPVAGPTTAVATAGQV

NMIDPWIVNNFVQSPQGEFTISPNNTPGDILFDLQLGPHLNPFLSHLSQ

MYNGWVGNMRVRILLAGNAFSAGKIIVCCVPPGFTSSSLTIAQATLFPH

VIADVRTLEPTEMPLEDVRNVLYHTNDNQPTMRLVCMLYTPLRTGGGSG

NSDSFVVAGRVLTAPSSDFSFLFLVPPTIEQKTRAFTVPNIPLQTLSNS

RFPSLIQGMILSPDASQVVQFQNGRCLIDGQLLGTTPATSGQLFRVRGK

INQGARTLNLTEVDGKPFMAFDSPAPVGFPDFGKCDWHMRISKTPNNTS

SGDPMRSVSVQTNVQGFVPHLGSIQFDEVFNHPTGDYIGTIEWISQPST

PPGTDINLWEIPDYGSSLSQAANLAPPVFPPGFGEALVYFVSAFPGPNN

RSAPNDVPCLLPQEYITHFVSEQAPTMGDAALLHYVDPDTNRNLGEFKL

YPGGYLTCVPNGVGAGPQQLPLNGVFLFVSWVSRFYQLKPVGTASTARG

RLGVRRI

GI.3 native VP1 sequence (GenBank Accession No. JQ743330)

(SEQ ID NO: 3)

MMMASKDAPPNMDGTSGAGQLVPEANTAEPISMEPVAGAATAAATAGQV

NMIDPWIMNNYVQAPQGEFTISPNNTPGDILFDLQLGPHLNPFLSHLAQ

MYNGWVGNMKVKVLLAGNAFTAGKIIISCIPPGFAAQNISIAQATMFPH

VIADVRVLEPIEVPLEDVRNVLFHNNDNTPTMRLVCMLYTPLRASGSSS

GTDPFVIAGRVLTCPSPDFSFLFLVPPNVEQKTKPFSVPNLPLNTLSNS

RVPSLIRSMMVSRDHGQMVQFQNGRVTLDGQLQGTTPTSASQLCKIRGS

VFHANGGNGYNLTELDGSPYHAFESPAPIGFPDLGECDWHMEASPTTQF

DTGDVIKQINVKQEAAFAPHLGTIQADGLSDVSVNTNMIAKLGWVSPVS

DGHRGSVDPWVIPRYGSTLTEAAQLAPPIYPPGFGEAIVFFMSDFPIAH

-continued

GANGLSVPCTIPQEFVTHFVNEQAPTRGEAALLHYLDPDTHRNLGEFKL

YPEGFMTCVPNSSGTGPQTLPINGVFAFVSWVSRFYQLKPVGTAGPARR

LGIRRS

GI.4 native VP1 sequence (GenBank Accession No. LN854563)

(SEQ ID NO: 4)

MMMASKDATPSADGATGAGQLVPEVNTADPIPIDPVAGSSTALATAGQV

NLIDPWIINNFVQAPQGEFTISPNNTPGDVLFDLQLGPHLNPFLSHLSQ

MYNGWVGNMRVRVVLAGNAFTAGKVIICCVPPGFQSRTLSIAQATLFPH

VIADVRTLDPVEVPLEDVRNVLYHNNDTQPTMRLLCMLYTPLRTGGASG

GTDSFVVAGRVLTCPGPDFNFLFLVPPTVEQKTRPFTVPNIPLKYLSNS

RIPNPIEGMSLSPDQTQNVQFQNGRCTIDGQPLGTTPVSVSQLCKFRGR

ITSGQRVLNLTELDGSPFMAFAAPAPAGFPDLGSCDWHIEMSKIPNSST

QNNPIVVNSVKPNSQQFVPHLSSITLDDIVSSGGDYIGTIQWTSPPSDS

GGANTNFWKIPDYGSSLSEASQLAPAVYPPGFNEVIVYFMASIPGPNQS

GSPNLVPCLLPQEYITHFISEQAPIQGEAALLHYVDPDTNRNLGEFKLY

PGGYLTCVPNSSSTGPQQLPLDGVFVFASWVSRFYQLKPVGTAGPARGR

LGVRR

GI.7 native VP1 sequence (GenBank Accession No. JN005886)

(SEQ ID NO: 5)

MMMASKDAPSNMDGTSGAGQLVPEVNAAEPLPLEPVVGAATAAATAGQV

NLIDPWIMNNFVQAPEGEFTISPNNTPGDILFDLHLGPHLNPFLQHLSQ

MYNGWVGNMRVRVMLAGNAFTAGKIIICCVPPGFASQNISIGQATMFPH

VIADVRVLEPIEIPLDDVRNVLFHTNENRPTMRLLCMLYTPLRAGGASS

GTDPFVIAGRVLTCPSPDFNFLFLVPPSVEQKTRQLTVPNIPLNNLANS

RVPAMINKMTVSTDQNQVVQFQNGRCTLEGQLLGTTPVSASQVARIRGK

VFSTASGKGLNLTELDGTPYHAFESPAPLGFPDIGACDWHVSTFKVDQN

LSGDPMSRLDVKQNAPFAPHLGSIEFTSDQDPTGDQLGTLAWVSPSTSG

ARVDPWKIPSYGSTVTESTHLAPPIFPPGFGEAIVYFMSDFPIVSGNTA

QVPCTLPQEFVSHFVEQQAPVRGEAALLHYVDPDTHRNLGEFKLYPDGF

ITCVPNTGGGPQNLPTNGVFVFSSWVSRYYQLKPVGTAGPARRLGVRRV

GI.8 native VP1 sequence (GenBank Accession No. AB081723)

(SEQ ID NO: 6)

MMMASKDAPTSPDGASGAGQLVPEANTAEQISMDPVAGASTAVATAGQV

NMIDPWIFNNFVQAPQGEFTISPNNTPGDILFDLQLGPHLNPFLAHLSQ

MYNGWVGNMRVRILLAGNAFTAGKIIICCVPPGFDARILTIAQATLFPH

LIADVRTLEPVELPLEDVRNVLYHNSSQPQPTMRLVAMLYTPLRTGGGS

GGTDAFVVAGRVLTCPAPDFSFLFLVPPSVEQKTRVFSVPNIPLKDLSN

SRVPVPIQGMFMSPDVNQSVQFQNGRCQIDGQLQGTTPVSLSQLCKIRG

KTSSNARVLNLSEVDGTPFIPLESPAPVGFPDLGGCDWHVNFTFQAQNQ

DPSQSVTFATNDASFVPYLGSISPHNGGDFHAGDIIGSLGWISAPSDNT

-continued

```
QLNVWTIPKYGSSLPDVTHLAPAVFPPGFGEVILYFYSTFPGSGQPSQL

QVPCLLPQEFITHFCNEQAPIAGEAALLHYVDPDTGRNLGEFKLYPDGF

MTCVPNSVSSGPQTLPINGVFVFVSWVSRFYQLKPVGTASAARRLGLRR

I
```

The amino acid numbering used herein for residues of the GI VP1 protein is with reference to the GI.1 VP1 sequence provided as SEQ ID NO: 1. With reference to the GI.1 VP1sequence provided as SEQ ID NO: 1, the shell (S) domain comprises residues 1-225, the Protruding domain (P) comprises residues 226-530) and is divided into subdomains P1 (residues 226-278 (P1 subdomain 1) and 406-530 (P1 subdomain 2) and P2 (amino acids 279-405). The position numbering of the VP1 protein may vary between GI VP1 protein stains, but the sequences can be aligned to determine relevant structural domains and residues of interest.

In some embodiments, the recombinant Norovirus VP1 VLP composed of GI VP1 proteins comprises a self-assembly of 90 Norovirus VP1 dimers into an icosahedral shaped VLP. The diameter of the recombinant Norovirus VP1 VLP composed of GI VP1 proteins is from about 35 to about 45 nm in the T=3 symmetry, such as from about 38 to about 40 nm, for example, about 37 nm, about 38 nm, about 39 nm, or about 40 nm. Human Norovirus VLPs can also self-assemble in T=1 and T=4 configuration. T=1 VLPs contain 60 VP1 monomers and are about 23 nm in diameter, while T=4 VLPs have 240 VP1 monomers and are about 55 nm in diameter. In several embodiments, the recombinant Norovirus VP1 VLP composed of GI VP1 proteins does not comprise a VP2 protein and/or genetic material.

Modification of the GI VP1 proteins with the one or more amino acid substitutions as described herein increases the stability (such as maintaining the assembled icosahedral VLP structure) of the corresponding VLP in the assembled compared to VLPs formed from unmodified GI VP1 proteins. For example, recombinant VLPs formed from the recombinant GI VP1 proteins comprising the one or more amino acid substitutions as described herein have increased thermal stability (such as maintaining the assembled icosahedral VLP structure at increased temperature) compared to VLPs formed from unmodified GI VP1 proteins.

As described in the examples, VLPs formed from native Norovirus GI VP1 proteins are prone to disassembly and in the presence of certain antibodies, such as mAb1227, the disassembly may be accelerated. Accordingly, VLPs formed from the recombinant GI VP1 proteins as described herein have increased resistance to disassembly when incubated with mAb1227, for example at a 1:2 molar ratio (1 VP1: 2 Fab) for 1 hour at room temperature in phosphate buffered saline (PBS), compared to corresponding VLPs formed from native GI VP1 proteins.

In some embodiments, a recombinant Norovirus VLP comprising a multimer of a recombinant Norovirus GI VP1 proteins is provided. In some embodiments, the recombinant Norovirus GI VP1 proteins in the VLP comprise amino acid substitutions set forth as one or more of the following pairs of cysteine substitutions that form a non-natural interprotomer disulfide bond: N116C/G193C, A37C/A44C, Q62C/A140C, L144C/P221C, G131C/N172C, and N167C/L169C. Formation of the interprotomer disulfide bond stabilizes the VLP in its assembled form.

In additional embodiments, the recombinant Norovirus GI VP1 proteins in the VLP comprise amino acid substitutions set forth as one or more of the following pairs of hydrophobic amino acid substitutions: Q141V/P221L and A37I/A44L substitutions. The hydrophobic residues are proximate to one another between protomers of the assembled VLP, and form hydrophobic interactions that stabilize the VLP in its assembled form.

The recombinant Norovirus GI VP1 protein in the VLP can be selected from any GI VP1 protein, such as a GI.1, GI.2, GI.3, GI.4, GI.7, or GI.8 VP1 protein that comprises the one or more amino acid substitutions. In several embodiments, the recombinant Norovirus GI VP1 protein in the VLP is a GI.1 VP1 protein comprising the one or more amino acid substitutions.

In some embodiments, the recombinant Norovirus GI VP1 protein comprises one or more of the following pairs of cysteine substitutions that form a non-natural interprotomer disulfide bond: N116C/G193C, A37C/A44C, Q62C/A140C, L144C/P221C, G131C/N172C, and N167C/L169C, and an amino acid sequence at least 80% (such as at least 90%, at least 95%, or at least 99%) identical to any one of SEQ ID NOs: 1-6.

In some embodiments, the recombinant Norovirus GI VP1 protein comprises N116C/G193C substitutions that form a non-natural interprotomer disulfide bond, and an amino acid sequence at least 80% (such as at least 90%, at least 95%, or at least 99%) identical to any one of SEQ ID NOs: 1-6. In some embodiments, the recombinant Norovirus GI VP1 protein comprises N116C/G193C substitutions that form a non-natural interprotomer disulfide bond, and an amino acid sequence at least 80% (such as at least 90%, at least 95%, or at least 99%) identical to SEQ ID NO: 1. The non-natural interprotomer disulfide bond formed by the N116C/G193C substitutions is located at the interface between each A-A monomer pair around the 5-fold symmetry axes and between each B-C monomer pair around the 3-fold symmetry axes in the capsid.

In some embodiments, the recombinant Norovirus GI VP1 protein comprises A37C/A44C substitutions that form a non-natural interprotomer disulfide bond, and an amino acid sequence at least 80% (such as at least 90%, at least 95%, or at least 99%) identical to any one of SEQ ID NOs: 1-6. In some embodiments, the recombinant Norovirus GI VP1 protein comprises A37C/A44C substitutions that form a non-natural interprotomer disulfide bond, and an amino acid sequence at least 80% (such as at least 90%, at least 95%, or at least 99%) identical to SEQ ID NO: 1. The non-natural interprotomer disulfide bond formed by the A37C/A44C substitutions is located within the icosahedral asymmetric unit of the VLP and links monomers A-B, B-C, and C-A).

In some embodiments, the recombinant Norovirus GI VP1 protein comprises Q62C/A140C substitutions that form a non-natural interprotomer disulfide bond, and an amino acid sequence at least 80% (such as at least 90%, at least 95%, or at least 99%) identical to any one of SEQ ID NOs: 1-6. In some embodiments, the recombinant Norovirus GI VP1 protein comprises Q62C/A140C substitutions that form a non-natural interprotomer disulfide bond, and an amino acid sequence at least 80% (such as at least 90%, at least 95%, or at least 99%) identical to SEQ ID NO: 1. The non-natural interprotomer disulfide bond formed by the Q62C/A140C substitutions is located at the interface between each A-A monomer pair around the 5-fold symmetry axes and between each B-C monomer pair around the 3-fold symmetry axes in the capsid.

In some embodiments, the recombinant Norovirus GI VP1 protein comprises L144C/P221C substitutions that form a non-natural interprotomer disulfide bond, and an amino acid sequence at least 80% (such as at least 90%, at least 95%, or at least 99%) identical to any one of SEQ ID NOs: 1-6. In some embodiments, the recombinant Norovirus GI VP1 protein comprises L144C/P221C substitutions that form a non-natural interprotomer disulfide bond, and an amino acid sequence at least 80% (such as at least 90%, at least 95%, or at least 99%) identical to SEQ ID NO: 1. The non-natural interprotomer disulfide bond formed by the L144C/P221C substitutions is located at the interface between each A-A monomer pair around the 5-fold symmetry axes and between each B-C monomer pair around the 3-fold symmetry axes in the capsid.

In some embodiments, the recombinant Norovirus GI VP1 protein comprises G131C/N172C substitutions that form a non-natural interprotomer disulfide bond, and an amino acid sequence at least 80% (such as at least 90%, at least 95%, or at least 99%) identical to any one of SEQ ID NOs: 1-6. In some embodiments, the recombinant Norovirus GI VP1 protein comprises G131C/N172C substitutions that form a non-natural interprotomer disulfide bond, and an amino acid sequence at least 80% (such as at least 90%, at least 95%, or at least 99%) identical to SEQ ID NO: 1. The non-natural interprotomer disulfide bond formed by the G131C/N172C substitutions is located at the interface between each A-A monomer pair around the 5-fold symmetry axes and between each B-C monomer pair around the 3-fold symmetry axes in the capsid.

In some embodiments, the recombinant Norovirus GI VP1 protein comprises N167C/L169C substitutions that form a non-natural interprotomer disulfide bond, and an amino acid sequence at least 80% (such as at least 90%, at least 95%, or at least 99%) identical to any one of SEQ ID NOs: 1-6. In some embodiments, the recombinant Norovirus GI VP1 protein comprises N167C/L169C substitutions that form a non-natural interprotomer disulfide bond, and an amino acid sequence at least 80% (such as at least 90%, at least 95%, or at least 99%) identical to SEQ ID NO: 1. The non-natural interprotomer disulfide bond formed by the N167C/L169C substitutions is located at the interface between each A-A monomer pair around the 5-fold symmetry axes and between each B-C monomer pair around the 3-fold symmetry axes in the capsid.

In some embodiments, the recombinant Norovirus GI VP1 protein further comprises one or more additional amino acid substitutions that stabilize the assembly of the recombinant Norovirus GI VP1 proteins in the VLP.

Exemplary protein sequences of recombinant GI VP1 proteins containing the amino acid substitutions as described herein are provided below. Norovirus VLPs composed of these recombinant VP1 proteins have increased stability (such as increased thermal stability) compared to Norovirus VLPs composed of corresponding unmodified VP1 proteins

```
GI.1 VP1 N116C/G193C
                                                    (SEQ ID NO: 7)
MMMASKDATSSVDGASGAGQLVPEVNASDPLAMDPVAGSSTAVATAGQVNPIDPWIINNFVQAPQGEFTISP

NNTPGDVLFDLSLGPHLNPFLLHLSQMYNGWVGNMRVRIMLAGCAFTAGKIIVSCIPPGFGSHNLTIAQATL

FPHVIADVRTLDPIEVPLEDVRNVLFHNNDRNQQTMRLVCMLYTPLRTCGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 F118C/G193C
                                                    (SEQ ID NO: 8)
MMMASKDATSSVDGASGAGQLVPEVNASDPLAMDPVAGSSTAVATAGQVNPIDPWIINNFVQAPQGEFTISP

NNTPGDVLFDLSLGPHLNPFLLHLSQMYNGWVGNMRVRIMLAGNACTAGKIIVSCIPPGFGSHNLTIAQATL

FPHVIADVRTLDPIEVPLEDVRNVLFHNNDRNQQTMRLVCMLYTPLRTCGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 Q62C/A140C
                                                    (SEQ ID NO: 9)
MMMASKDATSSVDGASGAGQLVPEVNASDPLAMDPVAGSSTAVATAGQVNPIDPWIINNFVCAPQGEFTISP

NNTPGDVLFDLSLGPHLNPFLLHLSQMYNGWVGNMRVRIMLAGNAFTAGKIIVSCIPPGFGSHNLTICQATL

FPHVIADVRTLDPIEVPLEDVRNVLFHNNDRNQQTMRLVCMLYTPLRTGGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ
```

-continued

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 A37C/A44C (SEQ ID NO: 10)

MMMASKDATSSVDGASGAGQLVPEVNASDPLAMDPVCGSSTAVCTAGQVNPIDPWIINNFVQAPQGEFTISP

NNTPGDVLFDLSLGPHLNPFLLHLSQMYNGWVGNMRVRIMLAGNAFTAGKIIVSCIPPGFGSHNLTIAQATL

FPHVIADVRTLDPIEVPLEDVRNVLFHNNDRNQQTMRLVCMLYTPLRTGGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 A37I/A44L (SEQ ID NO: 11)

MMMASKDATSSVDGASGAGQLVPEVNASDPLAMDPVIGSSTAVLTAGQVNPIDPWIINNFVQAPQGEFTISP

NNTPGDVLFDLSLGPHLNPFLLHLSQMYNGWVGNMRVRIMLAGNAFTAGKIIVSCIPPGFGSHNLTIAQATL

FPHVIADVRTLDPIEVPLEDVRNVLFHNNDRNQQTMRLVCMLYTPLRTGGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGISNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 Q141V/P221L (SEQ ID NO: 12)

MMMASKDATSSVDGASGAGQLVPEVNASDPLAMDPVAGSSTAVATAGQVNPIDPWIINNFVQAPQGEFTISP

NNTPGDVLFDLSLGPHLNPFLLHLSQMYNGWVGNMRVRIMLAGNAFTAGKIIVSCIPPGFGSHNLTIAVATL

FPHVIADVRTLDPIEVPLEDVRNVLFHNNDRNQQTMRLVCMLYTPLRTGGGTGDSFVVAGRVMTCPSPDFNF

LFLVLPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 P221C/L144C (SEQ ID NO: 13)

MMMASKDATSSVDGASGAGQLVPEVNASDPLAMDPVAGSSTAVATAGQVNPIDPWIINNFVQAPQGEFTISP

NNTPGDVLFDLSLGPHLNPFLLHLSQMYNGWVGNMRVRIMLAGNAFTAGKIIVSCIPPGFGSHNLTIAQATC

FPHVIADVRTLDPIEVPLEDVRNVLFHNNDRNQQTMRLVCMLYTPLRTGGGTGDSFVVAGRVMTCPSPDFNF

LFLVCPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

-continued

GI.1 VP1 G131C/N172C (SEQ ID NO: 14)

MMMASKDATSSVDGASGAGQLVPEVNASDPLAMDPVAGSSTAVATAGQVNPIDPWIINNFVQAPQGEFTISP

NNTPGDVLFDLSLGPHLNPFLLHLSQMYNGWVGNMRVRIMLAGNAFTAGKIIVSCIPPCFGSHNLTIAQATL

FPHVIADVRTLDPIEVPLEDVRNVLFHCNDRNQQTMRLVCMLYTPLRTGGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGTSNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.1 VP1 N167C/L169C (SEQ ID NO: 15)

MMMASKDATSSVDGASGAGQLVPEVNASDPLAMDPVAGSSTAVATAGQVNPIDPWIINNFVQAPQGEFTISP

NNTPGDVLFDLSLGPHLNPFLLHLSQMYNGWVGNMRVRIMLAGNAFTAGKIIVSCIPPGFGSHNLTIAQATL

FPHVIADVRTLDPIEVPLEDVRCVCFHNNDRNQQTMRLVCMLYTPLRTGGGTGDSFVVAGRVMTCPSPDFNF

LFLVPPTVEQKTRPFTLPNLPLSSLSNSRAPLPISSMGISPDNVQSVQFQNGRCTLDGRLVGTTPVSLSHVA

KIRGISNGTVINLTELDGTPFHPFEGPAPIGFPDLGGCDWHINMTQFGHSSQTQYDVDTTPDTFVPHLGSIQ

ANGIGSGNYVGVLSWISPPSHPSGSQVDLWKIPNYGSSITEATHLAPSVYPPGFGEVLVFFMSKMPGPGAYN

LPCLLPQEYISHLASEQAPTVGEAALLHYVDPDTGRNLGEFKAYPDGFLTCVPNGASSGPQQLPINGVFVFV

SWVSRFYQLKPVGTASSARGRLGLRR

GI.2 VP1 A37C/A44C (SEQ ID NO: 16)

MMMASKDASQSADGASGAGQLVPEVNTADPLPMEPVCGPTTAVCTAGQVNMIDPWIVNNFVQSPQGEFTISP

NNTPGDILFDLQLGPHLNPFLSHLSQMYNGWVGNMRVRILLAGNAFSAGKIIVCCVPPGFTSSSLTIAQATL

FPHVIADVRTLEPIEMPLEDVRNVLYHTNDNQPTMRLVCMLYTPLRTGGGSGNSDSFVVAGRVLTAPSSDFS

FLFLVPPTIEQKTRAFTVPNIPLQTLSNSRFPSLIQGMILSPDASQVVQFQNGRCLIDGQLLGTTPATSGQL

FRVRGKINQGARTLNLTEVDGKPFMAFDSPAPVGFPDFGKCDWHMRISKTPNNTSSGDPMRSVSVQTNVQGF

VPHLGSIQFDEVFNHPTGDYIGTIEWISQPSTPPGTDINLWEIPDYGSSLSQAANLAPPVFPPGFGEALVYF

VSAFPGPNNRSAPNDVPCLLPQEYITHFVSEQAPTMGDAALLHYVDPDTNRNLGEFKLYPGGYLTCVPNGVG

AGPQQLPLNGVFLFVSWVSRFYQLKPVGTASTARGRLGVRRI

GI.2 VP1 N116C/G193C (SEQ ID NO: 17)

MMMASKDASQSADGASGAGQLVPEVNTADPLPMEPVAGPTTAVATAGQVNMIDPWIVNNFVQSPQGEFTISP

NNTPGDILFDLQLGPHLNPFLSHLSQMYNGWVGNMRVRILLAGCAFSAGKIIVCCVPPGFTSSSLTIAQATL

FPHVIADVRTLEPIEMPLEDVRNVLYHTNDNQPTMRLVCMLYTPLRTCGGSGNSDSFVVAGRVLTAPSSDFS

FLFLVPPTIEQKTRAFTVPNIPLQTLSNSRFPSLIQGMILSPDASQVVQFQNGRCLIDGQLLGTTPATSGQL

FRVRGKINQGARTLNLTEVDGKPFMAFDSPAPVGFPDFGKCDWHMRISKTPNNTSSGDPMRSVSVQTNVQGF

VPHLGSIQFDEVFNHPTGDYIGTIEWISQPSTPPGTDINLWEIPDYGSSLSQAANLAPPVFPPGFGEALVYF

VSAFPGPNNRSAPNDVPCLLPQEYITHFVSEQAPTMGDAALLHYVDPDTNRNLGEFKLYPGGYLTCVPNGVG

AGPQQLPLNGVFLFVSWVSRFYQLKPVGTASTARGRLGVRRI

GI.3 VP1 A37C/A44C (SEQ ID NO: 18)

MMMASKDAPPNMDGTSGAGQLVPEANTAEPISMEPVCGAATAACTAGQVNMIDPWIMNNYVQAPQGEFTISP

NNTPGDILFDLQLGPHLNPFLSHLAQMYNGWVGNMKVKVLLAGNAFTAGKIIISCIPPGFAAQNISIAQATM

FPHVIADVRVLEPIEVPLEDVRNVLFHNNDNTPTMRLVCMLYTPLRASGSSSGTDPFVIAGRVLTCPSPDFS

FLFLVPPNVEQKTKPFSVPNLPLNTLSNSRVPSLIRSMMVSRDHGQMVQFQNGRVTLDGQLQGTTPTSASQL

-continued

CKIRGSVFHANGGNGYNLTELDGSPYHAFESPAPIGFPDLGECDWHMEASPTTQFDTGDVIKQINVKQEAAF

APHLGTIQADGLSDVSVNTNMIAKLGWVSPVSDGHRGSVDPWVIPRYGSTLTEAAQLAPPIYPPGFGEAIVF

FMSDFPIAHGANGLSVPCTIPQEFVTHFVNEQAPTRGEAALLHYLDPDTHRNLGEFKLYPEGFMTCVPNSSG

TGPQTLPINGVFAFVSWVSRFYQLKPVGTAGPARRLGIRRS

GI.3 VP1 N116C/G193C (SEQ ID NO: 19)

MMMASKDAPPNMDGTSGAGQLVPEANTAEPISMEPVAGAATAAATAGQVNMIDPWIMNNYVQAPQGEFTISP

NNTPGDILFDLQLGPHLNPFLSHLAQMYNGWVGNMKVKVLLAGCAFTAGKIIISCIPPGFAAQNISIAQATM

FPHVIADVRVLEPIEVPLEDVRNVLFHNNDNTPTMRLVCMLYTPLRACGSSSGTDPFVIAGRVLTCPSPDFS

FLFLVPPNVEQKTKPFSVPNLPLNTLSNSRVPSLIRSMMVSRDHGQMVQFQNGRVTLDGQLQGTTPTSASQL

CKIRGSVFHANGGNGYNLTELDGSPYHAFESPAPIGFPDLGECDWHMEASPTTQFDTGDVIKQINVKQEAAF

APHLGTIQADGLSDVSVNTNMIAKLGWVSPVSDGHRGSVDPWVIPRYGSTLTEAAQLAPPIYPPGFGEAIVF

FMSDFPIAHGANGLSVPCTIPQEFVTHFVNEQAPTRGEAALLHYLDPDTHRNLGEFKLYPEGFMTCVPNSSG

TGPQTLPINGVFAFVSWVSRFYQLKPVGTAGPARRLGIRRS

GI.4 VP1 A37C/A44C (SEQ ID NO: 20)

MMMASKDATPSADGATGAGQLVPEVNTADPIPIDPVCGSSTALCTAGQVNLIDPWIINNFVQAPQGEFTISP

NNTPGDVLFDLQLGPHLNPFLSHLSQMYNGWVGNMRVRVVLAGNAFTAGKVIICCVPPGFQSRTLSIAQATL

FPHVIADVRTLDPVEVPLEDVRNVLYHNNDTQPTMRLLCMLYTPLRTGGASGGTDSFVVAGRVLTCPGPDFN

FLFLVPPTVEQKTRPFTVPNIPLKYLSNSRIPNPIEGMSLSPDQTQNVQFQNGRCTIDGQPLGTTPVSVSQL

CKFRGRITSGQRVLNLTELDGSPFMAFAAPAPAGFPDLGSCDWHIEMSKIPNSSTQNNPIVVNSVKPNSQQF

VPHLSSITLDDIVSSGGDYIGTIQWTSPPSDSGGANTNFWKIPDYGSSLSEASQLAPAVYPPGFNEVIVYFM

ASIPGPNQSGSPNLVPCLLPQEYITHFISEQAPIQGEAALLHYVDPDTNRNLGEFKLYPGGYLTCVPNSSST

GPQQLPLDGVFVFASWVSRFYQLKPVGTAGPARGRLGVRR

GI.4 VP1 N116C/G193C (SEQ ID NO: 21)

MMMASKDATPSADGATGAGQLVPEVNTADPIPIDPVAGSSTALATAGQVNLIDPWIINNFVQAPQGEFTISP

NNTPGDVLFDLQLGPHLNPFLSHLSQMYNGWVGNMRVRVVLAGCAFTAGKVIICCVPPGFQSRTLSIAQATL

FPHVIADVRTLDPVEVPLEDVRNVLYHNNDTQPTMRLLCMLYTPLRTCGASGGTDSFVVAGRVLTCPGPDFN

FLFLVPPTVEQKTRPFTVPNIPLKYLSNSRIPNPIEGMSLSPDQTQNVQFQNGRCTIDGQPLGTTPVSVSQL

CKFRGRITSGQRVLNLTELDGSPFMAFAAPAPAGFPDLGSCDWHIEMSKIPNSSTQNNPIVVNSVKPNSQQF

VPHLSSITLDDIVSSGGDYIGTIQWTSPPSDSGGANTNFWKIPDYGSSLSEASQLAPAVYPPGFNEVIVYFM

ASIPGPNQSGSPNLVPCLLPQEYITHFISEQAPIQGEAALLHYVDPDTNRNLGEFKLYPGGYLTCVPNSSST

GPQQLPLDGVFVFASWVSRFYQLKPVGTAGPARGRLGVRR

GI.7 VP1 A37C/A44C (SEQ ID NO: 22)

MMMASKDAPSNMDGTSGAGQLVPEVNAAEPLPLEPVCGAATAACTAGQVNLIDPWIMNNFVQAPEGEFTISP

NNTPGDILFDLHLGPHLNPFLQHLSQMYNGWVGNMRVRVMLAGNAFTAGKIIICCVPPGFASQNISIGQATM

FPHVIADVRVLEPIEIPLDDVRNVLFHTNENRPTMRLLCMLYTPLRAGGASSGTDPFVIAGRVLTCPSPDFN

FLFLVPPSVEQKTRQLTVPNIPLNNLANSRVPAMINKMTVSTDQNQVVQFQNGRCTLEGQLLGTTPVSASQV

ARIRGKVFSTASGKGLNLTELDGTPYHAFESPAPLGFPDIGACDWHVSTFKVDQNLSGDPMSRLDVKQNAPF

APHLGSIEFTSDQDPTGDQLGTLAWVSPSTSGARVDPWKIPSYGSTVTESTHLAPPIFPPGFGEAIVYFMSD

FPIVSGNTAQVPCTLPQEFVSHFVEQQAPVRGEAALLHYVDPDTHRNLGEFKLYPDGFITCVPNTGGGPQNL

PTNGVFVFSSWVSRYYQLKPVGTAGPARRLGVRRV

-continued

GI.7 VP1 N116C/G193C (SEQ ID NO: 23)

MMMASKDAPSNMDGTSGAGQLVPEVNAAEPLPLEPVVGAATAAATAGQVNLIDPWIMNNFVQAPEGEFTISP

NNTPGDILFDLHLGPHLNPFLQHLSQMYNGWVGNMRVRVMLAGCAFTAGKIIICCVPPGFASQNISIGQATM

FPHVIADVRVLEPIEIPLDDVRNVLFHTNENRPTMRLLCMLYTPLRACGASSGTDPFVIAGRVLTCPSPDFN

FLFLVPPSVEQKTRQLTVPNIPLNNLANSRVPAMINKMTVSTDQNQVVQFQNGRCTLEGQLLGTTPVSASQV

ARIRGKVFSTASGKGLNLTELDGTPYHAFESPAPLGFPDIGACDWHVSTFKVDQNLSGDPMSRLDVKQNAPF

APHLGSIEFTSDQDPTGDQLGTLAWVSPSTSGARVDPWKIPSYGSTVTESTHLAPPIFPPGFGEAIVYFMSD

FPIVSGNTAQVPCTLPQEFVSHFVEQQAPVRGEAALLHYVDPDTHRNLGEFKLYPDGFITCVPNTGGGPQNL

PTNGVFVFSSWVSRYYQLKPVGTAGPARRLGVRRV

GI.8 VP1 A37C/A44C (SEQ ID NO: 24)

MMMASKDAPTSPDGASGAGQLVPEANTAEQISMDPVCGASTAVCTAGQVNMIDPWIFNNFVQAPQGEFTISP

NNTPGDILFDLQLGPHLNPFLAHLSQMYNGWVGNMRVRILLAGNAFTAGKIIICCVPPGFDARILTIAQATL

FPHLIADVRTLEPVELPLEDVRNVLYHNSSQPQPTMRLVAMLYTPLRTGGGSGGTDAFVVAGRVLTCPAPDF

SFLFLVPPSVEQKTRVFSVPNIPLKDLSNSRVPVPIQGMFMSPDVNQSVQFQNGRCQIDGQLQGTTPVSLSQ

LCKIRGKTSSNARVLNLSEVDGTPFIPLESPAPVGFPDLGGCDWHVNFTFQAQNQDPSQSVTFATNDASFVP

YLGSISPHNGGDFHAGDIIGSLGWISAPSDNTQLNVWTIPKYGSSLPDVTHLAPAVFPPGFGEVILYFYSTF

PGSGQPSQLQVPCLLPQEFITHFCNEQAPIAGEAALLHYVDPDTGRNLGEFKLYPDGFMTCVPNSVSSGPQT

LPINGVFVFVSWVSRFYQLKPVGTASAARRLGLRRI

GI.8 VP1 N116C/G193C (SEQ ID NO: 25)

MMMASKDAPTSPDGASGAGQLVPEANTAEQISMDPVAGASTAVATAGQVNMIDPWIFNNFVQAPQGEFTISP

NNTPGDILFDLQLGPHLNPFLAHLSQMYNGWVGNMRVRILLAGCAFTAGKIIICCVPPGFDARILTIAQATL

FPHLIADVRTLEPVELPLEDVRNVLYHNSSQPQPTMRLVAMLYTPLRTCGGSGGTDAFVVAGRVLTCPAPDF

SFLFLVPPSVEQKTRVFSVPNIPLKDLSNSRVPVPIQGMFMSPDVNQSVQFQNGRCQIDGQLQGTTPVSLSQ

LCKIRGKTSSNARVLNLSEVDGTPFIPLESPAPVGFPDLGGCDWHVNFTFQAQNQDPSQSVTFATNDASFVP

YLGSISPHNGGDFHAGDIIGSLGWISAPSDNTQLNVWTIPKYGSSLPDVTHLAPAVFPPGFGEVILYFYSTF

PGSGQPSQLQVPCLLPQEFITHFCNEQAPIAGEAALLHYVDPDTGRNLGEFKLYPDGFMTCVPNSVSSGPQT

LPINGVFVFVSWVSRFYQLKPVGTASAARRLGLRRI

B. Recombinant GII VLPs

In some embodiments, the recombinant Norovirus VP1 VLP is composed of GII VP1 proteins as provided herein. Non-limiting examples of native Norovirus GII VP1 proteins that can be modified as described herein by incorporation of one or more amino acid substitutions that stabilize the recombinant Norovirus VLP in its assembled form include:

GII.1 native VP1 sequence
Genbank: AJ277606
>GII.1 tr|Q9IV51|Q9IV51_9CALI Capsid protein OS = Human calicivirus NLV/Ludwigslust/218/99/DE OX = 122910 PE = 4 SV = 1

(SEQ ID NO: 26)

MKMASNDAAPSNDGAAGLVPXVNNETMALEPVAGASIAAPLTGQNNVIDPWIRMNFVQAPNGEFTVSPRNSP

GEILLNLELGPELNPFLAHLSRMXNGYAGGVEMQVLLAGNAFTAGKLLFAAIPPHFPIENLSPGQITMFPHV

IIDVRTLEPVLLPLPDVRNNFFHYNQEPEPRMWLVAMLYTPLRSNGSGDDVFTVSCRVPTRPSPDFDFNYLV

PPTVESKTKPFTLPILTIGELSNSRFPAPIDELYTSPNEGLVVQPQNGRTTLDGELLGTTQLVPSNICSLRG

RINAHLSDNQHRWNMQVTNANGTPFDPTEDVPAPLGTPDFLANIYGVTSQRNPDNTCRAHDGILATWSPKFT

-continued

PKLGSVVLGTWEDRDFDINQPTRFTPVGLYDTDHFNQWALPNYSGALTLNMNLAPSVAPLFPGEQLLFFRSH

IPLKGGTSNGAIDCLLPQEWVQHFYQESAPSSTDVALIRYTNPDTGRVLFEAKLHRQGFITVANTGSRPIVV

PPNGYFRFDSWVNQFYSLAPMGTGNGRRRVQ

GII.2 native VP1 sequence
Genbank:AY134748
>GII.2 tr|Q80RD6|Q80RD6_9CALI Viral protein 1 OS = Snow Mountain virus
OX = 52276 GN = ORF2 PE = 1 SV = 1

(SEQ ID NO: 27)

MKMASNDAAPSTDGAAGLVPESNNEVMALEPVAGAALAAPVTGQTNIIDPWIRANFVQAPNGEFTVSPRNAP

GEVLLNLELGPELNPYLAHLARMYNGYAGGMEVQVMLAGNAFTAGKLVFAAVPPHFPVENLSPQQITMFPHV

IIDVRTLEPVLLPLPDVRNNFFHYNQKDDPKMRIVAMLYTPLRSNGSGDDVFTVSCRVLTRPSPDFDFTYLV

PPTVESKTKPFTLPILTLGELSNSRFPVSIDQMYTSPNEVISVQCQNGRCTLDGELQGTTQLQVSGICAFKG

EVTAHLQDNDHLYNITITNLNGSPFDPSEDIPAPLGVPDFQGRVFGVITQRDKQNAAGQSQPANRGHDAVVP

TYTAQYTPKLGQVQIGTWQTDDLKVNQPVKFTPVGLNDTEHFNQWVVPRYAGALNLNTNLAPSVAPVFPGER

LLFFRSYLPLKGGYGNPAIDCLLPQEWVQHFYQEAAPSMSEVALVRYINPDTGRALFEAKLHRAGFMTVSSN

TSAPVVVPANGYFRFDSWVNQFYSLAPMGTGNGRRRIQ

GII.3 native VP1 sequence
Genbnak: EU187437
>GII.3 tr|A8W1Y2|A8W1Y2_9CALI Capsid OS = Norovirus Hu/5017.34/2003/JPN
OX = 478514 PE = 4 SV = 1

(SEQ ID NO: 28)

MKMASNDATPSNDGAAGLVPEINNEAMALDPVAGAAIAAPLIGQQNIIDPWIMNNFVQAPGGEFTVSPRNSP

GEVLLNLELGPEINPYLAHLARMYNGYAGGFEVQVVLAGNAFTAGKIIFAAIPPYFPIDNLSAAQITMCPHV

IVDVRQLEPVNLPMPDVRNNFFHYNQGSDSRLRLVAMLYTPLRANNSGDDVFTVSLRVLTRPSPDFSFNFLV

PPTVESKTKPFTLPILTISEMSNSRFPVPIDSLHTSPTENIVVQCQNGRVTLDGELMGTTQLLPSQICAFRG

VLTRSTSRASDQADTATPRLFNYYWHIQLDNLNGTPYDPAEDIPGPLGTPDFRGKVFGVASQRNPDSTTRAH

EAKVDTTAGRFTPKLGSLEISTESDDFDQNQPTRFTPVGIGVDHEADFQQWSLPDYSGQFTHNMNLAPAVAP

NFPGEQLLFFRSQLPSSGGRSNGILDCLVPQEWVQHFYQESAPAQTQVALVRYVNPDTGRVLFEAKLHKLGF

MTIAKNGDSPITVPPNGYFRFESWVNPFYTLAPMGTGNGRRRIQ

GII.4 native VP1 sequence
2012_sydney
Genbank:JX459908
>GII.4 tr K4LM89|K4LM89_9CALI VP1 OS = Norovirus
Hu/GII.4/Sydney/NSW0514/2012/AU OX = 1241973 PE = 1 SV = 1

(SEQ ID NO: 29)

MKMASSDANPSDGSAANLVPEVNNEVMALEPVVGAAIAAPVAGQQNVIDPWIRNNFVQAPGGEFTVSPRNAP

GEILWSAPLGPDLNPYLSHLARMYNGYAGGFEVQVILAGNAFTAGKVIFAAVPPNFPTEGLSPSQVTMFPHI

VVDVRQLEPVLIPLPDVRNNFYHYNQSNDPTIKLIAMLYTPLRANNAGDDVFTVSCRVLTRPSPDFDFIFLV

PPTVESRTKPFSVPVLIVEEMTNSRFPIPLEKLFTGPSSAFVVQPQNGRCTTDGVLLGTTQLSPVNICTFRG

DVTHITGSRNYTMNLASQNWNDYDPTEEIPAPLGTPDFVGKIQGVLTQTTRTDGSTRGHKATVYTGSADFAP

KLGRVQFETDTDRDFEANQNTKFTPVGVIQDGGTTHRNEPQQWVLPSYSGRNTHNVHLAPAVAPTFPGEQLL

FFRSTMPGCSGYPNMDLDCLLPQEWVQYFYQEAAPAQSDVALLRFVNPDTGRVLFECKLHKSGYVTVAHTGQ

HDLVIPPNGYFRFDSWVNQFYTLAPMGNGTGRRRAV

GII.5 native VP1 sequence
Genbank:AF397156
>GII.5 tr Q91165 Q91165_9CALI Capsid protein OS = Human calicivirus
NLV/MOH/99 OX = 168224 PE = 2 SV = 1

(SEQ ID NO: 30)

MASNDATPSNDGAAGLVPESNNEAMALEPVVGASLAAPVTGQTNIIDPWIRTNFVQAPNGEFTVSPRNSPGE

ILVNLELGPELNPYLAHLARMYNGYAGGMEVQVMLAGNAFTAGKIIFAAVPPYFPVENLSPSQITMFPHVII

DVRTLEPVLLPMPDVRSTLFHFNQKDEPKMRLVAMLYTPLRSNGSGDDVFTVSCRILTRPSPEFDFTYLVPP

-continued

TVESKTKPFTLPVLTLGELSNSRFPLSIDEMVTSPNESIVVQPQNGRVTLDGELLGTTQLQACNICSIRGKV

TGQVPNEQHMWNLEITNLNGTQFDPTDDVPAPLGVPDFAGEVFGVLSQRNRGESNPANRAHDAVVATYSDKY

TPKLGLVQIGTWNTNDVENQPTKFTPIGLNEVANGHRFEQWTLPRYSGALTLNMNLAPAVAPLFPGERLLFF

RSYVPLKGGFGNPAIDCLVPQEWVQHFYQESAPSLGDVALVRYVNPDTGRVLFEAKLHKGGFLTVSSTSTGP

VVVPANGYFRFDPWGNQFYSLAPMGTGNGRRRFQ

GII.6 native VP1 sequence
Genbank:AB039778
>GII.6 tr Q783X4|Q783X4_9CALI Capsid OS = Norwalk-like virus OX = 95340
PE = 4 SV = 1

(SEQ ID NO: 31)

MKMASNDAAPSNDGAANLVPEANNEVMALEPVVGASIAAPVVGQQNIIDPWIRENFVQAPQGEFTVSPRNSP

GEMLLNLELGPELNPYLSHLSRMYNGYAGGMQVQVVLAGNAFTAGKIIFAAVPPHFPVENISAAQITMCPHV

IVDVRQLEPVLLPLPDIRNRFFHYNQEDTPRMRLVAMLYTPLRANSGEDVFTVSCRVLTRPAPDFEFTFLVP

PTVESKTKPFTLPILTLGELSNSRFPAPIDMLYTDPNETIVVQPQNGRCTLDGTLQGTTQLVPTQICSFRGT

LISQTSRSADSTDSAPRVRNHPLHVQLKNLDGTPYDPTDEVPAVLGAIDFKGTVFGVASQRNTTGSSVGATR

AHEVHIDTTNPRYTPKLGSVLMYSESSDFDDGQPTRFTPIGMGADDWHQWELPEYSGHLTLNMNLAPAVAPA

FPGERILFFRSVVPSAGGYGSGQIDCLIPQEWVQHFYQEAAPSQSAVALIRYVNPDTGRNIFEAKLHREGFI

TVANSGNNPIVVPPNGYFRFEAWVNQFYTLTPMGTGQGRRRVQ

GII.7 native VP1 sequence
Genbank:AF414409
>GII.7 tr|Q918B0|Q918B0_9CALI Capsid protein OS = Norwalk-like virus
NLV/Gwynedd/273/1994/US OX = 171841 GN = orf2 PE = 4 SV = 1

(SEQ ID NO: 32)

MKMASNDAAPSNDGAAGLVPEINNEVMPLEPVAGASLATPVVGQQNIIDPWIRNNFVQAPAGEFTVSPRNSP

GEILLDLELGPELNPYLAHLARMYNGHAGGMEVQIVLAGNAFTAGKIIFAAIPPGFPYENLSPSQITMCPHV

IIDVRQLEPVLLPMPDIRNNFFHYNQGNDPKLRLVAMLYTPLRANNSGDDVFTVSCRVLTKPSPDFEFTFLV

PPTVESKTKQFTLPILKISEMTNSRFPVPVEMMYTSRNENQVVQPQNGRVTLDGELLGTTPLLAVNICKFKG

EVIAKNGDVRSYRMDMEITNTDGTPIDPTEDTPGPIGSPDFQGILFGVASQRNKNEQNPATRSHEANINTGG

DQYAPKLAQVKIFSQSQDFEVHQPTVFTPVGVAGDTSHPFRQWTLPRYGGHLTNNTHLAPAVAPLFPGEQIL

FFRSQIPSSGGHELGYMDCLVPQEWVQHFYQEAATAQSEVALIRFINPDTGRVLFEAKLHKQGFITVAHTGD

NPIVMPPNGYFRFEAWVNQFYSLAPVGTGNGRRRIQ

GII.8 native VP1 sequence
Genbank:AB039780
>GII.8 tr|Q783W9|Q783W9_9CALI Capsid OS = Norwalk-like virus OX = 95340
PE = 4 SV = 1

(SEQ ID NO: 33)

MKMASNDAAPSNDGAAGLVPEINHEVMAIEPVAGASLAAPVVGQLNIIDPWIRNNFVQAPAGEFTVSPRNAP

GEFLLDLELGPELNPYLAHLARMYNGHAGGMEVQIVLAGNAFTAGKILFAVIPPGFPYENLSPAQLTMCPHV

VVDVRQLEPILLPMPDIRNTFFHYNQSNGPKLRLVAMLYTPLRANNAGEDVFTVSCRVLTRPSPDFEFNFLV

PPSVESKTKAFTLPILKISEMTNSRFPIPVDQMYTSRNENIVVQPQNGRVTLDGELQGTTTLQPVSICGFRG

TLQTRLADQPNYTYQVHLENLDGSPVDPTDEVPAPLGTPDFQAQLFGVISQRSSDNATRAHEARVNTNDPTF

APQIAQVRFKSPSNDFFDNEPIKFTPVGISVDSQNSYNQWLLPRYGGHLTNNTHLAPSVSPMFPGEQILFFR

SFMPGASGHTDGAIDCLLPQEWVAHFYQEAATAQTDVALIRFVNPDTGRVLFEGKLHKQGFITISNSGDHPI

VMPANGYFRFEAWVNQFYSLAPVGTGSGRRRIQ

GII. 9 native VP1 sequence
Genbank: AY038599
>GII.9 tr Q91H09|Q91H09_9CALI Capsid OS = Human calicivirus
NLV/VA97207/1997 OX = 165510 PE = 1 SV = 2

(SEQ ID NO: 34)

MKMASNDAAPSSDGAAGVVPEINHEVMAIEPVAGASIAAPVVGQQNIIDPWIRNNFVQAPAGEFTVSPRNAP

GEFLLDLELGPDLNPYLAHLARMYNGHAGGMEVQIVLAGNAFTAGKILFAVIPPGFPYENLCPAQLTMCPHV

-continued

VVDVRQLEPVMLPMPDIRNTFFHYNQDGGPKLRLIAMLYTPLRANNSGDDVFTVSCRVLTRPAPDFEFTFLV

PPSIESKTKAFTIPVLKISEMTNSRFPVPVDQMYTSRSEGIVVQPQNGRATIDGELLGTTLVSPVSVCNFKG

NLQAEVPGQHQLYQLQLTNLDGSPIDPTDDTPGPLGCPDFTGLLYGVASQRGPGDATRAHEARIDTGSDTFA

PKIGQVRFYSTSSDFETNQPTHFTPIGIYIEGNSSDFNQWQLPRYGGHLANNNHLAPAVSPLFPGEQILFFR

SFIPGASGHTNGEMDCLLPQEFVQHFYQEAATARSEVALLRFVNPDTGRALFESKLHKQGFMTIASSGDHPI

IMPTNGYFRFEAWVNQFYSLAPVGTGSGRRRIQ

GII.10 native VP1 sequence
Genbank: AF427118
>GII.10 tr Q915C7|Q915C7_9CALI Capsid protein OS = Human calicivirus NLV/Erfurt/546/00/DE OX = 173929 PE = 4 SV = 1

(SEQ ID NO: 35)

MKMASNDAAPSSDGAAGLVPESNNEVMALEPVAGASLAAPVTGQTNIIDPWIRMNFVQAPNGEFTVSPRNSP

GEVLLNLELGPELNPYLAHLSRMYNGYAGGMEVQIMLAGNAFTAGKLIFAAVPPHFPIENLSPPQITMFPHV

IIDVRTLEPVLLPMPDIRNSFFHFIQRDEPKMRLVAMLYTPLRSNGSGDDVFTVSCRVLTRPTPDFDFTYLV

PPTVESKSKPFTLPILTLGELTNSRFPLPIDVLYTNPNESAIVQCQNGRCTLDGELQGTTQLLPTGICAFRG

KVTQQVQDEHRGTHWNMTVTNLNGTPFDPTEDVPAPLGTPDFSGQIYGVISQRNTNTVPGEGDLPANRAHEA

VIATYSPKFTPKLGNIQFSTWETQDVSSGQPTKFTPVGLASVDANSHFDQWTLPSYSGALTLNMNLAPSVAP

VFPGECLLFFRSFIPLKGGYGNPAIDCLMPQEWVQHLYQESAPSLSDVALVRYVNPETGRTLFEAKLHRNGF

LTVARNSAGPVVAPTNGYFRFDSWVNQFYTLAPMGNGSGRRRMQ

GII.11 native VP1 sequence
Genbank: AB074893
>GII.11 tr|Q8V713|Q8V713_9CALI Capsid protein OS = Swine norovirus OX = 70297 PE = 4 SV = 1

(SEQ ID NO: 36)

MKMASSDAPPSTDGSAGLVPEVNNETMALEPVVGAPLAAPVAGQHNIIDPWIKMNFVQAPNGEFTVSPRNAP

GEILLDLELGPDLNPYLSHLARMYNGYAGGMEVQVVLAGNAFTAGKIIFAAVPPNFPAENLSAAQVTMCPHV

IVDVRQLEPVMLPMPDIRNKLFHYNQVDDPKLRLLAYLYTPLRANNAGDDVFTVSCRVLTRPTPDFEFMFLV

PPTVESKTKPFSLPGLTLDELSNSRFPAPIVQLYTNPHDNLIVQPQNGRCTIDGLLQGTTQLVSCNVCSFRG

TMGEGQPAAHSEDEIMPMAFNVQREIMLENLDGSPYDPTDDIPAVLGSPDFQGVMFGILSQRNTDGQTRAHE

AKVDTRAARFAPKLGFVVATVESTDFHANQPSRFTPVGLGGDTNRDFNQWQLPAYGGALTNNTNLAPPVMPV

YPGEQLLFFRSQLPSSGGVVAGWLDCLLPQEWVQHFFQESATSQSDVALVRYVNPTTGRVLFEAKLHKQGFL

TVAASGSYPLVVPADGYFRFESWVNQFYTLAPMGNGSGRRRAR

GII.12 native VP1 sequence
Genbank: AB032758
>GII.12 tr Q9QMK6|Q9QMK6_9CALI Capsid protein OS = Chitta virus OX = 104901 PE = 4 SV = 1

(SEQ ID NO: 37)

MKMASNDAAPSNDGAAGLVPEANNETMALEPVAGASIAAPLTGQNNIIDPWIRLNFVQAPNGEFTVSPRNSP

GEVLLNLELGPELNPYLAHLSRMYNGYAGGVEVQVLLAGNAFTAGKLVFAAVPPHFPLENISPGQITMFPHV

IIDVRTLEPVLLPLPDVRNNFFHYNQQNEPRMRLVAMLYTPLRSNGSGDDVFTVSCRVLTRPSPDFDFNYLV

PPTLESKTKPFTLPILTIGELTNSRFPVPIDELYTSPNESLVVQPQNGRCALDGELQGTTQLLPTAICSFRG

RINQKVSGENHVWNMQVTNINGTPFDPTGDVPAPLGTPDFSGKLFGVLSQRDHDNACRSHDAVIATNSAKFT

PKLGAIQIGTWEEDDVHINQPTKFTPVGLFENEGFNQWTLPNYSGALTLNMGLAPPVAPTFPGEQILFFRSH

IPLKGGVADPVIDCLLPQEWIQHLYQESAPSQSDVALIRFTNPDTGRVLFEAKLHRSGYITVANTGSRPIVV

PANGYFRFDTWVNQFYSLAPMGTGNGRRRVQ

-continued

GII.13 native VP1 sequence
Genbank: AB078334
>GII.13 tr Q8JW45|Q8JW45_9CALI Capsid protein OS = Norwalk-like virus OX = 95340 GN = capsid PE = 4 SV = 1

(SEQ ID NO: 38)

MKMASNDAAPSNDGAASLVPEGINETMPLEPVAGASIAAPVAGQTNIIDPWIRTNFVQAPNGEFTVSPRNSP

GEILLNLELGPDLNPYLAHLSRMYNGYAGGVEVQVLLAGNAFTAGKILFAAIPPNFLVDMISPAQITMLPHL

IVDVRTLEPIMTPLPDVRNVFYHFNNQPQPRMRLVAMLYTPLRSNGSGDDVFTVSCRVLTRPTPDFEFIYLV

PPSVESKTKPFTLPILTISELTNSRFPIPIEQLYTAPNETNVVQCQNGRCTLDGELQGTTQLLSSAVCFLQG

RTVADNGDNWDQNLLQLTYPNGASYDPTDEVPAPLGTQDFSGMLYGVLTQDNVNVSTGEAKNAKGIYISTTS

GKFTPKIGSIGLHSITEHVHPNQQSRFTPVGVAVDENTPFQQWVLPHYAGSLALNTNLAPAVAPTFPGEQLL

FFRSRVPCVQGLQGQDAFIDCLLPQEWVNHFYQEAAPSQADVALIRYVNPDTGRTLFEAKLHRSGFITVSHT

GAYPLVVPPNGHFRFDSWVNQFYSLAPMGTGNGRRRIQ

GII.14 native VP1 sequence
Genbank: AY130761
>GII.14 tr Q8BAC6 Q8BAC6_9CALI Major capsid protein VP1 OS = Human calicivirus NLV/M7/1999/US OX = 207241 PE = 4 SV = 1

(SEQ ID NO: 39)

MKMASNDATPSDDGAAGLVPEINNEVMALEPVAGASIAAPVVGQQNIIDPWIRNNFVQAPAGEFTVSPRNSP

GELLLDLELGPELNPYLAHLARMYNGHAGGMEVQIVLAGNAFTAGKILFAAIPPSFPYENLSPAQLTMCPHV

IVDVRQLEPVLLPMPDIRNVFYHYNQNNSPKLRLVAMLYTPLRANNSGDDVFTVSCRVLTRPSPDFQFTFLV

PPTVESKTKNFTLPVLRVSEMTNSRFPVVLDQMYTSRNENIIVQPQNGRCTTDGELLGTTTLQSVSICNFRG

TMQAKLNEQPRYQLQLTNLDGSPIDPTDDMPAPLGTPDFQAMLYGVASQRSSRDNATRAHDAQIDTAGDTFA

PKIGQVRFKSSSDDFDLHDPTKFTPIGVNVDDQHPFRQWSLPNYGGHLALNNHLAPAVTPLFPGEQILFFRS

HIPSAGGHTDGAIDCLLPQEWIEHFYQEAAPSQSDIALVRFINPDTGRVLLEAKLHKQGFLTVAASGDHPIV

MPTNGYFRFEAWVNPFYTLAPVGTGSGRRRIQ

GII.15 native VP1 sequence
Genbank: AY130761
>GII.15 tr Q8BAC6|Q8BAC6_9CALI Major capsid protein VP1 OS = Human calicivirus NLV/M7/1999/US OX = 207241 PE = 4 SV = 1

(SEQ ID NO: 40)

MKMASNDATPSDDGAAGLVPEINNEVMALEPVAGASIAAPVVGQQNIIDPWIRNNFVQAPAGEFTVSPRNSP

GELLLDLELGPELNPYLAHLARMYNGHAGGMEVQIVLAGNAFTAGKILFAAIPPSFPYENLSPAQLTMCPHV

IVDVRQLEPVLLPMPDIRNVFYHYNQNNSPKLRLVAMLYTPLRANNSGDDVFTVSCRVLTRPSPDFQFTFLV

PPTVESKTKNFTLPVLRVSEMTNSRFPVVLDQMYTSRNENIIVQPQNGRCTTDGELLGTTTLQSVSICNFRG

TMQAKLNEQPRYQLQLTNLDGSPIDPTDDMPAPLGTPDFQAMLYGVASQRSSRDNATRAHDAQIDTAGDTFA

PKIGQVRFKSSSDDFDLHDPTKFTPIGVNVDDQHPFRQWSLPNYGGHLALNNHLAPAVTPLFPGEQILFFRS

HIPSAGGHTDGAIDCLLPQEWIEHFYQEAAPSQSDIALVRFINPDTGRVLLEAKLHKQGFLTVAASGDHPIV

MPTNGYFRFEAWVNPFYTLAPVGTGSGRRRIQ

GII.16 native VP1 sequence
Genbank: AY502010
>GII.16 tr|Q6EAW4|Q6EAW4_9CALI Capsid protein OS = Norovirus GII OX = 122929
GN = ORF2 PE = 4 SV = 1

(SEQ ID NO: 41)

MKMASNDAAPSNDGAAGLVPEVNNETMALEPVAGASIAAPLTGQNNVIDPWIRLNFVQAPNGEFTVSPRNSP

GEILLNLELGPELNPYLAHLARMYNGYAGGVEVQVLLAGNAFTAGKLVFAAIPPHFPVDNLSPGQITMFPHV

IIDVRTLEPVLLPLPDVRNNFFHYNQQSDQRMRLVAMLYTPLRSNGSGDDVFTVSCRVLTRPSPDFDFNYLV

PPTVESKTKPFSVPVLTLNELTNSRFPVPIDAMYTSPNDSIVVQPQNGRATIDGELLGTTQLIPSGICSFRG

KITTHLSDDRHLWNIQVSNLNGTPFDPTDDVPAPLGMPDFSGQIFGVVSQRDTGTNPANRAHDAVLATYSAK

YTPKLGSVQIGTWDTEDLLERQPVKFTPVGLNEIGQDKHFDQWVLPNYSGALGLNMHLAPAVSPLFPGERLL

-continued

FFRSYIPLKGGHGDPFIDCLVPQEWIQHFYQESAPAQSSVALLRYVNPDTGRTLFEAKLHKEGFITVSSTEN

RPVIVPPNGYFRFDSWVNQFYSLAPMGTGNGRRRMQ

GII.17 native VP1 sequence
Genbank: AY502009
>GII.17 tr|Q6EAX3|Q6EAX3_9CALI Capsid protein OS = Norovirus GII OX = 122929
PE = 4 SV = 1

(SEQ ID NO: 42)

MKMASNDAAPSNDGATGLVPEINNETLPLEPVAGAAIAAPVTGQNNIIDPWIRTNFVQAPNGEFTVSPRNSP

GEILLNLELGPDLNPYLAHLSRMYNGYAGGVEVQVLLAGNAFTAGKILFAAVPPNFPVEFLSPAQITMLPHL

IVDVRTLEPIMIPLPDVRNTFFHYNNQPANRMRLVAMLYTPLRSNGSGDDVFTVSCRVLTRPTPDFEFTYLV

PPSVESKTKPFSLPILTISELTNSRFPAPIDSLFTAQNNNLNVQCQNGRCTLDGELQGTTQLLPSGICAFRG

RLTADVDGSHDDRWHMQLTNLNGTPFDPTEDVPAPLGTPDFTGLLFGVASQRNVGSNPNTTRAHEAVVSTTS

SQFVPKLGSVNFGSTSTDFQLQQPTKFTPVGIKIESGHEFDQWALPRYSGHLTLNMNLAPPIAPNFPGEQLL

FFRSNVPCAGGVSDGVIDCLLPQEWIQHFYQESAPSQSDVALIRYVNPDTGRTLFEAKLHRTGYITVAHSGD

YPLVVPSNGYFRFDSWVNQFYSLAPMGTGNGRRRVQ

GII.18 native VP1 sequence
Genbank: AB983218
>GII.18 tr A0A077KVU6|A0A077KVU6_9CALI Capsid protein VP1 OS = Norovirus Hu/GII/JP/2014/GII.P17_GII.17/Kawasaki323 OX = 1537090 GN = VP1 PE = 4 SV = 1

(SEQ ID NO: 43)

MKMASNDAAPSNDGAAGLVPEGNNETLPLEPVAGAAIAAPVTGQNNIIDPWIRTNFVQAPNGEFTVSPRNSP

GEILLNLELGPDLNPYLAHLSRMYNGYAGGVEVQVLLAGNAFTAGKILFAAVPPNFPVEFLSPAQITMLPHL

IVDVRTLEPIMIPLPDVRNTFFHYNNQPNSRMRLVAMLYTPLRSNGSGDDVFTVSCRVLTRPTPDFEFTYLV

PPSVESKTKPFSLPILTLSELTNSRFPVPIDSLFTAQNNVLQVQCQNGRCTLDGELQGTTQLLPSGICAFRG

RVTAETDHRDKWHMQLQNLNGTTYDPTDDVPAPLGTPDFKGVVFGVASQRNVGNDAPGSTRAHEAVISTYSP

QFVPKLGSVNFRSNDNDFQLQPTKFTPVGINDDGDHPFRQWELPDYSGLLTLNMNLAPPVAPNFPGEQLLFF

RSFVPCSGGYNQGIVDCLIPQEWIQHFYQESAPSQSDVALIRYVNPDTGRTLFEAKLHRSGYITVAHSGDYP

LVVPANGYFRFDSWVNQFYSLAPMGTGNGRRRAQ

GII.19 native VP1 sequence
Genbank: AY823304
>GII.19 tr Q2VTK0|Q2VTK0_9CALI Capsid protein OS = Norovirus swine/GII/OH-QW101/03/US OX = 316619 PE = 4 SV = 1

(SEQ ID NO: 44)

MMMASNDATAPTDGAAGLVPEVTNETMALEPVAGAALAAPVVGQHNVIDPWIRGNFVQAPNGEFTVSPRNSP

GEVLLNLELGPELNPYLAHLARMYNGYAGGMEVQVVLAGNAFAAGKIIFAAVPPSFPVDALSAPTITMCPHV

IVDVRQLEPVLLPMPDVRNNFFHYNQSSDPKLRLVAMLYTPLRANSPTDDVFTVSCRVLTRPSPDFEFTFLI

PPTVESKSKPFTIPQLTLSELSNSRFPAPIDMLYTSPNDNIVVQPQNGRCTLDGELQGTTQLQPSLICSFRG

VTLNETSRMLVDQEEEEEGEVQRPQARAFNHEYHLQLQNLDGTDYDPAGDLPATLGAPDFIGTVYGVVSQRT

TRDSAARAHEAKITTSDPRYAPKLGSVEFVTESTDIVLNDQTKFTPVGLAHNRAVDYKQWELPHYAGELTAN

TNLAPPVAPVYPGEQLLFFRSNLPLAGGTAASVLDCLLPQEWIQHFYQESFAPQSDIALLRYVNPDTGRVLF

EAKLHRQGYITVAGAGTSPVAVPPNGYFRFESWVSQFYTLAPMGSGTGRRRNQ

GII.20 native VP1 sequence
Genbank: AY823306
>GII.20 tr Q2VTJ4|Q2VTJ4_9CALI Capsid protein OS = Norovirus swine/GII/OH-QW170/03/US OX = 316621 PE = 4 SV = 1

(SEQ ID NO: 45)

MKMASSDAAPSSDGSAGLVPEVNSETMALEPVVGAPLAAPVAGQHNIIDPWIKLNFVQAPNGEFTVSPRNAP

GEILLDLELGPDLNPYLAHLSRMYNAYAGGMEVQVILAGNAFTAGKIIFAAVPPNFPLENLSAAQITMCPHI

IVDVRQLEPVMLPMPDVRNRLFHYNQVREPRLRLVAYLYTPLRANNAGDDVFTVSCRVLTRPSQDFEFMFLV

PPSVESKTKPFSLPNLTLAELSNSRFPLPIEQLYTNPLDNLVVQPQNGRCTIDGILLGTTQLVPSLICSMRG

-continued

TLEADQASGHTDDESVQSRAFNRQRSLMLENPDGSAFDPSDEVPAVLGVPDFRGVVFGVLSQRNNGDTTRSH

EAKIDTRRPRYAPKLGFVEVLTESDDFQNGPPTKFTPVGLGGDGNPDFQQWALPDYGGALTNNTNLAPPVVP

VYPGEQILFFRSQLPSSGGTVAGWLDCLLPQEWIQHFYQDSAAAQSDVALVRYINPATGRVLFEAKLHRQGF

LTVSAAGPHPVVAPADGYFRFESWVNQFYTLAPMGNGSGRRRVY

GII.21 native VP1 sequence
Genbank: AB542917
>GII.21 tr E3WAN8|E3WAN8_9CALI Capsid protein VP1 OS = Norovirus
Hu/OC07118/2007/JPOX = 710666 PE = 4 SV = 1

(SEQ ID NO: 46)

MKMASNDANPSSDGSANLVPEISNEVMALEPVAGAAIAAPVAGQQNIIDPWIRNNFVQAPGGEFTVSPRNAP

GEVLLNLPLSPDINPYLAHLSRMYNGYAGGVEVEVVLAGNAFTAGKIIFAAVPPNFPPENLSPSQITMLPHI

IVDVRQLEPVRIPLPDVRNNFYHYSRENDSTLRLIAMLYTPLRANNAGDDVFTVSCRVLTRPSPDFDFIFLV

PPTVESKSKPFTIPMLTIEEMTNSRFPAPLELMTTGPSHDIVVQPQNGRCTIDGVLLGTTQLSPVNICSLRG

VPTKRINGNDNCFVQLENPNGSAYDPTEDIPAVLGSPDFVGELYGTITQRSSDNSTRAHPFTLNTGSPRYTP

KIGSVDIRVTDVSDLQDHDPVKLTPVGLSGDRGSIHQWQLPNYSGVATHNMHLAPSVAPLFPGEQILFFRST

VPGCGGYPNSNIDCLIPQEWVQHFYQEGAPARTDVALLRFINPDTGRVLFECKLHKHGFITVAYSGNHDLVM

PPNGYFRFESWVNQFHTLAPMGTGSGRRRIQ

GII.22 native VP1 sequence
Genbank: AB542917
>GII.22 tr|E3WAN8|E3WAN8_9CALI Capsid protein VP1 OS = Norovirus
Hu/OC07118/2007/JPOX = 710666 PE = 4 SV = 1

(SEQ ID NO: 47)

MKMASNDANPSSDGSANLVPEISNEVMALEPVAGAAIAAPVAGQQNIIDPWIRNNFVQAPGGEFTVSPRNAP

GEVLLNLPLSPDINPYLAHLSRMYNGYAGGVEVEVVLAGNAFTAGKIIFAAVPPNFPPENLSPSQITMLPHI

IVDVRQLEPVRIPLPDVRNNFYHYSRENDSTLRLIAMLYTPLRANNAGDDVFTVSCRVLTRPSPDFDFIFLV

PPTVESKSKPFTIPMLTIEEMTNSRFPAPLELMTTGPSHDIVVQPQNGRCTIDGVLLGTTQLSPVNICSLRG

VPTKRTNGNDNCFVQLENPNGSAYDPTEDIPAVLGSPDFVGELYGTITQRSSDNSTRAHPFTLNTGSPRYTP

KIGSVDIRVTDVSDLQDHDPVKLTPVGLSGDRGSIHQWQLPNYSGVATHNMHLAPSVAPLFPGEQILFFRST

VPGCGGYPNSNIDCLIPQEWVQHFYQEGAPARTDVALLRFINPDTGRVLFECKLHKHGFITVAYSGNHDLVM

PPNGYFRFESWVNQFHTLAPMGTGSGRRRIQ

GII.23 native VP1 sequence
Genbank: AJ844470
>GII.23 tr|Q3V574|Q3V574_9CALI Capsid protein OS = Norwalk virus
Hu/NV/Chiba/040502/2004/JPOX = 295718 PE = 4 SV = 1

(SEQ ID NO: 48)

MKMASKDASPSTDGAANLVPESQQEVLALQPVAGAQIAAPVAGQFNVIDPWIYQNFVQAPEGEFTVSPRNST

GEILMNLELGPQLNPYLAHLARMYNAYAGGFEVQVLLAGNAFTAGKIIVCAVPPNFPLQNISAAQATQLPHV

VVDVRQLEPVVLPLPDVRAGFYHYNQVEESRMRLVAILYTPLRTNSAGDDAFTVSCRILTRPAPDFSFFFLI

PPTIESKTTPFTLPRLPISEMTNSRFPLVIKGMVVDPNLPLQANFQNGRITLDGELQGTTLPTSTSIGRISG

TYMSSTPSRIIQHEDSGDSTQPRVFNPVWMDLTENNWTEFQPFNDQPAPLGCPDFKAKILGTLIRQPNNGSY

YFDAYLDTRQHGTFAPYTGHAAVHSDQQAGHLAQGYKIQFSPTGIESDQNTDLNQLPDYGGAMTVSKGLAPA

AAPDFPGEMILYFVSDMPVRNPNGERRDTEILCLLPQEMVTHFYEQQAPSQGDVALVRYINAETGRVMFEGK

LHRNGFFTVSATARTLIVPDGYFRFDSWVNRFYTLSPMGTGNGRRRARMLE

GII.24 native VP1 sequence
Genbank: KU306738
>GII.24 tr|A0A142KD02|A0A142KD02_9CALI Major capsid protein OS = Norovirus
GII OX = 122929 PE = 4 SV = 1

(SEQ ID NO: 49)

MKMASNDAAPSNDGASSLVPEINNETMALEPVAGGAIAAPLIGQTNFIDPWIRNNYVQAPNGEFTISPRNSP

GEILLNLELGPELNPFLAHLARMYNGYAGGVDVQVIMAGNAFTAGKVIFAAVPPHFPVESLSPPQITMFPHI

-continued

```
IVDVRTLEPINIPIPDVRNNFFHYNQNNEPRMRLVAMLYTPLRSNGSADDVFTVSCRVLTKPSADFEFNYLV

PPTVESRTKPFTIPILTIGEMTNSRFPVAIDMLYTSPTENLVVQPQNGRCTLEGELLGTTQLVTPNICSLRG

AITGHEGNDDNHKWHMTVTNPNGSAFDPTEDVPAPLGTPDFIGDVYGVLSQRNRNIESGQTAPANRSHEAVI

STRSNKFTPKLGSVMIATWNTNDVENQPTKFTPVGLENPGSFHQWELPNYSGALTLNMGLAPPVFPTYPGEQ

LLFFRSYIPLKGGFGNSIIDCLVPQEWIQHFYQESAPSQTDVALIRYVNPETGRVLFEAKLHRQGFITVAKT

GDSPINVPANGYFRFDSWVNSFYSLAPMGTGNGRRRIQ

GII.25 native VP1 sequence
Genbank: KY225989
>GII.25 tr|A0A1V0QSQ1|A0A1VOQSQ1_9CALI Major capsid protein OS = Norovirus
GII OX = 122929 GN = ORF2 PE = 4 SV = 1
                                                              (SEQ ID NO: 50)
MKMASNDAAPSNDGAANLVPEANKEVMALEPVAGGAIAAPLTGQTNIIDPWIMNNFVQAPNGEFTISPRNSP

GEVLLNLELGPDLNPFLAHLSRMYNGYAGGVEVQVIMAGNAFTAGKVIFAAVPPHFPVDNLSPPQVTMFPHV

IVDVRTFEPILLPLPDVRNSFYHYNQVNDSRMRLIAMLYTPLRSNGSSDDVFTVSCRVLTRPTPDFEFNYLV

PPTVESRTKPFSVPILTIGEMTNSRFPLPIDMLYTSPTENIVVQPQNGRCTLEGELLGTTQLVTPNICALRG

EIRGHEGSGDNHKWHFMVRSPNGAAFDPTEDVPAPLGTPDFIGDVFGVLSQRNRNTDSGQSGPANRSHDAVV

STRDSRFTPKLGSVMIATWETSDIQDQPTRFTPVGLENPDHYNQWQLPNYSGALTLNMGLAPSVFPTYPGEQ

ILFFRSYIPLKGGYGDSHIDCLVPQEWIQHFYQESAPSQTDVALIRYVNPETGRVLFEAKLHRQGYITVARS

GSSPINVPANGYFRFDSWVNQFYSLAPMGTGNGRRRIQ
```

In some embodiments, the one or more amino acid substitutions that stabilize the recombinant Norovirus VLP in its assembled form are incorporated into a modified GII VP1 sequence that represents a consensus of the GII VP1 protein strains, such as the consensus GII.4 VP1 protein described in Para et al. (Vaccine, 2012; 30(24:3580-3586) and provided as: GII.4c VP1 sequence (GenBank Accession No. QEN95698.1) (SEQ ID NO: 51)

```
MKMASSDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGNAFTAGKIIFAAVPPNFPTEGLSPSQVTMFPHIIVDVRQ

LEPVLIPLPDVRNNFYHYNQSNDPTIKLIAMLYTPLRANNAGDDVFTVSC

RVLTRPSPDFDFIFLVPPTVESRTKPFTVPILTVEEMTNSRFPIPLEKLF

TGPSGAFVVQPQNGRCTTDGVLLGTTQLSPVNICTFRGDVTHIAGTQEYT

MNLASQNWNNYDPTEEIPAPLGTPDFVGKIQGVLTQTTRGDGSTRGHKAT

VSTGSVHFTPKLGSVQFSTDTSNDFETGQNTKFTPVGVVQDGSTTHQNEP

QQWVLPDYSGRDSHNVHLAPAVAPTFPGEQLLFFRSTMPGCSGYPNMNLD

CLLPQEWVQHFYQEAAPAQSDVALLRFVNPDTGRVLFECKLHKSGYVTVA

HTGQHDLVIPPNGYFRFDSWVNQFYTLAPMGNGTGRRRAL
```

The amino acid numbering used herein for residues of the GII VP1 protein is with reference to the GII.4 VP1 sequence provided as SEQ ID NO: 29. With reference to the GII.4 VP1 sequence provided as SEQ ID NO: 29, the shell (S) domain comprises residues 1-221, the Protruding domain (P) comprises residues 222-540) and is divided into subdomains P1 (residues 222-274 (P1 subdomain 1) and 406-540 (P1 subdomain 2) and P2 (residues 275-405). The position numbering of the VP1 protein may vary between GII VP1 protein stains, but the sequences can be aligned to determine relevant structural domains and residues of interest.

In some embodiments, the recombinant Norovirus VP1 VLP composed of GII VP1 proteins comprises a self-assembly of 90 Norovirus VP1 dimers into an icosahedral shaped VLP. The diameter of the recombinant Norovirus VP1 VLP composed of GII VP1 proteins is from about 35 to about 45 nm in the T=3 symmetry, such as from about 38 to about 40 nm, for example, about 37 nm, about 38 nm, about 39 nm, or about 40 nm. Human Norovirus VLPs can also self-assemble in T=1 and T=4 configuration. T=1 VLPs contain 60 VP1 monomers and are about 23 nm in diameter, while T=4 VLPs have 240 VP1 monomers and are about 55 nm in diameter. In several embodiments, the recombinant Norovirus VP1 VLP composed of GII VP1 proteins does not comprise a VP2 protein and/or genetic material.

Modification of the GII VP1 proteins with the one or more amino acid substitutions as described herein increases the stability (such as maintaining the assembled icosahedral VLP structure) of the corresponding VLP in the assembled compared to VLPs formed from unmodified GII VP1 proteins. For example, recombinant VLPs formed from the recombinant GII VP1 proteins comprising the one or more amino acid substitutions as described herein have increased thermal stability (such as maintaining the assembled icosahedral VLP structure at increased temperature) compared to VLPs formed from unmodified GII VP1 proteins.

As described in the examples, VLPs formed from native Norovirus I VP1 proteins are prone to disassembly in the presence of certain antibodies, such as mAb1227. Accordingly, VLPs formed from the recombinant GII VP1 proteins as described herein have increased resistance to disassembly when incubated with mAb1227, for example at 1:2 molar ratio (1 VP1: 2 Fab) for 1 hour at room temperature in PBS, compared to corresponding VLPs formed from native GII VP1 proteins.

In some embodiments, a recombinant Norovirus VLP comprising a multimer of a recombinant Norovirus GII VP1 proteins is provided. In some embodiments, the recombinant Norovirus GII VP1 proteins in the VLP comprise amino acid substitutions set forth as one or more of the following pairs of cysteine substitutions that form a non-natural interprotomer disulfide bond: N112C/A116C, N189C/D194C, S134C/P60C, M140C/P217C, and P129C/R223C. Formation of the interprotomer disulfide bond stabilizes the VLP in its assembled form.

The recombinant Norovirus GI VP1 protein in the VLP can be selected from any GI VP1 protein, such as a GII.1, GII.2, GII.3, GII.4, GII.4c, GII.5, GII.6, GII.7, GII.8, GII.9, GII.10, GII.11, GII.12, GII.13, GII.14, GII.15, GII.16, GII.17, GII.18, GII.19, GII.20, GII.21, GII.22, GII.23, GII.24, or GII.25 VP1 protein that comprises the one or more amino acid substitutions. In several embodiments, the recombinant Norovirus GII VP1 protein in the VLP is a GII.4c VP1 protein comprising the one or more amino acid substitutions.

In some embodiments, the recombinant Norovirus GII VP1 protein comprises one or more of the following pairs of cysteine substitutions that form a non-natural interprotomer disulfide bond: N112C/A116C, N189C/D194C, S134C/P60C, M140C/P217C, and P129C/R223C, and an amino acid sequence at least 80% (such as at least 90%, at least 95%, or at least 99%) identical to any one of SEQ ID NOs: 26-51.

In some embodiments, the recombinant Norovirus GII VP1 protein comprises N112C/A116C substitutions that form a non-natural interprotomer disulfide bond, and an amino acid sequence at least 80% (such as at least 90%, at least 95%, or at least 99%) identical to any one of SEQ ID NOs: 26-51. In some embodiments, the recombinant Norovirus GII VP1 protein comprises N112C/A116C substitutions that form a non-natural interprotomer disulfide bond, and an amino acid sequence at least 80% (such as at least 90%, at least 95%, or at least 99%) identical to SEQ ID NO: 51. The non-natural interprotomer disulfide bond formed by the N112C/A116C substitutions is located at the interface between each A-A monomer pair around the 5-fold symmetry axes and between each B-C monomer pair around the 3-fold symmetry axes in the capsid.

In some embodiments, the recombinant Norovirus GII VP1 protein comprises N189C/D194C substitutions that form a non-natural interprotomer disulfide bond, and an amino acid sequence at least 80% (such as at least 90%, at least 95%, or at least 99%) identical to any one of SEQ ID NOs: 26-51. In some embodiments, the recombinant Norovirus GII VP1 protein comprises N189C/D194C substitutions that form a non-natural interprotomer disulfide bond, and an amino acid sequence at least 80% (such as at least 90%, at least 95%, or at least 99%) identical to SEQ ID NO: 51. The non-natural interprotomer disulfide bond formed by the N189C/D194C substitutions located at the interface between each A-A monomer pair around the 5-fold symmetry axes and between each B-C monomer pair around the 3-fold symmetry axes in the capsid.

In some embodiments, the recombinant Norovirus GII VP1 protein comprises S134C/P60C substitutions that form a non-natural interprotomer disulfide bond, and an amino acid sequence at least 80% (such as at least 90%, at least 95%, or at least 99%) identical to any one of SEQ ID NOs: 26-51. In some embodiments, the recombinant Norovirus GII VP1 protein comprises S134C/P60C substitutions that form a non-natural interprotomer disulfide bond, and an amino acid sequence at least 80% (such as at least 90%, at least 95%, or at least 99%) identical to SEQ ID NO: 51. The non-natural interprotomer disulfide bond formed by the S134C/P60C substitutions is located at the interface between each A-A monomer pair around the 5-fold symmetry axes and between each B-C monomer pair around the 3-fold symmetry axes in the capsid.

In some embodiments, the recombinant Norovirus GII VP1 protein comprises M140C/P217C substitutions that form a non-natural interprotomer disulfide bond, and an amino acid sequence at least 80% (such as at least 90%, at least 95%, or at least 99%) identical to any one of SEQ ID NOs: 26-51. In some embodiments, the recombinant Norovirus GII VP1 protein comprises M140C/P217C substitutions that form a non-natural interprotomer disulfide bond, and an amino acid sequence at least 80% (such as at least 90%, at least 95%, or at least 99%) identical to SEQ ID NO: 51. The non-natural interprotomer disulfide bond formed by the M140C/P217C substitutions is located within the icosahedral asymmetric unit of the VLP and links monomers A-B, B-C, and C-A).

In some embodiments, the recombinant Norovirus GII VP1 protein comprises P129C/R223C substitutions that form a non-natural interprotomer disulfide bond, and an amino acid sequence at least 80% (such as at least 90%, at least 95%, or at least 99%) identical to any one of SEQ ID NOs: 26-51. In some embodiments, the recombinant Norovirus GII VP1 protein comprises P129C/R223C substitutions that form a non-natural interprotomer disulfide bond, and an amino acid sequence at least 80% (such as at least 90%, at least 95%, or at least 99%) identical to SEQ ID NO: 51. The non-natural interprotomer disulfide bond formed by the P129C/R223C substitutions is located within the icosahedral asymmetric unit of the VLP and links monomers A-B, B-C, and C-A).

In some embodiments, the recombinant Norovirus GII VP1 protein further comprises one or more additional amino acid substitutions that stabilize the assembly of the recombinant Norovirus GII VP1 proteins in the VLP.

Exemplary protein sequences of recombinant GII VP1 proteins containing the amino acid substitutions as described herein are provided below. Norovirus VLPs composed of these recombinant VP1 proteins have increased stability (such as increased thermal stability) compared to Norovirus VLPs composed of corresponding unmodified VP1 proteins:

```
GII.4c N112C/A116C
                                          (SEQ ID NO: 52)
MKMASNDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGCAFTCGKIIFAAVPPNFPTEGLSPSQVTMFPHIIVDVRQ

LEPVLIPLPDVRNNFYHYNQSNDPTIKLIAMLYTPLRANNAGDDVFTVSC

RVLTRPSPDFDFIFLVPPTVESRTKPFTVPILTVEEMTNSRFPIPLEKLF

TGPSGAFVVQPQNGRCTTDGVLLGTTQLSPVNICTFRGDVTHIAGTQEYT

MNLASQNWNNYDPTEEIPAPLGTPDFVGKIQGVLTQTTRGDGSTRGHKAT

VSTGSVHFTPKLGSVQFSTDTSNDFETGQNTKFTPVGVVQDGSTTHQNEP

QQWVLPDYSGRDSHNVHLAPAVAPTFPGEQLLFFRSTMPGCSGYPNMNLD

CLLPQEWVQHFYQEAAPAQSDVALLRFVNPDTGRVLFECKLHKSGYVTVA

HTGQHDLVIPPNGYFRFDSWVNQFYTLAPMGNGTGRRRAL
```

-continued

GII.4c N189C/D194C (SEQ ID NO: 53)

MKMASNDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGNAFTAGKIIFAAVPPNFPTEGLSPSQVTMFPHIIVDVRQ

LEPVLIPLPDVRNNFYHYNQSNDPTIKLIAMLYTPLRACNAGDCVFTVSC

RVLTRPSPDFDFIFLVPPTVESRTKPFTVPILTVEEMTNSRFPIPLEKLF

TGPSGAFVVQPQNGRCTTDGVLLGTTQLSPVNICTFRGDVTHIAGTQEYT

MNLASQNWNNYDPTEEIPAPLGTPDFVGKIQGVLTQTTRGDGSTRGHKAT

VSTGSVHFTPKLGSVQFSTDTSNDFETGQNTKFTPVGVVQDGSTTHQNEP

QQWVLPDYSGRDSHNVHLAPAVAPTFPGEQLLFFRSTMPGCSGYPNMNLD

CLLPQEWVQHFYQEAAPAQSDVALLRFVNPDTGRVLFECKLHKSGYVTVA

HTGQHDLVIPPNGYFRFDSWVNQFYTLAPMGNGTGRRRAL

GII.4c P60C/S136C (SEQ ID NO: 54)

MKMASNDANPSDGSTANLVPEVNNEVMALEPVVGAAIAAPVAGQQNVIDP

WIRNNFVQACGGEFTVSPRNAPGEILWSAPLGPDLNPYLSHLARMYNGYA

GGFEVQVILAGNAFTAGKIIFAAVPPNFPTEGLSPCQVTMFPHIIVDVRQ

LEPVLIPLPDVRNNFYHYNQSNDPTIKLIAMLYTPLRANNAGDDVFTVSC

RVLTRPSPDFDFIFLVPPTVESRTKPFTVPILTVEEMTNSRFPIPLEKLF

TGPSGAFVVQPQNGRCTTDGVLLGTTQLSPVNICTFRGDVTHIAGTQEYT

MNLASQNWNNYDPTEEIPAPLGTPDFVGKIQGVLTQTTRGDGSTRGHKAT

VSTGSVHFTPKLGSVQFSTDTSNDFETGQNTKFTPVGVVQDGSTTHQNEP

QQWVLPDYSGRDSHNVHLAPAVAPTFPGEQLLFFRSTMPGCSGYPNMNLD

CLLPQEWVQHFYQEAAPAQSDVALLRFVNPDTGRVLFECKLHKSGYVTVA

HTGQHDLVIPPNGYFRFDSWVNQFYTLAPMGNGTGRRRAL

GII.4c M140C/P217C (SEQ ID NO: 55)

MKMASNDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGNAFTAGKIIFAAVPPNFPTEGLSPSQVTCFPHIIVDVRQ

LEPVLIPLPDVRNNFYHYNQSNDPTIKLIAMLYTPLRANNAGDDVFTVSC

RVLTRPSPDFDFIFLVCPTVESRTKPFTVPILTVEEMTNSRFPIPLEKLF

TGPSGAFVVQPQNGRCTTDGVLLGTTQLSPVNICTFRGDVTHIAGTQEYT

MNLASQNWNNYDPTEEIPAPLGTPDFVGKIQGVLTQTTRGDGSTRGHKAT

VSTGSVHFTPKLGSVQFSTDTSNDFETGQNTKFTPVGVVQDGSTTHQNEP

QQWVLPDYSGRDSHNVHLAPAVAPTFPGEQLLFFRSTMPGCSGYPNMNLD

CLLPQEWVQHFYQEAAPAQSDVALLRFVNPDTGRVLFECKLHKSGYVTVA

HTGQHDLVIPPNGYFRFDSWVNQFYTLAPMGNGTGRRRAL

GII.4c P129C/R223C (SEQ ID NO: 56)

MKMASNDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGNAFTAGKIIFAAVPPNFCTEGLSPSQVTMFPHIIVDVRQ

LEPVLIPLPDVRNNFYHYNQSNDPTIKLIAMLYTPLRANNAGDDVFTVSC

-continued

RVLTRPSPDFDFIFLVPPTVESCTKPFTVPILTVEEMTNSRFPIPLEKLF

TGPSGAFVVQPQNGRCTTDGVLLGTTQLSPVNICTFRGDVTHIAGTQEYT

MNLASQNWNNYDPTEEIPAPLGTPDFVGKIQGVLTQTTRGDGSTRGHKAT

VSTGSVHFTPKLGSVQFSTDTSNDFETGQNTKFTPVGVVQDGSTTHQNEP

QQWVLPDYSGRDSHNVHLAPAVAPTFPGEQLLFFRSTMPGCSGYPNMNLD

CLLPQEWVQHFYQEAAPAQSDVALLRFVNPDTGRVLFECKLHKSGYVTVA

HTGQHDLVIPPNGYFRFDSWVNQFYTLAPMGNGTGRRRAL

C. Additional Description of the Recombinant Norovirus VLPs

Analogs and variants of the recombinant Norovirus VP1 protein may be used in the methods and systems of the present disclosure. Through the use of recombinant DNA technology, variants of the recombinant Norovirus VP1 protein may be prepared by altering the underlying DNA. All such variations or alterations in the structure of the recombinant Norovirus VP1 protein resulting in variants are included within the scope of this disclosure. Such variants include insertions, substitutions, or deletions of one or more amino acid residues, glycosylation variants, unglycosylated recombinant Norovirus VP1 protein, organic and inorganic salts, covalently modified derivatives of the recombinant Norovirus VP1 protein, or a precursor thereof. Such variants may maintain one or more of the functional, biological activities of the recombinant Norovirus VP1 protein, such as binding to cell surface receptor. The recombinant Norovirus VP1 protein thereof can be modified, for example, by PEGylation, to increase the half-life of the protein in the recipient, to retard clearance from the pericardial space, and/or to make the protein more stable for delivery to a subject.

In some embodiments, a recombinant Norovirus VP1 protein useful within the disclosure is modified by replacement of one or more naturally occurring side chains of the 20 genetically encoded amino acids (or D-amino acids) with other side chains, for example with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,668; 4,301,144; 4,668,417; 4,791,192; and 4,179,337.

III. Polynucleotides and Expression

Polynucleotides encoding a recombinant VP1 protein of any of the disclosed recombinant Norovirus VLPs are also provided. These polynucleotides include DNA, cDNA and RNA sequences which encode the recombinant VP1 protein, as well as vectors including the DNA, cDNA and RNA sequences. The genetic code to construct a variety of functionally equivalent nucleic acids, such as nucleic acids which differ in sequence but which encode the same protein sequence, or encode a conjugate or fusion protein including the nucleic acid sequence.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013).

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed recombinant Norovirus VP1 protein can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed recombinant Norovirus VP1 protein can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed recombinant VP1 protein can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium,* SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques. Where the host is prokaryotic, such as, but not limited to, *E. coli*, competent cells which are capable of DNA uptake can be prepared from cells harvested after exponential growth phase and subsequently treated by the $CaCl_2$ method using standard procedures. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines.

Modifications can be made to a nucleic acid encoding a disclosed recombinant Norovirus VP1 protein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In some embodiments, the disclosed recombinant Norovirus VP1 protein can be expressed in cells under conditions where the recombinant Norovirus VP1 protein self-assembles into VLPs which are secreted from the cells into the cell media, such as described in the examples. The medium can be centrifuged and the recombinant Norovirus VLPs purified from the supernatant.

The presence of Norovirus VLPs following recombinant expression of viral proteins can be detected using any suitable techniques, such as by electron microscopy, biophysical characterization, dynamic light scattering (DLS), selective chromatographic separation (e.g., ion exchange, hydrophobic interaction, and/or size exclusion chromatographic separation of the VLPs) and density gradient centrifugation. Further, Norovirus VLPs can be isolated by any suitable technique, such as density gradient centrifugation and identified by characteristic density banding.

VI. Immunogenic Compositions

Immunogenic compositions comprising one or more of the disclosed recombinant Norovirus VLPs and a pharmaceutically acceptable carrier are also provided. Such pharmaceutical compositions can be administered to subjects by a variety of administration modes known to the person of ordinary skill in the art, for example, intramuscular, intradermal, subcutaneous, intravenous, intra-arterial, intra-articular, intraperitoneal, intranasal, sublingual, tonsillar, oropharyngeal, or other parenteral and mucosal routes. In several embodiments, pharmaceutical compositions including one or more of the disclosed immunogens are immunogenic compositions. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pennsylvania, 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some instances it may be desirable to combine a disclosed immunogen with other pharmaceutical products (e.g., vaccines) which induce protective responses to other agents. For example, a composition including a recombinant Norovirus VLP as described herein can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age), such as an influenza vaccine or a varicella zoster vaccine. As such, a disclosed immunogen including a recombinant Norovirus VLP as described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VII. Methods of Inducing an Immune Response

The disclosed recombinant Norovirus VLPs can be administered to a subject to induce an immune response to the VP1 protein of the recombinant Norovirus VLP in the subject. In a particular example, the subject is a human The immune response can be a protective immune response, for example a response that inhibits subsequent infection with Norovirus. Elicitation of the immune response can also be used to treat or inhibit Norovirus infection and illnesses associated with the Norovirus infection.

A subject can be selected for treatment that has or is at risk for developing Norovirus infection, for example because of exposure or the possibility of exposure to the Norovirus. Following administration of a disclosed immunogen, the subject can be monitored for infection or symptoms associated with Norovirus infection.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize Norovirus infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen is provided in advance of any symptom, for example, in advance of infection. The prophylactic administration of the immunogen serves to prevent or ameliorate any subsequent infection. When provided therapeutically, the immunogen is provided at or after the onset of a symptom of infection, for example, after development of a symptom of Norovirus infection or after diagnosis with the Norovirus infection. The immunogen can thus be provided prior to the anticipated exposure to the Norovirus so as to attenuate the anticipated severity, duration or extent of an infection and/or associated disease symptoms, after exposure or suspected exposure to the Norovirus, or after the actual initiation of an infection.

The immunogens described herein, and immunogenic compositions thereof, are provided to a subject in an amount effective to induce or enhance an immune response against the recombinant VP1 protein in the Norovirus VLP in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to Norovirus VP1 protein. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., prevention of infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg.

In some embodiments, the recombinant Norovirus VLP is administered at a dose of 100 □g. In some embodiments, the does includes 100 □g of a first recombinant Norovirus VLP formed from GI.1 VP1 Proteins and 100 □g of a second recombinant Norovirus VLP formed from GII.4 VP1 proteins.

The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a disclosed recombinant Norovirus VLP, can include an amount that is ineffective at eliciting an immune response by administration of a single dose, but that is effective upon administration of multiple dosages, for example in a prime-boost administration protocol.

Upon administration of an immunogenic composition comprising a disclosed recombinant Norovirus VLP of this disclosure, the immune system of the subject typically responds to the immunogenic composition by producing antibodies specific for the recombinant Norovirus VLP included in the composition. Such a response signifies that an immunologically effective dose was delivered to the subject.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, the recombinant Norovirus VLP included in the immunogenic composition.

Norovirus infection does not need to be completely eliminated or reduced or prevented for the methods to be effective. For example, elicitation of an immune response to the recombinant Norovirus VLP can reduce or inhibit Norovirus infection by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to Norovirus infection in the absence of the immunogen. In additional examples, Norovirus replication can be reduced or inhibited by the disclosed methods. Norovirus replication does not need to be completely eliminated for the method to be effective. For example, the immune response elicited using one or more of the disclosed immunogens can reduce Norovirus replication by a desired amount, for example, by at least 10%, at least 20%, at least 50%, at least 60%, at least 70%, at least 80%, at least 90%, at least 95%, at least 98%, or even at least 100% (elimination or prevention of detectable Norovirus replication, as compared to Norovirus replication in the absence of the immune response.

In some embodiments, the disclosed immunogen is administered to the subject simultaneously with the administration of the adjuvant. In other embodiments, the disclosed immunogen is administered to the subject after the administration of the adjuvant and within a sufficient amount of time to induce the immune response.

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity include, but are not limited to, plaque reduction neutralization (PRNT) assays, microneutralization assays, flow cytometry based assays, single-cycle infection assays.

VIII. Methods of Detection and Diagnosis

Methods are also provided for the detection of the presence of an antibody that specifically binds to a solvent-accessible epitope on a Norovirus VLP. In one example, the presence of an antibody that specifically binds to a solvent-accessible epitope on a stabilized Norovirus VLP as provided herein is detected in a biological sample from a subject and can be used to identify a subject with a neutralizing antibody response to Norovirus. The sample can be any sample, including, but not limited to, tissue from biopsies, autopsies, and pathology specimens. Biological samples also include sections of tissues, for example, frozen sections taken for histological purposes. Biological samples further include body fluids, such as blood, serum, plasma, sputum, spinal fluid or urine. The method of detection can include contacting a sample with a stabilized Norovirus VLP as described herein, or conjugate thereof under conditions sufficient to form an immune complex, and detecting the immune complex (e.g., by detecting a detectable marker conjugated to a secondary antibody that binds to antibodies in the biological sample).

In one embodiment, a method for identifying an antibody that specifically binds to a solvent-accessible epitope on a Norovirus VLP is provided. A stabilized Norovirus VLP as provided herein contacted with a test antibody under conditions sufficient to form an immune complex. Detecting the presence of the immune complex identifies that the test antibody specifically binds to a solvent-accessible epitope on the Norovirus VLP. Contacting the test antibody with the stabilized norovirus VLP, and detecting the presence of the immune complex, can be accomplished using any suitable means. In some embodiments, the stabilized Norovirus VLP is fixed to a solid support and contacted with the test antibody (the primary antibody). The primary antibody is unlabeled and a secondary antibody or other molecule that can bind the primary antibody is utilized for detection. The secondary antibody is chosen that is able to specifically bind the specific species and class of the primary antibody. For example, if the first antibody is a human IgG, then the secondary antibody may be an anti-human-IgG. Other molecules that can bind to antibodies include, without limitation, Protein A and Protein G, both of which are available commercially. Suitable labels for the antibody, antigen binding fragment or secondary antibody are known and described above, and include various enzymes, prosthetic groups, fluorescent materials, luminescent materials, magnetic agents and radioactive materials.

In another embodiment, identifying a sample from a subject with a neutralizing antibody response to Norovirus is provided (for example, to confirm that the subject produced a neutralizing antibody response following vaccination). A stabilized Norovirus VLP as provided herein contacted with a biological sample comprising antibodies from a test subject under conditions sufficient to form an immune complex. Detecting the presence of the immune complex identifies the sample as from a subject with a neutralizing antibody response to Norovirus. Contacting the biological sample with the stabilized norovirus VLP, and detecting the presence of the immune complex, can be accomplished using any suitable means. In some embodiments, the stabilized Norovirus VLP is fixed to a solid support and contacted with the biological sample contacting antibodies (the primary antibodies). The primary antibodies are unlabeled and can be detected as noted above.

EXAMPLES

The following examples are provided to illustrate particular features of certain embodiments, but the scope of the claims should not be limited to those features exemplified.

Example 1

Disulfide-Stabilized Norovirus GU Virus-Like Particles Elicit Durable Blockade Antibody Titers and Focus Immune Response Toward Neutralizing Epitopes This example shows that norovirus GI.1 VLPs are unstable and contain a substantial fraction of dissociated VLP components. Broadly reactive, non-neutralizing antibodies isolated from vaccinated donors bound to the dissociated particles, but not the intact VLPs. Engineering interprotomer disulfide bonds within the shell domain prevented disassembly of the VLPs while preserving antibody accessibility to neutralizing epitopes. Mice immunized with stabilized GI.1 VLPs without adjuvant developed faster blockade antibody titers compared to wild-type GI.1 VLPs. Additionally, immunization with stabilized particles focused immune responses toward surface exposed epitopes and away from occluded epitopes. Thus, the recombinant Norovirus VLPs elicit a superior immune response in an animal model compared to VLPs formed from unmodified VP1 proteins.

Noroviruses are single-stranded RNA viruses that cause pandemic outbreaks of acute gastroenteritis[1]. They are the major viral agents of food-borne diseases worldwide and they are responsible for more than 200,000 deaths per year (mostly among infants and elderly in developing countries)[2]. Due to high infectivity, noroviruses are also a significant threat to transplant patients and immunocompromised individuals[3,4]. Although discovered over 50 years ago, no vaccine nor drugs (antibodies or small molecules) are currently licensed to prevent or treat norovirus infections[5].

In the absence of a widely available tissue-culture system that can sustain replication of human noroviruses, virus-like particles have been used as a surrogate to study the structural features of the capsid and as immunogens to elicit protective humoral responses[6-8]. Recently, VLPs have emerged as valuable immunogens for the elicitation of durable protective serological memory[9,10]. The most advanced norovirus vaccine candidate to date is a bivalent formulation comprising a mixture of GI.1 and GII.4 VLPs, administered intramuscularly[11-13]. Results from phase IIb clinical trials have revealed that the vaccine is highly immunogenic and can elicit high titers of blockade antibodies[11,14]. However, the vaccine is less than 50% protective against GI.1 challenge and, at least for GII.4, serum blockade titers wane rapidly following immunization[15,16]. In a recent study, ten antibodies were isolated from three donors after immunization with the bivalent vaccine[17]. The antibodies could be classified into two broad classes: 1) cross-reactive (capable of binding VLPs from genogroups I and II), but non-neutralizing and 2) genotype-specific (only targeting GII.4 variants) and neutralizing. Structural analysis of the antibody Fab fragments in complex with the P domain of GII.4 (2002 Farmington Hills strain) revealed cross GI-GII reactive antibodies to target a site on the P domain that would be completely buried in the context of the intact viral particle[17]. Similar antibodies (herein referred to as occluded-site antibodies) have been previously observed after immunization with norovirus VLPs in mice[18-20]. Two questions arise: how can such antibodies be elicited, and can vaccine performance be improved by preventing their elicitation? To shed light on these issues, we investigated the interaction between GI.1 norovirus VLPs and one antibody belonging to each class. First, we observed that GI.1 VLP preparations contained dissociated VP1 components even after extensive purification, with a substantial amount of VP1 dimers. The cross-reactive, but non-neutralizing, antibody A1227 bound strongly to VP1 dimers, but not to the intact particles, while the GI.1 specific and blockade antibody 512 could bind to VP1 dimers as well as to intact particles. Structure-based design of interprotomer disulfide bonds resulted in GI.1 VLPs that did not dissociate and did not bind occluded-site antibodies. Crucially, stabilization did not compromise accessibility to known neutralizing epitopes. Finally, immunization with stabilized VLPs elicited blockade titers more rapidly and appeared to focus the immune responses toward accessible (and potentially neutralizing) epitopes. Together, the data suggest interprotomer disulfide stabilization as an avenue to improve VLP-based norovirus vaccines.

Results

Figure 1A:
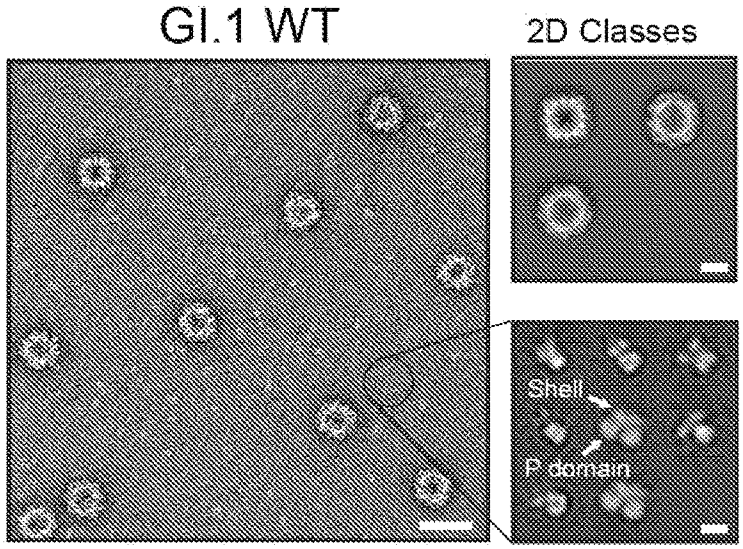
FIGS. 1A-1I. Dissociation of GI.1 Norovirus VLPs leads to exposure of occluded epitopes.
Figure 8:
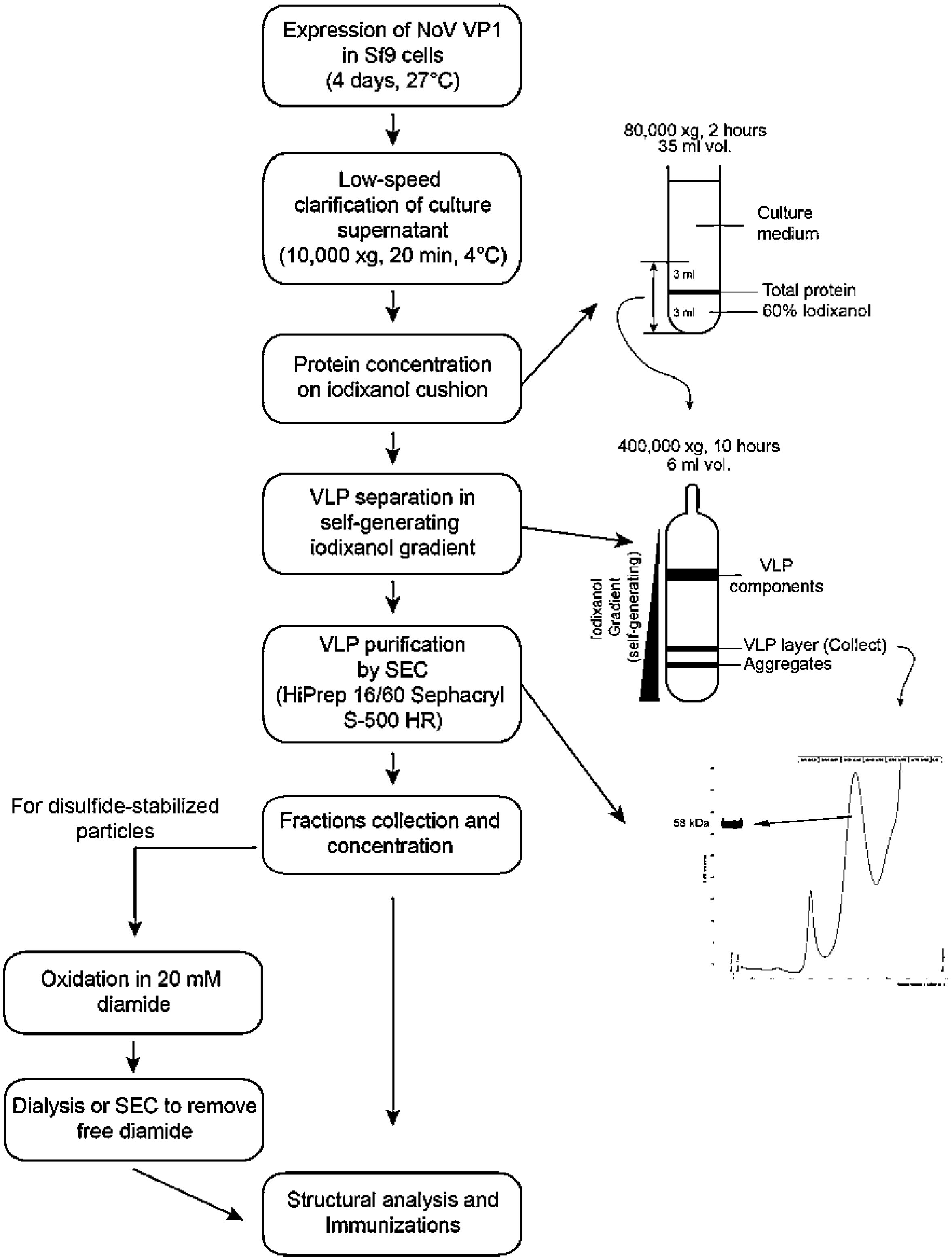
FIG. 8. Flow-chart for the production of GI.1 VLPs. Particles were expressed in Sf9 cells and collected from the cell culture supernatant. Iodixanol (OPTIPERP®) was used to concentrate and separate particles by ultracentrifugation. VLP layer was collected by side puncture and injected onto a Sephacryl S500 column. VLP peak eluted around 74 mL. Fractions were collected and concentrated in Amicon® spin column (50 kDa MWCO). To promote the formation of disulfide bonds, particles containing cysteine mutations were incubated with diamide for one hour and diamide removed by dialysis or by a second round of size-exclusion chromatography. Concentrated VLPs were used for EM analysis and mice immunizations.

GI.1 norovirus VLP preparations contain VP1 dimers and other oligomers that expose occluded-site epitopes. Serological analysis of antibody repertoires from humans vaccinated with a cocktail of GI.1 and GII.4 norovirus VLPs has identified broadly reactive, but non-neutralizing antibodies[17]. Binding data showed that one antibody belonging to this class (A1227) could bind to several VLPs from genogroup I and II, but no neutralization was observed against infectious GII.4 noroviruses in an organoid system[17]. The crystal structure of the A1227 Fab fragment bound to the GII.4 P domain revealed that the epitope for this antibody would be inaccessible when mapped on the surface of an intact GI.1 norovirus VLP (the only high-resolution structure of a human norovirus VLP available at the time)[17]. To determine how A1227 could interact with norovirus VLPs, we expressed the VP1 protein from GI.1 Norwalk strain (herein referred to as GI.1 WT) in insect cells and purified the self-assembled particles using a combination of gradient ultra-centrifugation and size-exclusion chromatography (FIG. 8). We first analyzed the GI.1 WT VLPs using negative staining electron microscopy (NS-EM). Although most of the particles were correctly formed and showed the expected diameter, analysis of 2D class averages of smaller proteins in the background revealed the presence of VLP components that appeared to be mostly VP1 dimers (FIG. 1*a*).

Figure 1B:
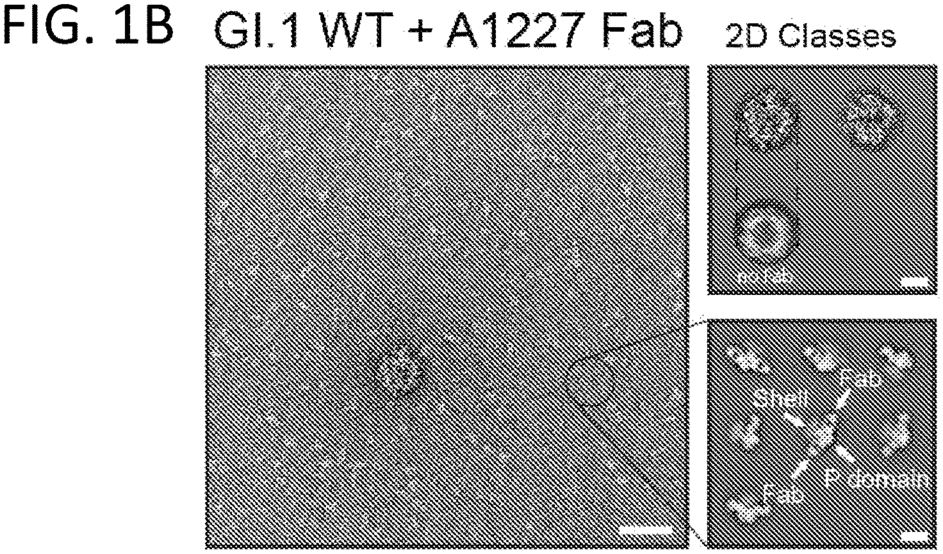
Figure 1C:
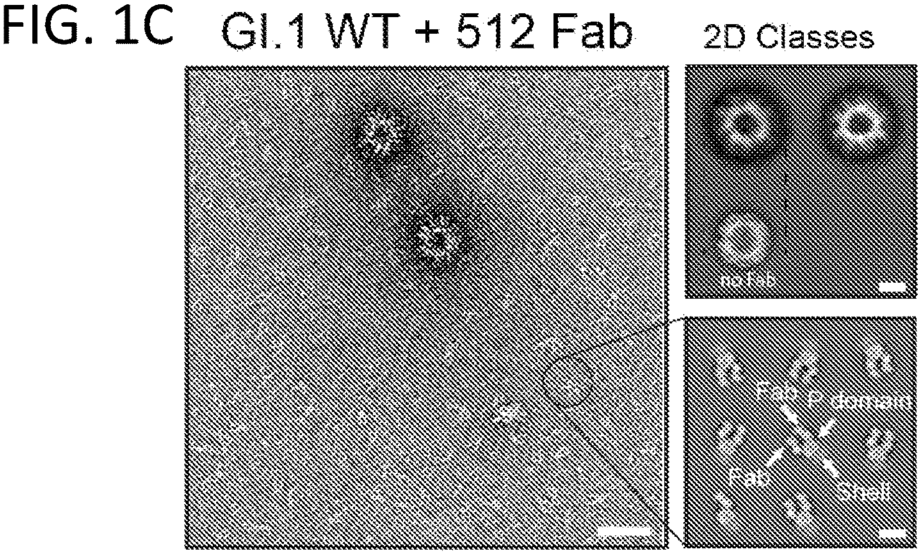
Figure 9A:
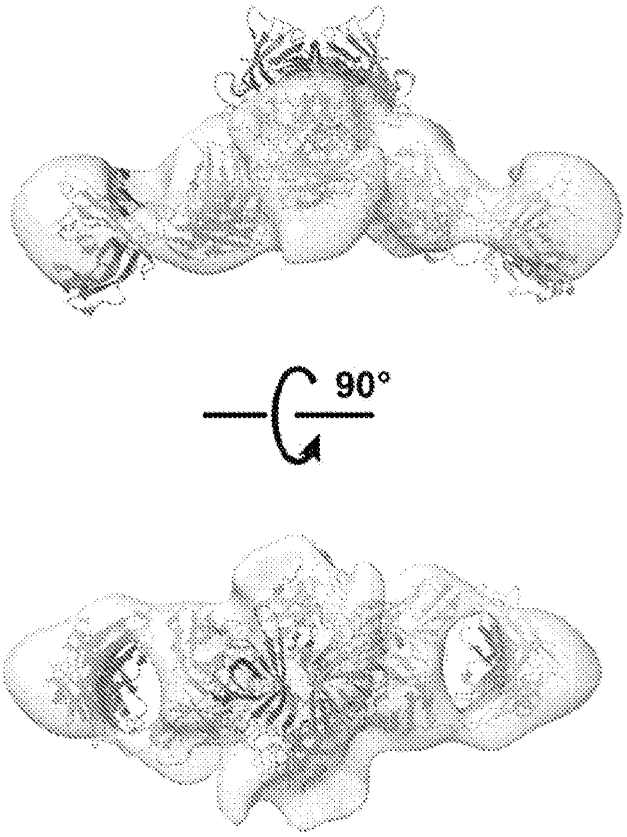
FIGS. 9A-9B. Three-dimensional reconstructions of VP1/A1227 Fab complex and VP1/512 Fab complex.
Figure 9B:
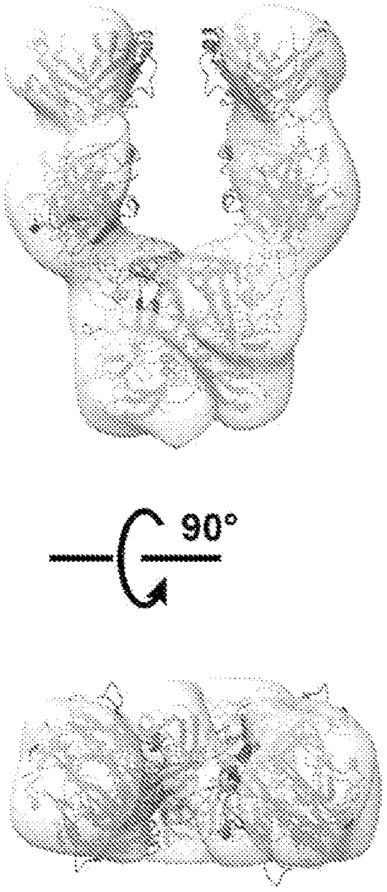
Figure 10A:
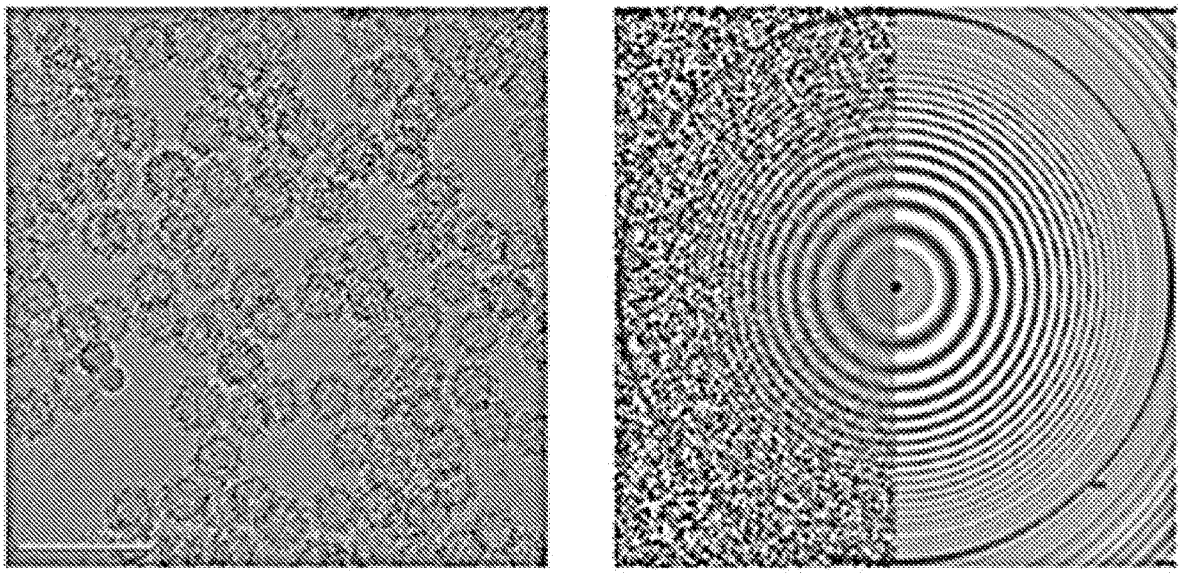
FIGS. 10A-10E. Cryo-EM data collection and map refinement.
Figure 10B:
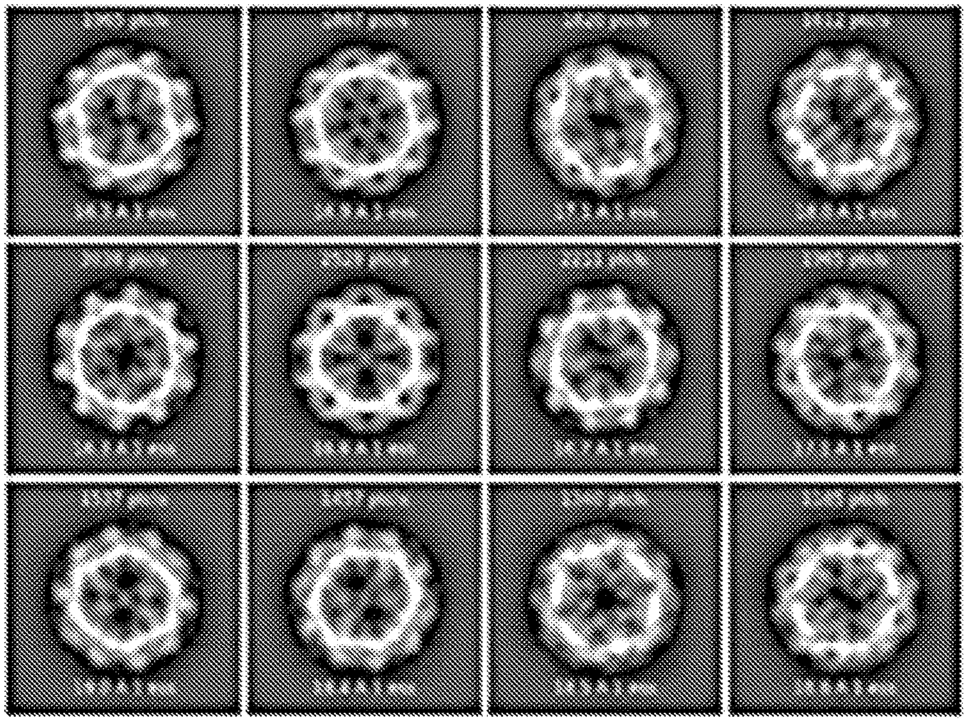
Figure 10C:
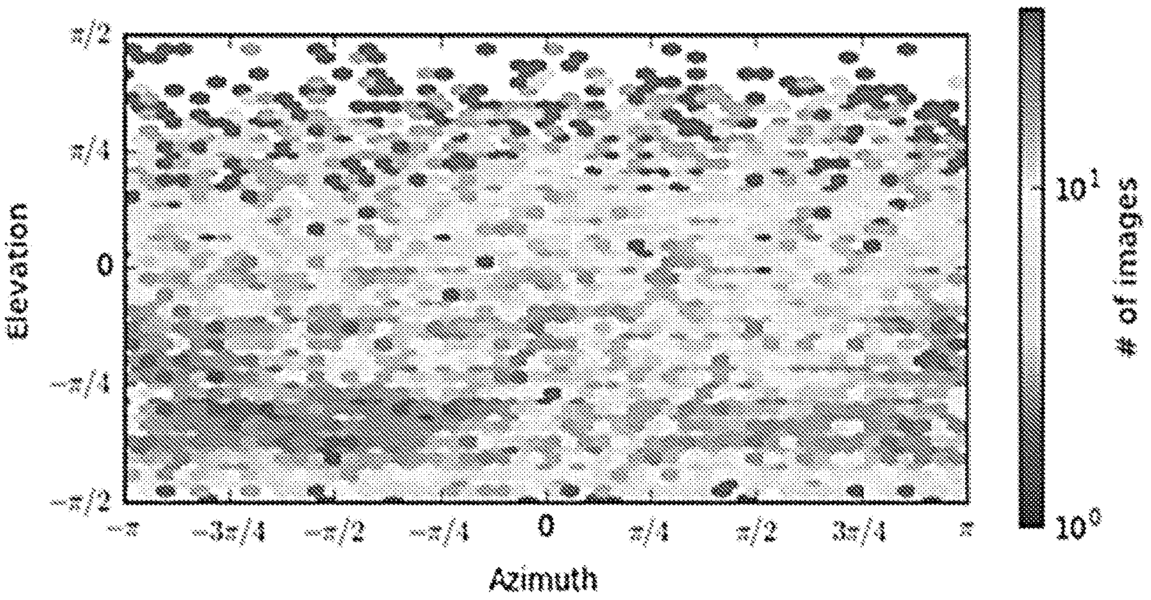
Figure 10D:
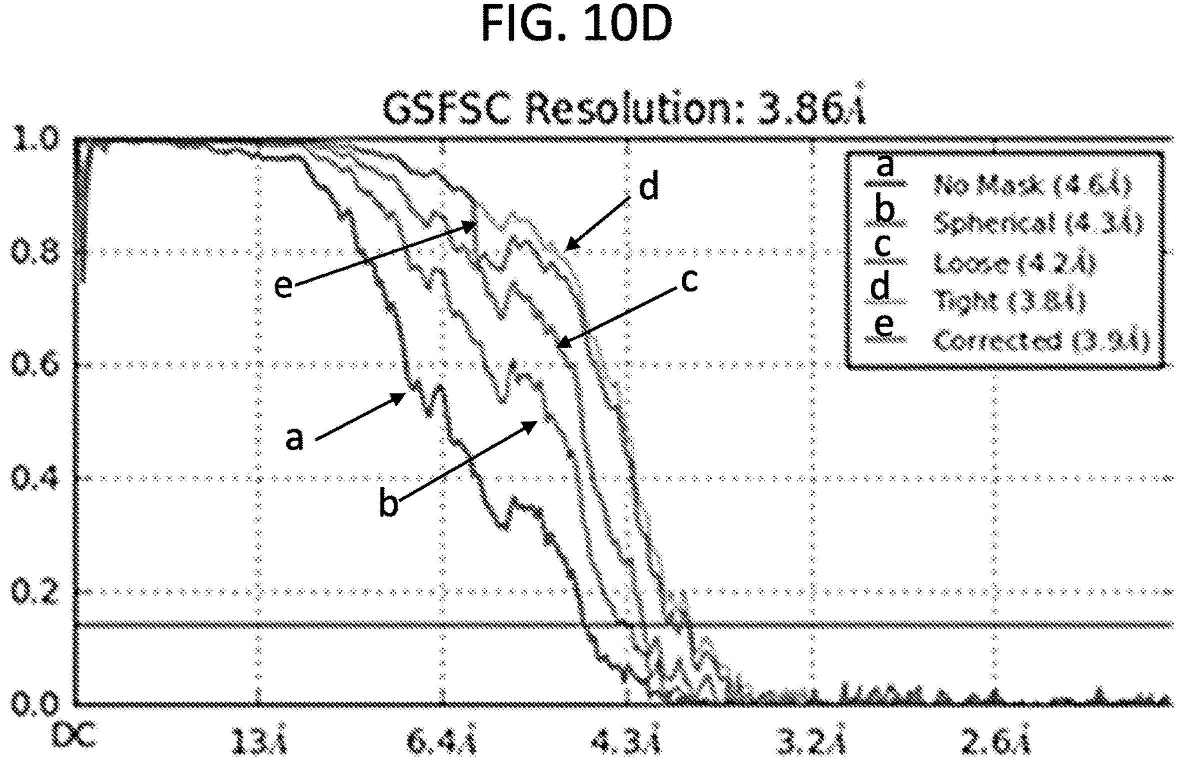
Figure 10E:
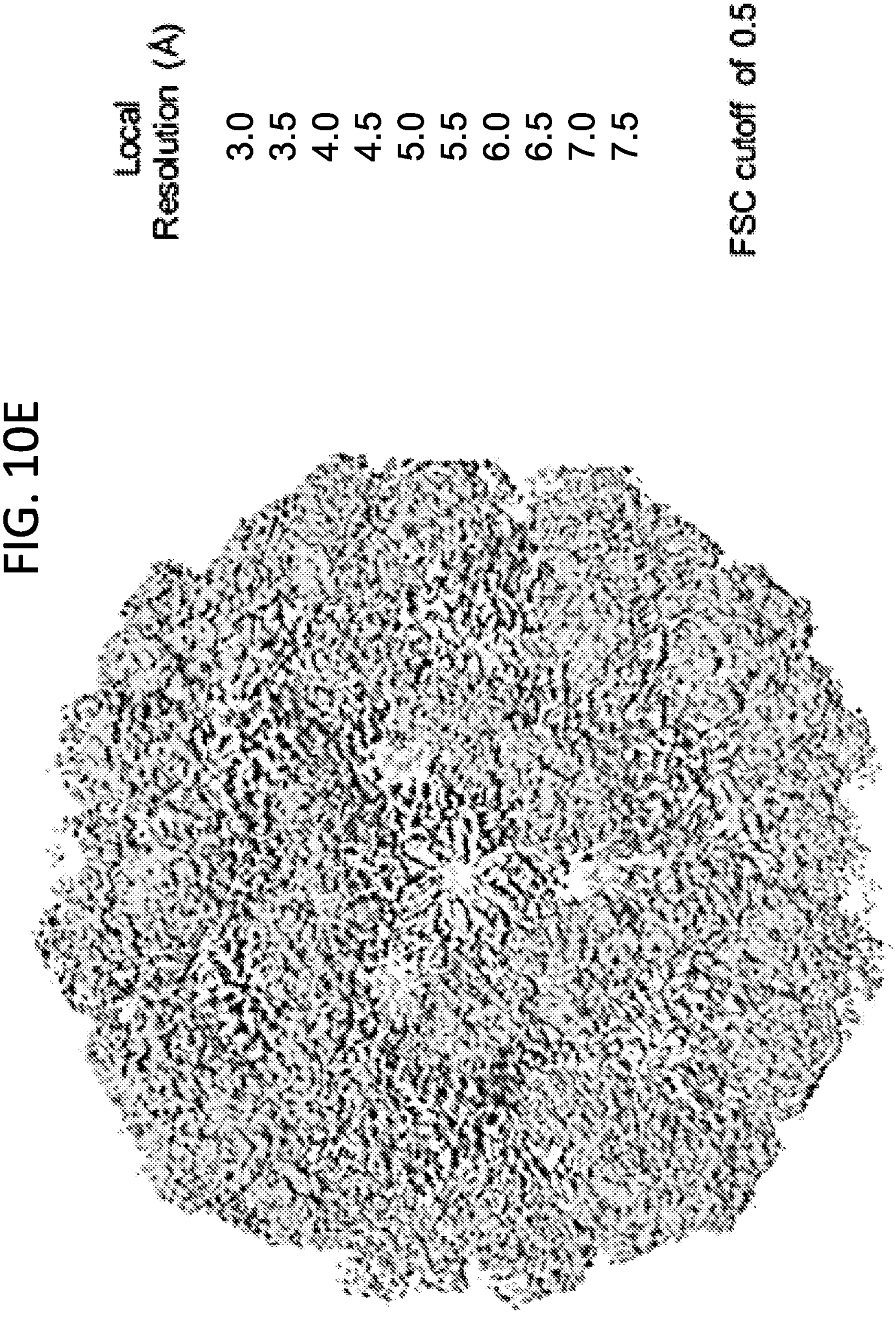
Figure 11A:
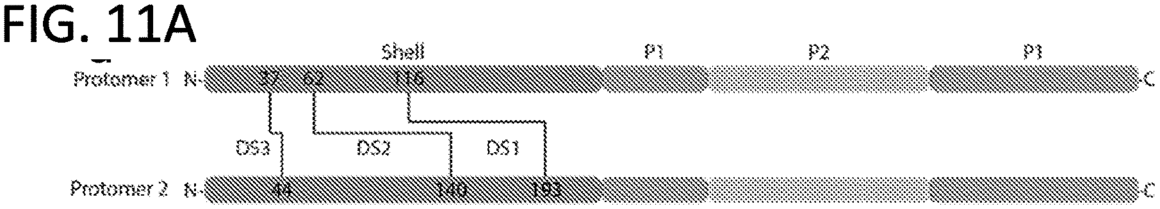
FIGS. 11A-11E. Schematic of interprotomer disulfide constructs used to stabilized GI.1 VLPs.
Figure 11B:
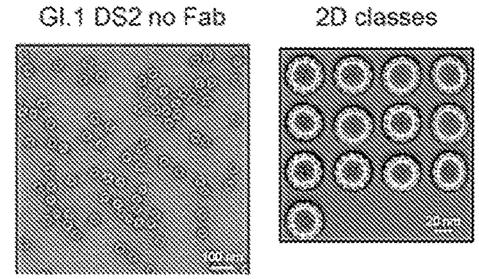
Figure 11C:
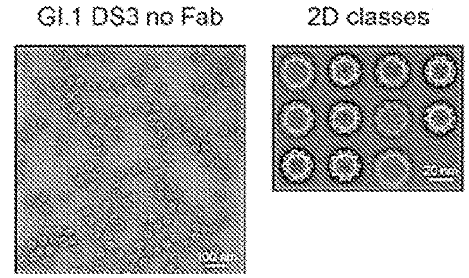
Figure 11D:
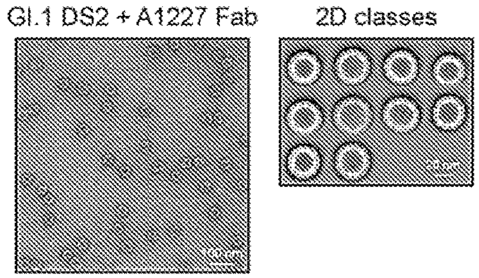
Figure 11E:
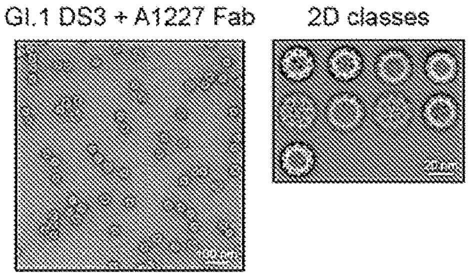

Next, we incubated A1227 Fab fragment with purified GI.1 WT VLPs. Surprisingly, after adding A1227 Fab (at a molar ratio of 1:2-VP1:Fab), we only observed complexes containing one VP1 dimer and two Fabs (FIG. 1*b*). Although not enough intact VLPs were available to produce 2D class averages, it appeared that A1227 Fab did not bind to intact particles (FIG. 1*b*). In contrast, addition of the GI.1 neutralizing antibody 512 (Fab fragment), which has been shown to bind to the P domain near the receptor binding site at the apex of the P domain[21], we saw VLPs decorated with 512 Fabs as well as VP1 dimers bound to two Fabs (FIG. 1*c*). Fitting of the A1227/GII.4c P domain crystal structure on the low-resolution 3D reconstruction of the complexes from NS-EM data showed that the Fabs bind to the GI.1 VP1 dimers with a similar angle as to the GII.4 P domain dimer (FIG. 9*a*), confirming that the epitope on the GI.1 P domain is similar for both GI.1 and GII.4 genotypes. The same results were obtained by fitting the crystal structure of GI.1 P domain/512 Fab complex onto the 3D map of the corresponding VP1/Fab complex (FIG. 9*b*).

Figure 1D:
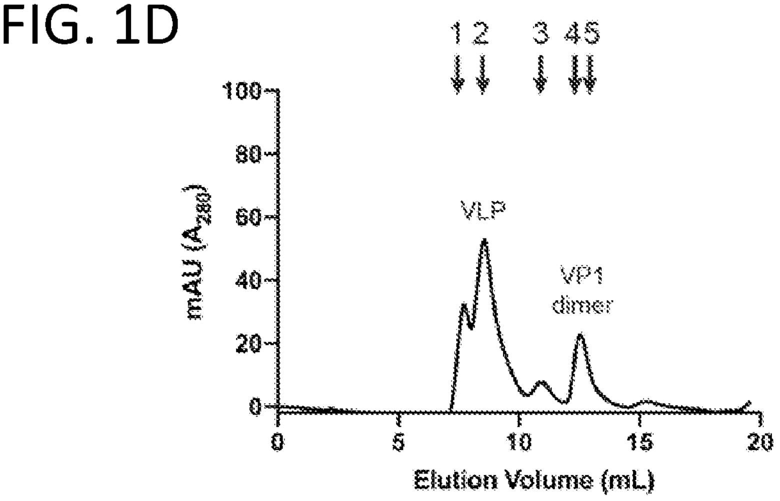
Figure 1E:
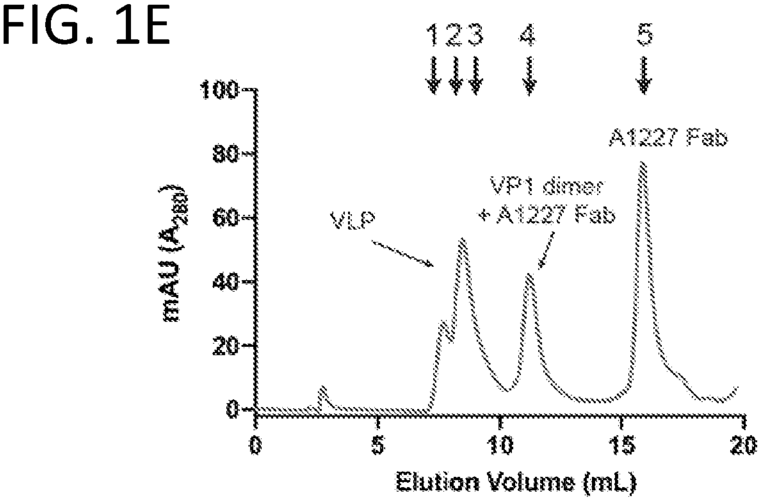
Figure 1F:
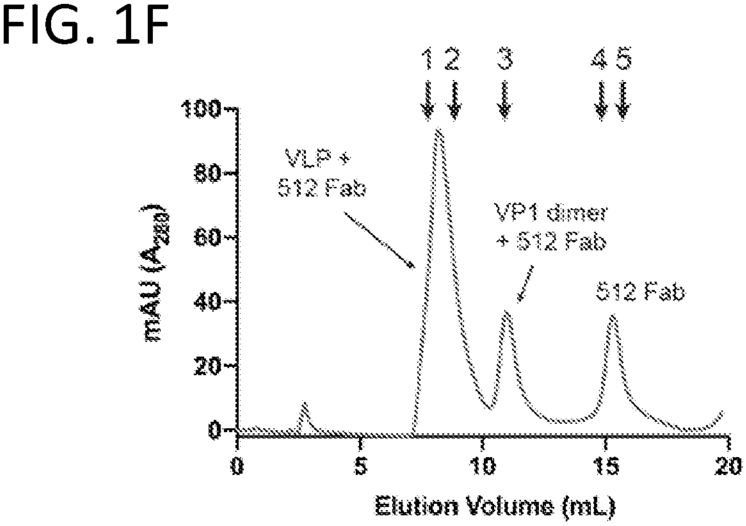
Figure 1G:
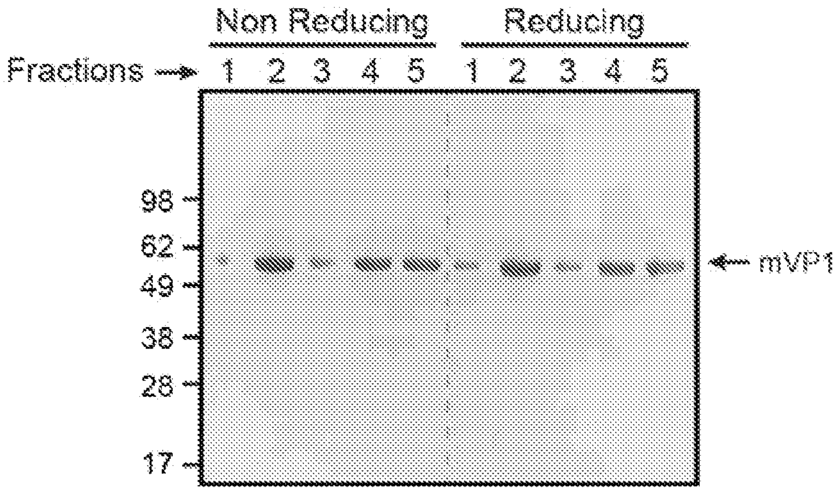
Figure 1H:
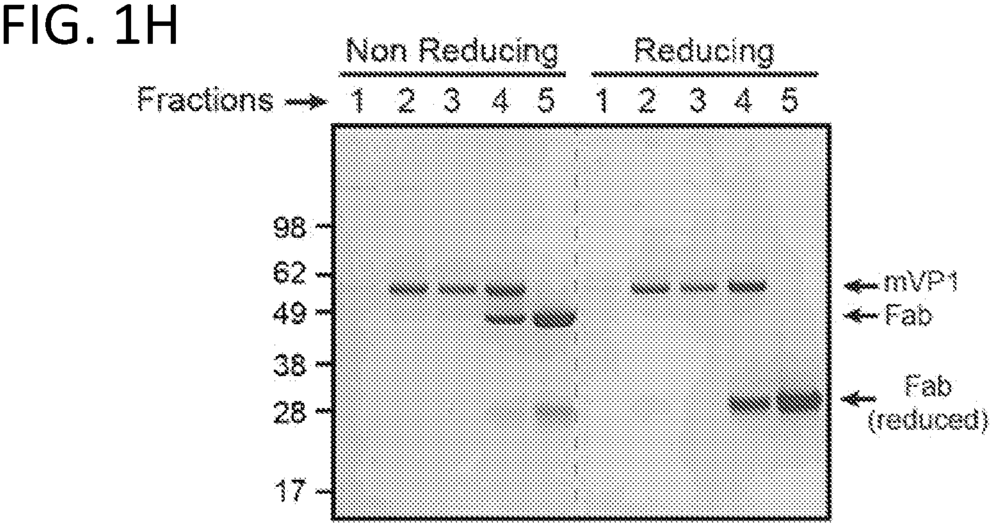
Figure 1I:
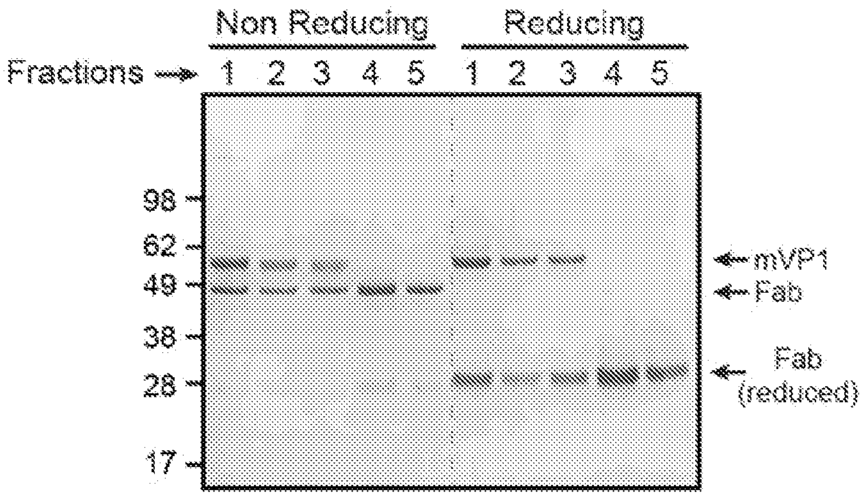

To rule out the possibility that VLP heterogeneity was due to artifacts from grid preparation for NS-EM, we used analytical size exclusion chromatography to assess particle dissociation and interaction with antibodies. In the absence of antibody A1227, GI.1 VLPs eluted in two main peaks (FIG. 1*d*), the first (fraction 1 and 2) corresponding to the void volume, indicative of non-dissociated VLPs and the second around 13 mL elution volume (fraction 4 and 5), consistent with VP1 dimers. Integration of the chromatogram indicates that about 20% of the sample is present as VP1 dimers. SDS-PAGE analysis confirmed the presence of VP1 protein in both peaks (FIG. 1*g*). When VLPs were incubated with A1227 Fab, the size and position of the void peak (fraction 1, 2, and 3) did not change, while the VP1 dimer peak shifted by 2 mL (fraction 4), indicative of complex formation, while the peak at 16 mL was consistent with free Fab (FIG. 1*e*). Analysis of the fractions by SDS-PAGE revealed that A1227 Fab is found in the VP1 dimer peak (fraction 4) and as free Fab (fraction 5), but not in the fractions with intact particles (FIG. 1*h*). These results were consistent with the NS-EM data showing no interaction between GI.1 VLPs and A1227, but strong interaction between A1227 and dissociated VP1 dimers. Finally, the addition of 512 Fab to GI.1 VLPs also resulted in three peaks (FIG. 1*f,i*). Antibody 512 Fabs were found in complex with the dissociated VP1 dimers (fraction 3) and in free form (fraction 4 and 5), but also in the void peak (fractions 1 and 2), indicative of Fab/VLP interaction.

In summary, expression of norovirus GI.1 VP1 protein in insect cells led to the production of intact VLPs as well a small population of dissociated particle components (primarily VP1 dimers). Cross-reactive, but non-neutralizing antibody A1227 bound only the dissociated VP1 dimers, while GI.1-specific and blockade antibody 512 bound to intact particles as well as to VP1 dimers.

Figure 2B:
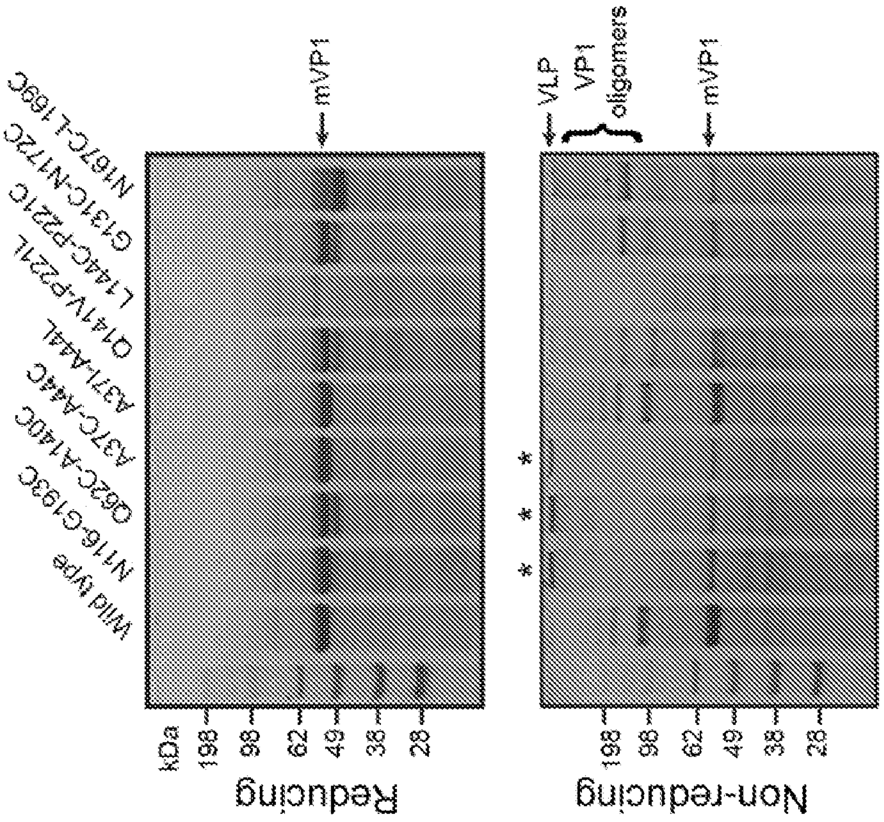
FIGS. 2A-2E. Structure-based design of interprotomer disulfides between VP1 monomers leads to stabilized particles with increased thermal stability of the shell domain.
Figure 2A:
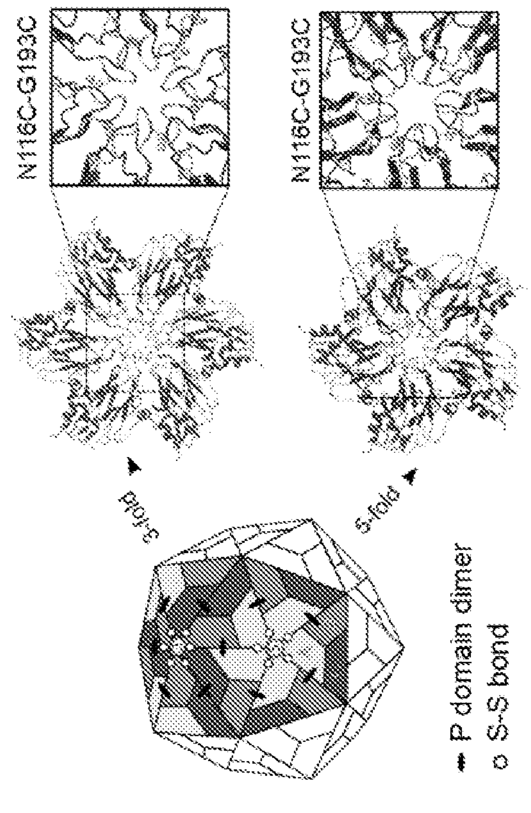
Figure 2C:
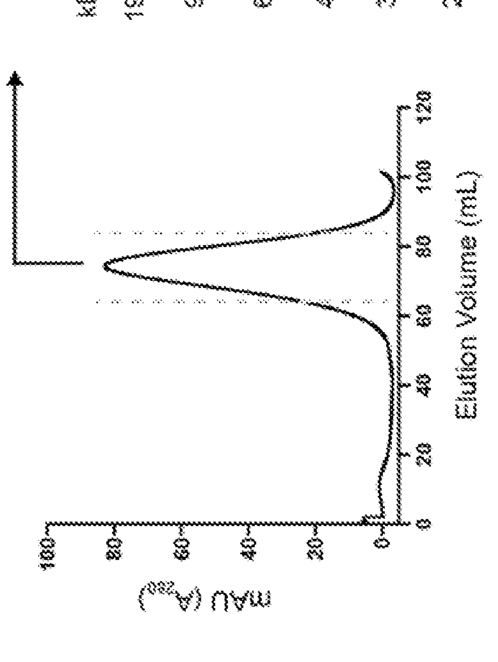
Figure 2D:
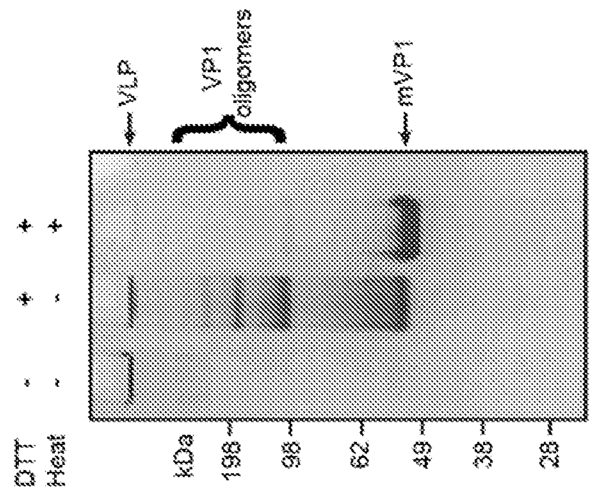
Figure 2E:
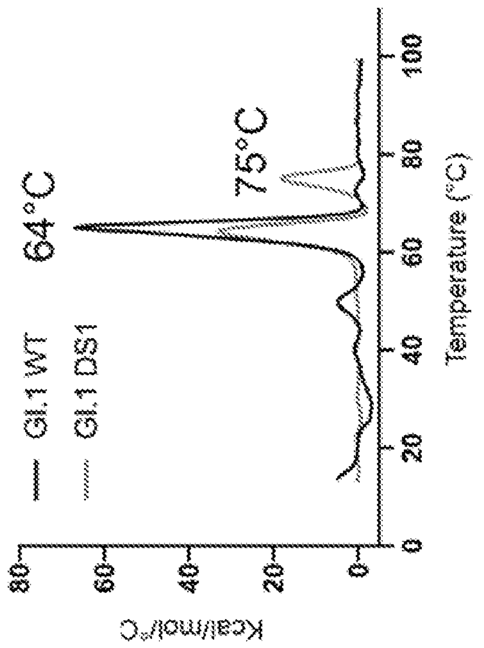

Structure-Based Design of disulfide Bonds between VP1 Monomers Leads to Stabilized Particles. Disassembly of multivalent antigen particles can decrease immunogenicity 22 and expose epitopes that would otherwise be inaccessible on the surface of an intact particle. Due to their highly conserved nature, antibodies directed toward these occluded epitopes would tend to dominate the immune response. In the T=3 icosahedral particle arrangement, Norovirus capsids are made of 180 identical copies of the VP1 protein. The icosahedral asymmetric unit contains three quasi-equivalent VP1 monomers (designated A, B, and C)[23]. Each monomer associates with another monomer to form P domain dimers (in either A-B or C-C configuration). To prevent disassembly of VLP and exposure of occluded non-neutralizing epitopes, we engineered interprotomer disulfides in the shell domain of GI.1 VLPs. Because of the symmetry of the norovirus VLPs, a cysteine pair introduced near the 5-fold symmetry axes would yield disulfides between every A-A monomer pairs. The same cysteine pair at the 3-fold symmetry axes would yield disulfide bonds between every B-C monomer pair. (FIG. 2*a*—top panel). A similar strategy could also be employed to generate disulfides between the A, B and C monomers of the icosahedral asymmetric unit (FIG. 2*a*—bottom panel). In both cases, the combination of engineered disulfides and the presence of the P domain dimers between A-B and C-C monomers would result in highly linked VLPs. Starting from the available high-resolution structures of GI.1 VLPs[23,24], we designed pairs of cysteine mutants that would result in interprotomer disulfides. To evaluate the stability of the different constructs, we used a screening approach developed for the stabilization of the hepatitis B core antigen VLPs[25]. Supernatants from insect cells expressing VP1 were incubated with diamide (to establish an oxidizing environment) and subsequently separated by SDS-PAGE under reducing or non-reducing conditions. VLPs in which each protomer was covalently linked to the neighboring protomer by disulfide links, did not dissociate in the presence of SDS and thus failed to enter the separating gel due to the large size of the particle (~10 MDa), remaining at the top of the well. In the presence of DTT, the disulfides were reduced, and the particle could be dissociated by SDS, resulting in a single band corresponding to the VP1 monomer. Three constructs showed significant stabilization after oxidation in diamide (FIG. 2*b* and FIG. 11). GI.1 with N116C and G193C mutations (herein referred to as GI.1 DS1) was chosen for large scale production and characterization (FIG. 2*c,d*). The resulting particles showed increased thermal stability as evidenced by the appearance of a second melting transition at 75° C. compared to a single transition at 64° C. for the wild-type particles (FIG. 2*e*). The lower temperature transition corresponds to the unfolding of the P domain, while the higher temperature transition likely corresponds to the stabilized shell domain. These results are in agreement with previous studies on the thermal stability of GI.1 shell domain[26]. We also tested the possibility of introducing hydrophobic interactions (A37I-A44L and Q141V-P221L) to promote stabilization of the VLPs. However, none of the constructs resulted in a stabilizing effect comparable to the disulfides (FIG. 2*b*).

Figures 3A, 3B, 3C, 3D, 3E:
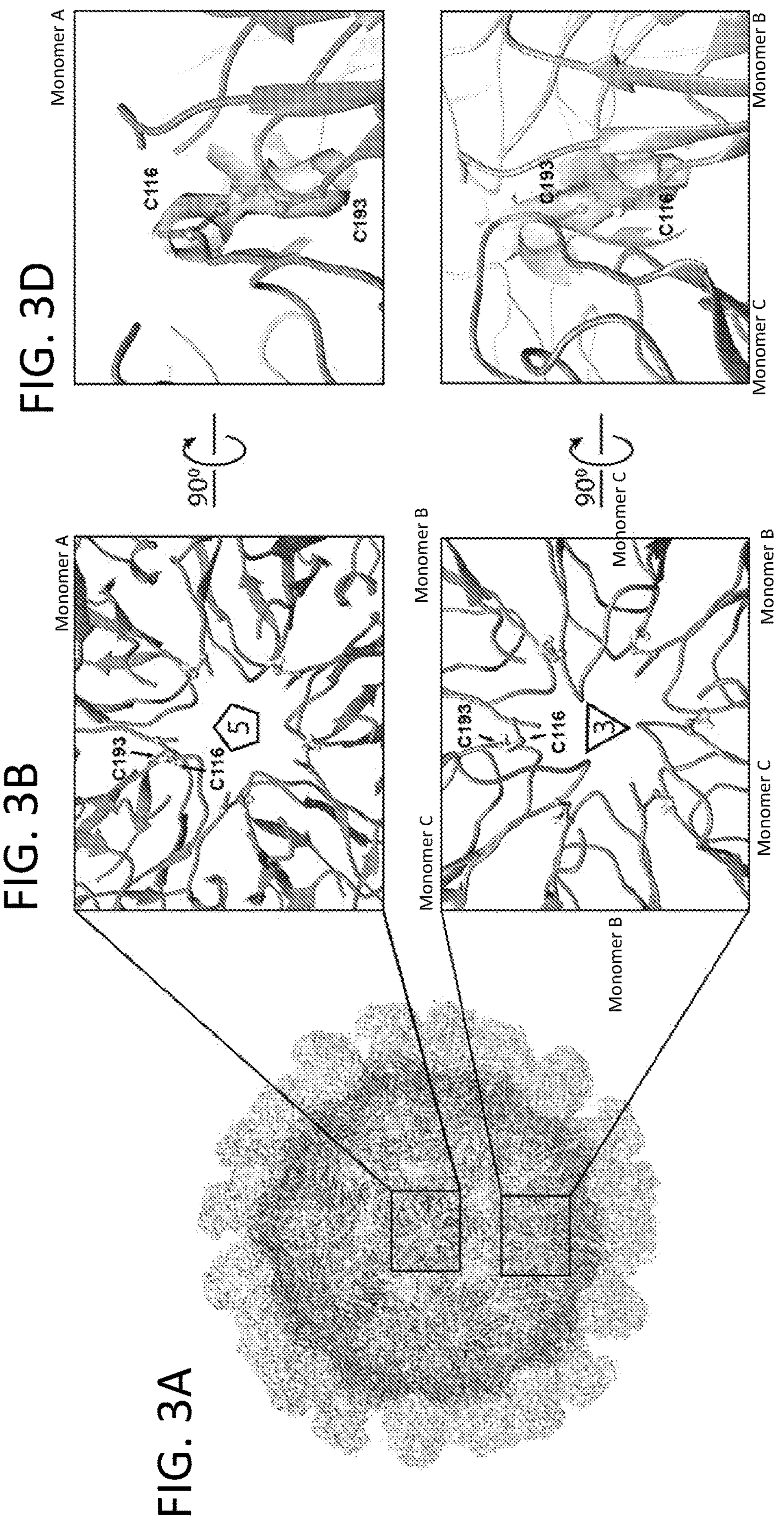
FIGS. 3A-3E. Cryo-EM reconstruction of GI.1 DS1 VLP provides details of inter-protomer disulfide bonds between Cys116 and Cys193.

To verify the formation of the disulfides, we determined the structure of the GI.1 DS1 VLP at 3.9 Å resolution using single-particle cryo-electron microscopy (FIG. 7, FIG. 3 and FIG. 10). GI.1 DS1 VLPs showed the characteristic icosahedral symmetry with T=3 arrangement. Clear densities for the formation of the interprotomer disulfide between Cys116 and Cys193 were visible around the 5-fold and 3-fold symmetry axes (FIG. 3*b-e*). In summary, we successfully designed cysteine mutations in the GI.1 shell domain that resulted in interprotomer disulfides, stabilizing the entire capsid.

Figure 17A:
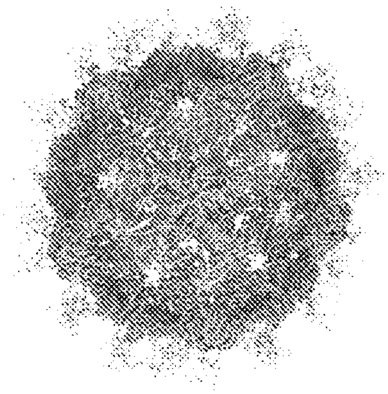
FIGS. 17A-17B. Introduction of second disulfide within the icosahedral asymmetric unit leads to further structural stabilization of the VLP. (17A) Cryo-electron density map of GI.1 DS1. Single disulfide between residues C116 and C193 causes lower electron densities within the shell domain and p domain, due to heterogeneity in the p domain region. (FIG.
Figure 17B:
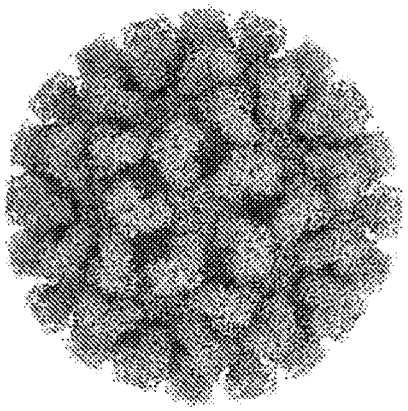

Introduction of second disulfide within the icosahedral asymmetric unit leads to further structural stabilization of the VLP (FIG. 17). A A37C/A44C disulfide was introduced into the GI.1 DS1 VLP to generate GI.1 DS2 VLP. Cryo-electron density mapping showed that the single disulfide between residues 116 and 193 led to lower electron densities within the shell domain and p domain relative to GI.1 DS2 VLP, due to constraints on the symmetry imposed by the disulfide or increased dynamics Introduction of the second disulfide bond between positions 37 and 44 leads to homogenous electron densities for shell and p domains.

Figure 4A:
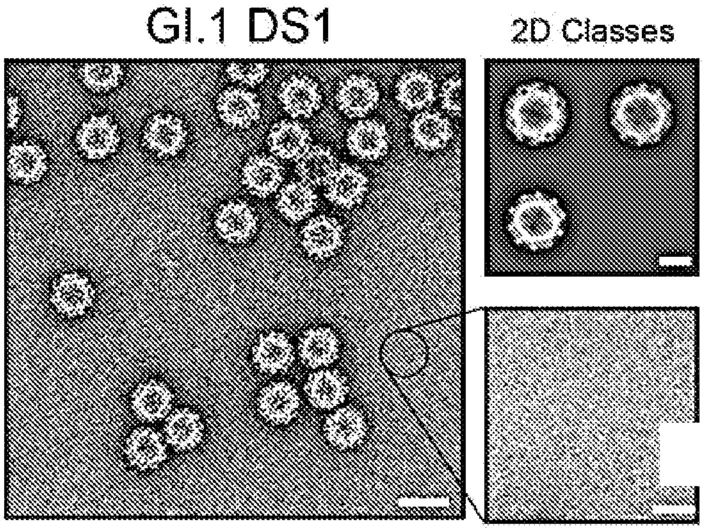
FIGS. 4A-4I. Stabilization of GI.1 VLPs prevents VLPs from disassembling but preserves accessibility to 512 blockade epitope.
Figure 4B:
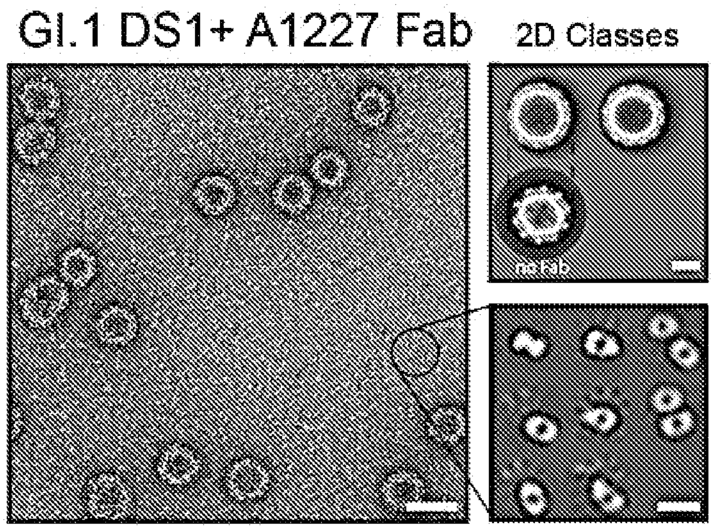
Figure 4C:
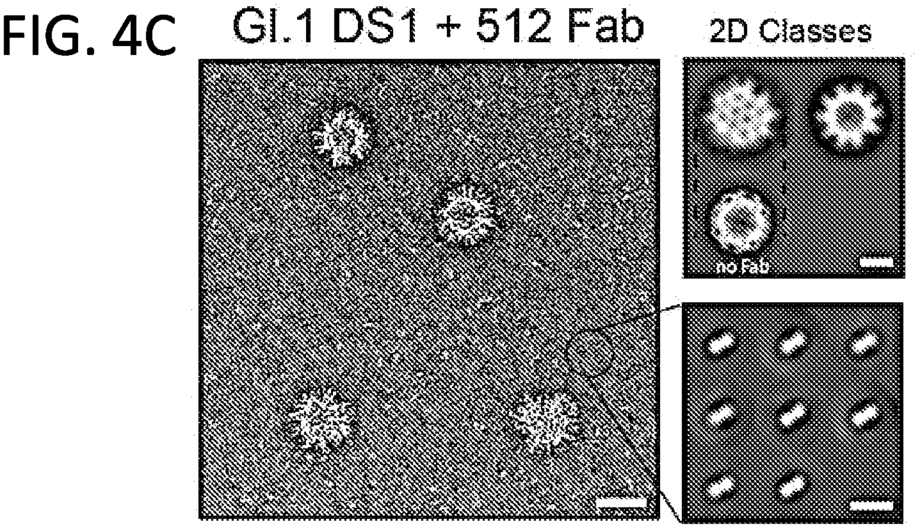
Figure 4D:
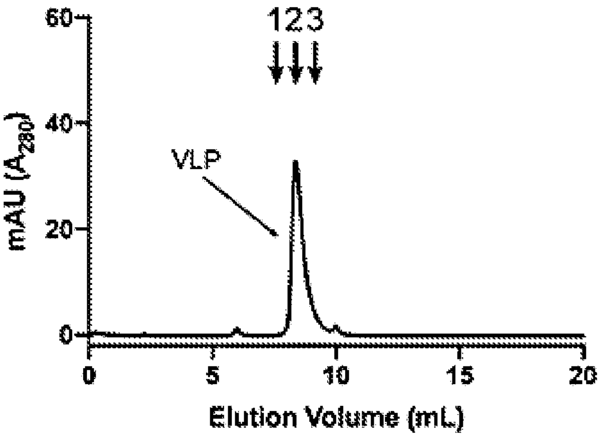
Figure 4E:
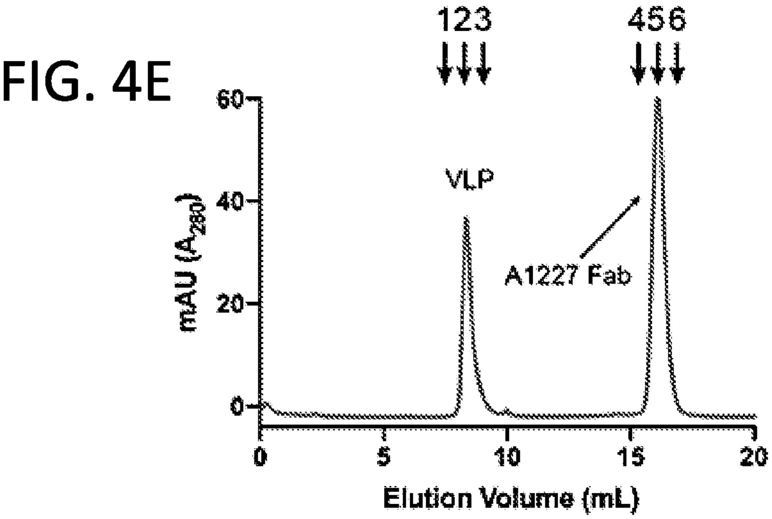
Figure 4F:
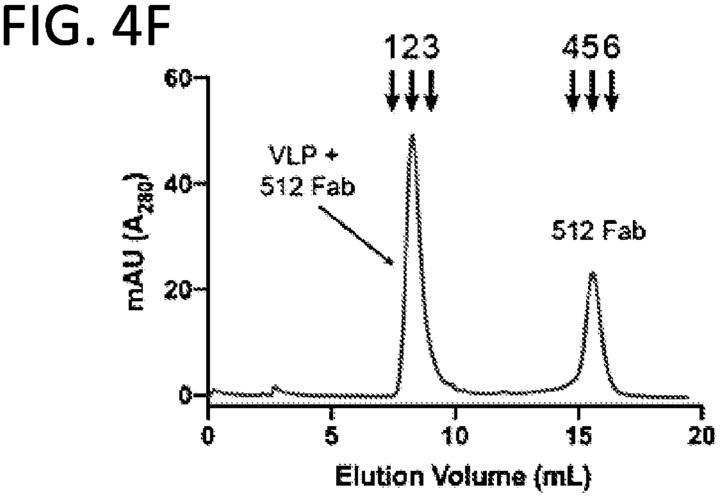
Figure 4G:
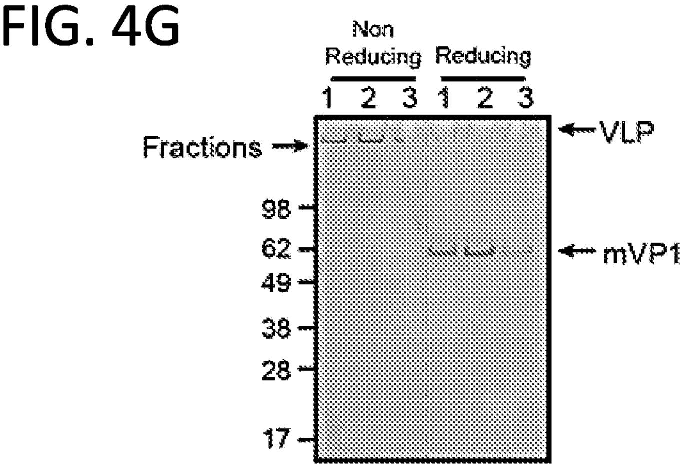
Figure 4H:
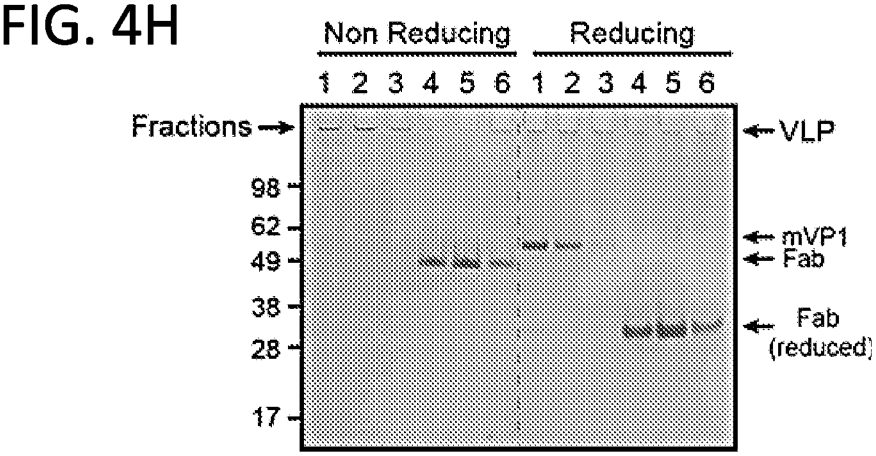
Figure 4I:
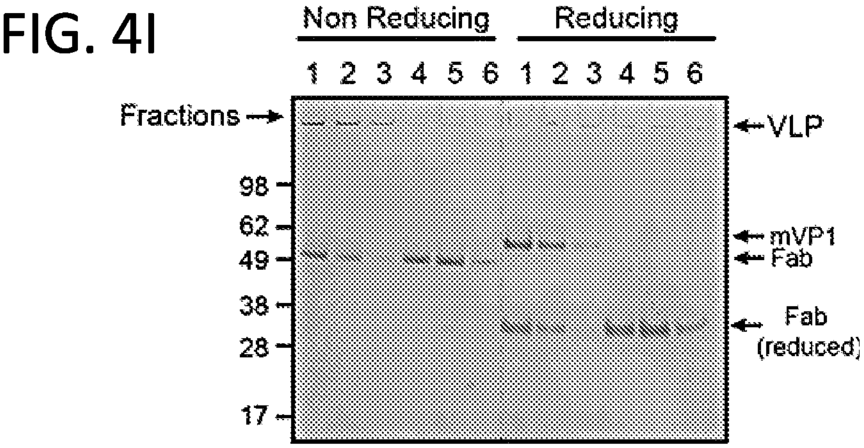

Stabilized GI.1 VLPs do not Expose Occluded Epitopes but Retain Antigenicity of Blockade Epitopes. Stabilization of the VLPs should prevent the binding of occluded-site antibodies while maintaining accessibility of blockade epitopes. First, NS-EM analysis of GI.1 DS1 revealed very homogenous VLPs with undetectable amounts of dissociated particles (FIG. 4*a*). Size-exclusion chromatography (FIG. 4*d*) and analysis of fractions (FIG. 4*g*). Critically, addition of A1227 Fab did not lead to any detectable interaction with the stabilized particles and because no dissociated VLP components were present in the sample, no complexes could be observed with VP1 dimers (FIG. 4*b*). From 2D class averages, it appeared that the presence of A1227 Fab did not lead to any significant differences in particle diameter and the smaller components visible in the background were free Fabs (FIG. 4*b*). In contrast, addition of 512 Fab to GI.1 DS1 resulted in particles fully decorated with Fabs (FIG. 4*c*). The diameter of the VLP in complex with the 512 Fab increased by about 7 nm, consistent with a shell of Fabs bound to the surface of the particle. Again, the small objects in the background represented free Fabs (FIG. 4*c*). Size-exclusion chromatography of VLPs in the presence of Fabs and analysis of fractions by SDS-PAGE confirmed the NS-EM data (FIG. 4*e,h* and FIG. 4*f,i*).

Figure 12A:
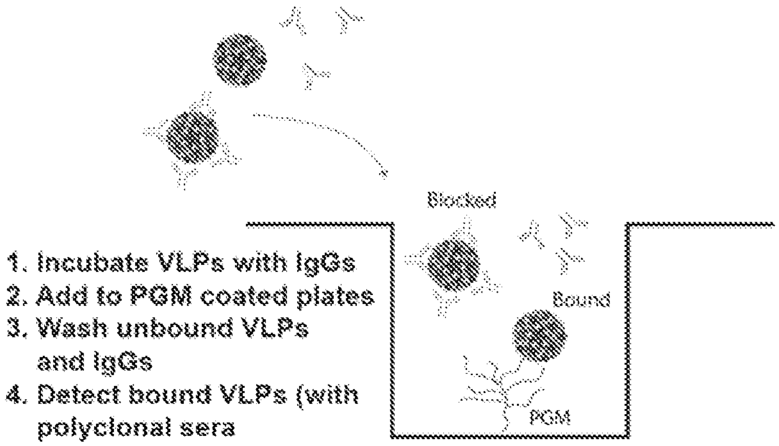
FIGS. 12A-12G. Stabilization of GI.1 VLPs preserves neutralizing epitopes but prevents binding of non-blockade antibodies.
Figure 12B:
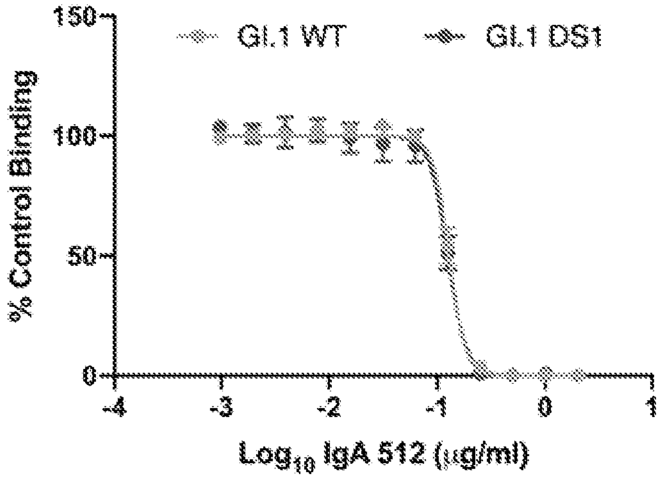
Figure 12C:
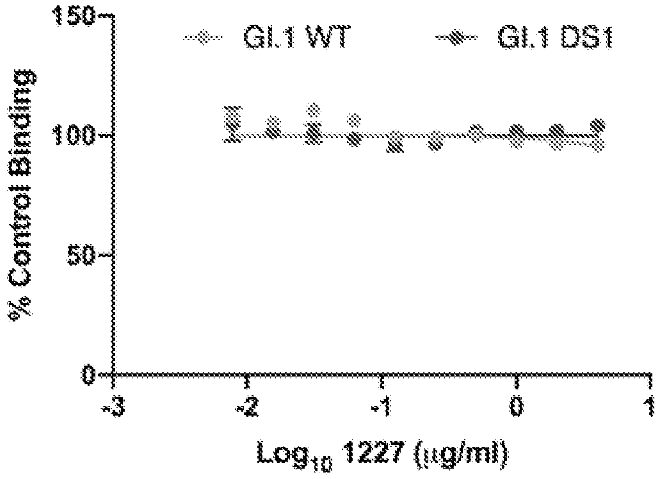
Figure 12F:
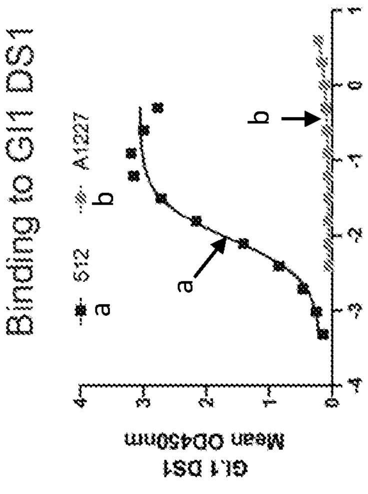
Figure 12H:
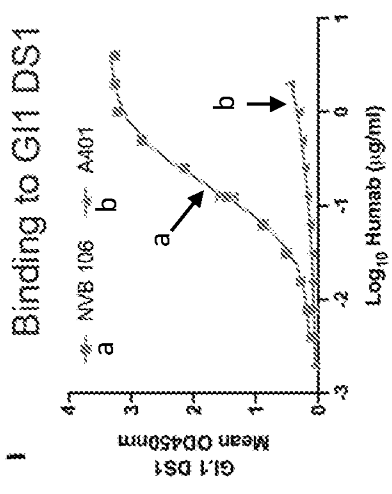
(FIG. 12H) The same experiment in (FIG. 12G) was repeated using GI.1 DS1 VLPs. Very low binding of A401 was observed, while NVB106 did not show any difference in binding.
Figure 12E:
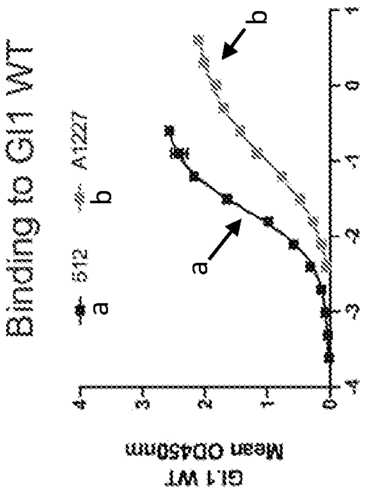
Figure 12G:
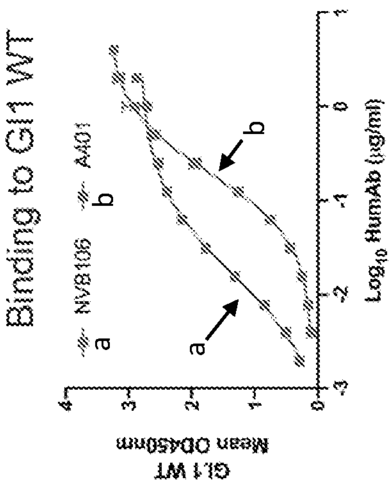
Figure 12D:
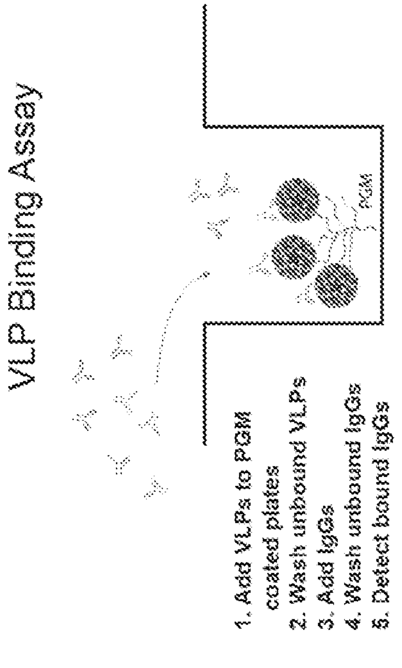
Figure 13A:
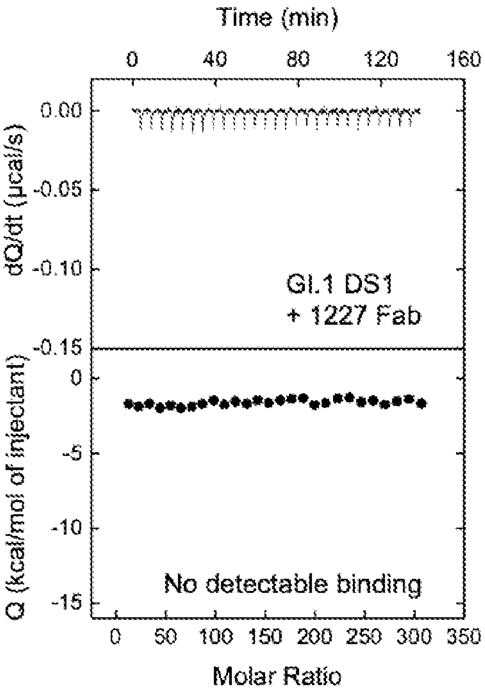
FIGS. 13A-13B. Isothermal titration calorimetry shows no detectable binding of A1227 Fab to stabilized particles but high affinity for 512 Fab. Purified GI.1 DS1 VLPs were titrated with A1227 Fab (FIG. 13A) or 512 Fab (FIG. 13B). Notice that no detectable binding was observed when A1227 was titrated into GI.1-DS1 .
Figure 13B:
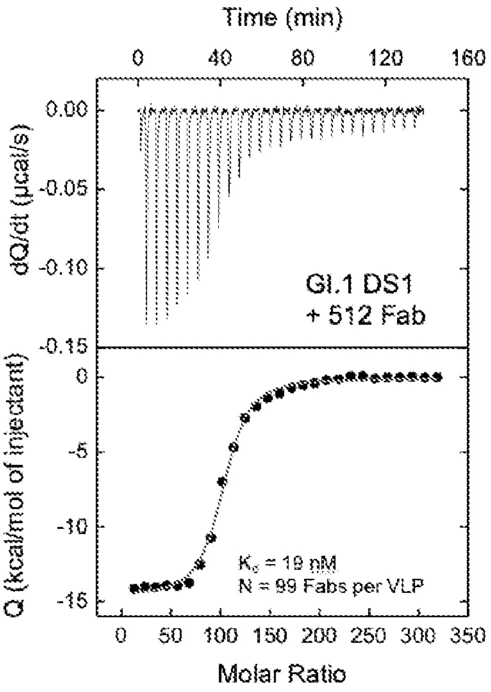

To verify that the stabilization of the GI.1 VLPs did not compromise the blockade activity of GI.1 specific antibodies, we performed blockade and binding assays using pig gastric mucin (PGM)[15] (FIG. 12*a,d*). Binding of both GI.1 WT and GI.1 DS1 was blocked by antibody 512, while occluded-site antibody A1227 did not show any blockade activity (FIG. 12*b,c*). When VLPs were captured on PGM-coated plates, antibody A1227 could only bind to the GI.1 WT VLPs, but negligible binding was observed to GI.1 DS1 (FIG. 12*e,f*). The same experiments were repeated using blockade antibody NVB106[27] and cross-reactive, but non-blockade antibody A401[17]. Both NVB106 and A401 could bind to wild type particles (FIG. 12*g*). However, when tested against GI. DS1, only NVB106 showed similar binding, while A401 did not bind. (FIG. 12*h*). To further confirm that stabilization prevented binding of A1227 while preserving binding of 512, we used isothermal titration calorimetry (FIG. 13). As expected, no binding was detected when A1227 Fab was titrated into GI.1 DS1 VLPs (FIG. 13*a*), while 512 Fab bound with high affinity to the particles. Analysis of the thermograms showed that around one hundred 512 Fabs were bound to each particle. (FIG. 13*b*). Overall, our data showed that stabilizing GI.1 VLPs by engineering interprotomer disulfide bonds in the shell domain prevented dissociation of the particles but retained antigenicity of blockade epitopes (512 and NVB106). In addition, non-neutralizing antibodies (A1227 and A401) were no longer capable of binding the intact particles.

Stabilized VLPs Elicit Blockade Antibodies Faster than Wild Type and Focus Immune Responses toward Blockade Epitopes. Current clinical trials using norovirus VLPs have proven partially successful. The bivalent GI.1/GII4 VLP vaccine, currently in phase IIb clinical trials, is highly immunogenic; however blockade titers wane very quickly and, for some individuals, boosting fails to increase blockade responses[15]. We reasoned that lack of particle stability could promote exposure of immunodominant epitopes (mostly located at the base of the P domain and within the shell region). The resulting antibodies (targeting these occluded sites) would appear cross-reactive but would fail to neutralize the virus. Using stabilized particles would allow greater availability of intact particles to B cells in vivo for elicitation of higher blockade titers. In addition, since the stabilized particles would not present occluded site epitopes, they could help focus the immune response toward accessible (and potentially neutralizing) epitopes.

Figure 5A:
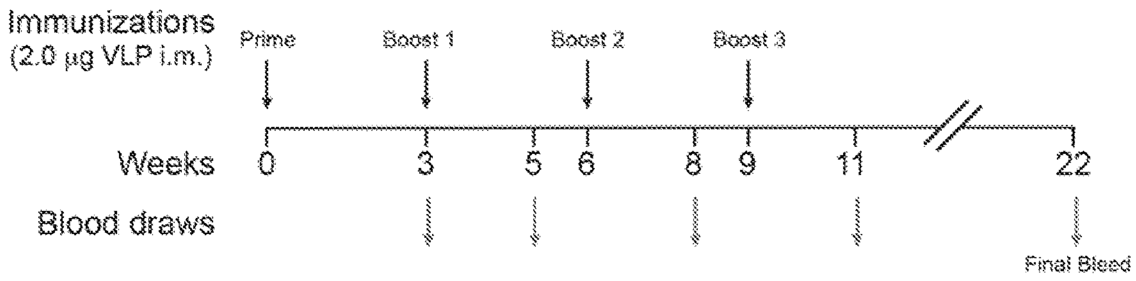
FIGS. 5A-5C. Mice immunizations with stabilized GI.1 VLPs produces high titers of blockade antibody responses after two injections without alum.
Figure 5B:
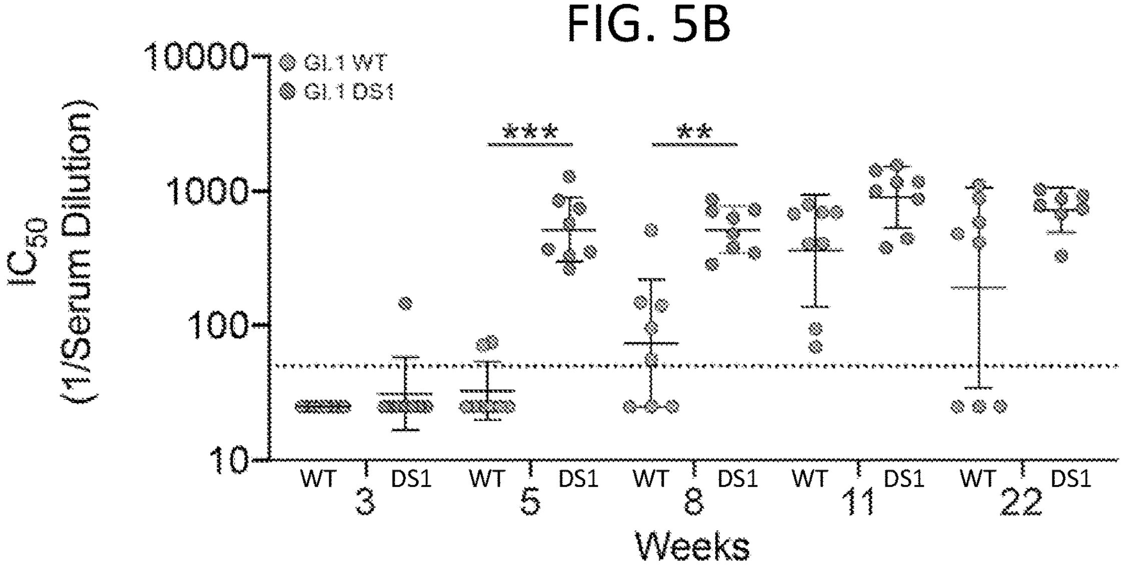
Figure 5C:
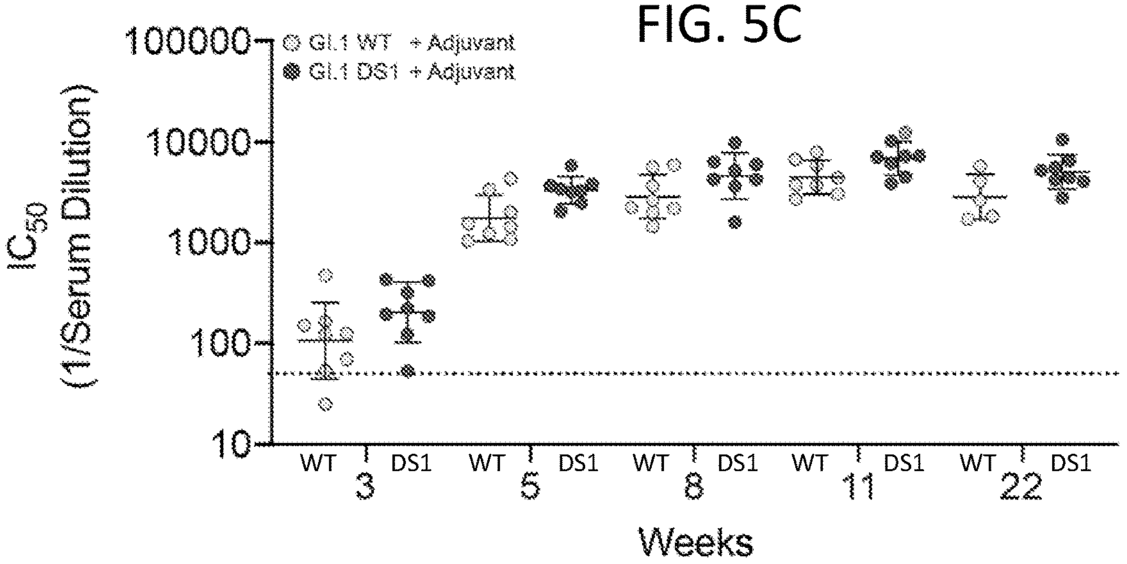
Figure 14:
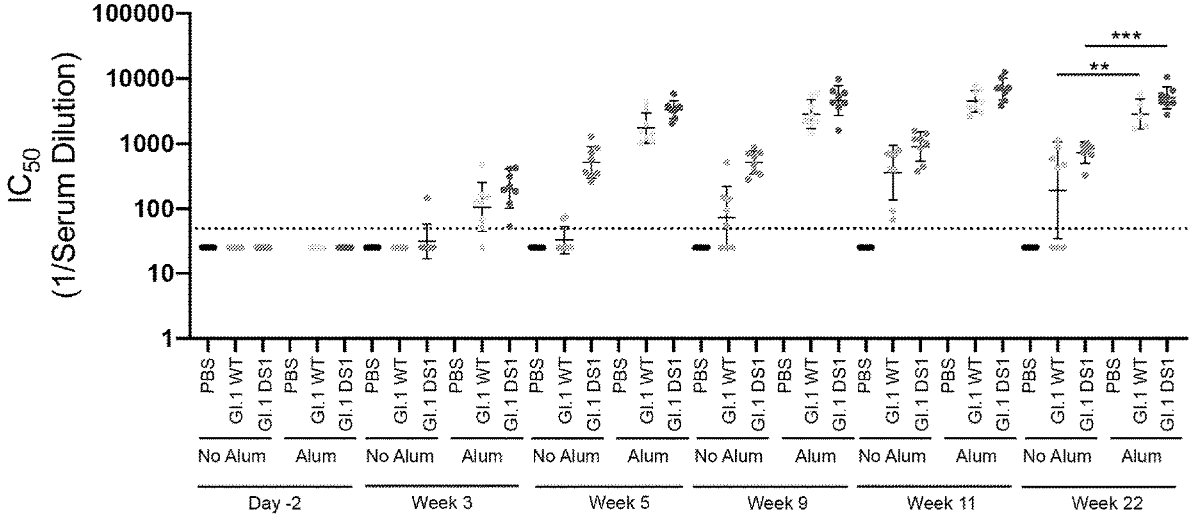
FIG. 14. HBGA blockade titers for all groups at all time points. Comparison of blockade antibody titers between each group in the presence and absence of alum. Groups are displayed according to blood draw week. Limit of detection (titer=80) is indicated with a horizontal dotted line. Geometric mean titers±geometric SD are shown in scatter dot plot. P values were determined by two-tailed Mann-Whitney tests.  indicates P≤0.01, * indicates P≤0.001.

Accordingly, we immunized mice with GI.1 WT and GI.1 DS1 VLPs. Each group was tested with and without adjuvant (alum). The first boost was administered three weeks after the prime, followed by a second and third boost at week 6 and 9, respectively. Blood draws were performed at weeks 3, 5, 8 and 11 and final bleed was performed at week 22 (FIG. 5*a*). Blockade assays were performed after each blood draw (FIG. 5*b,c* and FIG. 14). In the absence of alum, mice immunized with the stabilized particles showed high blockade titers after only two immunizations, but the titers did not increase significantly with subsequent boosts (FIG. 5*b*—red circles). In contrast, blockade titers using GI.1 wild type particles were undetectable until the third immunization was administered. Even after four immunizations with GI.1 WT particles, some animals showed barely detectable blockade titer (FIG. 5*b*—grey circles). However, when VLPs were administered with adjuvant, we did not see any significant difference at any time point between stabilized and wild-type particles (FIG. 5*c*), suggesting a stabilizing effect of adjuvant on the wild-type particles.

Figure 6A:
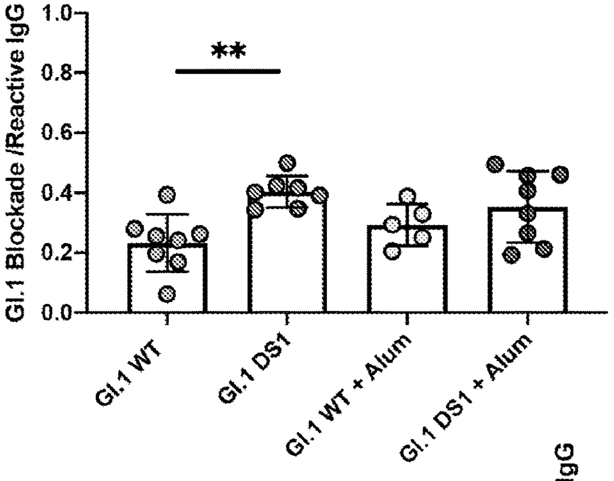
FIGS. 6A-6C. Stabilization of GI.1 VLPs focuses immune responses toward blockade epitopes and away from occluded epitopes.
Figure 6B:
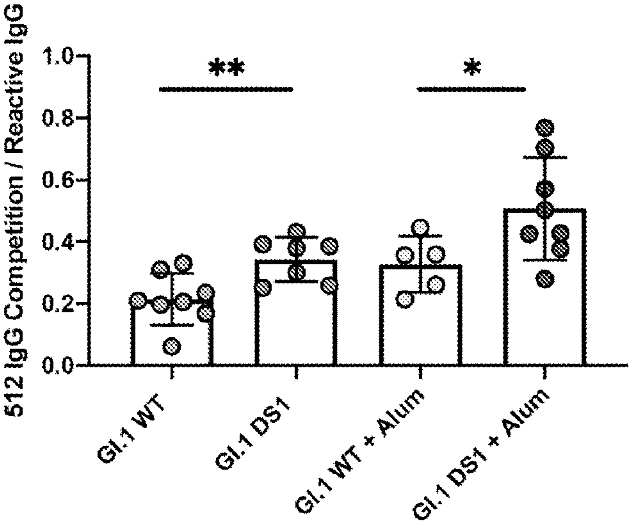
Figure 6C:
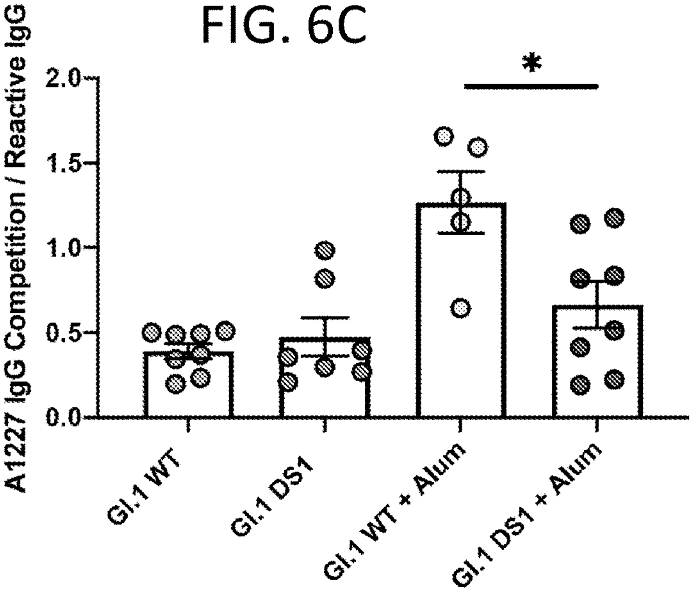
Figure 15A:
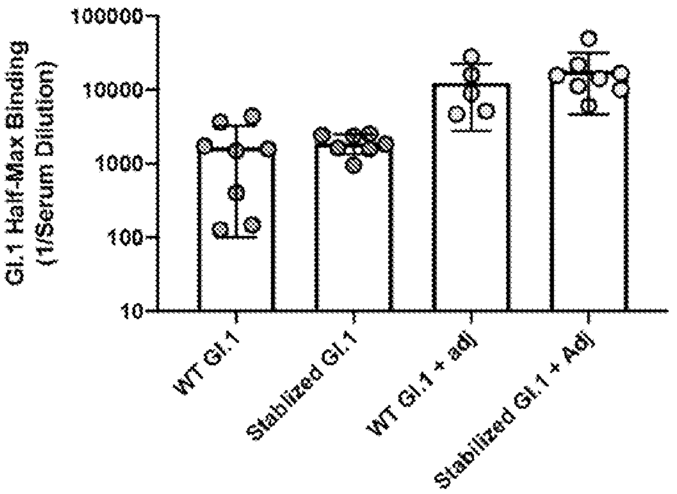
FIGS. 15A-15C. GI.1 reactive serum tiers and serum dilution that blocks 512 or A1227 binding.
Figure 15B:
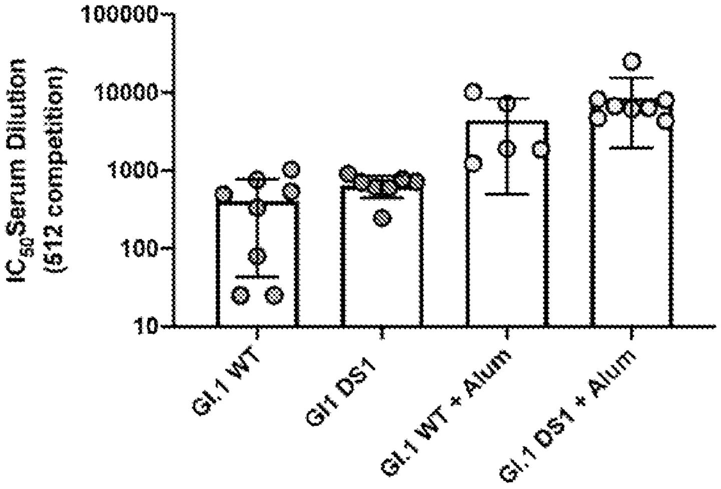
Figure 15C:
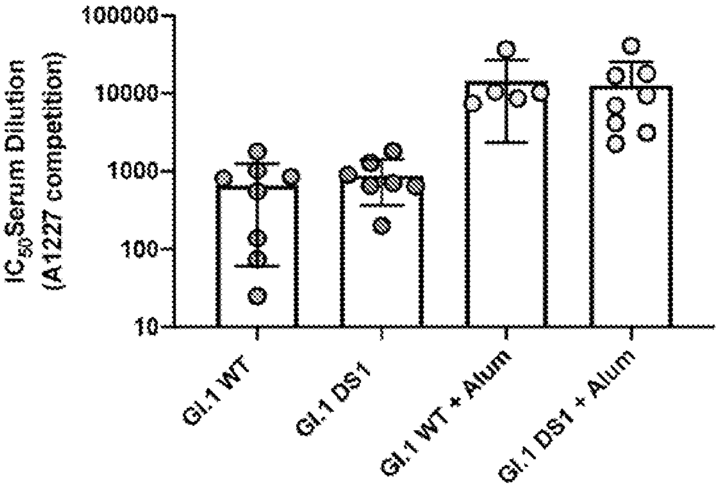
Figure 16A:
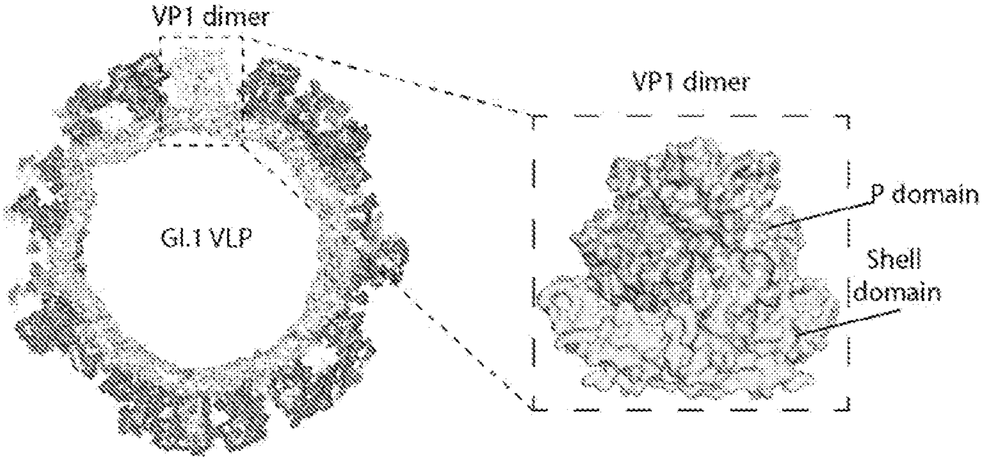
FIGS. 16A-16G. Residual binding titers after capturing VP1 dimer with 512 or A1227 IgG.
Figure 16B:
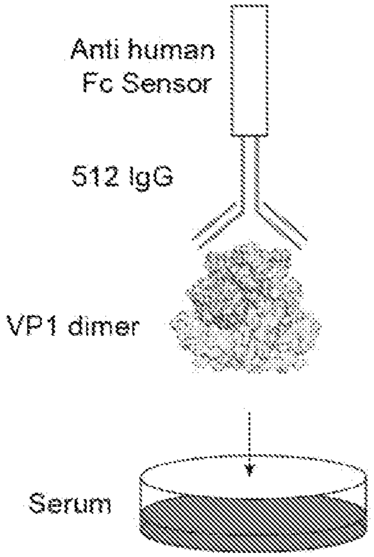
Figure 16C:
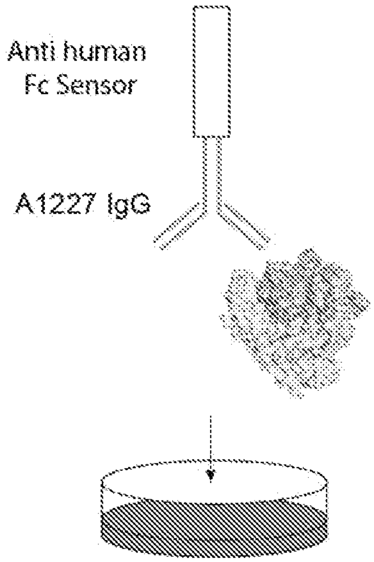
Figure 16D:
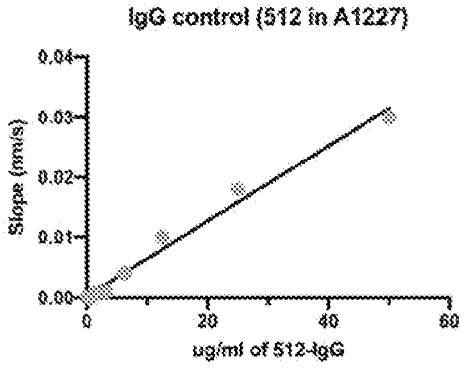
Figure 16E:
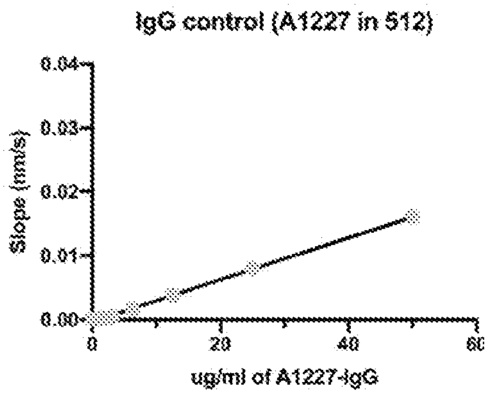
Figure 16F:
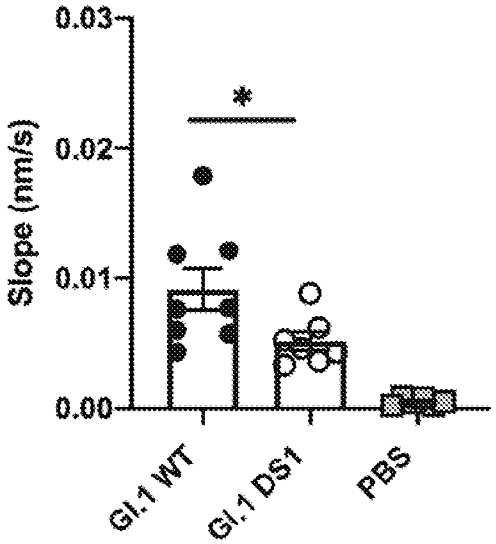
Figure 16G:
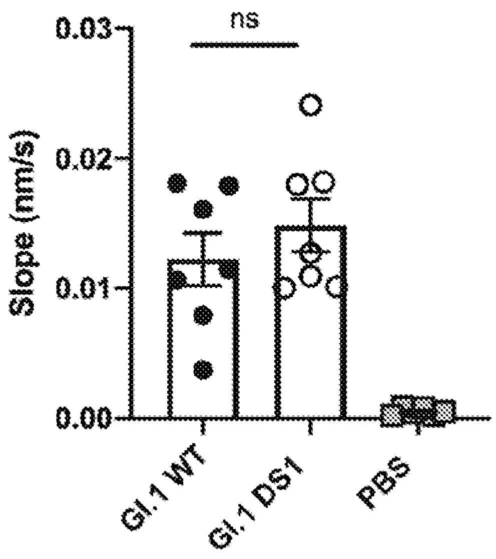
Figure 16H:
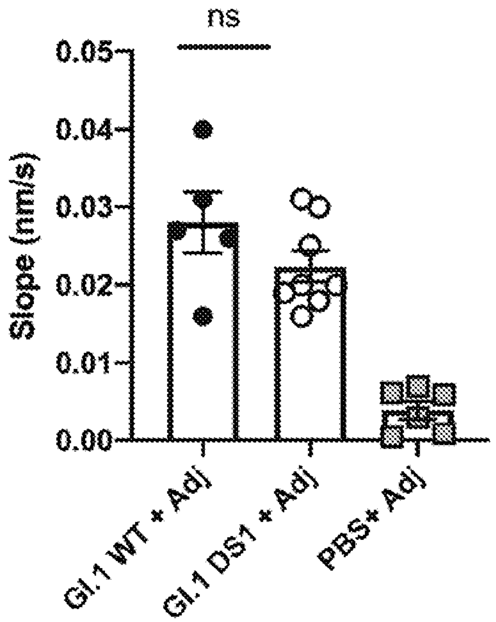
(FIG. 16H,16I) Same experiment as in (FIG. 16F,16G), but with sera from adjuvanted groups. PBS controls correspond to sera from mice immunized with PBS or PBS+adjuvant. In all cases, the initial slope of each curve is plotted. Average slopes±SEM are shown in each box plot. P values were determined by two-tailed Mann-Whitney tests. * indicates P≤0.05. ns=non significant.
Figure 16I:
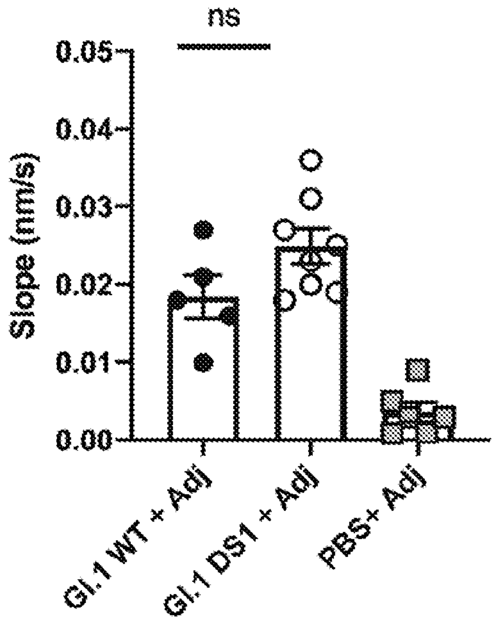

Stabilized GI.1 VLPs should elicit higher titers of blockade antibodies (relative to GI.1—reactive antibody titers) compared to GI.1 WT. Indeed, immunization with stabilized particles led to a two-fold increase of blockade antibodies relative to total binding responses in the absence of alum (FIG. 6*a* and FIG. 15*a*). Additionally, when sera from immunized mice were used in a competition assay with the blockade antibody 512 for binding to the VLPs, we observed more competition for sera from stabilized particles compared to sera from wild type particles, when normalized to total GI.1-binding titers (FIG. 6*b* and FIG. 15*a,b*). The same experiment was repeated using the occluded-site antibody A1227. At least for the adjuvanted groups, the sera from mice immunized with wild-type particle were able to compete with the A1227 binding to VLPs more than sera from mice immunized with stabilized VLPs (FIG. 6*c* and FIG. 14*a-c*). As an orthogonal approach, we used biolayer interferometry to measure the residual serum binding to VP1 dimers after complex formation with either 512 or A1227 antibodies (FIG. 16*a,b*). VP1 dimers were purified from dissociated GI.1 VLP samples (FIG. 1*d*). After capturing VP1 dimers with 512-IgG, sera from mice immunized with stabilized particles showed significantly reduced residual binding to the dimer, compared to sera from wild type immunization at the same dilution (FIG. 16*c*). Although not statistically significant, the results from the same experiment using A1227 bound to VP1 dimers showed an opposite trend. Sera from mice immunized with wild-type particles had less residual binding to the VP1/A1227 complex, while sera from mice immunized with stabilized VLPs had a higher residual binding (FIG. 16*d*). In the presence of alum, sera from mice immunized with GI.1 WT and GI.1 DS1 had similar residual binding to VP1 dimers (FIG. 16*e,f*).

Taken together, these data show that preventing norovirus particles from dissociating can lead to antibody responses that are more focused toward blockade epitopes; further, the stabilized VLPs showed faster development of blockade titers, compared to wild type VLPs.

Discussion

In this study, we found that purification of GI.1 wild-type VLPs consistently resulted in a mixture of intact particles and partially dissociated VLP components. Even after extensive purification with size exclusion chromatography, it was still possible to detect disassembled particle components. Negative staining EM analysis of these smaller components revealed that the primary species were VP1 dimers. Interestingly, the cross-reactive but non-neutralizing antibody A1227 (Fab fragment) bound exclusively to VP1 dimers, while no Fab could be detected on the surface of intact particles. Conversely, the blocking antibody 512 could be found in complex with both intact particles and VP1 dimers. This suggests a potential route for the elicitation of cross-reactive but non-neutralizing antibodies, previously isolated from humans and mice immunized with norovirus VLPs[17-19]. When animals are immunized with VLPs, the partially dissociated particles expose highly conserved sites (mostly located at the base of the P domain and the shell domain) leading to the elicitation of antibodies capable of binding dissociated particles from several genogroups. It has been shown that cross-reactive but non-neutralizing antibodies are also elicited in people infected with GI.1 viruses, indicating that even infectious noroviruses could present occluded epitopes[27]. It is currently unclear if noroviruses can naturally present occluded sites as results of assembly defects or metastability of the capsid. It has been suggested that the flexibility of the P domain could allow some of these occluded epitopes to be (at least transiently) exposed[28,29]. On the other hand, to date, there are no EM studies showing direct evidence of VLPs bound to occluded-site antibodies. In our experiments, we could not detect any A1227 Fab bound to intact particles by NS-EM. However, we cannot exclude that binding of A1227 Fab at very low occupancy (few Fabs per VLP) could happen due to the transient exposure of occluded epitopes. The resolution of negatively stained samples is not sufficient to detect few Fabs that bind at the base of the P domain. Although infectious norovirus particles appear to be in a T=3 icosahedral configuration[30], there is evidence that heterologous expression of VP1 proteins can lead to the assembly of T=1, T=3, and T=4 icosahedral VLPs[24,30].

In addition to preventing disassembly, stabilization of VLPs also impacted immunogenicity. In particular, stabilized VLPs elicited a more focused immune response toward accessible epitopes and the development of blockade titers was much faster than immunization with wild type particles. Interestingly, the presence of adjuvant drastically improved the immunogenicity of wild type particles. We speculate that adsorption of VLPs on adjuvant could exert a stabilizing effect, thereby alleviating their propensity to dissociate. Furthermore, the particle stabilization can be used to improve immunogenicity of other human norovirus genogroups and genotypes, such as the medically important GII.4 or emerging strains such as GII.2 and GII.6. Finally, the ability of stabilized norovirus VLPs to discriminate between antibodies binding to irrelevant epitopes and surface-exposed epitopes can be exploited in antibody isolation campaigns to search for broadly neutralizing antibodies.

METHODS

Production of Norovirus Virus-Like Particles

The gene for GI.1 VP1 protein (accession number: Q83884, identical VP1 sequence to GenBank Accession No. M87661) was synthesized, cloned in a pFastBacl vector and codon optimized for insect cell expression (GenScript). Mutation were performed by GeneImmune using the original pFastBac vector. All plasmids were sequenced before use. Generation of recombinant bacmid DNA was done using the Bac-to-Bac Baculovirus Expression System according to manufacturer instructions (Invitrogen).

Sf9 cells were maintained in ESF921 medium (Expression systems) and transfected with recombinant bacmid DNA using a mixture of 1 μg of DNA and 8 μL of Cellfectin II (Invitrogen) in a final volume of 100 μL. After incubation for 1 hour at room temperature, 800 μL of transfection reagent (Expression system) was added. Transfection was carried out in 6-well plates containing a total of 0.9×10^6 cells per well by dropwise addition of transfection mixture. After incubation for 4 hours at 27° C., the medium was removed and 3 mL of ESF931 medium was added. Cells were incubated at 27° C. for 6 days. Cell culture medium containing recombinant baculovirus (P1 generation) was collected from each well and filter sterilized through 0.2 μm filters. High titer baculovirus was obtained by infecting 50 mL Sf9 cells at a density of 1×10^6 cell/mL with 0.5 mL of P1 virus and incubating for 6 days (27° C., 140 rpm). Medium containing baculovirus (P2 generation) was subsequently clarified by centrifugation (4000 x g, 45 mM, 4° C.) and filter sterilized through 0.2 um filters and kept at 4° C. protected from light until needed. To test expression of VP1 proteins, 50 mL of Sf9 at 3×10^6 cells/mL were infected with 5 mL of P2 virus and incubated for 4 days (27° C., 140 rpm) before clarification of medium. Expression levels were assessed by SDS-PAGE of samples from clarified medium.

Large scale preparation of VLPs were carried out in 200 mL of SF9 cells at $3\times10^6$ cells/mL by addition of baculovirus at MOI of 1:5 (Sf9:PFU) for 4 days at 27° C. Clarified supernatant were prepared as described above. VLPs were concentrated by centrifugation (54,000 xg for 2 hours at 4° C.) on a cushion of 3 mL of 60% iodixanol (Optiprep). Most of the content of the tube was removed by pipetting, leaving the bottom 3 mL, the concentrated protein layer and additional 3 mL above the layer. The final concentration of the iodixanol in the sample being 30%. The mixture was transferred to 5.5 mL Quick-Seal® Ultra-Clear tubes (Beckmann) and centrifugation at 300,000 xg for 8 hours at 4° C. in a NVT100 rotor. The clearly visible VLP layer was collected by side-puncture and injected onto a 16/60 Sephacryl S-500 gel filtration column equilibrated with PBS. The VLP peak eluted at about 74 mL and fractions were pooled, concentrated to about 1 mg/mL in Amicon Ultra Filters (MWCO 30 kDa), and stored at 4° C. until needed. In the case of stabilized mutants, the pooled VLP peak was incubated with a final concentration of 20 mM diamide for one hour at room temperature and subsequently dialyzed overnight against PBS or re-injected onto Sephacryl S-500 columns to remove free diamide. Confirmation of disulfide formation was assessed by SDS-PAGE, with samples run in reducing and non-reducing conditions.

Production of Antibodies

Antibodies and Fab fragments were produced as previously described[17]. Briefly, heavy and light chain plasmids (IgG format) containing secretion signals were co-transfected in Expi293F cells (ThermoFisher) using Turbo293 transfection reagent (Speed Biosystem). Cells were incubated for one day at 37° C., followed by 4 days at 37° C. All subsequent steps were performed at 4° C. Supernatant was collected by centrifugation and loaded onto Protein A resin (GE MabSelect) pre-equilibrated with PBS. Bound antibodies were washed with 50 ml of PBS and eluted dropwise in 1 mL fractions with Pierce IgG Elution buffer (Pierce). Elution was neutralized with 1M Tris-Cl, pH 8.0 (final concentration 0.1M). Fractions with highest A280 absorption were pooled and dialyzed overnight against PBS. Dialyzed protein concentrated to ~10 mg/mL, filter sterilized and kept at 4° C. until needed. For the production of Fab fragment, the purified antibodies were incubated with HRV-3C protease (Millipore-Sigma) overnight at 4° C. Cleavage reaction was loaded onto Protein A resin and flow through was collected. Fabs were purified by size exclusion chromatography on a Superdex 200 16/60 column in PBS. Fractions corresponding to Fab were pooled, concentrated to ~5 mg/mL, filter sterilized and kept at 4° C. until needed.

Negative Staining Electron Microscopy

VLP samples were diluted to approximately 0.1 mg/ml with 10 mM HEPES, pH 7.0, 150 mM NaCl. Higher dilutions, in the range of 0.01-0.05 mg/ml, were used when dissociated VLP fragments or Fab fragments were present. Material was adsorbed to a glow-discharged carbon-coated copper grid, washed with the same buffer, and negatively stained with 0.75% uranyl formate. Datasets were collected at magnifications of 50,000 and 100,000 (pixel size: 0.44 and 0.22 nm, respectively) using SerialEM[35] on an FEI Tecnai T20 electron microscope equipped with a 2 k x 2k Eagle CCD camera and operated at 200 kV, as well as at a magnification of 57,000 (pixel size: 0.25 nm) using EPU on a ThermoFisher Talos F200C electron microscope equipped with a ThermoFisher Ceta CCD camera and operated at 200 kV. Particles were picked automatically using in-house developed automatic software (unpublished) or using e2boxer from the EMAN2 software package[36], followed by manual correction. Reference-free 2D classifications and 3D reconstructions were performed using Relion[37].

Analytical Size-Exclusion Chromatography to Evaluate Dissociated VP1 Components

Norovirus VLPs (200 μg) were incubated with either 512 Fab or A1227 Fab to a final molar ratio of 1:2 (VP1:Fab) on ice for 1 hour. Mixture was subsequently injected onto a Supredex 200 Increase 10/300 GL connected to an Äkta Pure system (GE Healthcare) equilibrated in PBS. Fractions (0.5 mL each) were collected and 20 μL from each fraction was mixed with 20 μL of 2X sample buffer (with and without reduction agent). Fifteen microliters of each fraction was loaded onto a NuPAGE™ 4 to 12%, Bis-Tris gel, which were subsequently stained with Coomassie. Each gel was derived from the same experiment and was processed in parallel. Integration of peaks from chromatograms was performed with the Evaluation option in the Unicorn 7.3 software.

Differential Scanning Calorimetry

VLP samples were prepared by diluting stock solutions (at 2 mg/mL) in PBS to a final concentration of 300 μg/mL. Four hundred microliter of diluted VLPs were loaded on a 96 well plate next to PBS only samples and heat capacities were measured using a high-precision differential scanning VP-DSC microcalorimeter (GE Healthcare/MicroCal). The scan rate was set at 1° C. per minute from 18° C. to 110° C.

Isothermal Titration Calorimetry

Binding experiments by ITC were performed at 25° C. using a VP-ITC microcalorimeter from MicroCal-Malvern Instruments (Northampton, MA, USA). GI.1 VLP and the 512 and 1227 antibody fragments were prepared and dialyzed against PBS, pH 7.4. In each titration, the solution containing the antibody fragment was added stepwise in 10 μL aliquots to the stirred calorimetric cell (v ~1.4 mL) containing GI.1 DS1 VLP at 12-17 nM. The concentration of Fab in the syringe was 16-27 μM. All reagents were thoroughly degassed prior to the experiments. The results are expressed per mole of Fab fragment and the stoichiometry, N, denotes the number of binding sites per mole of VLP. The heat evolved upon each injection was obtained from the integral of the calorimetric signal and the heat associated with binding was obtained after subtraction of the heat of dilution. The enthalpy change, ΔH, the association constant, $K_\alpha$ (the dissociation constant, $K_d=1/K_\alpha$) and the stoichiometry, N, were obtained by nonlinear regression of the data to a single-site binding model using Origin with a fitting function made inhouse. Gibbs energy, ΔG, was calculated from the binding affinity using $\Delta G=-RT \ln K_a$, (R=1.987 cal/(K×mol)) and T is the absolute temperature in kelvin). The entropy contribution to Gibbs energy, −TΔS, was calculated from the relation $\Delta G=\Delta H-T\Delta S$.

Determination of GI.1-v1 VLP Structure by Cryo-EM

Cryo-EM Data Collection and Processing

GI.1 DS1 was deposited on a C-flat grid 1.2/1.3 (protochip.com) with 2.3 □1 of volume at 1 mg/ml concentration. The grid was vitrified with an FEI Vitrobot Mark IV with a wait time of 30 seconds, blot time of 3 seconds and a blot force of 1. Data collection was performed on a Titan Krios microscope using Leginon software[38]. The camera was a Gatan K2 Summit direct detection device. High magnification exposures were collected in movie mode for a 10 s with the total dose of 70.48 e-/Å$^2$ fractionated over 50 raw frames. Images were initially processed using Appion[39, 41]; frames were aligned using MotionCor2[41]. CTFFind4[42,43] was used to calculate the CTF and DoG Picker[39,40] was used for initial particle picking. RELION[37] was then used for particle extraction and the particle stack was imported to cryoSPARC. CryoSPARC 2.12[44] was used for 2D classifications, ab initio 3D reconstruction in C1, and the volume was subjected to homogeneous refinement using I1 symmetry.

Model Building

UCSF Chimera[45] was used to fit the asymmetric unit of human norovirus GI.1 Norwalk VLP (PDB 6OUT) into cryo-EM density and determine symmetry operators. Residues corresponding to the P domain were excluded from the model because the resolution in this region was insufficient for model building, leaving residues 51-222 of chains A-C. The model was subjected to alternating rounds of real space refinement in Phenix[46] and manual building in Coot[47].

Several loops located around the 3-fold symmetry axis were deleted because of weak density in this region. The FSC curve between the map and the model was calculated using phenix.mtriage. Model validation was performed with MolProbity[48] and EMRinger[49]. Figures were generated in UCSF Chimera and PyMOL (www.pymol.org).

EIA and Blockade, and Competition Assays

EIA and blockade assays were done as previously reported[17]. For VLP capture assays, plates were coated with PGM as for blockade assays, followed by addition of 0.25 μg/ml VLP for 1 hour at 37° C. and bound mAb detected as for EIA.

The competition between mouse polyclonal serum and human monoclonal antibodies for binding to immobilized VLPs (0.25 μg/ml) was measured by EIA as described previously[50]. Briefly, mouse s era were added to VLP-coated plates at different dilutions. After 1 h, human mAb were added at a concentration required to achieve 50% maximal binding [$EC_{50}$] at room 37C for 1 h. The plates were then washed with phosphate-buffered saline (PBS)-0.05% Tween 20, and bound human mAb was detected using anti-human-IgG HRP (GE Healthcare). The concentration of sera that blocked binding of 50% of the mab was determined as described above for blockade of binding assays.

Mouse Immunization

Mouse studies were executed in accordance with the recommendations for the care and use of animals by the Office of Laboratory Animal Welfare (OLAW) at NIH. The Institutional Animal Care and Use Committee (IACUC) at UNC-CH approved the animal studies performed here (protocol, IACUC 17-059). Six-week-old Balb/c mice (Jackson Labs) were immunized intramuscularly with 2 μg of VLP plus either PBS or 50 μg alhydrogel (Invivogen). Identical booster vaccinations were performed at week 3, 6, 9 with bleeds at week 3, 5, 8 and 11. Mice were euthanized with isoflurane at week 22, for terminal bleed. Each VLP group contained 8 mice, while 6 mice were used in PBS control groups.

Statistical Analysis

Statistical analyses were performed using two-tailed Mann-Whitney tests with GraphPad Prism 8.0 software (La Jolla, CA). Differences were considered statistically significant at $P<0.05$.

Biolayer Interferometry

A fortéBio Octet Red384 instrument was used to measure binding of sera from immunized mice after capture of VP1 dimer with 512 or A1227 IgG. All assays were performed at 1,000 rpm agitation. Assays were performed at 30° C. in tilted black 384-well plates (Geiger Bio-One) with final volumes of 50 μl/well. Anti Human-Fc sensor tips were used to capture either 512 or A1228 IgG. Biosensor tips were equilibrated for 30 minutes in PBS before each experiment. Capture levels were between 1.2 and 1.3 nm, and variability for each tip did not exceed 0.1 nm. Biosensor tips were then equilibrated for 300 s in PBS before a second association step (600 s) with VP1 dimers at 30 ug/mL. Biosensor tips were then equilibrated for 300 s in PBS prior to measuring association to serum samples from final bleed (300 s). All sera were diluted 50-fold in PBS. Initial slopes were determined by linear regression of the signal in first 30 seconds of association.

References for Example 1

1. Ahmed, S. M. et al. Global prevalence of norovirus in cases of gastroenteritis: a systematic review and meta-analysis. Lancet Infect. Dis. 14, 725-730 (2014).
2. Lopman, B. A., Steele, D., Kirkwood, C. D. & Parashar, U. D. The Vast and Varied Global Burden of Norovirus: Prospects for Prevention and Control. PLoS Med. 13, (2016).
3. Bok, K. & Green, K. Y. Norovirus Gastroenteritis in Immunocompromised Patients. N. Engl. J. Med. 368, 971 (2013).
4. Mattner, F. et al. Risk groups for clinical complications of norovirus infections: an outbreak investigation. Clin. Microbiol. Infect. 12, 69-74 (2006).

5. Arias, A., Emmott, E., Vashist, S. & Goodfellow, I. Progress towards the prevention and treatment of norovirus infections. Future Microbiol. 8, 1475-1487 (2013).
6. Ball, J. M., Hardy, M. E., Atmar, R. L., Conner, M. E. & Estes, M. K. Oral Immunization with Recombinant Norwalk Virus-Like Particles Induces a Systemic and Mucosal Immune Response in Mice. J. Virol. 72, 1345-1353 (1998).
7. Cortes-Penfield, N. W., Ramani, S., Estes, M. K. & Atmar, R. L. Prospects and Challenges in the Development of a Norovirus Vaccine. Clin. Ther. 39, 1537-1549 (2017).
8. Jiang, X., Wang, M., Graham, D. Y. & Estes, M. K. Expression, self-assembly, and antigenicity of the Norwalk virus capsid protein. J. Virol. 66, 6527-6532 (1992).
9. Slifka, M. K. & Amanna, I. J. Role of Multivalency and Antigenic Threshold in Generating Protective Antibody Responses. Front. Immunol. 10, 956 (2019).
10. Mohsen, M. O., Zha, L., Cabral-Miranda, G. & Bachmann, M. F. Major findings and recent advances in virus-like particle (VLP)-based vaccines. Semin. Immunol. 34, 123-132 (2017).
11. Atmar, R. L. et al. Norovirus Vaccine against Experimental Human Norwalk Virus Illness. N. Engl. J. Med. 365, 2178-2187 (2011).
12. Bernstein, D. I. et al. Norovirus Vaccine Against Experimental Human GII.4 Virus Illness: A Challenge Study in Healthy Adults. J. Infect. Dis. 211, 870-878 (2015).
13. Treanor, J. J. et al. A Novel Intramuscular Bivalent Norovirus Virus-Like Particle Vaccine Candidate-Reactogenicity, Safety, and Immunogenicity in a Phase 1 Trial in Healthy Adults. J. Infect. Dis. 210, 1763-1771 (2014).
14. Ramani, S. et al. Mucosal and Cellular Immune Responses to Norwalk Virus. J. Infect. Dis. 212, 397-405 (2015).
15. Lindesmith, L. C. et al. Broad Blockade Antibody Responses in Human Volunteers after Immunization with a Multivalent Norovirus VLP Candidate Vaccine Immunological Analyses from a Phase I Clinical Trial. PLOS Med. 12, e1001807 (2015).
16. Atmar, R. L. et al. Persistence of Antibodies to 2 Virus-Like Particle Norovirus Vaccine Candidate Formulations in Healthy Adults: 1-Year Follow-up With Memory Probe Vaccination. J. Infect. Dis. 220, 603-614 (2019).
17. Lindesmith, L. C. et al. Sera Antibody Repertoire Analyses Reveal Mechanisms of Broad and Pandemic Strain Neutralizing Responses after Human Norovirus Vaccination Immunity 50, 1530-1541.e8 (2019).
18. Hansman, G. S. et al. Structural Basis for Broad Detection of Genogroup II Noroviruses by a Monoclonal Antibody That Binds to a Site Occluded in the Viral Particle. J. Virol. 86, 3635-3646 (2012).
19. Parker, T. D., Kitamoto, N., Tanaka, T., Hutson, A. M. & Estes, M. K. Identification of Genogroup I and Genogroup II Broadly Reactive Epitopes on the Norovirus Capsid. J. Virol. 79, 7402-7409 (2005).
20. Shiota, T. et al. Characterization of a Broadly Reactive Monoclonal Antibody against Norovirus Genogroups I and II: Recognition of a Novel Conformational Epitope. J. Virol. 81, 12298-12306 (2007).
21. Shanker, S. et al. Structural basis for norovirus neutralization by an HB GA blocking human IgA antibody. Proc. Natl. Acad. Sci. U. S. A. 113, E5830-E5837 (2016).
22. Chackerian, B. & Peabody, D. S. Factors That Govern the Induction of Long-Lived Antibody Responses. Viruses 12, 74 (2020).
23. Prasad, B. V. V. X-ray Crystallographic Structure of the Norwalk Virus Capsid. Science 286, 287-290 (1999).
24. Jung, J. et al. High-resolution cryo-EM structures of outbreak strain human norovirus shells reveal size variations. Proc. Natl. Acad. Sci. 116, 12828-12832 (2019).
25. Lu, Y., Chan, W., Ko, B. Y., VanLang, C. C. & Swartz, J. R. Assessing sequence plasticity of a virus-like nanoparticle by evolution toward a versatile scaffold for vaccines and drug delivery. Proc. Natl. Acad. Sci. 112, 12360-12365 (2015).
26. Ausar, S. F., Foubert, T. R., Hudson, M. H., Vedvick, T. S. & Middaugh, C. R. Conformational Stability and Disassembly of Norwalk Virus-like Particles: EFFECT OF pH AND TEMPERATURE. J. Biol. Chem. 281, 19478-19488 (2006).
27. Lindesmith, L. C. et al. Serum Immunoglobulin A Cross-Strain Blockade of Human Noroviruses. Open Forum Infect. Dis. 2, ofv084 (2015).
28. Song, C. et al. Dynamic rotation of the protruding domain enhances the infectivity of norovirus. PLOS Pathog. 16, e1008619 (2020).
29. Young, V. L. et al. High-Resolution Cryo-Electron Microscopy Structures of Murine Norovirus 1 and Rabbit Hemorrhagic Disease Virus Reveal Marked Flexibility in the Receptor Binding Domains. J. Virol. 84, 5836-5841 (2010).
30. Devant, J. M., Hofhaus, G., Bhella, D. & Hansman, G. S. Heterologous expression of human norovirus GII.4 VP1 leads to assembly of T=4 virus-like particles. Antiviral Res. 168, 175-182 (2019).
31. Bundy, B. C. & Swartz, J. R. Efficient disulfide bond formation in virus-like particles. J. Biotechnol. 154, 230-239 (2011).
32. Malik, N. et al. Structures of foot and mouth disease virus pentamers: Insight into capsid dissociation and unexpected pentamer reassociation. PLOS Pathog. 13, e1006607 (2017).
33. Perez-Martin, E. et al. Structure-based energetics of protein interfaces guides foot-and-mouth disease virus vaccine design. Nat. Struct. Mol. Biol. 22, 788-794 (2015).
34. Li, K. et al. Bioengineered Norovirus S 60 Nanoparticles as a Multifunctional Vaccine Platform. ACS Nano 12, 10665-10682 (2018).
35. Mastronarde, D. N. Automated electron microscope tomography using robust prediction of specimen movements. J. Struct. Biol. 152, 36-51 (2005).
36. Tang, G. et al. EMAN2: An extensible image processing suite for electron microscopy. J. Struct. Biol. 157, 38-46 (2007).
37. Scheres, S. H. W. RELION: Implementation of a Bayesian approach to cryo-EM structure determination. J. Struct. Biol. 180, 519-530 (2012).
38. Suloway, C. et al. Automated molecular microscopy: The new Leginon system. J. Struct. Biol. 151, 41-60 (2005).

39. Lander, G. C. et al. Appion: An integrated, database-driven pipeline to facilitate EM image processing. J. Struct. Biol. 166, 95-102 (2009).
40. Voss, N. R., Yoshioka, C. K., Radermacher, M., Potter, C. S. & Carragher, B. DoG Picker and TiltPicker: Software tools to facilitate particle selection in single particle electron microscopy. J. Struct. Biol. 166, 205-213 (2009).
41. Zheng, S. Q. et al. MotionCor2: anisotropic correction of beam-induced motion for improved cryo-electron microscopy. Nat. Methods 14, 331-332 (2017).
42. Rohou, A. & Grigorieff, N. CTFFIND4: Fast and accurate defocus estimation from electron micrographs. J. Struct. Biol. 192, 216-221 (2015).
43. Zhang, K. Gctf: Real-time CTF determination and correction. J. Struct. Biol. 193, 1-12 (2016).
44. Punjani, A., Rubinstein, J. L., Fleet, D. J. & Brubaker, M. A. cryoSPARC: algorithms for rapid unsupervised cryo-EM structure determination. Nat. Methods 14, 290-296 (2017).
45. Pettersen, E. F. et al. UCSF Chimera? A visualization system for exploratory research and analysis. J. Comput. Chem. 25, 1605-1612 (2004).
46. Liebschner, D. et al. Macromolecular structure determination using X-rays, neutrons and electrons: recent developments in Phenix. Acta Crystallogr. Sect. Struct. Biol. 75, 861-877 (2019).
47. Emsley, P., Lohkamp, B., Scott, W. G. & Cowtan, K. Features and development of Coot. Acta Crystallogr. D Biol. Crystallogr. 66, 486-501 (2010).
48. Chen, V. B. et al. MolProbity : all-atom structure validation for macromolecular crystallography. Acta Crystallogr. D Biol. Crystallogr. 66, 12-21 (2010).
49. Barad, B. A. et al. EMRinger: side chain—directed model and map validation for 3D cryo-electron microscopy. Nat. Methods 12, 943-946 (2015).
50. Corti, D. et al. Particle Conformation Regulates Antibody Access to a Conserved GII.4 Norovirus Blockade Epitope. J. Virol. 88, 8826-8842 (2014).

Example 2

Stabilized Virus-Like Particles Formed from Recombinant GII.4 VP1 Proteins

Norovirus GII VLPs are metastable and can be disrupted by interaction with specific antibodies. Norovirus GII VLPs produced in insect cells using the baculovirus system have been 20 used extensively as immunogens in both mice and humans.

Using negative staining electron microscopy, the presence of distorted VLPs as well as VLP components were observed (FIG. 18). The majority of smaller objects are made of VP1 dimers, which are presumably stabilized by the p-domain dimer interface.

Further and surprisingly, adding A1227-Fab to GII.4.1997 VLPs lead to rapid (<60 min) 25 and complete disassembly of the VLP (FIG. 19). The only 2D-class averages were obtained for VP1 dimers with two 1227-Fab bound. The angle of binding is consistent with the crystal structures of the p-domain in complex with 1227-Fab (Lindesmith et al., Immunity 50(6): 1530-1541, 2019).

In contrast, A1227 has no inhibitory effect towards GII.4 viruses, as assessed by an enteroid culture system (Lindesmith et al., Immunity 50(6): 1530-1541, 2019). Therefore, it appears that A1227 (and other occluded site antibodies) bind partially disassembled VLPs, but do not interact with intact viruses.

Stabilization of GII VLPs

To prevent particle disassembly, intermolecular disulfide bonds and hydrophobic substitutions were designed within the shell domain of GII.4. The template GII.4 sequence used was the following:

```
Template GII.4c VP1
                                            (SEQ ID NO: 51)
MKMASNDANPSDGSTANLVPEVNNEVMALEPVVGAAIAAPVAGQQNVID

PWIRNNFVQAPGGEFTVSPRNAPGEILWSAPLGPDLNPYLSHLARMYNG

YAGGFEVQVILAGNAFTAGKIIFAAVPPNFPTEGLSPSQVTMFPHIIVD

VRQLEPVLIPLPDVRNNFYHYNQSNDPTIKLIAMLYTPLRANNAGDDVF

TVSCRVLTRPSPDFDFIFLVPPTVESRTKPFTVPILTVEEMTNSRFPIP

LEKLFTGPSGAFVVQPQNGRCTTDGVLLGTTQLSPVNICTFRGDVTHIA

GTQEYTMNLASQNWNNYDPTEEIPAPLGTPDFVGKIQGVLTQTTRGDGS

TRGHKATVSTGSVHFTPKLGSVQFSTDTSNDFETGQNTKFTPVGVVQDG

STTHQNEPQQWVLPDYSGRDSHNVHLAPAVAPTFPGEQLLFFRSTMPGC

SGYPNMNLDCLLPQEWVQHFYQEAAPAQSDVALLRFVNPDTGRVLFECK

LHKSGYVTVAHTGQHDLVIPPNGYFRFDSWVNQFYTLAPMGNGTGRRRA

L
```

Amino acid substitutions were introduced into the template sequence as follows:

1. GII.4c F114W
2. GII.4c F114Y
3. GII.4c A113W
4. GII.4c A113F
5. GII.4c N112C/T115C
6. GII.4c N112C/A116C (SEQ ID NO: 52)
7. GII.4c N189C/D194C (SEQ ID NO: 53)
8. GII.4c F165W
9. GII.4c F165Y
10. GII.4c N164C
11. GII.4c T139C/V57C
12. GII.4c H414C/T314C
13. GII.4c H414C/T314GC
14. GII.4c H414C/T314CG
15. GII.4c R187C/F196C
16. GII.4c N163C/N164C
17. GII.4c P125F
18. GII.4c P125W
19. GII.4c F128W
20. GII.4c S136C/P60C (SEQ ID NO: 54)
21. GII.4c S134C/D518C
22. GII.4c H91M
23. GII.4c H91L
24. GII.4c L246W
25. GII.4c L246Y
26. GII.4c P142F
27. GII.4c P142W
28. GII.4c V47C
29. GII.4c N46W
30. GII.4c A191F
31. GII.4c A191C/N189C
32. GII.4c A191GC/N189C
33. GII.4c M140D/Y88R
34. GII.4c M140C/P217C (SEQ ID NO: 55)
35. GII.4c P129C/R223C (SEQ ID NO: 56)

GII.4 VP1 proteins with the sequences of variants 1-35 were expressed in insect cells as described in Example 1 for the GI VLPs. Supernatants from the insect cells were incubated with diamide (to establish an oxidizing environment) and subsequently separated by SDS-PAGE under reducing or non-reducing conditions. VLPs in which each protomer was covalently linked to the neighboring protomer by disulfide links, did not dissociate in the presence of SDS and thus failed to enter the separating gel due to the large size of the particle (~10 MDa), remaining at the top of the well. In the presence of DTT, the disulfides were reduced, and the particle could be dissociated by SDS, resulting in a single band corresponding to the VP1 monomer. Three constructs showed significant stabilization after oxidation in diamide, variants 6, 7, and 20 (FIG. 20). Variant 7 (GII.4c N189C/D194C, SEQ ID NO: 53) was selected for large scale production and characterization according to the method described in FIG. 8. Subsequent analysis showed that GII.4c variant 7 VLPs are approximately 40.3 nm in diameter and are resistant to deformation when incubated with mAb 1227 Fab (FIG. 21).

Example 3

Norovirus VLPs for Detection and Isolation of Norovirus Neutralizing Antibodies

This example describes use of the stabilized Norovirus VLPs described herein to detect and isolate antibodies that specifically bind to solvent-exposed epitopes on the surface of the VLPs.

The GI.1 DS1 VLPs (SEQ ID NO: 7) were fixed to detection plate surface in three difference ways (FIG. 22), by direct binding to the plate surface, by binding to HBGA bound to the plate surface, or by a biotin/streptavidin interaction with biotinylated VLP and streptavidin-coated plates. The stabilized virus-like particles were biotinylated using sulfo-NHS biotin regent (labeling of primary amines). Monoclonal primary antibodies (human) against norovirus GI.1 were used to bind the particles on the plates. Anti-human Fc secondary antibodies conjugated to HRP were used to detect the particles. Three mAbs were used: VRC01 (an HIV directed antibody) as negative control, mAb 512 (a blockade/neutralizing human antibody that binds a surface accessible epitope on GI.1 VLP), and mAb 1227 (a non-neutralizing antibody that binds to an occluded epitope that is only exposed when the particle dissociates). When the VLPs were bound directly to the plate surface, mAbs 512 and 1227 showed similar binding curves, indicating VLP disassociation and exposure of occluded epitopes. When the VLPs were captured using HBGA-coated plates, mAb 512 completed with HBGA binding to VLP at higher antibody concentrations, leading to VLP disassociation and exposure of occluded epitopes. In contrast, when VLPs were captured using biotin/streptavidin, there was clear separation between mAb 512 and mAb 1227 binding, particularly at concentrations below 12 μg/mL, indicating that this protocol is sufficient to detect and isolate antibodies that bind to solvent-exposed epitopes on the surface of the stabilized VLPs. Such antibodies are predicted to be neutralizing/blockade antibodies that block Norovirus infection.

Also, using Streptavidin coated plates makes the difference much larger than coating the VLP directly to the plate. This may be due to deformation of the particle when interacting with the plastic. Capturing of VLPs using the receptor (HBGA) is also not ideal because at higher concentration, the 512 antibody competes with the receptor and the particles detaches from the plate.

To further illustrate the effectiveness of the stabilized Norovirus VLP as diagnostic tools for identification of a subject that has produced a neutralizing antibody response to Norovirus VLP, assessment of total IgG, IgA and IgM antibody titers using stabilized GI.1 VLPs as probe was performed on samples from human patients before and after oral GI.1 Norovirus challenge. Serum from 15 different patients was collected before (day 1) and on day 28 following oral GI.1 Norovirus challenge. IgG, IgA and IgM antibody titers were determined against GI.1 DS1 VLP linked to plates using biotin/streptavidin as described above. As shown in FIG. 23, in nearly all patients, the concentration of antibody binding to the stabilized VLP increased following Norovirus challenge.

Accordingly, detection and/or isolation of antibodies that bind to solvent-exposed epitopes on the surface of the stabilized VLPS described herein can be used to identify a subject that elicits a neutralizing antibody response following Norovirus infection and/or receipt of a Norovirus vaccine, as also as tools to isolate neutralizing/blockade antibodies from immunized or naturally infected subjects.

It will be apparent that the precise details of the methods or compositions described may be varied or modified without departing from the spirit of the described embodiments. We claim all such modifications and variations that fall within the scope and spirit of the claims below.

We claim:

1. A recombinant Norovirus Virus-Like Particle (VLP) comprising:

- a multimer of a recombinant Norovirus GI VP1 protein comprising amino acid substitutions set forth as one or more of the following pairs of cysteine substitutions that form a non-natural interprotomer disulfide bond: N116C/G193C, A37C/A44C, Q62C/A140C, L144C/P221C, G131C/N172C, and N167C/L169C, wherein the amino acid positions are according to the reference GI VP1 protein sequence set forth as SEQ ID NO: 1; or
- a multimer of a recombinant Norovirus GII VP1 protein comprising amino acid substitutions set forth as one or more of the following pairs of cysteine substitutions that form a non-natural interprotomer disulfide bond: N112C/A116C, N189C/D194C, P60C/S136C, M140C/P217C, P129C/R223C, wherein the amino acid positions are according to the reference GII VP1 protein sequence set forth as SEQ ID NO: 51.

2. The recombinant Norovirus VLP of claim 1, comprising the multimer of the recombinant Norovirus GI VP1 protein.

3. The recombinant Norovirus VLP of claim 2, wherein the recombinant Norovirus GI VP1 protein comprises the one or more of the following pairs of cysteine substitutions that form a non-natural interprotomer disulfide bond: N116C/G193C, A37C/A44C, Q62C/A140C, L144C/P221C, G131C/N172C, and N167C/L169C within an amino acid sequence at least 90% identical to any one of SEQ ID NOS: 1-6.

4. The recombinant Norovirus VLP of claim 2, wherein the recombinant Norovirus GI VP1 protein in the VLP comprises the N116C/G193C substitutions.

5. The recombinant Norovirus VLP of claim 4, wherein the non-natural disulfide bond between the N116C/G193C substitutions is located at 5-fold and quasi-6 fold axes of the VLP, and wherein the VLP has T=3 symmetry.

6. The recombinant Norovirus VLP of claim 2, wherein the recombinant Norovirus GI VP1 protein in the VLP comprises the A37C/A44C substitutions.

7. The recombinant Norovirus VLP of claim 6, wherein the non-natural disulfide bond between the A37C/A44C substitutions is located at a 3-fold axis of the VLP, and wherein the VLP has T=3 symmetry.

8. The recombinant Norovirus VLP of claim 1, wherein the recombinant Norovirus GI VP1 protein in the VLP comprises the N116C/G193C and A37C/A44C substitutions.

9. The recombinant Norovirus VLP of claim 2, wherein the recombinant Norovirus GI VP1 protein is a GI.1, GI.2, GI.3, GI.4, GI.7, or GI.8 VP1 protein comprising the one or more of the following pairs of cysteine substitutions that form a non-natural interprotomer disulfide bond: N116C/G193C, A37C/A44C, Q62C/A140C, L144C/P221C, G131C/N172C, and N167C/L169C.

10. The recombinant Norovirus VLP of claim 9, wherein the recombinant Norovirus GI VP1 protein is a GI.1 VP1 protein comprising the one or more of the following pairs of cysteine substitutions that form a non-natural interprotomer disulfide bond: N116C/G193C, A37C/A44C, Q62C/A140C, L144C/P221C, G131C/N172C, and N167C/L169C.

11. The recombinant Norovirus VLP of claim 2, wherein the recombinant Norovirus GI VP1 protein comprises or consists of the amino acid sequence set forth as any one of SEQ ID NOs: 7-25.

12. The recombinant Norovirus VLP of claim 1, comprising the multimer of the recombinant Norovirus GII VP1 protein.

13. The recombinant Norovirus VLP of claim 12, wherein the recombinant Norovirus GII VP1 protein comprises the amino acid substitutions set forth as one or more of the following pairs of cysteine substitutions that form a non-natural interprotomer disulfide bond: N112C/A116C, N189C/D194C, P60C/S136C, M140C/P217C, P129C/R223C within an amino acid sequence at least 90% identical to any one of SEQ ID NOs: 26-51.

14. The recombinant Norovirus VLP of claim 12, wherein the recombinant Norovirus GII VP1 protein in the VLP comprises the N112C/A116C substitutions.

15. The recombinant Norovirus VLP of claim 14, wherein the non-natural disulfide bond between the N112C/A116C substitutions is located at a 3-fold axis of the VLP, and wherein the VLP has T=3 symmetry.

16. The recombinant Norovirus VLP of claim 12, wherein the recombinant Norovirus GII VP1 protein in the VLP comprises the N189C/D194C substitutions.

17. The recombinant Norovirus VLP of claim 16, wherein the non-natural disulfide bond between the N189C/D194C substitutions is located at a 3-fold axis of the VLP, and wherein the VLP has T=3 symmetry.

18. The recombinant Norovirus VLP of claim 12, wherein the recombinant Norovirus GII VP1 protein in the VLP comprises the P60C/S136C substitutions.

19. The recombinant Norovirus VLP of claim 18, wherein the non-natural disulfide bond between the P60C/S136C substitutions is located at a 3-fold axis of the VLP, and wherein the VLP has T=3 symmetry.

20. The recombinant Norovirus VLP of claim 12, wherein the recombinant Norovirus GII VP1 protein is a GII.1, GII.2, GII.3, GII.4, GII.4c, GII.5, GII.6, GII.7, GII.8, GII.9, GII.10, GII.11, GII.12, GII.13, GII.14, GII.15, GII.16, GII.17, GII.18, GII.19, GII.20, GII.21, GII.22, GII.23, GII.24, or GII.25 VP1 protein comprising the one or more of the following pairs of cysteine substitutions that form a non-natural interprotomer disulfide bond: N112C/A116C, N189C/D194C, P60C/S136C, M140C/P217C, P129C/R223C.

21. The recombinant Norovirus VLP of claim 12, wherein the recombinant Norovirus GII VP1 protein is a GII.4c VP1 protein comprising the one or more of the following pairs of cysteine substitutions that form a non-natural interprotomer disulfide bond: N112C/A116C, N189C/D194C, P60C/S136C, M140C/P217C, P129C/R223C.

22. The recombinant Norovirus VLP of claim 12, wherein the recombinant Norovirus GII VP1 protein comprises or consists of the amino acid sequence set forth as any one of SEQ ID NOs: 52-56.

23. The recombinant Norovirus VLP of claim 1, wherein the recombinant Norovirus VP1 protein further comprises one or more amino acid substitutions that stabilize the assembly of the recombinant Norovirus VP1 proteins in the VLP.

24. The recombinant Norovirus VLP of claim 1, wherein the multimer is a self-assembly of 90 Norovirus VP1 dimers into an icosahedral shaped VLP.

25. The recombinant Norovirus VLP of claim 24, wherein the one or more amino acid substitutions stabilize the assembly of the Norovirus VP1 dimers in the icosahedral shape.

26. The recombinant Norovirus VLP of claim 1, comprising increased thermal stability compared to a control Norovirus VLP without the one or more amino acid substitutions.

27. The recombinant Norovirus VLP of claim 1, comprising a diameter of from about 20 nm to about 60 nm.

28. The recombinant Norovirus VLP of claim 1, comprising a T=3 symmetry and a diameter of about 38 nm.

29. The recombinant Norovirus VLP of claim 1, wherein the recombinant Norovirus VLP does not comprise a VP2 protein and/or genetic material.

30. The recombinant Norovirus VLP of claim 1, wherein the VP1 proteins of the recombinant Norovirus VLP do not dissociate following incubation with mAb1227 Fab for 1 hour at room temperature in phosphate buffered saline at a 1:2 molar ratio of GI VP1 to mAb1227 Fab.

31. An immunogenic composition comprising the recombinant Norovirus VLP of claim 1, and a pharmaceutically acceptable carrier.

32. A method for generating an immune response to a Norovirus VP1 protein in a subject, comprising administering to the subject an effective amount of the recombinant Norovirus VLP of claim 1 to generate the immune response.

33. The method of claim 32, wherein the immune response inhibits Norovirus infection in the subject.

34. The method of claim 32, wherein the immune response inhibits replication and/or shedding of the Norovirus in the subject.

* * * * *